(12) United States Patent
Schnell et al.

(10) Patent No.: US 11,571,576 B2
(45) Date of Patent: Feb. 7, 2023

(54) BRAIN STIMULATION AND SENSING

(71) Applicant: Medtronic, Inc., Minneapolis, MN (US)

(72) Inventors: Evan D. Schnell, North Oaks, MN (US); Scott R. Stanslaski, Shoreview, MN (US); Ilan D. Gordon, Crystal, MN (US); Steven M. Goetz, North Oaks, MN (US); Hijaz M. Haris, Plymouth, MN (US); Eric J. Panken, Edina, MN (US); Timothy R. Abraham, Lino Lakes, MN (US); Thomas L. Chouinard, Maple Grove, MN (US); Susan Heilman Kilbane, Deephaven, MN (US); Karan Chitkara, Plymouth, MN (US); Christopher M. Arnett, Dayton, MN (US); Alicia W. Thompson, Coon Rapids, MN (US); Kevin C. Johnson, Zimmerman, MN (US); Ankush Thakur, Fridley, MN (US); Lukas Valine, Forest Lake, MN (US); Christopher L. Pulliam, Plymouth, MN (US); Brady N. Fetting, Hudson, WI (US); Rucha Gokul G. Samant, Fridley, MN (US); Andrew H. Houchins, Hugo, MN (US); Caleb C. Zarns, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 113 days.

(21) Appl. No.: 17/139,316

(22) Filed: Dec. 31, 2020

(65) Prior Publication Data

US 2021/0196958 A1 Jul. 1, 2021

Related U.S. Application Data

(60) Provisional application No. 62/955,861, filed on Dec. 31, 2019.

(51) Int. Cl.
*A61N 1/372* (2006.01)
*A61N 1/36* (2006.01)
(Continued)

(52) U.S. Cl.
CPC .......... *A61N 1/36139* (2013.01); *A61B 5/318* (2021.01); *A61B 5/37* (2021.01);
(Continued)

(58) Field of Classification Search
CPC .............. A61N 1/36139; A61N 1/0534; A61N 1/3606; A61N 1/36135; A61N 1/37241;
(Continued)

(56) References Cited

U.S. PATENT DOCUMENTS 5,593,431 A 1/1997 Sheldon
7,231,254 B2 6/2007 DiLorenzo
(Continued)

OTHER PUBLICATIONS

Goetz et al., "Movement Disorder Society-Sponsored Revision of the Unified Parkinson's Disease Rating Scale (MDS-UPDRS): Scale Presentation and Clinimetric Testing Results," Movement Disorders, vol. 23, No. 15, Nov. 15, 2008, pp. 2129-2170.
(Continued)

*Primary Examiner* — Eugene T Wu
(74) *Attorney, Agent, or Firm* — Shumaker & Sieffert, P.A.

(57) ABSTRACT

Devices, systems, and techniques are disclosed for managing electrical stimulation therapy and/or sensing of physiological signals such as brain signals. For example, a system may assist a clinician in identifying one or more electrode combinations for sensing a brain signal. In another example,
(Continued)

a user interface may display brain signal information and values of a stimulation parameter at least partially defining electrical stimulation delivered to a patient when the brain signal information was sensed.

20 Claims, 76 Drawing Sheets

(51) Int. Cl.

| | | |
|---|---|---|
| A61B 5/384 | (2021.01) | |
| A61B 5/37 | (2021.01) | |
| A61B 5/318 | (2021.01) | |
| A61B 5/372 | (2021.01) | |
| A61B 5/00 | (2006.01) | |
| A61N 1/05 | (2006.01) | |

(52) U.S. Cl.
CPC .............. *A61B 5/372* (2021.01); *A61B 5/384* (2021.01); *A61B 5/7221* (2013.01); *A61B 5/7257* (2013.01); *A61B 5/7264* (2013.01); *A61N 1/0534* (2013.01); *A61N 1/3606* (2013.01); *A61N 1/36135* (2013.01); *A61N 1/37241* (2013.01); *A61N 1/37247* (2013.01)

(58) Field of Classification Search
CPC ............ A61N 1/37247; A61N 1/36185; A61N 1/36064; A61N 1/36067; A61N 1/36082; A61N 1/3718; A61B 5/318; A61B 5/37; A61B 5/372; A61B 5/384; A61B 5/7221; A61B 5/7257; A61B 5/7264; A61B 5/293; A61B 5/4064; A61B 5/7207
See application file for complete search history.

(56) References Cited

U.S. PATENT DOCUMENTS

| | | | |
|---|---|---|---|
| 9,717,439 B2 | 8/2017 | Giftakis et al. | |
| 9,888,861 B2 | 2/2018 | Carlson et al. | |
| 10,016,606 B2 | 7/2018 | Afshar et al. | |
| 10,596,379 B2 | 3/2020 | Arlotti et al. | |
| 10,820,819 B2 | 11/2020 | Afshar et al. | |
| 2009/0083070 A1* | 3/2009 | Giftakis ................ | G16H 20/40 705/2 |
| 2011/0245629 A1* | 10/2011 | Giftakis ................ | A61B 5/1116 600/301 |
| 2011/0270357 A1 | 11/2011 | Torgerson et al. | |
| 2013/0053722 A1* | 2/2013 | Carlson ................. | A61B 5/316 607/45 |
| 2014/0135870 A1 | 5/2014 | Carlson et al. | |
| 2014/0148723 A1 | 5/2014 | Nierenberg et al. | |
| 2014/0358024 A1 | 12/2014 | Nelson et al. | |
| 2018/0085572 A1 | 3/2018 | Stanslaski et al. | |
| 2018/0085586 A1* | 3/2018 | Stanslaski ............ | A61B 5/4836 |
| 2020/0139113 A1* | 5/2020 | Shin ..................... | A61N 1/0456 |

OTHER PUBLICATIONS

Arlotti et al., "Eight-Hours Adaptive Deep Brain Stimulation in Patients with Parkinson Disease," Neurology, vol. 90, No. 11, Mar. 13, 2018, pp. e971-e976.

Little et al., "Beta Band Stability Over Time Correlates with Parkinsonian Rigidity and Bradykinesia," Experimental Neurology, No. 236, Aug. 2012, pp. 383-388.

Connolly et al., "Guiding Deep Brain Stimulation Contact Selection Using Local Field Potentials Sensed by a Chronically Implanted Device in Parkinson's Disease Patients," 2015 7th International IEEE/EMBS Conference on Neural Engineering (NER), Apr. 22-24, 2015, 4 pp.

Eusebio et al., "Deep Brain Stimulation Can Suppress Pathological Synchronisation in Parkinsonian Patients," Journal of Neurology, Neurosurgery & Psychiatry, vol. 82, No. 5, Oct. 2010, pp. 569-573.

Tinkhauser et al., "Directional Local Field Potentials: A Tool to Optimize Deep Brain Stimulation," Movement Disorders, vol. 33, No. 1, Jan. 2018, pp. 159-164.

Alonso-Frech et al., "Slow Oscillatory Activity and Levodopa-Induced Dyskinesias in Parkinson's Disease," Brain, vol. 129, Issue 7, Jul. 2006, pp. 1748-1757.

Swann et al., "Gamma Oscillations in the Hyperkinetic State Detected with Chronic Human Brain Recordings in Parkinson's Disease," The Journal of Neuroscience, vol. 36, No. 4, Jun. 15, 2016, pp. 6445-6458.

Kuhn et al., "Pathological Synchronisation in the Subthalamic Nucleus of Patients with Parkinson's Disease Relates tc Both Bradykinesia and Rigidity," Experimental Neurology, vol. 215, Feb. 2009, pp. 380-387.

Ince et al., "Selection of Optimal Programming Contacts Based on Local Field Potential Recordings From Subthalamic Nucleus in Patients With Parkinson's Disease," Neurosurgery, vol. 67, No. 2, Aug. 2010, pp. 390-397.

Odekerken et al., "Subthalamic Nucleus Versus Globus Pallidus Bilateral Deep Brain Stimulation for Advanced Parkinson's Disease (NSTAPS Study): a Randomised Controlled Trial," Lancet Neurology, vol. 12, No. 1, Jan. 1, 2013, pp. 37-44.

* cited by examiner

BRAIN STIMULATION AND SENSING

This application claims priority to U.S. Provisional Patent Application No. 62/955,861, filed Dec. 31, 2019 and entitled "BRAIN STIMULATION AND SENSING," the entire contents of which are incorporated by reference herein.

TECHNICAL FIELD

This disclosure generally relates to electrical stimulation therapy.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current amplitude, a pulse width, and a pulse frequency as stimulation parameters. A set of parameters, such as a set including electrode combination, electrode polarity, voltage or current amplitude, pulse width and pulse rate, may be referred to as a program in the sense that they define the electrical stimulation therapy to be delivered to the patient.

SUMMARY

In general, the disclosure describes devices, systems, and techniques for managing DBS therapy, which may include monitoring brain signals, stimulation parameter values, patient events, or other aspects related to the patient and the DBS therapy. For example, a programming device may be configured to present a user interface configured to present information related to DBS therapy and/or brain signal monitoring. The system may include a medical device (e.g., an implantable medical device) configured to sense physiological signals such as electrical signals originating in the patient's brain. The system may employ aspects of these signals for presenting information to the user and/or guiding the user to select various parameters for sensing and/or delivering stimulation.

For example, an external device (e.g., an external programmer) may include a user interface that is configured to receive user input selecting one or more electrode configurations for delivering stimulation and/or sensing brain signals. The system may suggest and/or receive user input defining one or more thresholds that determine therapy parameter values or request patient data. In some examples, the user interface may be configured to present stored and/or real-time brain signal data alone or together with one or more stimulation parameter values defining stimulation delivered when the brain signal data is sensed. In some examples, the external programming device may control a medical device to perform one or more signal tests for one or more electrode combinations (e.g., one or more signal pathways) of an implanted lead. The programming devices, user interfaces, and techniques described herein may thus enable a user (e.g., a clinician or patient) to manage one or more aspects of DBS therapy.

In one example, a method includes obtaining, by processing circuitry, brain signal information for at least one electrode combination of a plurality of electrode combinations of one or more electrical leads; determining, by the processing circuitry and based on the brain signal information, a respective frequency for the at least one electrode combination; outputting, for display, a plurality of selectable lead icons, wherein each selectable lead icon of the plurality of selectable lead icons represents a different electrode combination of the plurality of electrode combinations; outputting, for display, the respective frequency determined for the at least one electrode combination in association with the respective selectable lead icon associated with the at least one electrode combination; receiving user input selecting one selectable lead icon of the plurality of selectable lead icons; and responsive to receiving the user input, selecting, by the processing circuitry and for subsequent brain signal sensing, a sense electrode combination associated with the one selectable lead icon selected by the user input.

In another example, a method includes obtaining, by processing circuitry, a brain signal representative of electrical activity of a brain of a patient; controlling, by the processing circuitry, a medical device to deliver electrical stimulation defined by at least a first value of a stimulation parameter; adjusting, by the processing circuitry, the first value of the stimulation parameter to a second value of the stimulation parameter at which a patient condition is identified; and determining, by the processing circuitry, a threshold value for the brain signal associated with the patient condition, wherein the medical device is configured to limit automatic adjustment of the stimulation parameter to the second value associated with the threshold value.

In another example, a method includes obtaining, by processing circuitry, a brain signal representative of electrical activity of a brain of a patient; obtaining, by the processing circuitry, one or more values of a stimulation parameter that at least partially defines electrical stimulation deliverable to a portion of the brain of the patient; and outputting, for display by a user interface, a graph comprising a first trace of the brain signal for a period of time and a second trace of the one or more values of the stimulation parameter for the period of time.

In another example, a method includes obtaining, by processing circuitry and from a first memory, brain signal information representative of electrical activity of a brain of a patient over a period of time; obtaining, by the processing circuitry, stimulation parameter information comprising one or more values of a stimulation parameter that at least partially defines electrical stimulation delivered to a portion of the brain of the patient during the period of time; and outputting, for display by a user interface, a graph comprising a first trace of the brain signal information for the period of time and a second trace of the one or more values of the stimulation parameter for the period of time.

In another example, a method includes obtaining, by processing circuitry, brain signal information representative of electrical activity of a brain of a patient over a period of time; determining, by the processing circuitry, a first amount of time an amplitude of the brain signal information was greater than an upper threshold during the period of time; determining, by the processing circuitry, a second amount of time the amplitude of the brain signal information was less than a lower threshold during the period of time; determining, by the processing circuitry, a third amount of time the amplitude of the brain signal information was between the upper threshold and the lower threshold during the period of time; and outputting, for display via a user interface, a representation of the first amount of time, the second amount of time, and the third amount of time.

In another example, a method includes receiving, by processing circuitry, an indication of an event at a time; responsive to receiving the indication of the event, storing spectral information for a brain signal recorded at the time; and outputting, for display by a user interface, a graph indicating the spectral information for the brain signal recorded at the time.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
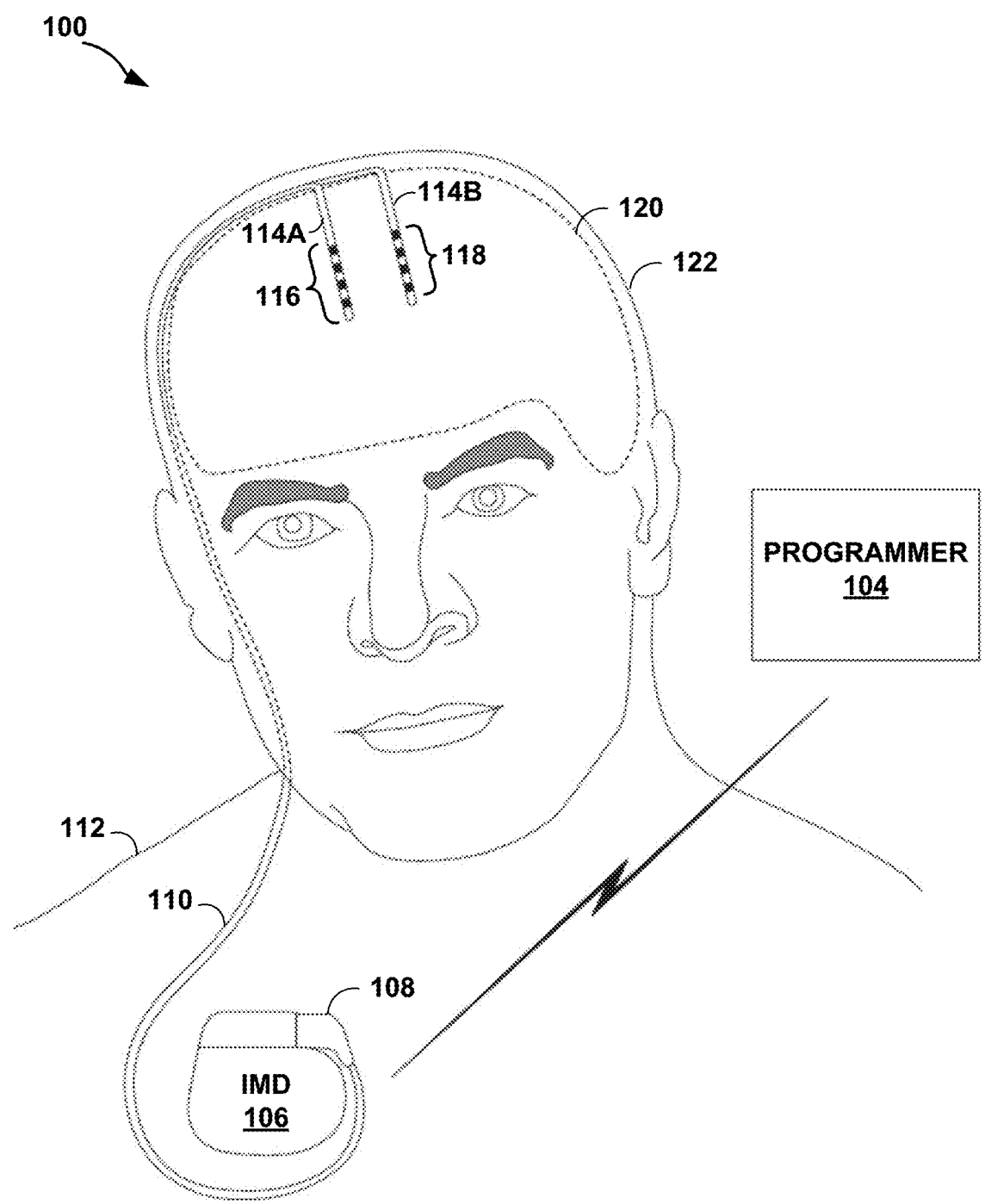
FIG. 1 is a conceptual diagram illustrating an example system that includes an implantable medical device (IMD) configured to deliver DBS to a patient according to an example of the techniques of the disclosure.

A patient may suffer from one or more symptoms treatable by electrical stimulation therapy. For example, a patient may suffer from brain disorder such as Parkinson's disease, Alzheimer's disease, or another type of movement disorder. Deep brain stimulation (DBS) may be an effective treatment to reduce the symptoms associated with such disorders. However, it may be time consuming for a clinician to manually determine appropriate stimulation parameters that define effective electrical stimulation therapy. Moreover, DBS is typically delivered continuously in an open loop fashion for the patient. Not only does this open loop delivery consume more battery power due to stimulation being delivered when not needed by the patient, but the system is not able to adjust stimulation parameters to provide more targeted therapy as the condition of the patient changes over time or under certain conditions. In addition, it can be challenging for clinicians to identify patient events and conditions and what types of adjustments could be made to improve therapy over time.

As described herein, various devices, systems, and techniques enable management of DBS therapy and/or brain sensing for a patient. For example, systems described herein may be configured to sense and record brain signals (e.g., electroencephalogram (EEG signals), local field potentials (LFP signals), or other brain signals) associated with brain disorders. The system may identify appropriate frequencies for different electrode combinations and/or suggest an electrode combination for sensing. The system may also display the recorded brain signals or aspects thereof for review by a user such as a clinician. In some examples, the system may operate in an adaptive DBS mode in which the system adjusts the value of one or more stimulation parameters in order to maintain the brain signals above or below one or more respective thresholds. The system may receive user input specifying or adjusting any of these thresholds. In addition, the system may employ a setup mode in which the clinician can capture brain signal thresholds that correspond to respective stimulation parameter values. In some examples, the system may be configured to record and store brain signal information in response to a user identified event and/or a system identified event, where the system can later present information regarding the brain signal to enable a clinician to view the brain signal associated with the event that occurred.

These various features may provide advantages over other systems and improve system functionality and patient outcomes. For example, the system may capture brain signals from multiple different electrode combinations and suggest an electrode combination to use for brain signal sensing, which reduces clinician trial and error during patient setup. The system may also guide a clinician through setup of one or more thresholds employed to provide adaptive DBS therapy and enable fine adjustments to these thresholds. This guide may reduce clinician time and improve therapeutic results for the patient by increasing therapeutic stimulation efficacy and reducing side effects. The system may also correlate patient condition and events with sensed brain signals and display such information for clinician review. The clinician can then identify brain signals sensed during a specific patient event, and stimulation status during such events, to monitor stimulation efficacy and adjust stimulation over time to reduce patient symptoms.

FIG. 1 is a conceptual diagram illustrating an example system 100 that includes an implantable medical device (IMD) 106 configured to deliver adaptive deep brain stimulation to a patient 112. DBS may be adaptive in the sense that IMD 106 may adjust, increase, or decrease the magnitude of one or more stimulation parameters of the DBS in response to changes in patient activity or movement, a severity of one or more symptoms of a disease of the patient, a presence of one or more side effects due to the DBS, or one or more sensed signals of the patient, etc. For example, one or more sensed signals of the patient may be used as a control signal such that the IMD 106 correlates the magnitude of the one or more parameters of the electrical stimulation to the magnitude of the one or more sensed signals. According to the techniques of the disclosure, system 100, via IMD 106, delivers electrical stimulation therapy having one or more parameters, such as voltage or current amplitude, adjusted in response to a signal deviating from a range defined by a homeostatic window (e.g., a window defined by one or more thresholds for a brain signal, such as a lower threshold and upper threshold).

In other examples, the system delivers electrical stimulation therapy having the one or more parameters, such as voltage or current amplitude, adjusted in response to multiple signals, each signal deviating from a range defined by a respective homeostatic window. For example, the system may sense a first neurological signal, such as a signal within a Beta frequency band of the brain 120 of patient 112 within a first respective homeostatic window and a second neurological signal, such as a signal within a Gamma frequency band of the brain 120 of patient 112 within a second respective homeostatic window. In one example system, IMD 16 dynamically selects one of the first signal or the second signal for controlling adjustment of the one or more parameters based on a determination of which of the first signal or second signal most accurately corresponds to the severity of one or more symptoms of the patient. In another example system, IMD 106 adjusts the one or more parameters based on a ratio of the first signal to the second signal. In some examples, amplitudes of one or more frequencies in the Gamma frequency band increase with greater stimulation intensity such that higher Gamma frequency amplitudes may be associated with side effects. Conversely, amplitudes of one or more frequencies in the Beta frequency band decrease with greater stimulation intensity such that lower Gamma frequency amplitudes may be associated with side effects (e.g., dyskinesia).

In some examples, the medication taken by patient 112 is a medication for controlling one or more symptoms of Parkinson's disease, such as tremor or rigidity due to Parkinson's disease. Such medications include extended release forms of dopamine agonists, regular forms of dopamine agonists, controlled release forms of carbidopa/levodopa (CD/LD), regular forms of CD/LD, entacapone, rasagiline, selegiline, and amantadine. Typically, to set the upper threshold and lower threshold of the homeostatic window, the patient has been off medication, i.e., the upper and lower thresholds are set when the patient is not taking medication selected to reduce the symptoms. The patient may be considered to be not taking the medication when the patient, prior to the time the upper bound is set, has not taken the medication for at least approximately 72 hours for extended release forms of dopamine agonists, the patient has not taken the medication for at least approximately 24 hours for regular forms of dopamine agonists and controlled release forms of CD/LD, and the patient has not taken the medication for at least approximately 12 hours for regular forms of CD/LD, entacapone, rasagiline, selegiline, and amantadine. If only stimulation is suppressing brain signals (e.g., LFP signals), then the system can measure these brain signals for various values of stimulation parameters without outside inputs. Once the upper threshold and lower threshold is established, the system can identify when medication wears off because the brain signals will cross the lower or upper threshold. In response to identifying the brain signal crossing a threshold, the system may turn on electrical stimulation to bring back brain signal amplitudes back between the lower threshold and the upper threshold. Programmer 104 may enable the user to initially set the lower threshold and the upper threshold and make adjustments over time. Programmer 104 may also determine and display information regarding the amount of time stimulation amplitude is above, below, or between the thresholds.

As described herein, "reducing" or "suppressing" the symptoms of the patient refer to alleviating, in whole or in part, the severity of one or more symptoms of the patient. In one example, a clinician makes a determination of the severity of one or more symptoms of Parkinson's disease of patient 112 with reference to the Unified Parkinson's Disease Rating Scale (UPDRS) or the Movement Disorder Society-Sponsored Revision of the Unified Parkinson's Disease Rating Scale (MDS-UPDRS). A discussion of the application of the MDS-UPDRS is provided by Movement Disorder Society-Sponsored Revision of the Unified Parkinson's Disease Rating Scale (MDS-UPDRS): Scale Presentation and Clinimetric Testing Results, C. Goetz et al, Movement Disorders, Vol. 23, No. 15, pp. 2129-2170 (2008), the content of which is incorporated herein in its entirety.

As described herein, a clinician can determine the upper threshold of the homeostatic window while the patient is not taking medication, and while, via IMD 106, electrical stimulation therapy is delivered to the brain 120 of patient 112. In one example, a clinician determines the point at which increasing the magnitude of one or more parameters defining the electrical stimulation therapy, such as voltage amplitude or current amplitude, begins to cause one or more side effects for the patient 112. For example, the clinician may gradually increase the magnitude of one or more parameters defining the electrical stimulation therapy and determine the point at which further increase to the magnitude of one or more parameters defining the electrical stimulation therapy causes a perceptible side effect for patient 112. As described herein, IMD 106 may sense LFPs during this process and display the LFP signal and/or LFP signal magnitude that may correspond to the respective thresholds.

As also described above, a clinician determines the lower threshold while the patient is off medication and while, via IMD 106, electrical stimulation therapy is delivered to the brain 120 of patient 112. In one example, a clinician determines the point at which decreasing the magnitude of one or more parameters defining the electrical stimulation therapy causes break-through of one or more symptoms of the patient 112. This break-through of symptoms may refer to re-emergence of at least some symptoms that were substantially suppressed up to the point of re-emergence due to the decrease in magnitude of the one or more electrical stimulation therapy parameters. For example, the clinician may gradually decrease the magnitude of one or more parameters defining the electrical stimulation therapy and determine the point at which the symptoms of Parkinson's disease in patient 112 emerge, as measured by sudden increase with respect to tremor or rigidity, in the score of patient 112 under the UPDRS or MDS-UPDRS. In another example, the clinician measures a physiological parameter of patient 112 correlated to one or more symptoms of the disease of patient 112 (e.g., wrist flexion of patient 112) and determines the point at which further decrease to the magnitude of one or more parameters defining the electrical stimulation therapy causes a sudden increase in the one or more symptoms of the disease of patient 112 (e.g., onset of lack of wrist flexion of patient 112).

At the magnitude of one or more parameters defining the electrical stimulation therapy at which further decrease to the magnitude of one or more parameters defining the electrical stimulation therapy causes a sudden increase in the one or more symptoms of the disease of patient 112, the clinician measures the magnitude of the signal of the patient 112 and sets this magnitude as the lower threshold of the homeostatic window. In some examples, the clinician may select a lower threshold of the homeostatic window to be a predetermined amount, e.g., 5% or 10%, higher than the magnitude at which the symptoms of the patient 112 first emerge during decrease in the magnitude of one or more electrical stimulation parameters to prevent emergence of the symptoms of the patient 112 during subsequent use.

In another example, the clinician sets the lower threshold by first ensuring that the patient is off medication for the one or more symptoms. In this example, the clinician delivers electrical stimulation having a value for the one or more parameters approximately equal to the upper threshold of the therapeutic window. In some examples, the clinician delivers electrical stimulation having a value for the one or more parameters slightly below the magnitude which induces side effects in the patient 112. Typically, this causes greater reduction of the one or more symptoms of the disease of the patient 112, and therefore greater reduction of the signal. At this magnitude of the one or more parameters, the clinician measures the magnitude of the signal of the patient 112 and sets, via external programmer 104, this magnitude as the lower threshold of the homeostatic window. In some examples, the clinician may select a value for the lower threshold of the homeostatic window to be a predetermined amount, e.g., 5% or 10%, higher than the magnitude at which the symptoms of the patient 112 emerge to prevent emergence of the symptoms of the patient 112 during subsequent use.

Additionally, in one example of the techniques of the disclosure, the system monitors a signal of the patient. In one example, the signal is a neurological signal of a patient, such as a signal within a Beta frequency band or a Gamma frequency band of the brain of the patient. In yet a further example, the signal is a signal indicative of a physiological parameter of the patient, such as a severity of a symptom of the patient, a posture of the patient, a respiratory function of the patient, or an activity level of the patient. For example, the monitored signal may be a power of the respective Beta frequency band and/or Gamma frequency band.

The system, via IMD 106, delivers electrical stimulation to the patient, wherein one or more parameters defining the electrical stimulation are proportional to the magnitude of the monitored signal.

System 100 may be configured to treat a patient condition, such as a movement disorder, neurodegenerative impairment, a mood disorder, or a seizure disorder of patient 112. Patient 112 ordinarily is a human patient. In some cases, however, therapy system 100 may be applied to other mammalian or non-mammalian, non-human patients. While movement disorders and neurodegenerative impairment are primarily referred to herein, in other examples, therapy system 100 may provide therapy to manage symptoms of other patient conditions, such as, but not limited to, seizure disorders (e.g., epilepsy) or mood (or psychological) disorders (e.g., major depressive disorder (MDD), bipolar disorder, anxiety disorders, post-traumatic stress disorder, dysthymic disorder, and obsessive-compulsive disorder (OCD)). At least some of these disorders may be manifested in one or more patient movement behaviors. As described herein, a movement disorder or other neurodegenerative impairment may include symptoms such as, for example, muscle control impairment, motion impairment or other movement problems, such as rigidity, spasticity, bradykinesia, rhythmic hyperkinesia, nonrhythmic hyperkinesia, and akinesia. In some cases, the movement disorder may be a symptom of Parkinson's disease. However, the movement disorder may be attributable to other patient conditions.

Example therapy system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes are located at different positions around the perimeter of the respective lead.

In some examples, the neurological signals sensed within brain 120 may reflect changes in electrical current produced by the sum of electrical potential differences across brain tissue. Examples of neurological brain signals include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120 of patient 112.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, in some examples, the electrodes used for delivering electrical stimulation may be different than the electrodes used for sensing neurological brain signals. In other examples, the same electrodes may be used to deliver electrical stimulation and sense brain signals. However, this configuration would require the system to switch between stimulation generation and sensing circuitry and may reduce the time the system can sense brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. Other lead 114 and IMD 106 implant sites are contemplated. For example, IMD 106 may be implanted on or within cranium 122, in some examples. Or leads 114 may be implanted within the same hemisphere or IMD 106 may be coupled to a single lead implanted in a single hemisphere.

Existing lead sets include axial leads carrying ring electrodes disposed at different axial positions and so-called "paddle" leads carrying planar arrays of electrodes. Selection of electrode combinations within an axial lead, a paddle lead, or among two or more different leads presents a challenge to the clinician. In some examples, more complex lead array geometries may be used.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because they are relatively simple to program and are capable of delivering an electrical field to any tissue adjacent to electrodes 116, 118. In other examples, electrodes 116, 118 may have different configurations. For example, in some examples, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode. In this manner, electrical stimulation may be directed in a specific direction from leads 114 to enhance therapy efficacy and reduce possible adverse side effects from stimulating a large volume of tissue. In some examples, a housing of IMD 106 may include one or more stimulation and/or sensing electrodes. In alternative examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114). In addition, or as an alternative, to programmer 104, a different external computing device may perform any of the functionality of programmer 104. The external computing device may be a networked device and in communication with IMD 106 directly or via programmer 104.

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combination with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 112 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 104 is described as delivering electrical stimulation therapy to brain 120, IMD 106 may be configured to direct electrical stimulation to other anatomical regions of patient 112 in other examples. In other examples, system 100 may include an implantable drug pump in addition to, or in place of, IMD 106. Further, an IMD may provide other electrical stimulation such as spinal cord stimulation to treat a movement disorder.

According to the techniques of the disclosure, system 100 defines a homeostatic window and a therapeutic window for delivering adaptive DBS to patient 112. System 100 may adaptively deliver electrical stimulation and adjust one or more parameters defining the electrical stimulation within a parameter range defined by upper and lower limits of the therapeutic window based on the activity of the sensed signal (e.g., LFP signal) within the homeostatic window. For example, system 100 may adjust the one or more parameters defining the electrical stimulation in response to the sensed signal falling below the lower threshold or exceeding the upper threshold of the homeostatic window, but may not adjust the one or more parameters defining the electrical stimulation such that they fall below the lower limit or exceed the upper limit of the therapeutic window.

In one example, external programmer 104 issues commands to IMD 106 causing IMD 106 to deliver electrical stimulation therapy via electrodes 116, 118 via leads 114. As described above, the therapeutic window defines an upper bound and a lower bound for one or more parameters defining the delivery of electrical stimulation therapy to patient 112. For example, the one or more parameters include a current amplitude (for a current-controlled system) or a voltage amplitude (for a voltage-controlled system), a pulse rate or frequency, and a pulse width. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. In one example, the therapeutic window defines an upper bound and a lower bound for one or more parameters, such as upper and lower threshold for a current amplitude of the electrical stimulation therapy (in current-controlled systems) or upper and lower threshold of a voltage amplitude of the electrical stimulation therapy (in voltage-controlled systems). While the examples herein are typically given with respect to adjusting a voltage amplitude or a current amplitude, the techniques herein may equally be applied to a homeostatic window and a therapeutic window using other parameters, such as, e.g., pulse rate or pulse width. Example implementations of the therapeutic window are provided in further detail below.

Typically, a patient programmer 104 may not have access to adjustments to any thresholds or limits for sensing or stimulation related to adaptive DBS. For example, patient programmer 104 may only enable a patient to adjust a stimulation parameter value between limits set by the clinician programmer. However, in other examples, system 100 may provide adaptive DBS by permitting a patient 112, e.g., via a patient programmer 104, to indirectly adjust the activation, deactivation, and magnitude of the electrical stimulation by adjusting the lower and upper threshold of the homeostatic window. In one example, the patient programmer 104 may only be enabled to adjust an upper or lower threshold a small magnitude or percentage of the clinician-set value. In another example, by adjusting one or both thresholds of the homeostatic window, patient 112 may adjust the point at which the sensed signal deviates from the homeostatic window, triggering system 100 to adjust one or more parameters of the electrical stimulation within a parameter range defined by the lower and upper threshold of the therapeutic window.

In some examples, a patient may provide feedback, e.g., via programmer 104, to adjust one or both threshold of the homeostatic window. In another example, programmer 104 and/or IMD 106 may automatically adjust one or both threshold of the homeostatic window, as well as one or more parameters of the electrical stimulation within the parameter range defined by the lower and upper threshold of the therapeutic window. For example, IMD 106 may adjust the delivery of adaptive DBS by automatically adjusting one or more thresholds (e.g., an upper and a lower threshold in some examples) of the homeostatic window, e.g., in response to a physiological parameter sensed by one or more sensors 109 of system 100. As a further example, programmer 104 and/or IMD 106 may automatically adjust one or more thresholds of the homeostatic window based on one or more physiological or neurological signals of patient 112 sensed by IMD 106. For example, in response to deviations in the signal of the patient outside of the homeostatic window, system 100 (e.g., IMD 106 or programmer 104) may automatically adjust one or more parameters defining the electrical stimulation therapy delivered to the patient in a manner that is proportional to the magnitude of the sensed signal and within the therapeutic window defining lower and upper thresholds for the one or more parameters. The adjustment to the one or more stimulation therapy parameters based on the deviation of the sensed signal may be proportional or inversely proportional to the magnitude of the signal.

Hence, in some examples, system 100, via programmer 104 or IMD 106, may adjust one or more parameters of the electrical stimulation, such as voltage or current amplitude, within the therapeutic window based on patient input that adjusts the homeostatic window, or based on one or more signals, such as sensed physiological parameters or sensed neurological signals, or a combination of two or more of the above. In particular, system 100 may adjust a parameter of the electrical stimulation, automatically and/or in response to patient input that adjusts the homeostatic window, provided the value of the electrical stimulation parameter is constrained to remain within a range specified by the upper and lower threshold of the therapeutic window. This range may be considered to include the upper and lower threshold themselves.

In some examples where system 100 adjusts multiple parameters of the electrical stimulation, system 100 may adjust at least one of a voltage amplitude or current amplitude, a stimulation frequency, a pulse width, or a selection of electrodes, and the like. In such an example, the clinician may set an order or sequence for adjustment of the parameters (e.g., adjust voltage amplitude or current amplitude, then adjust stimulation frequency, and then adjust the selection of electrodes). In other examples, system 100 may randomly select a sequence of adjustments to the multiple parameters. In either example, system 100 may adjust a value of a first parameter of the parameters of the electrical stimulation. If the signal does not exhibit a response to the adjustment of the first parameter, system 100 may adjust a value of a second parameter of the parameters of the electrical stimulation, and so on until the signal returns to within the homeostatic window.

To adaptively adjust DBS based on a neurological signal, for example, two or more electrodes 116, 118 of IMD 106 may be configured to monitor a neurological signal (e.g., an LFP signal) of patient 112. In some examples, at least one of electrodes 116, 118 may be provided on a housing of IMD 106, providing a unipolar stimulation and/or sensing configuration. In one example, the neurological signal is a signal within a Beta frequency band of brain 120 of patient 112. For example, neurological signals within the Beta frequency band of patient 112 may correlate to one or more symptoms of Parkinson's disease in patient 112. Generally speaking, neurological signals within the Beta frequency of patient 112 may be approximately proportional to the severity of the symptoms of patient 112. For example, as tremor induced by Parkinson's disease increases, neurological signals within the Beta frequency of patient 112 increase (e.g., magnitude of the signal and/or spectral power). Moreover, neurological signals within the Beta frequency are considered proportional because system 100 may be configured such that an increase in signal magnitude may trigger system 100 to increase delivered stimulation therapy magnitude according to disclosed techniques. Similarly, as tremor induced by Parkinson's disease decreases, neurological signals within the Beta frequency of patient 112 decrease (e.g., magnitude of the signal and/or spectral power), and the decrease may trigger system 100 to decrease the magnitude of delivered stimulation.

In some examples, each of a sensor within IMD 106 is an accelerometer, a bonded piezoelectric crystal, a mercury switch, or a gyro. In some examples, these sensors may provide a signal that indicates a physiological parameter of the patient, which in turn varies as a function of patient activity. For example, the device may monitor a signal that indicates the heart rate, electrocardiogram (ECG) morphology, electroencephalogram (EEG) morphology, respiration rate, respiratory volume, core temperature, subcutaneous temperature, or muscular activity of the patient.

In some examples, the sensors generate a signal both as a function of patient activity and patient posture. For example, accelerometers, gyros, or magnetometers may generate signals that indicate both the activity and the posture of a patient 112. External programmer 104 may use such information regarding posture to determine whether external programmer 104 should perform adjustments to the therapeutic window.

For example, in order to identify posture, the sensors such as accelerometers may be oriented substantially orthogonally with respect to each other. In addition to being oriented orthogonally with respect to each other, each of the sensors used to detect the posture of a patient 112 may be substantially aligned with an axis of the body of a patient 112. When accelerometers, for example, are aligned in this manner, the magnitude and polarity of DC components of the signals generate by the accelerometers indicate the orientation of the patient relative to the Earth's gravity, e.g., the posture of a patient 112. Further information regarding use of orthogonally aligned accelerometers to determine patient posture may be found in a commonly assigned U.S. Pat. No. 5,593,431, which issued to Todd J. Sheldon, the entire content of which is incorporated by reference herein.

Other sensors that may generate a signal that indicates the posture of a patient 112 include electrodes that generate a signal as a function of electrical activity within muscles of a patient 112, e.g., an electromyogram (EMG) signal, or a bonded piezoelectric crystal that generates a signal as a function of contraction of muscles. Electrodes or bonded piezoelectric crystals may be implanted in the legs, buttocks, chest, abdomen, or back of a patient 112, and coupled to one or more of external programmer 104 and IMD 106 wirelessly or via one or more leads. Alternatively, electrodes may be integrated in a housing of the IMD 106 or piezoelectric crystals may be bonded to the housing when IMD 106 is implanted in the buttocks, chest, abdomen, or back of a patient 112. The signals generated by such sensors when implanted in these locations may vary based on the posture of a patient 112, e.g., may vary based on whether the patient is standing, sitting, or lying down.

Further, the posture of a patient 112 may affect the thoracic impedance of the patient. Consequently, sensors may include an electrode pair, including one electrode integrated with the housing of IMDs 106 and one of electrodes 116, 118, that generate a signal as a function of the thoracic impedance of a patient 112, and IMD 106 may detect the posture or posture changes of a patient 112 based on the signal. In one example (not depicted), the electrodes of the pair may be located on opposite sides of the patient's thorax. For example, the electrode pair may include electrodes located proximate to the spine of a patient for delivery of SCS therapy, and IMD 106 with an electrode integrated in its housing may be implanted in the abdomen or chest of patient 112. As another example, IMD 106 may include electrodes implanted to detect thoracic impedance in addition to leads 114 implanted within the brain of patient 112. The posture or posture changes may affect the delivery of DBS or SCS therapy to patient 112 for the treatment of any type of neurological disorder, and may also be used to detect patient sleep, as described herein.

Additionally, changes of the posture of a patient 112 may cause pressure changes with the cerebrospinal fluid (CSF) of the patient. Consequently, sensors may include pressure sensors coupled to one or more intrathecal or intracerebroventricular catheters, or pressure sensors coupled to IMDs 106 wirelessly or via one of leads 114. CSF pressure changes associated with posture changes may be particularly evident within the brain of the patient, e.g., may be particularly apparent in an intracranial pressure (ICP) waveform.

Accordingly, in some examples, instead of monitoring a neurological signal of the patient, the system 100 monitors one or more signals from sensors indicative of a magnitude of a physiological parameter of patient 112. Upon detecting that one or more signals from sensors exceed the upper bound of the homeostatic window, the system 100 increases stimulation at a maximum ramp rate determined by the clinician until one or more signals from sensors return to within the homeostatic window, or until the magnitude of the electrical stimulation reaches an upper limit of a therapeutic window determined by the clinician. Similarly, upon detecting that one or more signals from sensors falls below the lower bound of the homeostatic window, the system decreases stimulation at a maximum ramp rate determined by the clinician until one or more signals from sensors return to within the homeostatic window, or until the magnitude of the electrical stimulation reaches a lower limit of a therapeutic window determined by the clinician. Upon detecting that one or more signals from sensors are within the threshold of the homeostatic window, the system holds the magnitude of the electrical stimulation constant.

Such a system 100 for delivering adaptive DBS to the patient by monitoring a physiological parameter may provide advantages over other techniques that use a neurological signal as a threshold in that the techniques of the disclosure allow an IMD to control delivery of therapy using hysteresis. In other words, such a system 100 uses the physiological parameter of the patient to create a control loop for not only controlling the delivery of therapy, but also controlling the magnitude of the delivered therapy. Such a system may be less intrusive on the activity of a patient because the system 100 adapts the stimulation to the current needs of the patient, and thus may reduce the side effects that the patient experiences.

Further, such a system 100 may use external sensors, such as accelerometers, instead of internal sensors, such as electrodes, to detect symptoms of the disease of the patient and control adjustments to the magnitude of one or more parameters of the therapy. For example, the system 100 may use a wrist sensor to detect wrist flexion or tremor of a patient suffering from Parkinson's disease. Thus, such an IMD the monitoring of a physiological parameter may be less invasive than other IMD systems because the system of the present disclosure may not require sensing electrodes to be implanted in the brain of the patient 112.

In some circumstances, system 100, as described herein, may deliver, based on the upper and lower threshold of the homeostatic window, a lower magnitude of electrical stimulation than patient 112 requires to prevent breakthrough of his or her symptoms. For example, a patient receiving therapy from an IMD 106 that controls delivery of electrical stimulation therapy using the homeostatic window may, in certain circumstances, experience results that are less optimal than if the patient received continuous electrical stimulation therapy at a maximum therapy magnitude. To prevent this occurrence, system 100 may determine a value for the at least one electrical stimulation parameter as defined by the homeostatic window, as described above. Further, the IMD 106 of system 100 may increase the value for the at least one electrical stimulation parameter by a bias amount greater than the determined magnitude defined by the homeostatic window so as to further prevent breakthrough of the symptoms of patient 112. Thus, system 100 may avoid delivering electrical stimulation therapy that is of a magnitude that may be insufficient for prevention of symptom breakthrough.

The architecture of system 100 illustrated in FIG. 1 is shown as an example. The techniques as set forth in this disclosure may be implemented in the example system 100 of FIG. 1, as well as other types of systems not described specifically herein. For example, a clinician may determine the upper threshold and lower threshold of the homeostatic window. In other examples, one of the external programmer 104 and IMD 104 determines the upper threshold and lower threshold of the homeostatic window. Furthermore, either external programmer 104 or IMD 106 may receive the signal representative of the signal of patient 112 and determine an adjustment to one or more parameters defining the electrical stimulation therapy that IMD 106 delivers to patient 112. Nothing in this disclosure should be construed so as to limit the techniques of this disclosure to the example architecture illustrated by FIG. 1.

Figure 2:
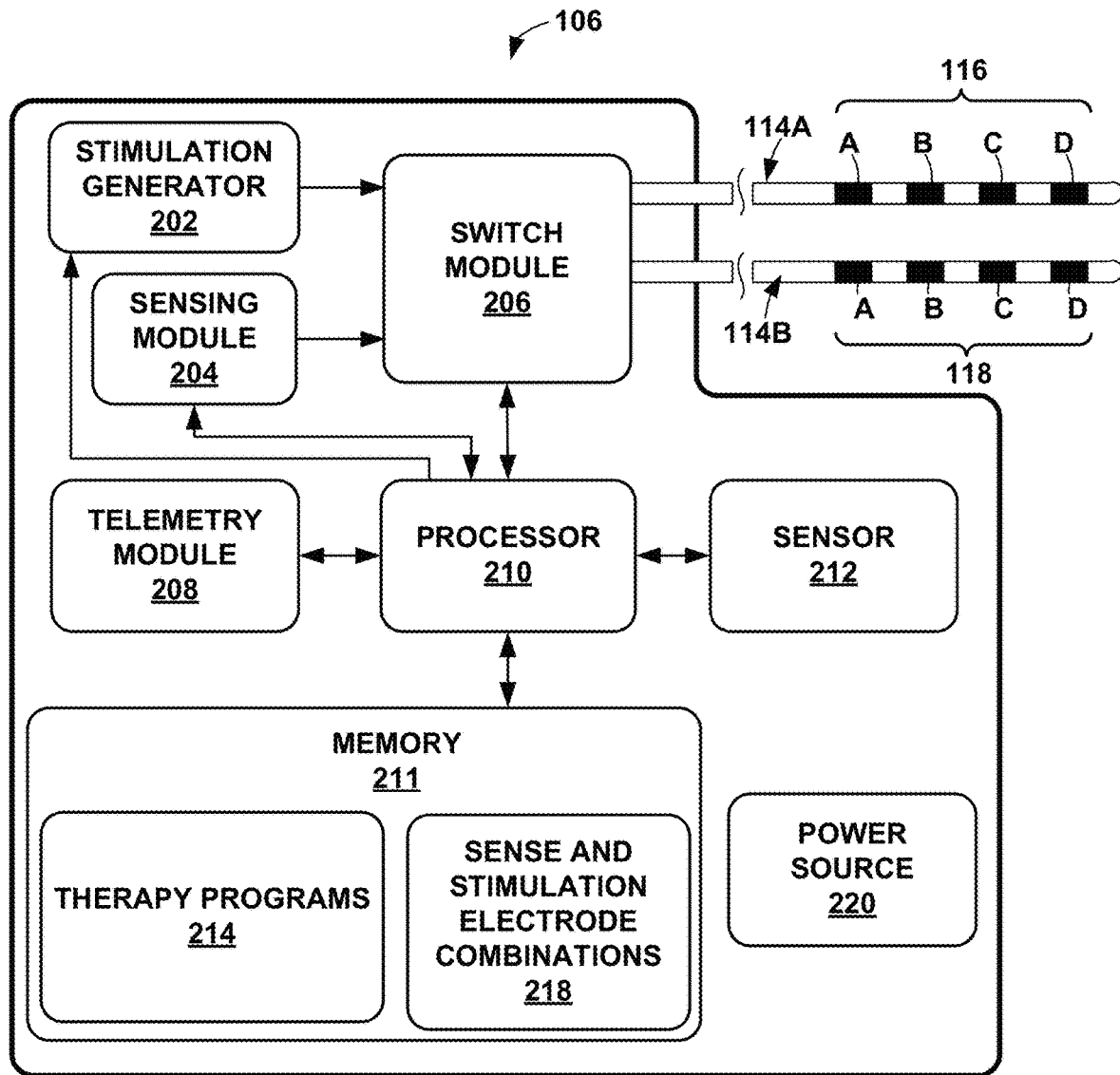
FIG. 2 is a block diagram of the example IMD of FIG. 1 for delivering DBS therapy according to an example of the techniques of the disclosure.

FIG. 2 is a block diagram of the example IMD 106 of FIG. 1 for delivering adaptive deep brain stimulation therapy. In the example shown in FIG. 2, IMD 106 includes processor 210, memory 211, stimulation generator 202, sensing module 204, switch module 206, telemetry module 208, sensor 212, and power source 220. Each of these modules may be or include electrical circuitry configured to perform the functions attributed to each respective module. For example, processor 210 may include processing circuitry, switch module 206 may include switch circuitry, sensing module 204 may include sensing circuitry, and telemetry module 208 may include telemetry circuitry. Switch module 204 may not be necessary for multiple current source and sink configurations. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 106 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Sense and stimulation electrode combinations 218 stores sense electrode combinations and associated stimulation electrode combinations. As described above, in some examples, the sense and stimulation electrode combinations may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate any irregular oscillations or other irregular brain activity within the tissue site associated with the sense electrode combination.

Stimulation generator 202, under the control of processor 210, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 40 Hertz and approximately 500 Hertz, such as between approximately 40 to 185 Hertz or such as approximately 140 Hertz.

2. In the case of a voltage controlled system, Voltage Amplitude: between approximately 0.1 volts and approximately 50 volts, such as between approximately 2 volts and approximately 3 volts.

3. In the alternative case of a current controlled system, Current Amplitude: between approximately 0.2 milliamps to approximately 100 milliamps, such as between approximately 1.3 milliamps and approximately 2.0 milliamps.

4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 202 generates electrical stimulation signals in accordance with the electrical stimulation parameters noted above, subject to application of the upper and lower threshold of a therapeutic window to one or more of the parameters, such that an applicable parameter resides within the range prescribed by the window. Other ranges of therapy parameter values may also be useful, and may depend on the target stimulation site within patient 112. While stimulation pulses are described, stimulation signals may be of any form, such as continuous-time signals (e.g., sine waves) or the like.

Processor 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 may control stimulation generator 202 according to therapy programs 214 stored in memory 211 to apply particular stimulation parameter values specified by one or more of programs, such as voltage amplitude or current amplitude, pulse width, or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processor 210 also controls switch module 206 to apply the stimulation signals generated by stimulation generator 202 to selected combinations of electrodes 116, 118. In particular, switch module 204 may couple stimulation signals to selected conductors within leads 114, which, in turn, deliver the stimulation signals across selected electrodes 116, 118. Switch module 206 may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generator 202 is coupled to electrodes 116, 118 via switch module 206 and conductors within leads 114. In some examples, however, IMD 106 does not include switch module 206.

Stimulation generator 202 may be a single channel or multi-channel stimulation generator. In particular, stimulation generator 202 may be capable of delivering a single stimulation pulse, multiple stimulation pulses, or a continuous signal at a given time via a single electrode combination or multiple stimulation pulses at a given time via multiple electrode combinations. In some examples, however, stimulation generator 202 and switch module 206 may be configured to deliver multiple channels on a time-interleaved basis. For example, switch module 206 may serve to time divide the output of stimulation generator 202 across different electrode combinations at different times to deliver multiple programs or channels of stimulation energy to patient 112. Alternatively, stimulation generator 202 may comprise multiple voltage or current sources and sinks that are coupled to respective electrodes to drive the electrodes as cathodes or anodes. In this example, IMD 106 may not require the functionality of switch module 206 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D. On one example, the electrodes may be electrically coupled to switch module 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 114. These and other constructions may be used to create a lead with a complex electrode geometry.

Although sensing module 204 is incorporated into a common housing with stimulation generator 202 and processor 210 in FIG. 2, in other examples, sensing module 204 may be in a separate housing from IMD 106 and may communicate with processor 210 via wired or wireless communication techniques. Example neurological brain signals include, but are not limited to, a signal generated from local field potentials (LFPs) within one or more regions of brain 28. EEG and ECoG signals are other examples of electrical signals that may be measured within brain 120 or by electrodes placed in other locations with respect to brain 120.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient).

Telemetry module 208 supports wireless communication between IMD 106 and an external programmer 104 or another computing device under the control of processor 210. Processor 210 of IMD 106 may receive, as updates to programs, values for various stimulation parameters such as magnitude and electrode combination, from programmer 104 via telemetry module 208. The updates to the therapy programs may be stored within therapy programs 214 portion of memory 211. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104. Accordingly, telemetry module 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

According to the techniques of the disclosure, processor 210 of IMD 106 delivers, electrodes 116, 118 interposed along leads 114 (and optionally switch module 206), electrical stimulation therapy to patient 112. The adaptive DBS therapy is defined by one or more therapy programs 214 having one or more parameters stored within memory 211.

For example, the one or more parameters include a current amplitude (for a current-controlled system) or a voltage amplitude (for a voltage-controlled system), a pulse rate or frequency, and a pulse width, or quantity of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time. In one example, the therapeutic window defines an upper limit and a lower limit for a voltage amplitude of the electrical stimulation therapy. In another example, the therapeutic window defines an upper limit and a lower limit for a current amplitude of the electrical stimulation therapy. In particular, a parameter of the electrical stimulation therapy, such as voltage or current amplitude, is constrained to a therapeutic window having an upper limit and a lower limit, such that the voltage or current amplitude may be adjusted provided the amplitude remains greater than or equal to the lower limit and less than or equal to the upper limit. It is noted that a single limit may be used in some examples.

In one example, processor 210, via electrodes 116, 118 of IMD 106, monitors the behavior of a signal of patient 112 that correlates to one or more symptoms of a disease of patient 112 within a homeostatic window. Processor 210, via electrodes 116, 118, delivers to patient 112 adaptive DBS and may adjust one or more parameters defining the electrical stimulation within a parameter range defined by lower and upper thresholds of a therapeutic window based on the activity of the sensed signal within the homeostatic window.

In one example, the signal is a neurological signal (e.g., a LFP signal) within the Beta frequency band of brain 120 of patient 112. The signal within the Beta frequency band of patient 112 may correlate to one or more symptoms of Parkinson's disease in patient 112. Generally speaking, neurological signals within the Beta frequency band of patient 112 may be approximately proportional to the severity of the symptoms of patient 112. For example, as tremor induced by Parkinson's disease increases, one or more of electrodes 116, 118 detect an increase in the magnitude of neurological signals within the Beta frequency band of patient 112.

Similarly, as tremor induced by Parkinson's disease decreases, processor 210, via the one or more of electrodes 116, 118, detects a decrease in the magnitude of the neurological signals within the Beta frequency band of patient 112. In another example, the signal is a neurological signal within the Gamma frequency band of brain 120 of patient 112. The signal within the Gamma frequency band of patient 112 may also correlate to one or more side effects of the electrical stimulation therapy. However, in contrast to neurological signals within the Beta frequency band, generally speaking, neurological signals within the Gamma frequency band of patient 112 may be approximately inversely proportional to the severity of the side effects of the electrical stimulation therapy. For example, as side effects due to electrical stimulation therapy increase, processor 210, via the one or more of electrodes 116, 118, detects a decrease in the magnitude of the signal within the Gamma frequency band of patient 112. Similarly, as side effects due to electrical stimulation therapy decrease, processor 210, via the one or more of electrodes 116, 118, detects an increase in the magnitude of the signal within the Gamma frequency band of patient 112.

In response to detecting that the signal of the patient, e.g., a sensed physiological parameter signal or a sensed neurological signal, has deviated from the homeostatic window, processor 210 dynamically adjusts the magnitude of the one or more parameters of the electrical stimulation therapy such as, e.g., pulse current amplitude or pulse voltage amplitude, to drive the signal of the patient back into the homeostatic window. For example, wherein the signal is a neurological signal within the Beta frequency band of brain 120 of patient 112, processor 210, via the one or more of electrodes 116, 118, monitors the beta magnitude of patient 112. Upon detecting that the beta magnitude of patient 112 exceeds the upper bound of the homeostatic window, processor 210 increases a magnitude of the electrical stimulation delivered via electrodes 116, 118 at a maximum ramp rate, e.g., determined automatically or by the clinician until the magnitude of the neurological signal within the Beta band falls back to within the homeostatic window, or until the magnitude of the electrical stimulation reaches an upper limit of a therapeutic window determined by the clinician. Similarly, upon detecting that the beta magnitude of patient 112 falls below the lower bound of the homeostatic window, processor 210 decreases stimulation magnitude at a maximum ramp rate determined by the clinician until the beta magnitude rises back to within the homeostatic window, or until the magnitude of the electrical stimulation reaches a lower limit of a therapeutic window determined by the clinician. Upon detecting that the beta magnitude is presently within the threshold of the homeostatic window, or has returned to within the threshold of the homeostatic window, processor 210 holds the magnitude of the electrical stimulation constant. In other examples, processing 210 may automatically determine the ramp rate at which stimulation parameters are adjusted to cause the brain signal to fall back within the target range. The ramp rate may be selected based on prior data indicating general patient comfort or comfort or preferences of the specific patient.

In some examples, processor 210 continuously measures the signal in real time. In other examples, processor 210 periodically samples the signal according to a predetermined frequency or after a predetermined amount of time. In some examples, processor 210 periodically samples the signal at a frequency of approximately 150 Hertz.

Furthermore, processor 210 delivers electrical stimulation therapy that is constrained by an upper limit and a lower limit of a therapeutic window. In some examples, values defining the therapeutic window are stored within memory 211 of IMD 106. For example, in response to detecting that the brain signal has deviated from the homeostatic window, processor 210 of IMD 106 may adjust one or more parameters of the electrical stimulation therapy to provide responsive treatment to patient 112. For example, in response to detecting that the signal has exceeded an upper threshold of the homeostatic window and prior to delivering the electrical stimulation therapy, processor 210 increases an amplitude of stimulation (e.g., but not above the upper limit) in order to bring the signal back down below the upper threshold. For example, in a voltage-controlled system wherein the clinician has set the upper limit of the therapeutic window to be 3 Volts, processor 210 can increase the voltage amplitude to values no greater than 3 Volts in an attempt to decrease the brain signal below the upper threshold.

In another example, in response to detecting that the signal has fallen below a lower threshold of the homeostatic window and prior to delivering the electrical stimulation therapy, processor 210 decreases the voltage amplitude, for example, but not lower than the magnitude of the lower limit. For example, in the above voltage-controlled system wherein the clinician has set the lower bound of the therapeutic window to be 1.2 Volts, processor 210 can decrease the voltage amplitude down to no lower than 1.2 Volts in an attempt to raise the brain signal back above the lower threshold and into the homeostatic window. Thus, processor 210 of IMD 106 may deliver adaptive DBS to patient 112 wherein the one or more parameters defining the adaptive DBS is within the therapeutic window defined by a lower and upper limit for the parameter.

In the foregoing example, the limit of the therapeutic window are inclusive (i.e., the upper and lower limit are valid values for the one or more parameters). However, in other examples, the limit of the therapeutic window are exclusive (i.e., the upper and lower limits are not valid values for the one or more parameters). In such an example of an exclusive therapeutic window, processor 210 instead sets the adjustment to the one or more parameters to be the next highest valid value (in the case of an adjustment potentially exceeding the upper limit) or the next lowest valid value (in the case of an adjustment potentially exceeding the lower limit).

In another example, values defining the therapeutic window are stored within a memory 311 of external programmer 104. In this example, in response to detecting that the signal has deviated from the homeostatic window, processor 210 of IMD 106 transmits, via telemetry module 208, data representing the measurement of the signal to external programmer 104. In one example, in response to detecting that the signal has exceeded an upper threshold of the homeostatic window, processor 210 of IMD 106 transmits, via telemetry module 208, data representing the measurement of the signal to external programmer 104. External programmer 104 may determine to adjust a parameter value to reduce the signal below the upper threshold as long as the parameter value remains within the one or more limits to the parameter.

In another example, processor 210, via telemetry module 208 and from external programmer 104, receives instructions to adjust one or more limits of the therapeutic window. For example, such instructions may be in response to patient feedback on the efficacy of the electrical stimulation therapy, or in response to one or more sensors that have detected a signal of the patient. Such signals from sensors may include neurological signals, such as a signal within the Beta frequency band or signal within the Gamma frequency band of brain 120 of patient 112, or physiological parameters and measurements, such as a signal indicating one or more of a patient activity level, posture, and respiratory function. Further, such signals from sensors may indicate a lack of reduction of one or more symptoms of the patient 112, such as tremor or rigidity or the presence of side effects due to electrical stimulation therapy, such as paresthesia. In response to these instructions, processor 210 may adjust one or more thresholds of the homeostatic window. For example, processor 210 may adjust the magnitude of the upper threshold, the lower threshold, or shift the overall position of the homeostatic window such that the threshold, defined by the homeostatic window, for adjustment of the one or more parameters of electrical stimulation, is itself adjusted. Thereafter, processor 210, via electrodes 116 and 118, delivers the adjusted electrical stimulation to patient 112.

Figure 3:
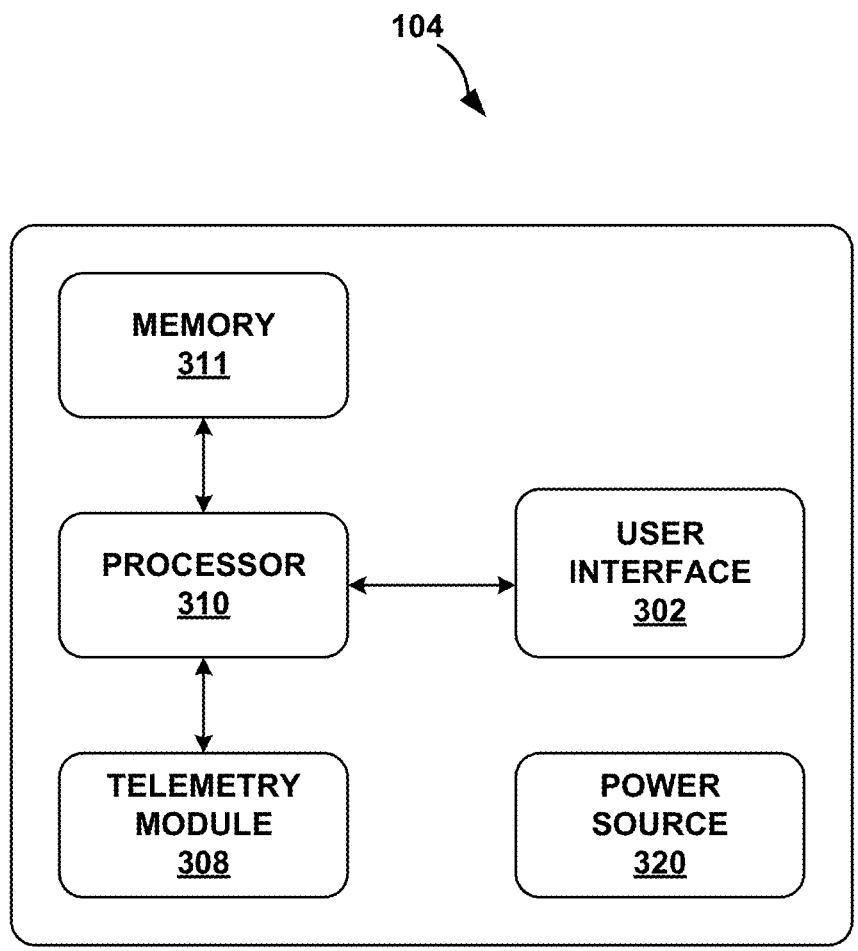
FIG. 3 is a block diagram of the external programmer of FIG. 1 for controlling delivery of DBS therapy according to an example of the techniques of the disclosure.

FIG. 3 is a block diagram of the external programmer 104 of FIG. 1. Although programmer 104 may generally be described as a hand-held device, programmer 104 may be a larger portable device or a more stationary device. In some examples, programmer 104 may be referred to as a tablet computing device. In addition, in other examples, programmer 104 may be included as part of an external charging device or include the functionality of an external charging device. As illustrated in FIG. 3, programmer 104 may include a processor 310, memory 311, user interface 302, telemetry module 308, and power source 320. Memory 311 may store instructions that, when executed by processor 310, cause processor 310 and external programmer 104 to provide the functionality ascribed to external programmer 104 throughout this disclosure. Each of these components, or modules, may include electrical circuitry that is configured to perform some or all of the functionality described herein. For example, processor 310 may include processing circuitry configured to perform the processes discussed with respect to processor 310.

In general, programmer 104 comprises any suitable arrangement of hardware, alone or in combination with software and/or firmware, to perform the techniques attributed to programmer 104, and processor 310, user interface 302, and telemetry module 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processor 310 and telemetry module 308 are described as separate modules, in some examples, processor 310 and telemetry module 308 may be functionally integrated with one another. In some examples, processor 310 and telemetry module 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. For example, memory 311 may include instructions that cause processor 310 to obtain a parameter set from memory, select a spatial electrode movement pattern, or receive a user input and send a corresponding command to IMD 104, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen. User interface 302 may refer to hardware configured to present information to a user and/or receive input from the user. In some examples, processor 310 directly controls this hardware. In other examples, processor 310 may communicate with drive hardware that controls hardware of user interface 302. In some example, user interface 302 may include display and/or interactive display configurations as described herein.

Telemetry module 308 may support wireless communication between IMD 106 and programmer 104 under the control of processor 310. Telemetry module 308 may also be configured to communicate with another computing device via wireless communication techniques, or direct communication through a wired connection. In some examples, telemetry module 308 provides wireless communication via an RF or proximal inductive medium. In some examples, telemetry module 308 includes an antenna, which may take on a variety of forms, such as an internal or external antenna.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry module 308 may be configured to transmit a spatial electrode movement pattern or other stimulation parameter values to IMD 106 for delivery of stimulation therapy.

According to the techniques of the disclosure, in some examples, processor 310 of external programmer 104 defines the parameters of a homeostatic therapeutic window, stored in memory 311, for delivering adaptive DBS to patient 112. In one example, processor 311 of external programmer 104, via telemetry module 308, issues commands to IMD 106 causing IMD 106 to deliver electrical stimulation therapy via electrodes 116, 118 via leads 114.

Figure 4:
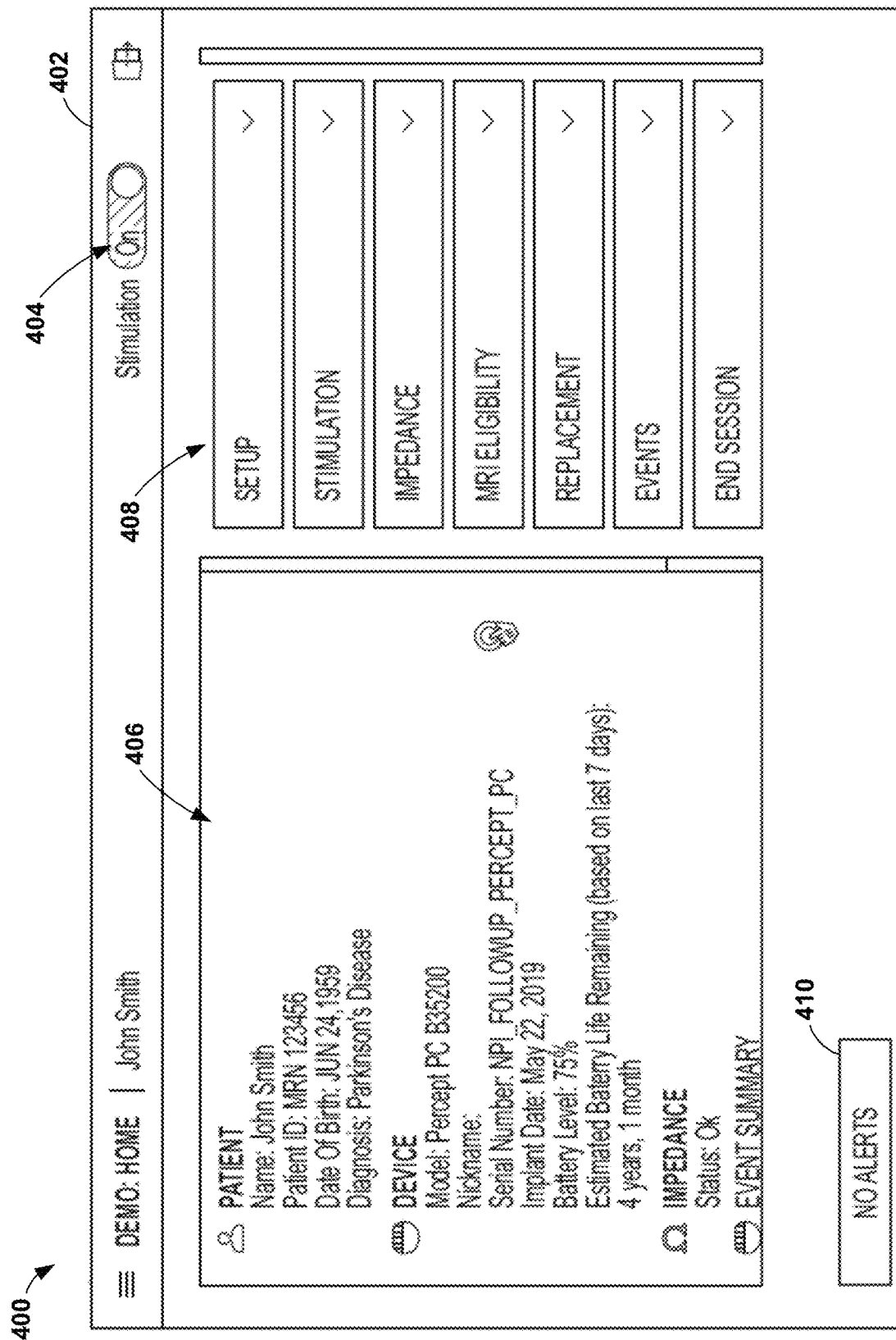
FIG. 4 is a conceptual diagram illustrating an example home screen for navigating within a user interface.

The following examples illustrate various user interfaces and techniques for managing the sensing of physiological signals, such as brain signals, and managing electrical stimulation as described above. Programmer 104, or another external computing device, may output the user interfaces and screens described herein. FIG. 4 is a conceptual diagram illustrating an example home screen 402 for navigating within an example user interface 400. User interface 400 may include several different screens as the user can navigate to different functions to view sensed information, view stored data, or adjust various stimulation parameter values. As shown in the example of FIG. 4, home screen 402 includes information associated with patient 122, such as patient specific information 406 such as name, patient ID, date of birth, and patient diagnosis. Other information may include device specific information such as model number, implant date, battery level, and estimated batter life remaining. Information such as impedance status for the system and event summary may also be provided in the home screen 402. Screen 402 may also include stimulation toggle switch 404 that, when selected, toggles between turning stimulation on or turning stimulation off. Stimulation toggle switch 404 may be provided in some, most, or all of the different screens within user interface 400 to enable the user to turn stimulation on or off at any time. Alert button 410 shows "no alerts" because there are no alerts to be shown. However, if there are alerts for the user, alert button 410 may indicate that there are alerts, or the number of alerts, and alert button 410 may be selectable to cause user interface 400 to show a list of the alerts for the user.

The home screen 402 in FIG. 4 may also include a menu 408 that includes several selectable buttons that enable a user to navigate to other screen and functionality supported by user interface 400. These selectable buttons include "setup," "stimulation," "impedance," "MRI eligibility," "replacement," "events," and "end session." Programmer 104 may switch to the appropriate screen in response to user selection of the respective selectable button.

The setup button takes the user to screens associated with selecting electrode configurations for sensing and/or stimulation. The setup portion of user interface 400 may also provide screens that receive user input for capturing upper and/or lower thresholds for a homeostatic window and/or upper and/or lower limits for the therapeutic window. The stimulation button takes the user to screens associated with managing electrical stimulation therapy for the patient. The impedance button takes the user to screens associated with viewing impedances of one or more electrode combinations and/or leads and running impedance testing for any electrical pathways.

The MRI eligibility button takes the user to screens associated with checking MRI eligibility of any implanted device (e.g., IMD 106) and/or placing the implanted device into an MRI eligible mode. The replacement button causes user interface 400 to displace screens related to when the IMD 106 should be replaced (e.g., remaining operational life for a primary cell non-rechargeable power supply). The events button enables the user to navigate to various screens that display events and data associated with sensing and delivering electrical stimulation. The end session button enables a user to terminate the management session via user interface 400. In addition to the menu, user interface 400 may include a stimulation toggle switch that enables the user to request turning stimulation on or off.

User interface 400 may be configured for a clinician programmer that enables a clinician to manage all aspects of stimulation therapy and/or sensing. In some examples, user interface 400 may enable the language of the clinician programmer to be different from a patient programmer configured to enable the patient to control a subset of features related to IMD 106. For example, user interface 400 may enable the clinician to set up the patient programmer language in the setup button, where the patient programmer language is different from the language of user interface 400 presented by the clinician programmer. For example, user interface 400 may enable the clinician to set up therapy group names, device names, and patient events to appear in a patient's local language irrespective of the primary or supported clinician language of user interface 400. In this manner, user interface 400 may enable the clinician (or a translator assisting the clinician) to program group names and patient events in the desired language for the patient even if it is not the primary language of the clinician.

Figure 5:
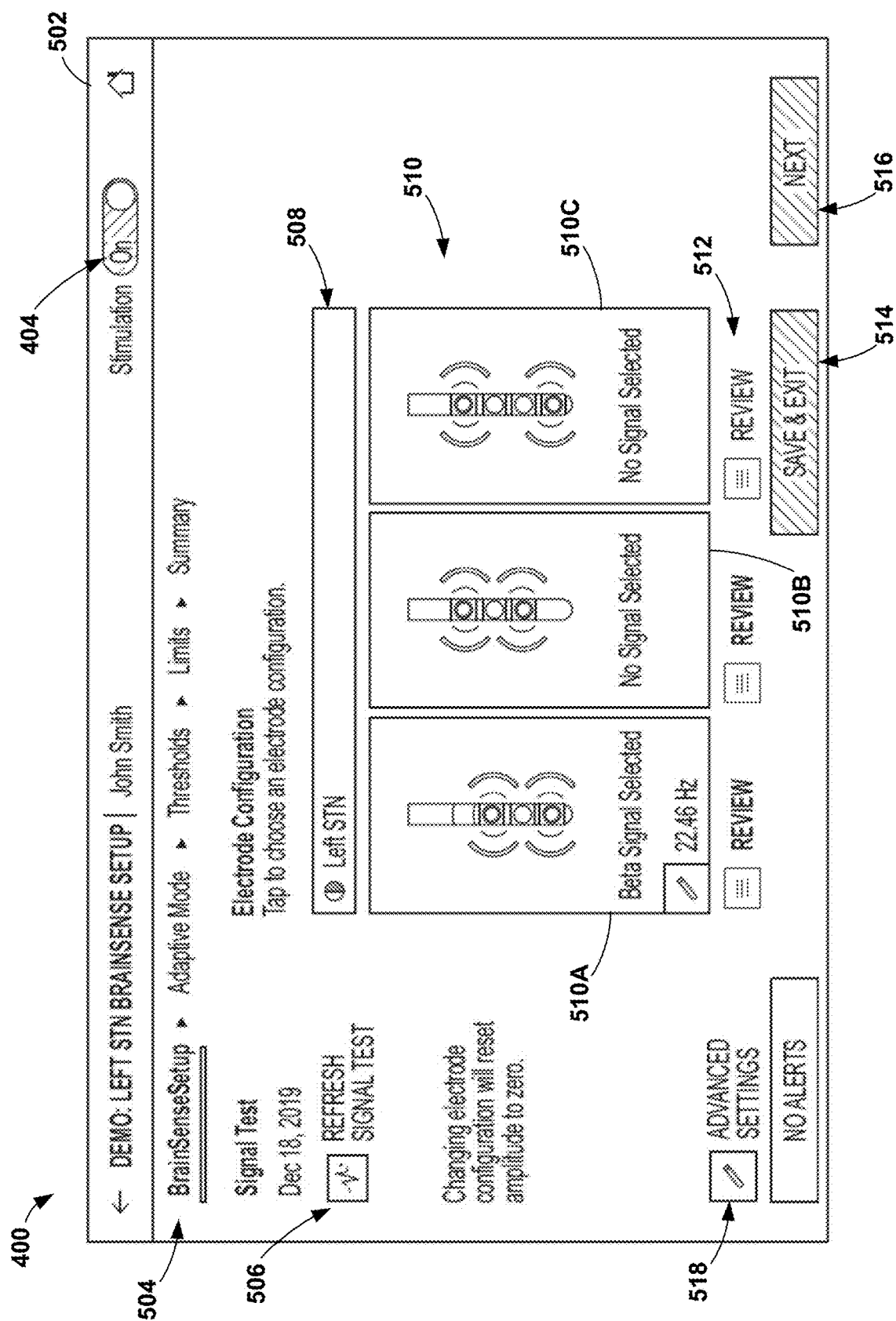
FIGS. 5 and 6 are conceptual diagrams illustrating example setup screens for managing electrode configurations.
Figure 6:
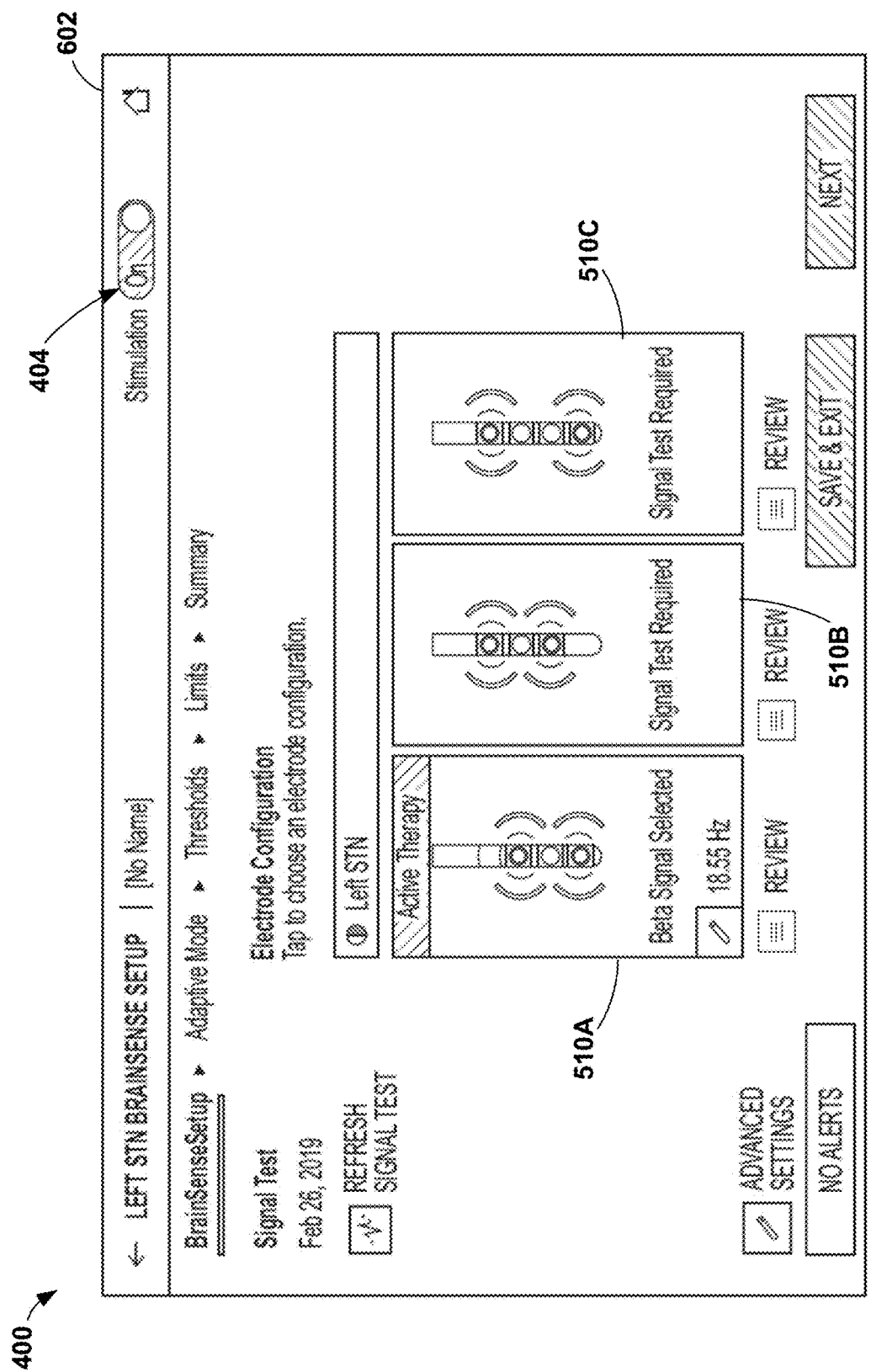

FIGS. 5 and 6 are conceptual diagrams illustrating example setup screens for managing electrode configurations. Programmer 104 may be configured to control display of user interface 400 that includes screens for reviewing and selecting electrode configurations for sensing brain signals. In some examples, programmer 104 may control IMD 106 to check signal quality across all electrodes and leads (e.g., in different hemispheres) for the purpose or guiding the user to selection of an appropriate sensing electrode configuration. This appropriate sensing configuration may also be appropriate for stimulation because the sensing electrode configuration may be compatible with an efficacious stimulation electrode configuration for therapy.

Figure 8:
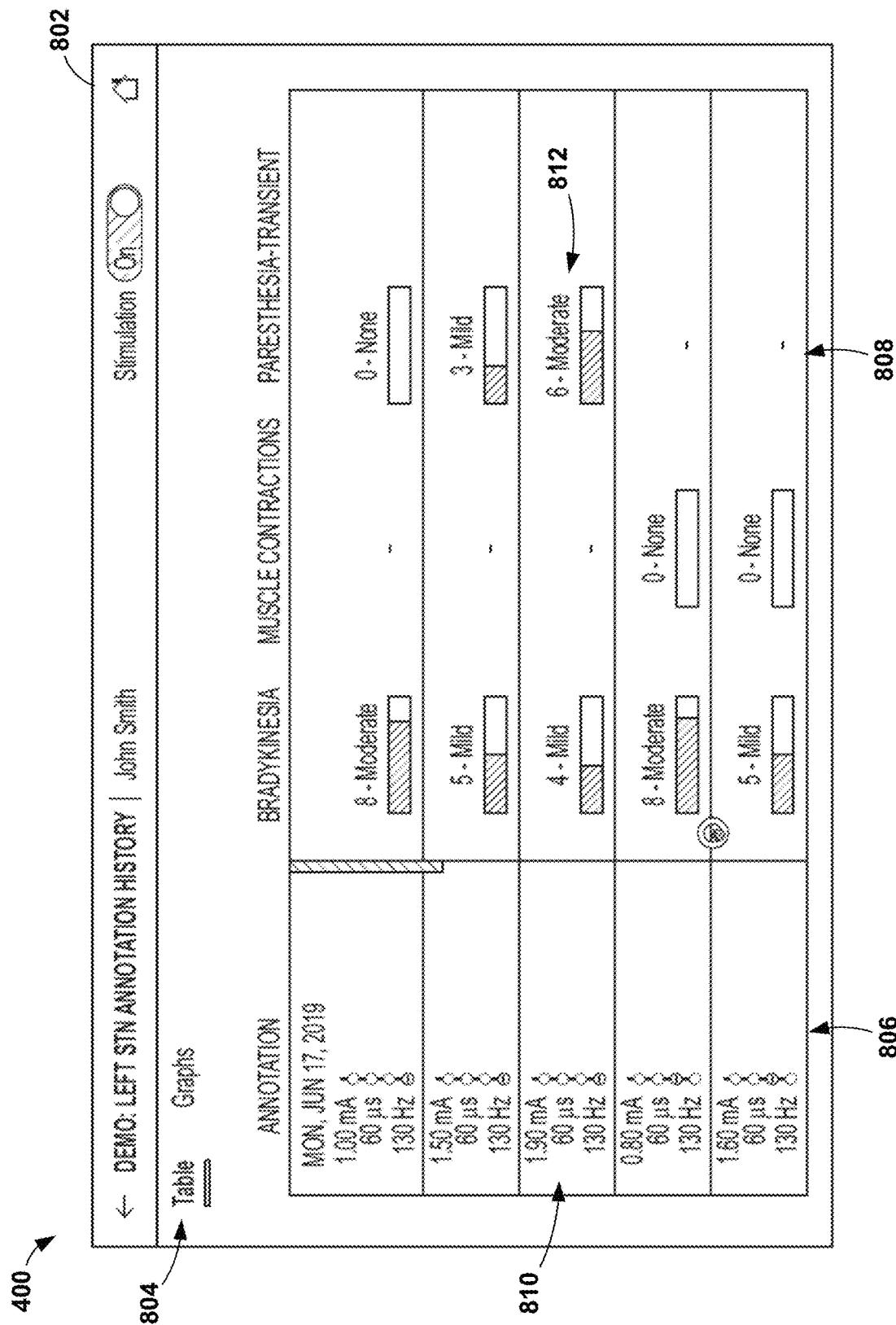
FIGS. 8 and 9 are conceptual diagrams illustrating example screens illustrating information associated with stimulation effects for a patient.
Figure 9:
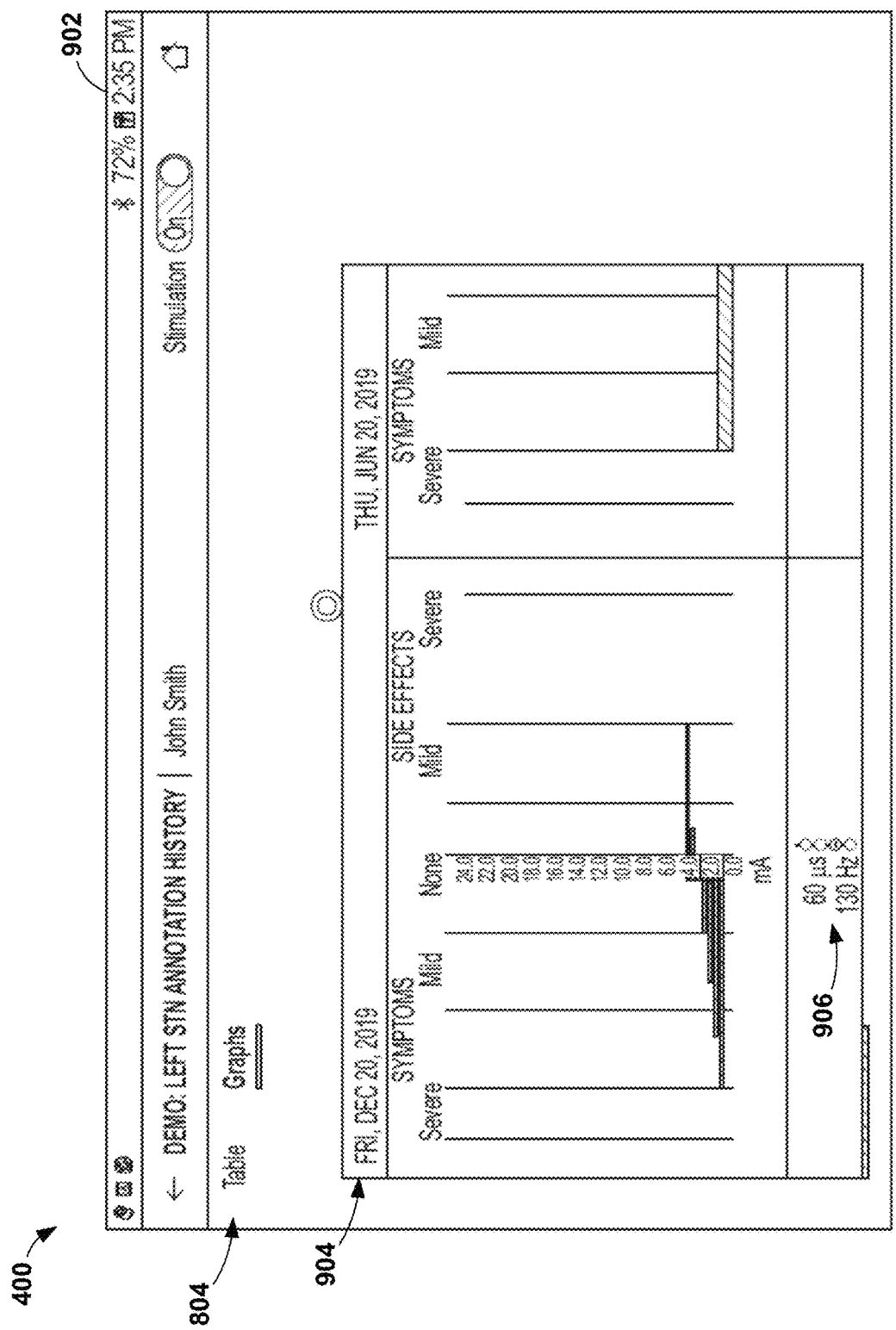

In some examples, programmer 104 may evaluate all constraints and known information of stimulation outcomes, such as electrode impedances, signal powers in one or more frequency bands, electrode combinations selected for therapy, or other such factors. For example, for each lead or hemisphere, programmer 104 may suggest a sensing electrode configuration based on one, some, or all of the following factors: electrodes available for sensing due to concurrent stimulation electrodes used, sensed signals of interest (e.g., one or more of a predetermined signal range or a peak power for a specific frequency band such as a Beta or Gamma band), previously collected information regarding effects and/or side effects for various electrodes at certain stimulation parameter values (e.g., as shown in FIGS. 8 and 9), or identified sources of artifacts due to other signals such as electrocardiogram (ECG) artifacts.

Figure 10:
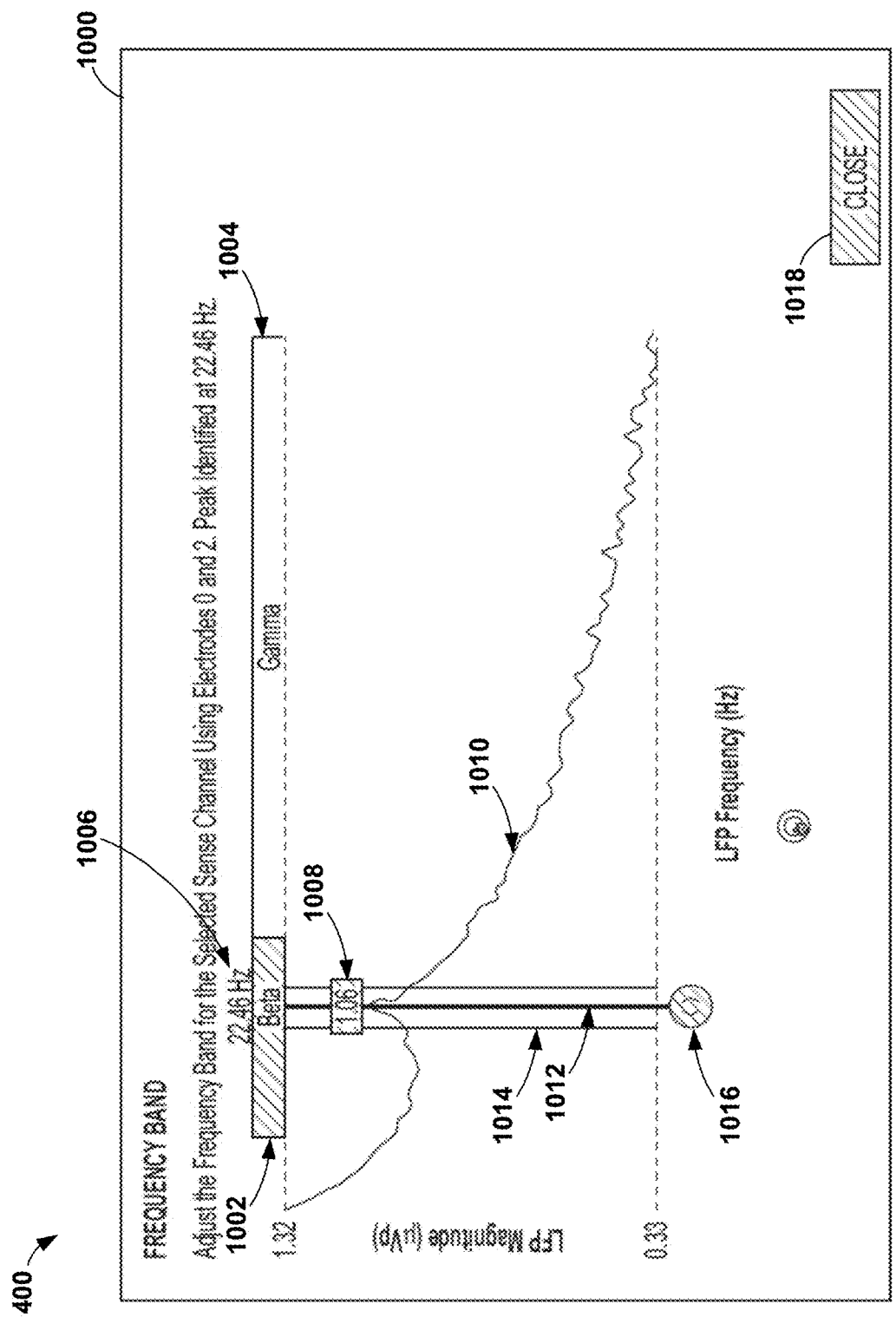
FIG. 10 is a conceptual diagram illustrating an example screen for adjusting a frequency band for an electrode configuration.
Figure 11:
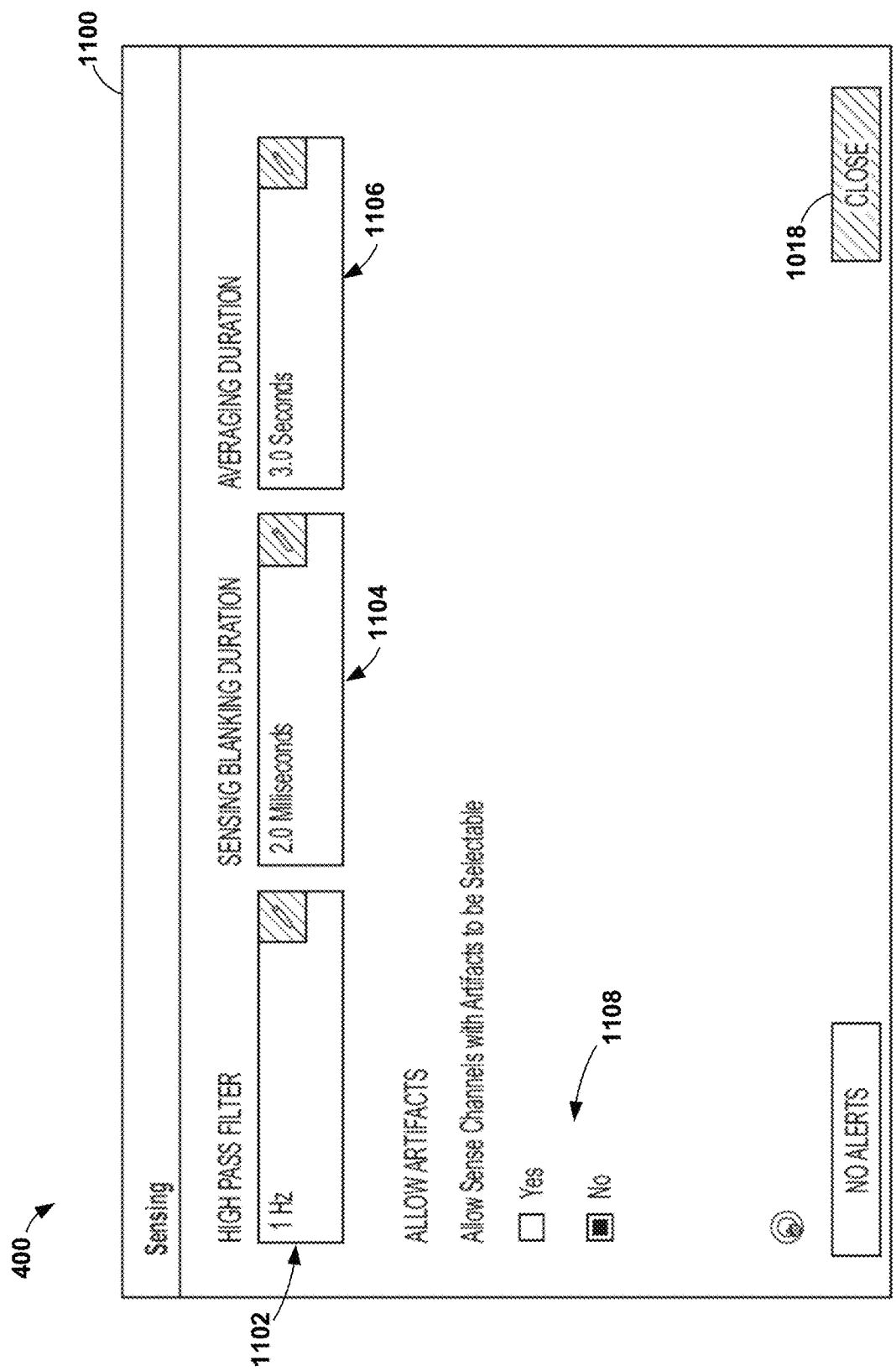
FIG. 11 is a conceptual diagram illustrating an example screen for setting various sensing parameters for an electrode configuration.

User interface 400 may include configuration options that enable a user to configure, or adjust, one or more aspects of sensing electrode configuration setup process. For example, programmer 104 may provide a frequency selection input (as shown in FIG. 10) that adjusts the frequency of signals for feedback in response the user selecting a different frequency. Programmer 104 may provide this frequency selection input for one or more frequency bands, such as the Beta band and Gamma band. In addition, user interface 400 may provide selectable inputs that enable the user to adjust the frequency of a high pass filter or type of filter, sensing blanking duration, averaging duration for the signal, or whether or not electrodes (or electrode combinations) that capture artifacts (e.g., ECG or EMG artifacts) can be selectable for sensing brain signals (e.g., as shown in FIG. 11). In other examples, user interface 400 may enable artifact contrast input that may enable a user specified magnitude of artifact (or several selectable levels of artifact) to be acceptable for sensing electrode configurations.

In some examples, user interface 400 may provide additional features. For example, programmer 104 may include different default settings for sensing electrode configuration setup based on the indication of therapy for the patient. For example, the user may input the specific type of condition or therapy desired (e.g., Parkinson's disease, tremor, epilepsy, depression, etc.), and programmer 104 may control user interface 400 to set default settings for the sensing electrode configurations (e.g., target frequency bands, electrode configurations, filters, blanking intervals, averaging durations, etc.) that may reduce adjustments needed from the user. Programmer 104 may also include automatic selection of frequency band powers when multiple peaks are present in a certain frequency band. For example, programmer 104 may be configured to select one of the multiple peaks for sensing based on the magnitude of each peak with respect to adjacent frequencies, the position of the frequencies within respect to commonly used frequencies, the closeness of peaks to each other, or any other such factors. In some examples, programmer 104 may set or suggest (for user confirmation) a specific bandwidth for sensing the power of sensed signals. This specific bandwidth may be set to a predetermined, and fixed, range such as 5 Hz, for example. However, programmer 104 may select a different fixed range based on the frequency width of a power peak in the power spectrum, the presence of neighboring peaks, the absence of neighboring peaks, or indication of the patient. In some examples, programmer 104 may enable a bandwidth selection input that is configured to receive user input selecting a different frequency range desired by the user (e.g., less or greater than the suggested bandwidth). Such a bandwidth input could be provided as a slider or other input on FIG. 10, for example. User interface 400 may show the changed bandwidth on the graph by widening or narrowing a column of different color around the target frequency shown.

In another example, programmer 104 may suggest different default settings for signal quality based on the type of lead selected (or indicated as implanted in the patient). For example, programmer 104 may use different electrode combinations for sensing from a lead with all ring electrodes than a lead with some electrodes at different circumferential positions around the lead. In addition, programmer 104 may change filter settings, blanking durations, averaging durations, frequency bands, etc. based on the type of lead indicated as implanted within the patient.

In the example of FIG. 5, the BrainSense setup screen 502 has been entered in order to select the electrode configuration for sensing brain signals, such as LFP signals. Menu 504 indicates the current stage in the setup, which is shown as "BrainSenseSetup" in FIG. 5. As the user moves through the different stages of the setup, the respective stage is underlined to show the current status. The "refresh signal test" button 506 causes, when selected by a user, programmer 104 to control IMD 106 to run a signal test on one or more pathways (e.g., different electrode combinations). Each pathway is a different electrode combination possible for the electrodes implanted within the patient. For each pathway, IMD 106 gathers brain signals for a period of time, such as 30 seconds. Each pathway may be a pathway between two or more different electrodes of the lead (e.g., a sensing electrode combination).

The screen of FIG. 5 may display all pairs of electrode combinations a particular lead. Lead selector 508 indicates which lead, or hemisphere in which the lead is located, has been selected (e.g., the left STN in the example of FIG. 5). Although a four electrode lead is shown in the example of FIG. 5, other leads having fewer or greater numbers of electrodes can be used in other examples. In some examples, the lead may have multiple electrodes located at different circumferential positions around the perimeter of the lead alone or in combination with ring electrodes or other electrode patterns. FIG. 5 illustrates a screen in which all pathways (or all sensing electrode combinations) are shown on respective selectable cards 510. Each card 510 may provide the frequency of the brain signal that provides the greatest amplitude. For example, the selected card 510A in FIG. 5 indicates a frequency of 22.46 Hz that is within the Beta frequency band. No signal has been selected for the respective different pathways of cards 510B and 510C. In other examples, user interface 400 may be controlled to only show the cards of pathways that provide better signal when there are too many pathways to show on the screen of FIG. 5. In other examples, user interface 400 may group combinations according to type of electrode combinations (e.g., which position the electrodes are in the lead) or other factors. Advanced settings 518 is a selectable icon that, when selected, causes programmer 104 to show additional settings for stimulation.

In this manner, processing circuitry 310 of programmer 104 may be configured to obtain brain signal information for at least one electrode combination of a plurality of electrode combinations of one or more electrical leads, determine, based on the brain signal information, a respective frequency for the at least one electrode combination, and output, for display, a plurality of selectable lead icons (e.g., cards 510), wherein each selectable lead icon of the plurality of selectable lead icons represents a different electrode combination of the plurality of electrode combinations. In addition, processing circuitry 310 may output, for display, the respective frequency determined for the at least one electrode combination in association with the respective selectable lead icon associated with the at least one electrode combination, receive user input selecting one selectable lead icon of the plurality of selectable lead icons, and, responsive to receiving the user input, select, for subsequent brain signal sensing, a sense electrode combination associated with the one selectable lead icon selected by the user input.

Processing circuitry 310 may also output, for display, a selectable signal test icon, receive user input selecting the selectable signal test icon, and responsive to receiving the user input selecting the selectable signal test icon, control a medical device to obtain brain signal information for at least one electrode combination of the plurality of electrode combinations. The plurality of electrode combinations may include all electrode combinations possible for the one or more electrical leads implanted within a patient, but less than all combinations may be shown in other examples.

In some examples, processing circuitry 310 may analyze the brain signal information for presence of an artifact associated with at least one of electrocardiogram sensing or motion of the one or more electrical leads, determine that the artifact is not present in the brain signal information, and, responsive to determining that the artifact is not present, approving the one or more electrode combinations for selection by a user for subsequent brain signal sensing. In this manner, processing circuitry 310 may determine if an electrode or electrode combination may be suited for sensing or potentially problematic and unable to provide accurate and/or consistent sensed data. Processing circuitry 310 may perform the ECG artifact detection in several different ways, alone or in combination. In some examples, processing circuitry 310 analyzes the brain signal information for presence of the artifact by applying a logistic regression classifier to at least a portion of the brain signal information. This logistic regression classifier may be a machine learning approach using LFP data collected from prior group of patients for training. Other types of machine learning algorithms may be used in other examples, such as neural networks, support vector machines, extra trees, random forests, or other types of classifiers.

A logistic regression classifier may include spectral band power features and time domain threshold crossing statistic features. Processing circuitry 310 may initially filter the sensed brain signal, such as removing a first portion (e.g., 10 seconds) and a last portion (e.g., 2.5 seconds) to avoid transient signals. Processing circuitry 310 may determine spectral features by computing band power over several frequency intervals. In one example, these frequency bands may include 0-3 Hz, 3-5 Hz, 5-10 Hz, 10-20 Hz, 20-30 Hz, 40-50 Hz, 50-60 Hz, 70-80 Hz, and 80-90 Hz. Processing circuitry 310 may then normalize the power by dividing the power for each band by the total power calculated in the band from 0-90 Hz. Processing circuitry 310 may then compute the entropy of normalized band powers. In some examples, the entropy of normalized band powers will be summed for used by the logistic regression classifier.

The time domain features may be determined by computing the threshold crossings from the rectified normalized LFP signal. Processing circuitry 310 may determine the rate of threshold crossings for several different thresholds. Processing circuitry 310 may then determine the inter threshold crossing interface (e.g., the number of seconds between consecutive threshold crossings. Processing circuitry 310 may then determine the entropy for each inter threshold crossing interval. These time domain features may be used in addition to the spectral features by the logistic regression classifier or other machine learning algorithms in other examples.

The inputs for the logistic regression classifier may include an amplitude or power from selected frequency ranges of a brain signal such that frequency domain and/or time domain inputs may be employed. In one example, processing circuitry 310 may determine a plurality of signal features from the brain signal information, the plurality of signal features including entropies for a plurality of frequency bands within the brain signal information and a plurality of time domain threshold crossing features. Then, processing circuitry 310 may apply the logistic regression classifier to the portion of the brain signal information by applying the logistic regression classifier to the plurality of signal features. In some examples, the probability threshold for the logistic regression classifier may be set to 0.5, wherein anything greater than 0.5 is output as the brain signal including an ECG artifact and anything 0.5 or less is output as the brain signal not including an ECG artifact.

As another way of identifying ECG artifacts, processing circuitry 310 may analyze the brain signal information for a fast Fourier transform (FFT) amplitude separation at approximately 8 Hz between a first brain signal detected during delivery of electrical stimulation and a second brain signal detecting during an absence of electrical stimulation delivery. In this manner, the FFT amplitude separation less than a separation threshold indicates that the artifact is not present. In some examples, IMD 106 may be more susceptible to ECG artifact with stimulation being delivered at 0 mA, so this check helps to identify those cases. In one example, the absolute value of the FFT amplitude difference at 8 Hz between stimulation off and stimulation at 0 mA is compared to a threshold (e.g., 200 nV/rtHz). If this FFT amplitude difference is greater than the threshold, then the system determines that the separation is too large and the electrode configuration is susceptible to ECG artifacts.

In this manner, processing circuitry 310 may evaluate the recorded brain signal from each electrode combination for several issues. Processing circuitry 310 may evaluate the brain signal to determine that no ECG artifact is present. In addition, processing circuitry 310 may analyze the brain signal to determine that no movement artifacts are present. In addition, processing circuitry 310 may determine that the brain signal amplitude is above a predetermined threshold. For the example of LFP signals, the threshold may be 1.2 uVp (microvolt peak).

Processing circuitry 310 may automatically select the frequency from the brain signal that has the largest amplitude, or power, in the frequency domain. This frequency may then be used by the electrode combination to monitor changes to the brain signal. However, user interface 400 may receive user selection of an edit button that enables the user to select a different frequency from the automatically selected frequency. For example, the user may select the frequency from a graph of power vs. frequency from the test signal for the electrode combination.

The "review" button 512 provides a summary about effects, side effects, amplitudes, etc. that has already been established by a clinician for this pathway and for the specific patient. For example, the clinician may have previously performed a monopolar review of all electrode pathways in order to identify any effects and side effects associated with stimulation for each electrode. In this manner, the user may be able to access these annotations about each electrode combination from the card for that specific electrode combination. The user may then be able to balance sensing with therapy. For example, the user can select a different electrode combination based on information other than the frequencies of the sensed brain signal for that electrode combination.

Once the electrode configuration has been selected, the user can select "save and exit" button 514 which causes processing circuitry 310 to enter a different screen where sensing and therapy can begin. Alternatively, processing circuitry 310 may receive user selection of the "next" button 516 and responsively move to the next screen in which thresholds may be established for adaptive DBS therapy. In the example of FIG. 6, screen 602 is similar to screen 502 and illustrates that the highlighted card 510A of the selected electrode combination indicates that therapy is being delivered using the electrode combination of the selected card 510A.

Figure 7:
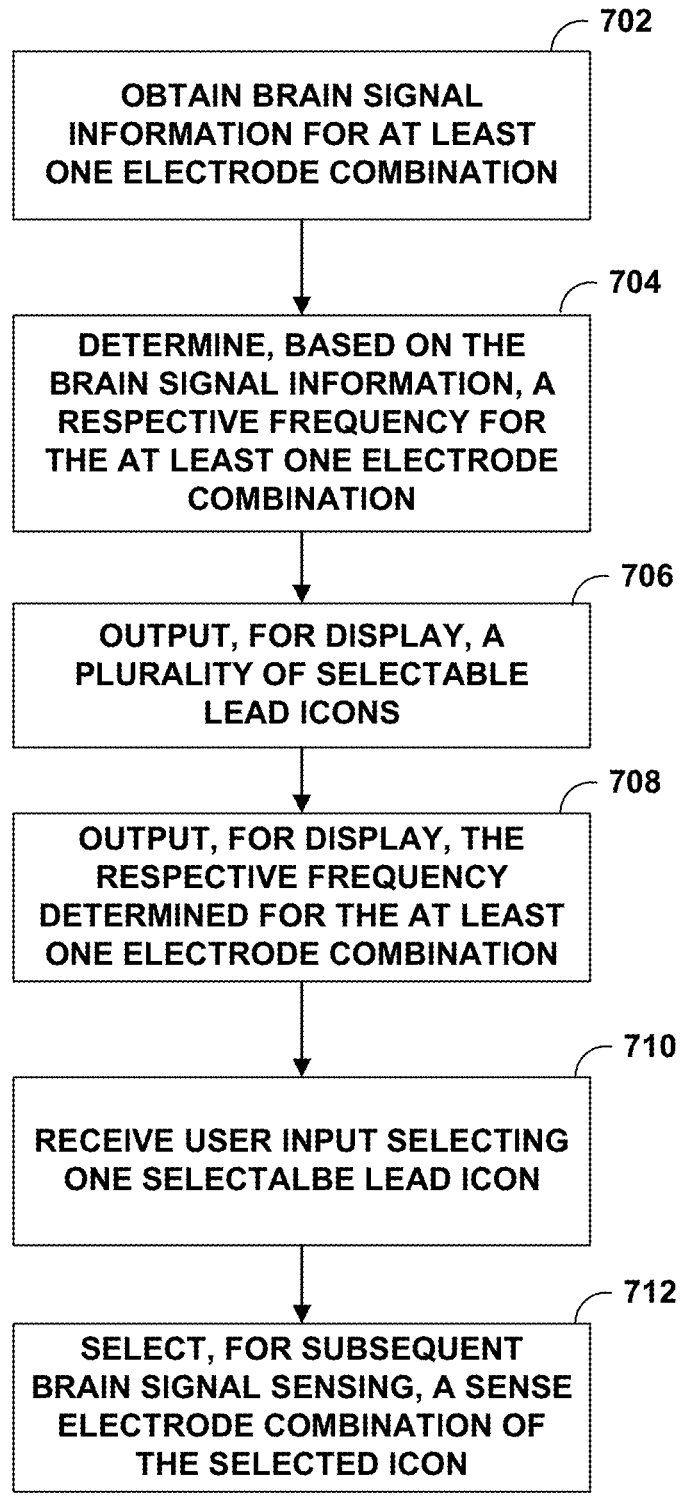
FIG. 7 is a flowchart illustrating an example technique for running a signal test that evaluates one or more aspects of an electrode configuration.

FIG. 7 is a flowchart illustrating an example technique for running a signal test that evaluates one or more aspects of an electrode configuration. The signal test is configured to assess the presence and/or prevalence of particular brain signals across all available electrode configurations to a medical device. Such a process may utilize portions of user interface 400 shown in FIGS. 4, 5, and 6.

In the example if FIG. 7, processing circuitry 310 obtains brain signal information for at least one electrode combination of a plurality of electrode combinations of one or more electrical leads (702) and then determines, based on the brain signal information, a respective frequency for the at least one electrode combination (704). Example signals obtained during this process may be similar to the signals shown in FIGS. 58 and 59. Processing circuitry 310 then outputs, for display, a plurality of selectable lead icons (706), such as selectable cards 510 of FIG. 5. Each selectable lead icon of the plurality of selectable lead icons represents a different electrode combination of the plurality of electrode combinations. Processing circuitry 310 then outputs, for display, the respective frequency determined for the at least one electrode combination in association with the respective selectable lead icon associated with the at least one electrode combination (708). Processing circuitry 310 receives user input selecting one selectable lead icon of the plurality of selectable lead icons (710) and, responsive to receiving the user input, selects, for subsequent brain signal sensing, a sense electrode combination associated with the one selectable lead icon selected by the user input (712). The user may repeat this process at any time during therapy or monitoring of the patient.

FIGS. 8 and 9 are conceptual diagrams illustrating example user interface screens 802 and 902 illustrating information associated with stimulation effects for a patient. The information of FIGS. 8 and 9 of user interface 400 may provide accessibility to previously captured clinician evaluation of electrode viability for one or more electrode combinations. In some examples, the previously captured clinician evaluation may have been performed using monopolar electrode combinations (e.g., one electrode on a lead and another electrode distal from the lead, such as an electrode carried by the housing of the IMD). By providing this evaluation information for electrodes as integrated with the signal selection and evaluation process, the clinician and/or automated system, may have quick access to additional background information when making the most appropriate signal selection for sensing and/or stimulation. The screens of FIGS. 8 and 9 may be accessed via the "review" button 512 from FIG. 5.

As shown in FIG. 8, screen 802 displays the severity of various side effects, such as bradykinesia, muscle contractions, and paresthesia in data field 808, for respective stimulation parameter sets 806. Each parameter set 810 shows values of amplitude, pulse width, and frequency. Each data point for the various side effects may include a numerical indicator, a word indicator, and/or a graph indicator. Menu 804 indicates that screen 802 shows the table of this information. As shown in the example of FIG. 9, screen 902 illustrates an example graph 904 showing the severity of side effects in conjunction with the severity of symptoms for different current amplitudes of stimulation. Each graph is provided for a single day, but multiple days may be combined in other examples. Parameter values 906 indicate the pulse width and frequency for the delivered stimulation. Menu 804 indicates that screen 802 shows the graph version of this information.

Programmer 104 may utilize historical data for the patient, or other patients with similar conditions, when generating a suggested sensing electrode configuration. For example, programmer 104 may identify those electrode combinations that can provide efficacious therapy (e.g., therapeutic effects with no or limited side effects) and suggest only sensing configurations compatible with those electrode combinations for therapy. Programmer 104 may identify those electrode combinations that would not be used for therapy. In some examples, programmer 104 may control user interface 400 may indicate which sensing electrodes are available for the stimulation electrode combinations that can provide effective therapy. The screens 802 and 902 of FIGS. 8 and/or 9 may also indicate the therapeutic windows, thresholds, or other stimulation parameters associated with the identified electrode combinations. Programmer 104 may control the user interface to present a therapeutic window, for example, for each electrode combination when available to identify those electrode combinations that can provide larger therapeutic windows and likely better stimulation therapy.

FIG. 10 is a conceptual diagram illustrating an example screen 1000 for adjusting a frequency band used for sensing brain signals using an electrode configuration. As shown in FIG. 10, the brain signal 1010 recorded for an electrode configuration during the signal check of FIG. 5 is shown in the frequency domain. Processing circuitry 310 has automatically selected the frequency 1012 having a peak 1008 in the Beta frequency band 1002 as the frequency from which to monitor during brain signal sensing. Frequency indicator 1006 indicates that this frequency is 22.46 Hz. This peak 1008 may be selected because it may provide the best sensing for changes to brain signal information. However, via the screen 1000 of FIG. 10, the user interface 400 provides a user movable slider 1016 that, when selected, enables the user to drag slider 1016 along the x-axis and select a different frequency. Frequency range 1014 indicates the range of frequencies from which the power of signal 1010 will be used to monitor brain activity. In some examples, frequency range 1014 may be a preset variance from frequency 1012, such as 5 Hz on either side of frequency 1012. In other examples, screen 1000 may include an adjustment input via which the user can change frequency range 1014. In other examples programmer 104 may automatically select the width of frequency range 1014 based on the width of peak 1008 or some other feature of signal 1010. Although both Beta band 1002 and Gamma band 10004 are shown, other examples may only include one frequency band. In response to user selection of close button 1018, user interface 400 may close screen 1000 and return to a setup screen such as screen 502.

FIG. 11 is a conceptual diagram illustrating an example screen 1100 for setting various sensing parameters for an electrode configuration. As shown in the example of FIG. 11, user interface 400 may provide screen 100 which includes sensing parameters such as the frequency of the high pass filter 1102, the sensing blanking duration 1104, and the average duration for sensing 1106. Each of these parameters may be selected and changed by a user. In addition, the user may be able to determine whether or not electrode combinations that include artifacts are selectable for sensing, via selection of one of the allow artifacts input boxes 1108.

Figure 12:
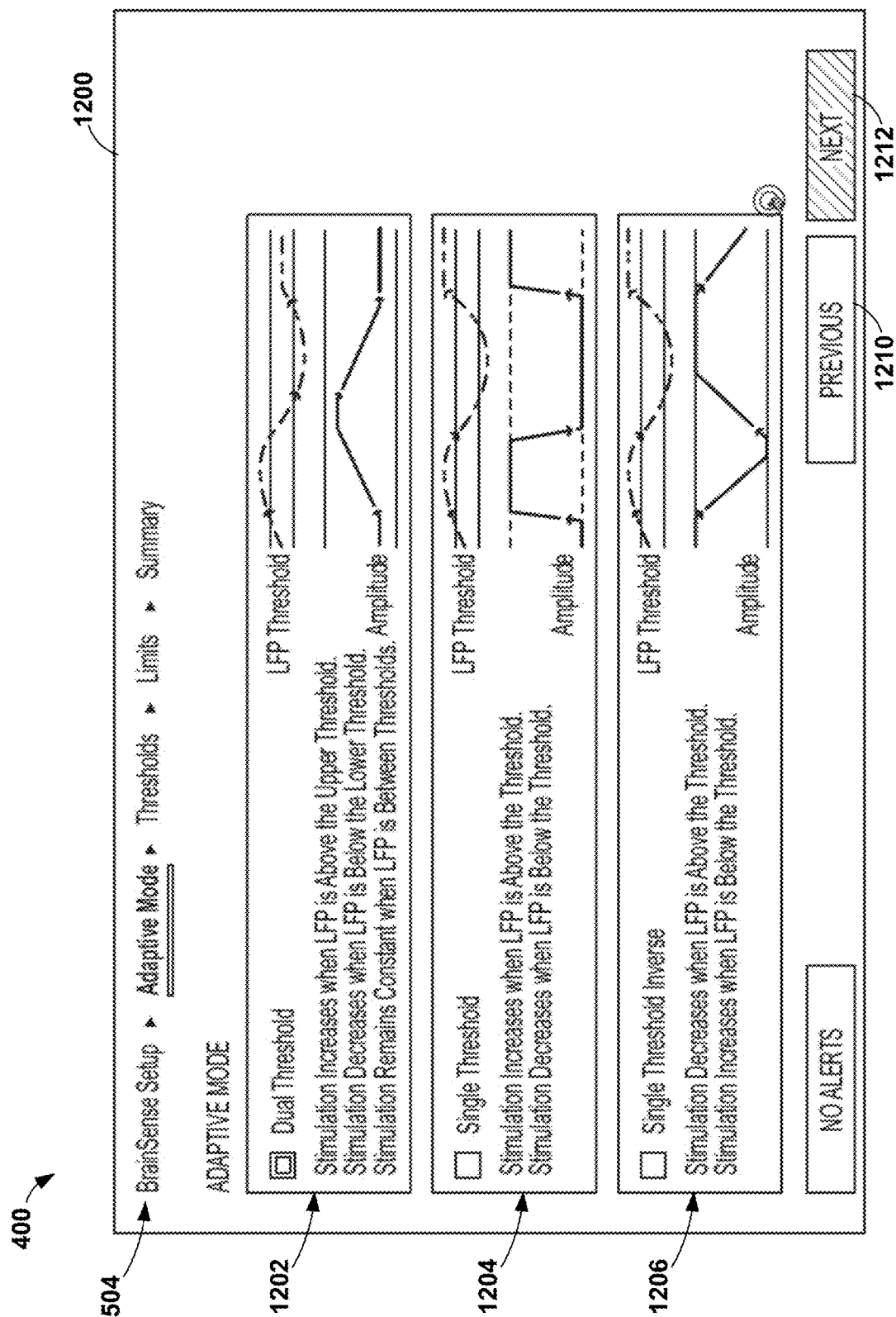
FIG. 12 is a conceptual diagram illustrating an example screen for selecting a type of adaptive DBS mode.

FIG. 12 is a conceptual diagram illustrating an example screen 1200 for selecting a type of adaptive DBS mode. As shown in the example of FIG. 12, user interface 400 may include a screen 1200 that enables selection of dual threshold mode 1202, single threshold mode 1204, or single threshold inverse mode 1206. Dual threshold mode 1202 is shown as selected. Dual threshold mode 1202 enables the system to adjust stimulation amplitude based on upper and lower thresholds of the LFP signals. Single threshold mode 1204 enables the system to increase stimulation when LFP signals are above the threshold, and single threshold inverse mode 1206 enables the system to decrease stimulation when LFP signals are below the threshold.

This feature of adaptive DBS is intended to allow a clinician to configure therapy to automatically adjust, within clinician defined limits, based on changes in brain state. A patient's brain state will be measured using a brain signal, such as LFPs, recorded chronically from the implanted electrodes. The goal of the automatic adjustment of therapy may be to maintain the brain state (as defined by these signals) within a clinician specified range (e.g., the range between an upper and lower threshold in the dual threshold mode example), understanding that clinical symptoms and side effects may be well correlated with these detected brain states. In this manner of managing brain states, the user may be able to manage clinical symptoms and side effects. This feature is referred to as closed loop DBS or "aDBS" (adaptive DBS). "cDBS" refers to continuous DBS (i.e. manually controlled and open loop, as in legacy DBS systems).

Figure 22:
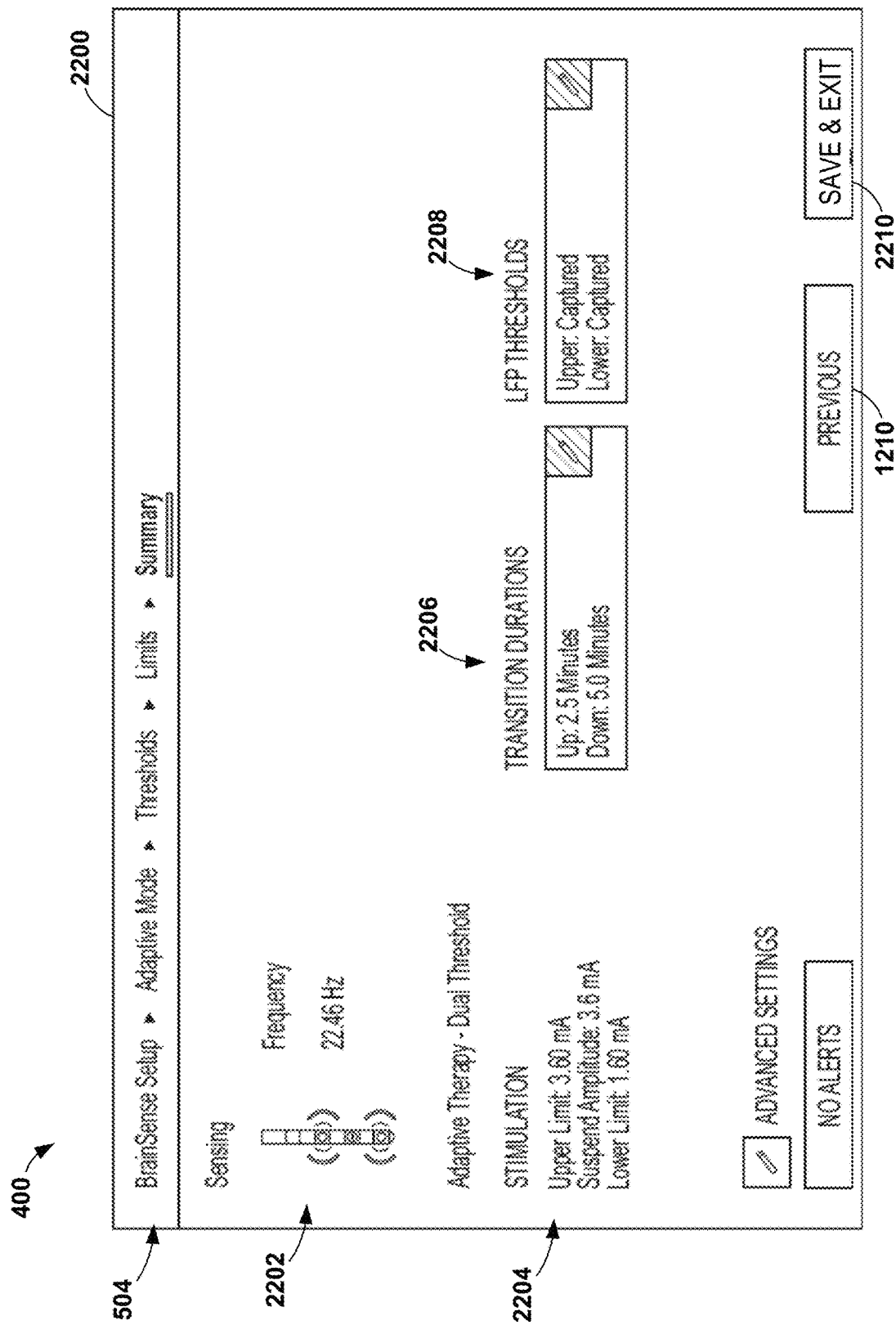
FIG. 22 is a conceptual diagram illustrating an example screens summarizing parameters selected for adaptive DBS therapy.
Figure 23:
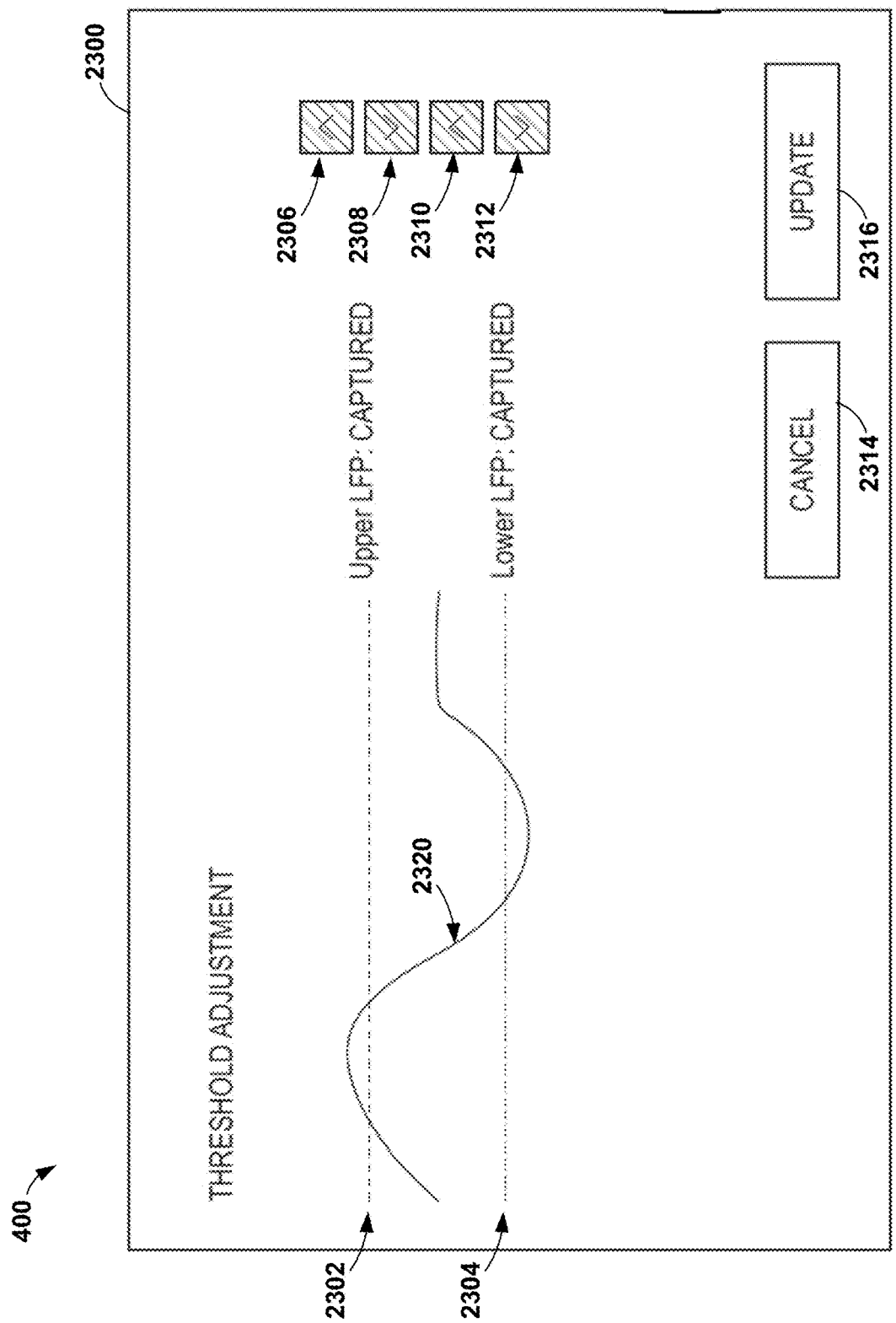
FIGS. 23 and 24 are conceptual diagrams illustrating example screens for manually adjusting one or more thresholds associated with adaptive DBS therapy.

In this manner, user interface 400 enables the user to configure adaptive therapy by selecting algorithm, thresholds, and/or stimulation settings for adaptive stimulation modes. In addition to selecting one of the threshold modes, user interface 400 enables the user to configure and adjust one or more thresholds that instruct the system to automatically adapt, or change, stimulation parameter values (e.g., such as shown in FIGS. 13-21). User interface 400 also enables the user to configure other stimulation settings, changes, limits, transition times, and other settings such as shown in FIGS. 22 and 23. In some examples, user interface 400 enables the user to view, measure, and assess the performance of the adaptive stimulation using the set thresholds (e.g., as shown in FIGS. 25-32). User interface 400 may also include other tools to assess stimulation such as tracking events, LFP signals, and stimulation parameters over time.

In other examples, programmer 104 may provide additional features. For example, programmer 104 may automatically propose a threshold mode (e.g., dual or signal threshold) based on historical timeline data. In some examples, programmer 104 may detect poor or reduced performance based on one or more factures, such as a signal quality check, oscillations in stimulation amplitude of LFP signals, time LFP signals are outside of thresholds exceeds a threshold time, LFP values remain at upper or lower thresholds longer than a predetermined amount of time, the patient turns off stimulation greater than a predetermined number of times or frequency, or any other such events. In some examples, user interface 400 may enable the user to adjust one or more thresholds for stimulation and/or stimulation parameter values while viewing LFP data and/or stimulation parameter values in real-time.

FIGS. 13-20 are conceptual diagrams illustrating example screens for capturing one or more thresholds associated with adaptive DBS therapy. In this manner, user interface 400 enables a user to define thresholds to quantify changes in a signal over time. These thresholds may be used to summarize large stretches of data to understand patterns of find anomalies worthy of further inspection. FIGS. 13-20 illustrate examples in which user interface 400 enables the user to configure, view, and measure signals against one or more thresholds. For example, a user may set upper and lower thresholds for LFP signals and adjust stimulation amplitude values to put the brain in a state consistent with a desired threshold. User interface 400 may enable the user to manually adjust an LFP threshold and display the thresholds over stored data and/or real-time data. User interface 400 can also show the amount of time the LFP signals are below, between, or above the thresholds.

In other examples, user interface 400 may display one or more thresholds on the same display as event data or enable the user to set threshold values from timeline, trend, or event data screens. In some examples, user interface 400 may enable the user to adjust non-stimulation threshold settings such as settings related to drug state during stimulation or other patient conditions. User interface 400 may also, or alternatively, show information such as long term averages of LFP values or time below, between, or above thresholds, identification of days or times in which LFP data is a statistical outlier with respect to other data, differences between night and day (or awake and asleep), or other averages or statistics for each stimulation parameter value.

Figure 13:
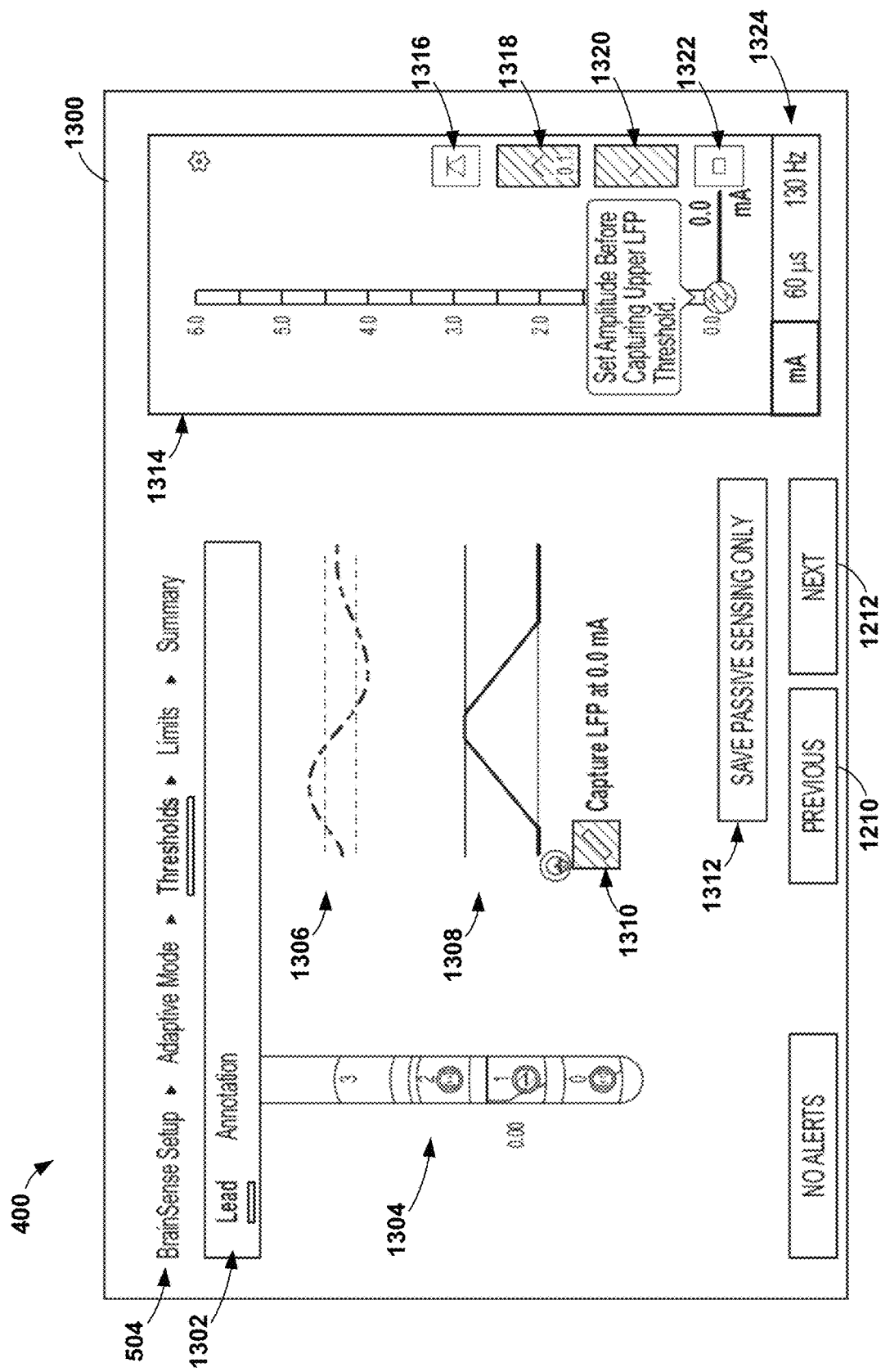
FIGS. 13-20 are conceptual diagrams illustrating example screens for capturing one or more thresholds associated with adaptive DBS therapy.

As shown in the example of FIG. 13, a representation of a lead and the electrodes carried thereon is displayed in screen 1300. The cathode and anode electrodes are also indicated to show the selected electrode configuration as part of lead view 1304. Menu 1302 indicates that lead view 1304 is currently displayed, but that annotation of the electrode configuration can be shown instead. To the right of the lead view 1304, an LFP graph 1306 and a stimulation parameter graph 1308 are displayed. Capture button 1310 enables the user to request capture of the LFP at the current amplitude. On the very right of the screen 1300 is parameter view 1314 which includes inputs selectable by the user to increase (button 1318) and decrease (button 1320) the stimulation parameter, which is current amplitude in the example of FIG. 13. Button 1316 jumps to the upper amplitude limit that has been set. Button 1322 jumps to the lower amplitude limit when set. Parameter buttons 1324 enable the user to select the desired parameter, such as amplitude, pulse width, or frequency, to adjust. On this screen of FIG. 13, the user may set parameter value limits that correspond to respective thresholds for the brain signal, such as LFPs. Passive sensing button 1312 causes programmer 104 to save the LFP values for sensing only, instead of adaptive stimulation. The user can move between different screens of user interface 400 via previous button 1210 and next button 1212.

Using these screens of user interface 400, the user can capture thresholds of the LFP that correspond to respective stimulation parameter values. In this manner, the system can determine a LFP Classification threshold using stimulation as the actuator. In one example, each threshold may be set based on measuring LFPs for 25 seconds at particular amplitude levels as defined by the patient's tolerance and symptom relief. Other durations of sensing may be used in other examples.

Typically, to set the upper threshold and lower threshold for brain signal monitoring, the patient has been off medication, i.e., the upper and lower thresholds are set when the patient is not taking medication selected to reduce the symptoms. The patient may be considered to be not taking the medication when the patient, prior to the time the upper bound is set, has not taken the medication for at least approximately 72 hours for extended release forms of dopamine agonists, the patient has not taken the medication for at least approximately 24 hours for regular forms of dopamine agonists and controlled release forms of CD/LD, and the patient has not taken the medication for at least approximately 12 hours for regular forms of CD/LD, entacapone, rasagiline, selegiline, and amantadine. If only stimulation is suppressing brain signals (e.g., LFP signals), then the system can measure these brain signals for various values of stimulation parameters without outside inputs. Once the upper threshold and lower threshold is established, the system can identify when medication wears off because the brain signals will cross the lower or upper threshold. In response to identifying the brain signal crossing a threshold, the system may turn on electrical stimulation to bring back brain signal amplitudes back between the lower threshold and the upper threshold. Thresholds may be set for certain brain signals, such as signals within the Beta frequency band, when the patient is off medication. In some examples, such as when assessing signals within the Gamma frequency band, thresholds may be set when the patient is on medication.

Figure 14:
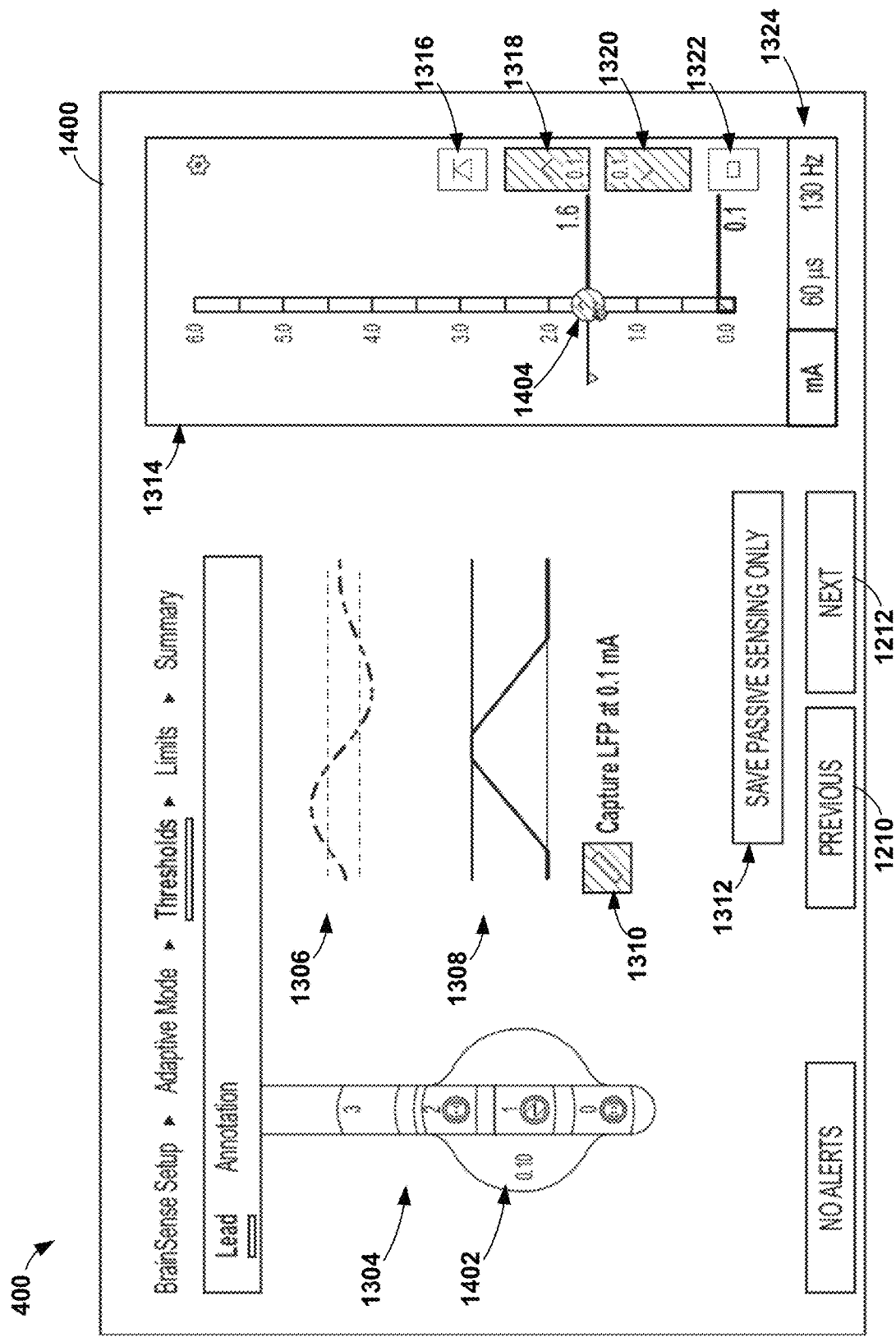
Figure 15:
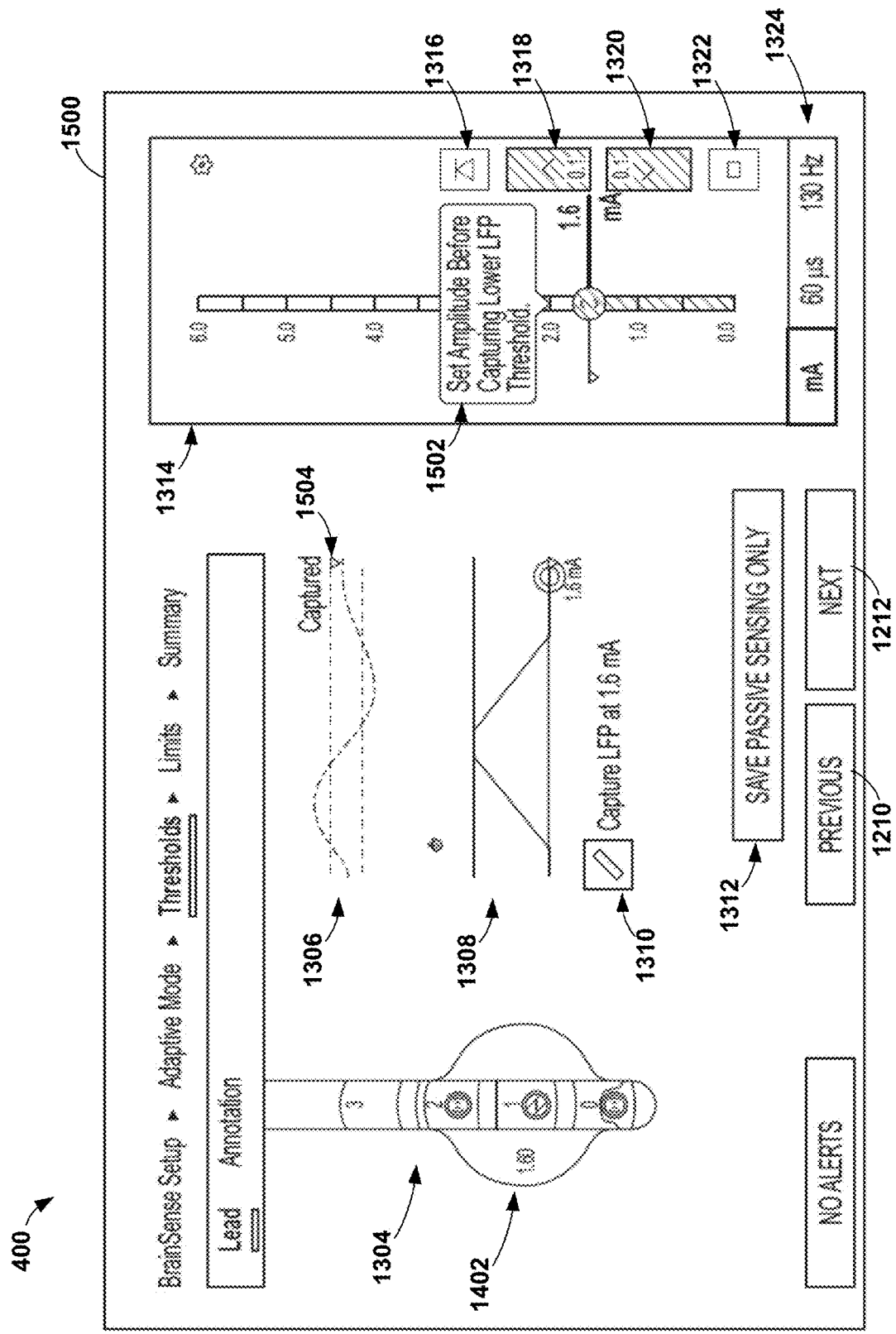
Figure 16:
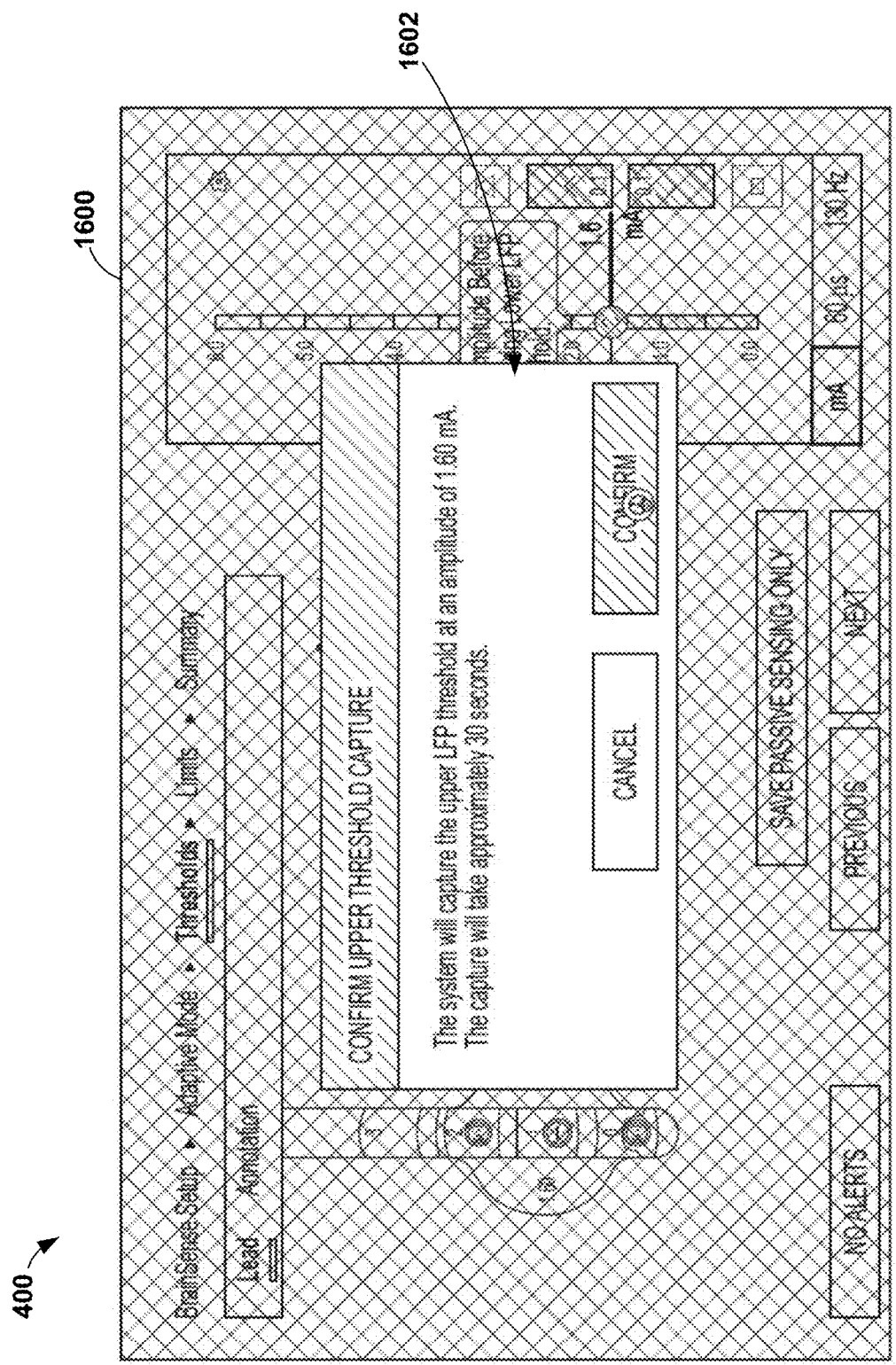

Since the patient is not getting any medication, LFP activity may be present above a threshold, such as greater than or equal to 1.2 uVp. In this procedure, the user will identify the lowest current amplitude where symptoms are controlled, which will correlate to the upper threshold for the LFP signal. FIG. 14 illustrates an increasing stimulation amplitude with the resulting volume of activation (VOA) shown on the representation of the lead. In the example of FIG. 14, screen 1400 shows that an increase of stimulation amplitude has caused deliver of stimulation to the patient as indicated by stimulation field 1402. Slider 1404 may be selected and dragged by the user to increase or decrease the amplitude of stimulation. This lowest amplitude will also be set as the lower limit for the stimulation parameter. FIG. 15 illustrates via screen 1500 that the upper threshold is present and can be captured as upper threshold 1504. Bubble 1502 informs the user to set the amplitude before capturing the lower LFP threshold. The Beta signal will be high since there is little stimulation amplitude to suppress the brain activity. FIG. 16 shows screen 1600 which includes an example pop-up window 1602 requesting that the patient confirm upper threshold capture at the current amplitude. The system will set the upper threshold here in response to the user selecting the confirm button.

Figure 17:
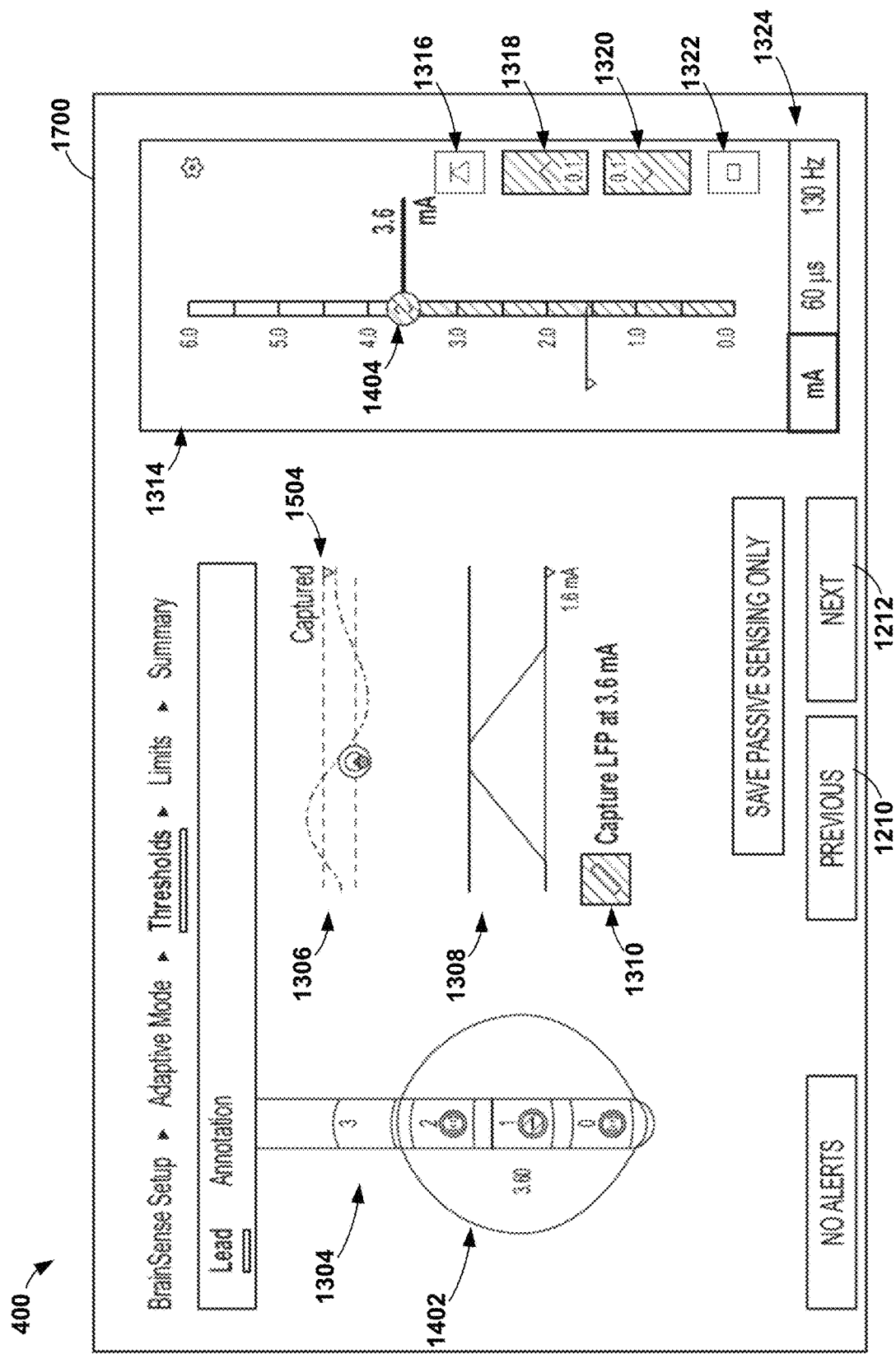
Figure 18:
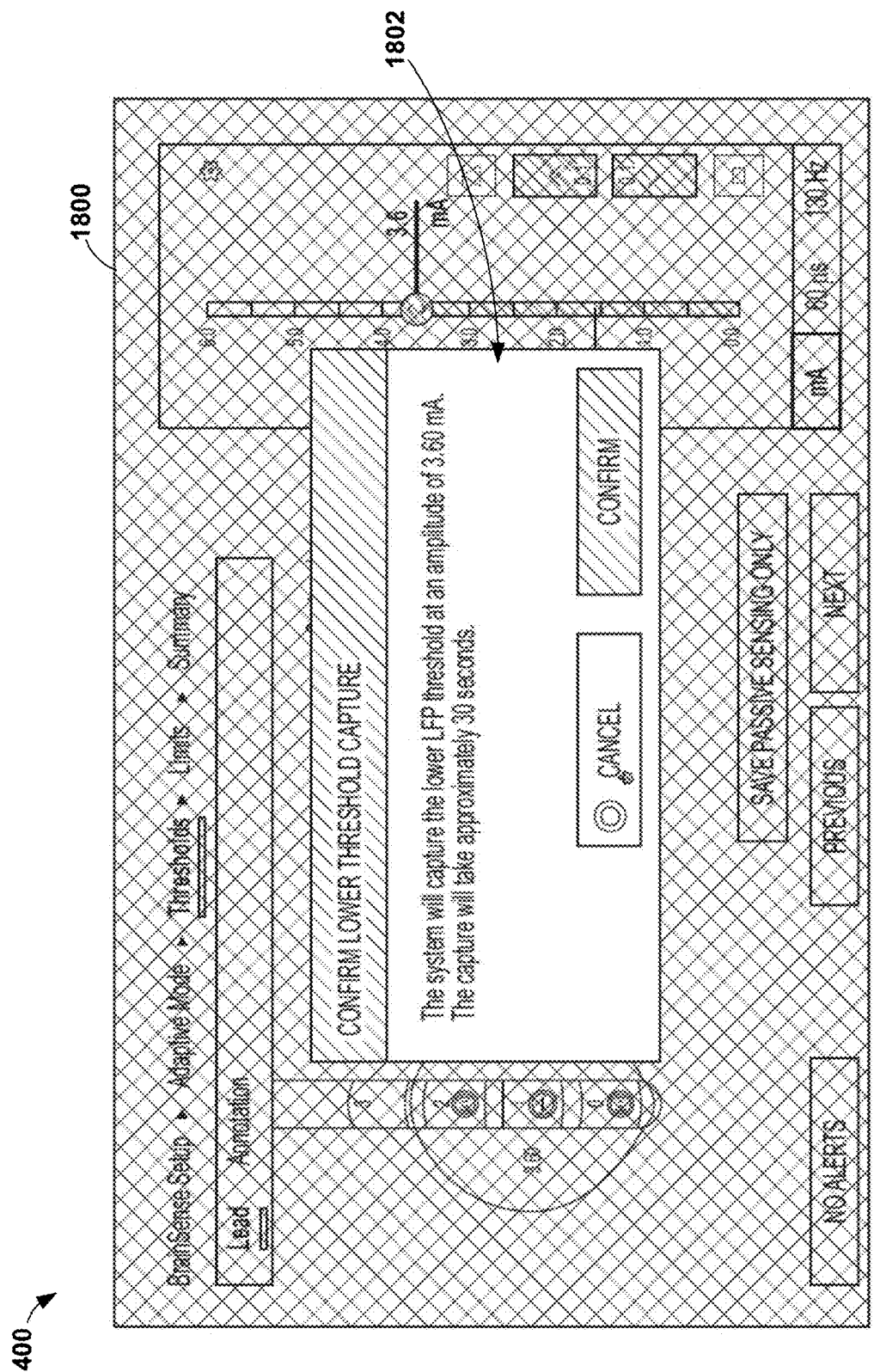
Figure 19:
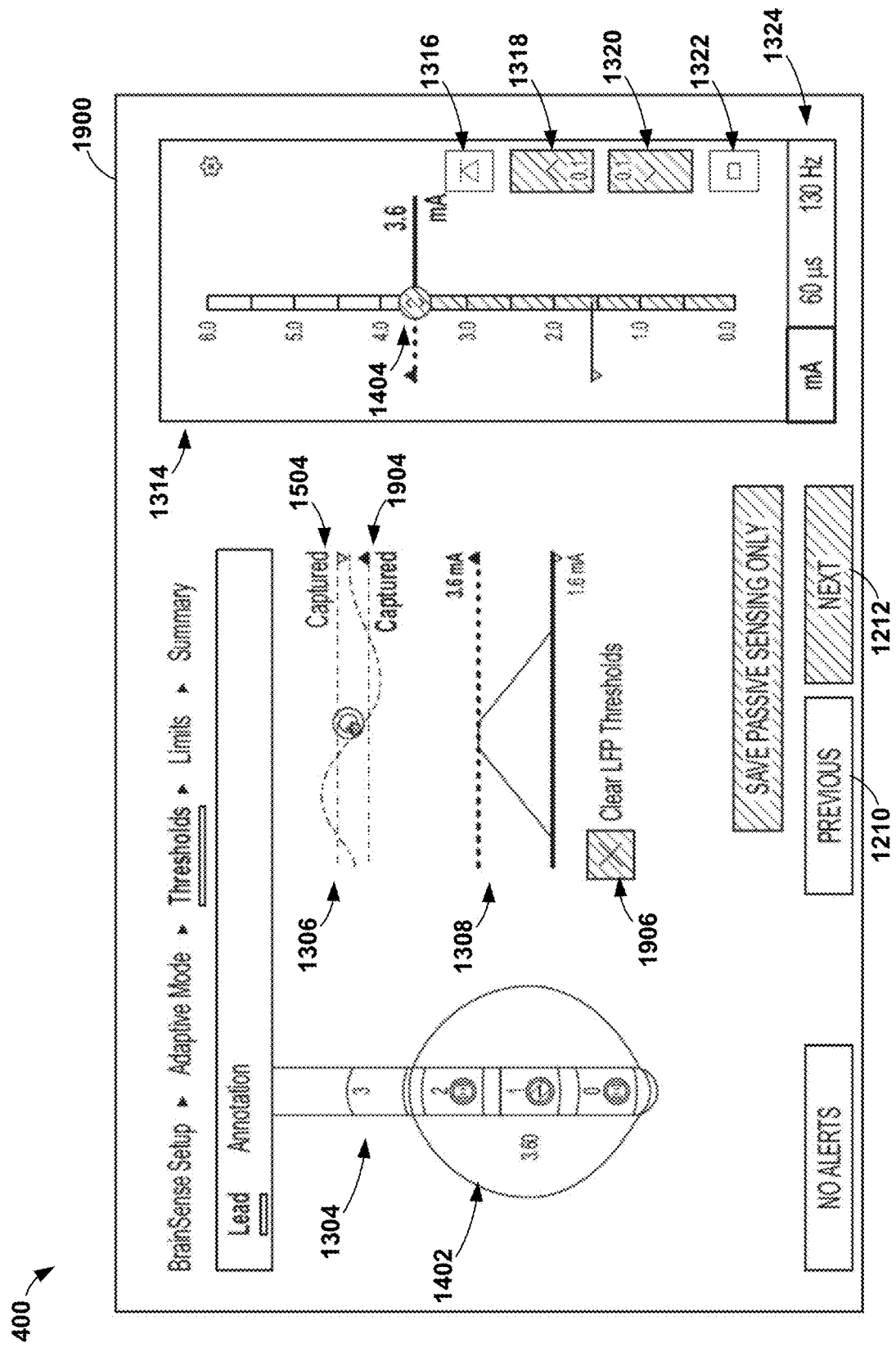

FIG. 17 illustrates screen 1700 in which the upper threshold 1504 has been captured and the lower limit of current amplitude has been set. Then, the user will increase the current amplitude to highest amplitude at which there are no side effects (or acceptable side effects for the patient in other examples). As shown in FIG. 17, the current amplitude has been increased to 3.6 mA using slider 1404, along with the VOA or stimulation field 1402 shown with the representation of the lead 1304. User selection of the capture button 1310 will capture the sensed LFP amplitude as the lower threshold and set the current amplitude as the upper limit for the amplitude range. FIG. 18 illustrates screen 1800 which includes an example pop-up window 1802 requesting that the patient confirm lower threshold capture at the current amplitude in response to the user selecting the capture button 1310. The system will set the lower threshold here in response to the user selecting the confirm button. As shown in FIG. 19, screen 1900 indicates that the upper threshold 1504 has been set and color coordinated to the lower limit for current amplitude (e.g., shown as the same color). The lower threshold 1904 has been set and color coordinated to the upper limit for current amplitude (e.g., shown as the same color different from the upper threshold/lower limit color). In addition to color, the upper threshold 1504 and lower limit has a similar pointing arrow, while the lower threshold 1904 and the upper limit has a similar pointing arrow. In this manner, the system can adjust the current amplitude automatically between the lower and upper limit in order to maintain the LFP signal between the lower and upper thresholds.

As shown herein, increasing current amplitude (or other stimulation parameters that increase stimulation intensity) may decrease the amplitude of the LFP signal at the selected frequency. Conversely, decreasing current amplitude (or other stimulation parameters that decrease stimulation intensity) may increase the amplitude of the LFP signal at the selected frequency. LFPs below the lower threshold may indicate that the patient is receiving too much stimulation and having dyskinesia, while LFPs above the upper threshold may indicate that the patient's symptoms are not being controlled effectively. In some examples, the average power for the selected frequency over 30 seconds is captured as the upper threshold and the lower threshold. In some examples, processing circuitry 310 may employ error checking on the upper and lower thresholds. For example, processing circuitry 310 may reject capturing a threshold if that capture would result in the upper threshold being below the lower threshold. In addition, or alternatively, processing circuitry may perform a statistical threshold check to ensure that the thresholds are adequately separated from one another.

As shown in FIG. 19, the system can capture LFPs during delivery of stimulation. This may be possible because the stimulation electrodes are different from the sensing electrodes. One benefit to this capability of capturing LFPs while delivering stimulation is that the LFP data may be identified when the patient is home so that the system can monitor the LFP thresholds.

As discussed herein, processing circuitry 310 may obtain a brain signal representative of electrical activity of a brain of a patient, control a medical device (e.g., IMD 106) to deliver electrical stimulation defined by at least a first value of a stimulation parameter, adjust the first value of the stimulation parameter to a second value of the stimulation parameter at which a patient condition is identified, and determine a threshold value for the brain signal associated with the patient condition. The IMD 106 may be configured to limit automatic adjustment of the stimulation parameter to the second value associated with the threshold value. The threshold value for the brain signal may be associated with one of an upper threshold associated with a therapeutic benefit or a lower threshold for the brain signal associated with a side effect.

In some examples, processing circuitry 310 may adjust the stimulation parameter to a third value at which a side effect is identified, the third value different than the second value and determine a second threshold value for the brain signal associated with the side effect, the second threshold value associated with a lower threshold. The medical device may be configured to limit automatic adjustment of the stimulation parameter to between the second value and the third value such that the brain signal remains between the upper threshold and the lower threshold. As discussed above, processing circuitry 310 may control a user interface to display the upper threshold and the lower threshold on a first graph and display the second value and the third value on a second graph. In some examples, the upper threshold and the second value are represented with a first color, and the lower threshold and the third value are represented with a second color different than the first color. As shown in FIG. 19, processing circuitry 310 may control the user interface to display the threshold value of the brain signal on a first graph, display the second value of the stimulation parameter on a second graph, display a representation of electrodes via which the electrical stimulation is delivered, and display a stimulation field representing the electrical stimulation with respect to the representation of the electrodes. In some examples, user selection of the clear LFP thresholds button 1906 will cause processing circuitry 310 to discard the captured upper and lower threshold.

Figure 20:
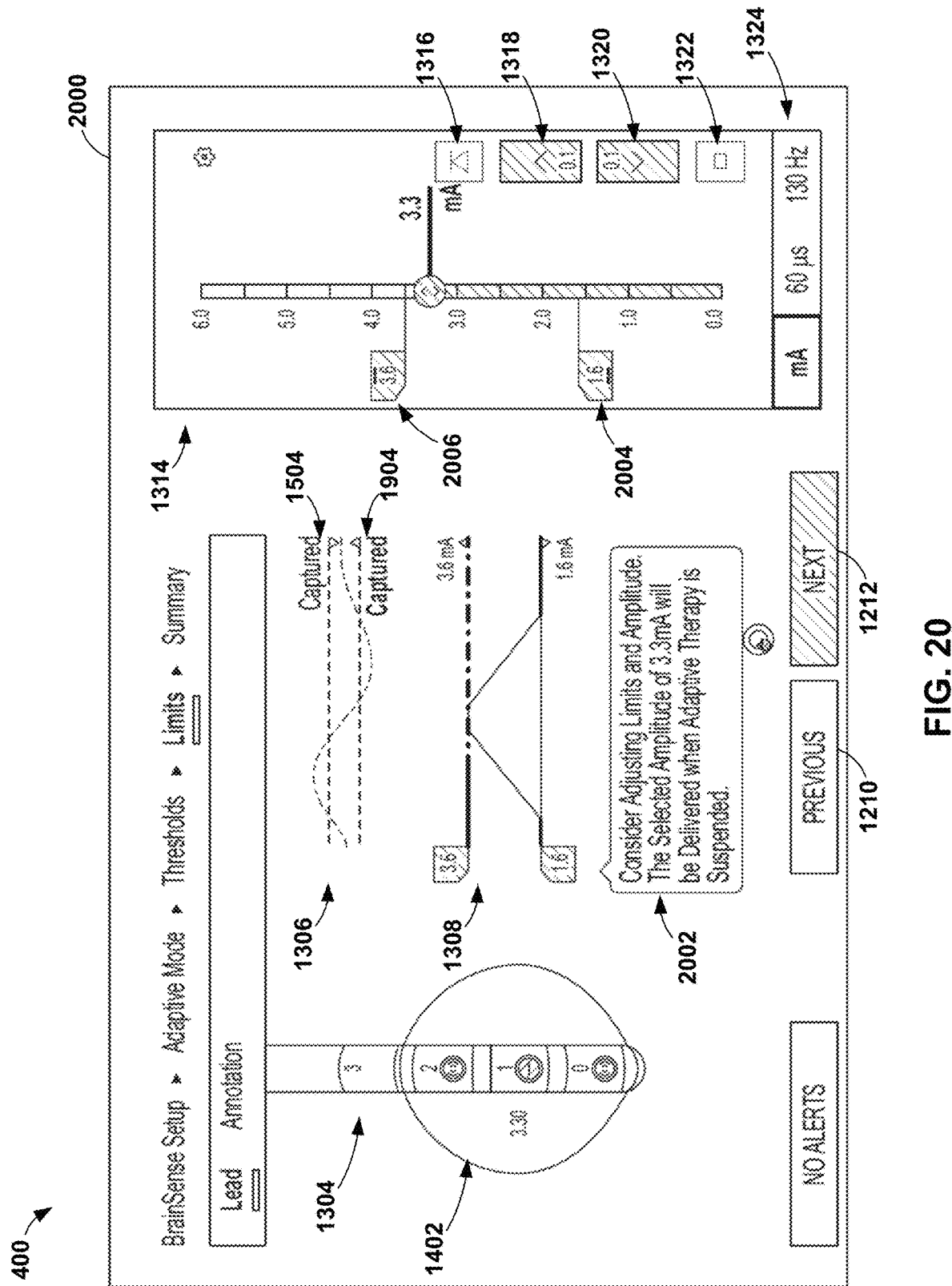

FIG. 20 illustrates an example screen 2000 in which user interface 400 indicates a prompt 2002 regarding the amplitude of stimulation. Although the amplitude is within the upper and lower limits, the system may indicate that this stimulation may be too high if adaptive DBS is turned off. Upper limit 2006 is the upper limit of amplitude and lower limit 2004 is the lower limit of amplitude.

Figure 21:
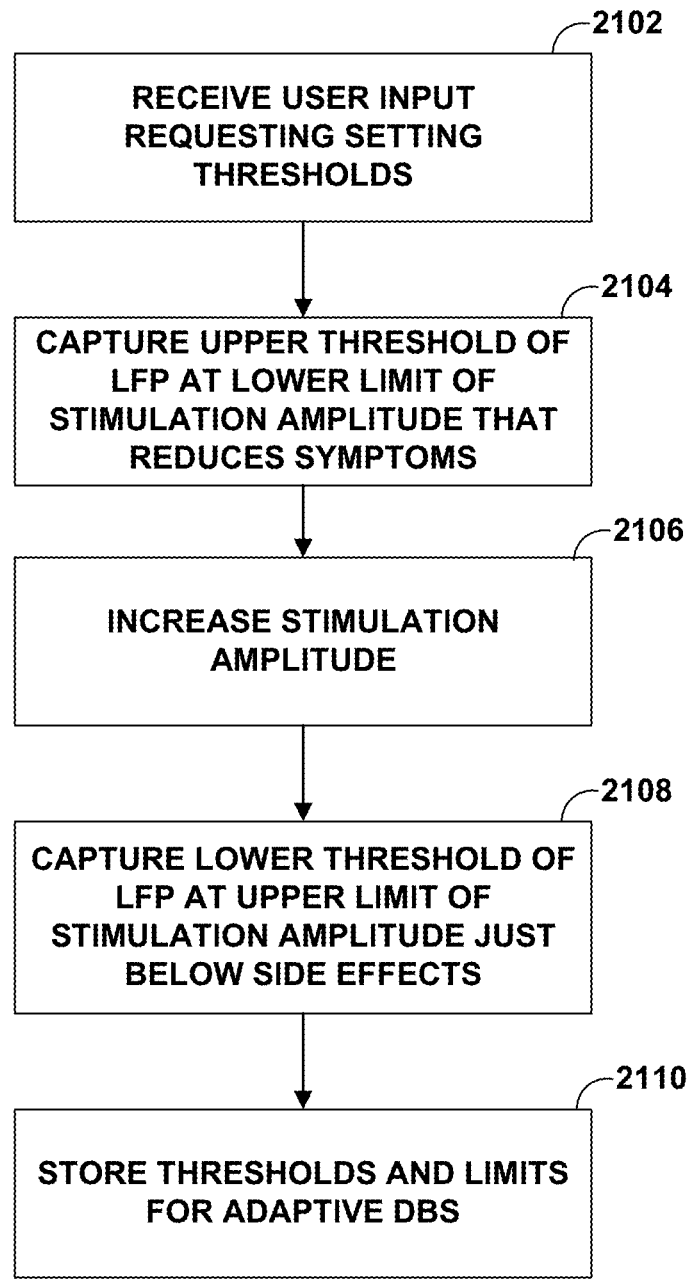
FIG. 21 is a flowchart illustrating an example technique for setting one or more thresholds associated with adaptive DBS therapy.

FIG. 21 is a flowchart illustrating an example technique for setting dual thresholds associated with adaptive DBS therapy, which may be done using various screens of user interface 400 described herein. In the example of FIG. 21, processing circuitry 310 receives user input requesting setting of thresholds for adaptive DBS (2102). Processing circuitry 310 captures the upper threshold of the LFP brain signal at the lower limit of stimulation amplitude that reduces symptoms for the patient (2104). Processing circuitry 310 then increases stimulation amplitude according to user input (2106). Processing circuitry 310 captures the lower threshold of the LFP brain signal at the upper limit of stimulation amplitude that is just below side effects for the patient (2108). Processing circuitry 310 then stores the thresholds and limits for adaptive DBS (2110). The user may adjust these thresholds and limits manually in some examples.

FIG. 22 is a conceptual diagram illustrating an example screen 2200 summarizing parameters selected for adaptive DBS therapy. In the example screen 2200 of FIG. 22, set transitions for moving stimulation up or down are provided along with an indication that the thresholds have been captured. Electrode configuration 2202 shows the electrodes used to sense brain signals. Stimulation settings 2204 indicates the upper limit, lower limit, and suspended amplitude for stimulation therapy. Field 2206 indicates the transition durations when moving between the upper and lower limit of amplitudes, and field 2208 indicates whether the LFP thresholds have been captured or now. User selection of the thresholds edit button for the respective fields 2206 and 2208 will cause processing circuitry 310 to display the screens shown in FIGS. 23 and 24.

Figure 24:
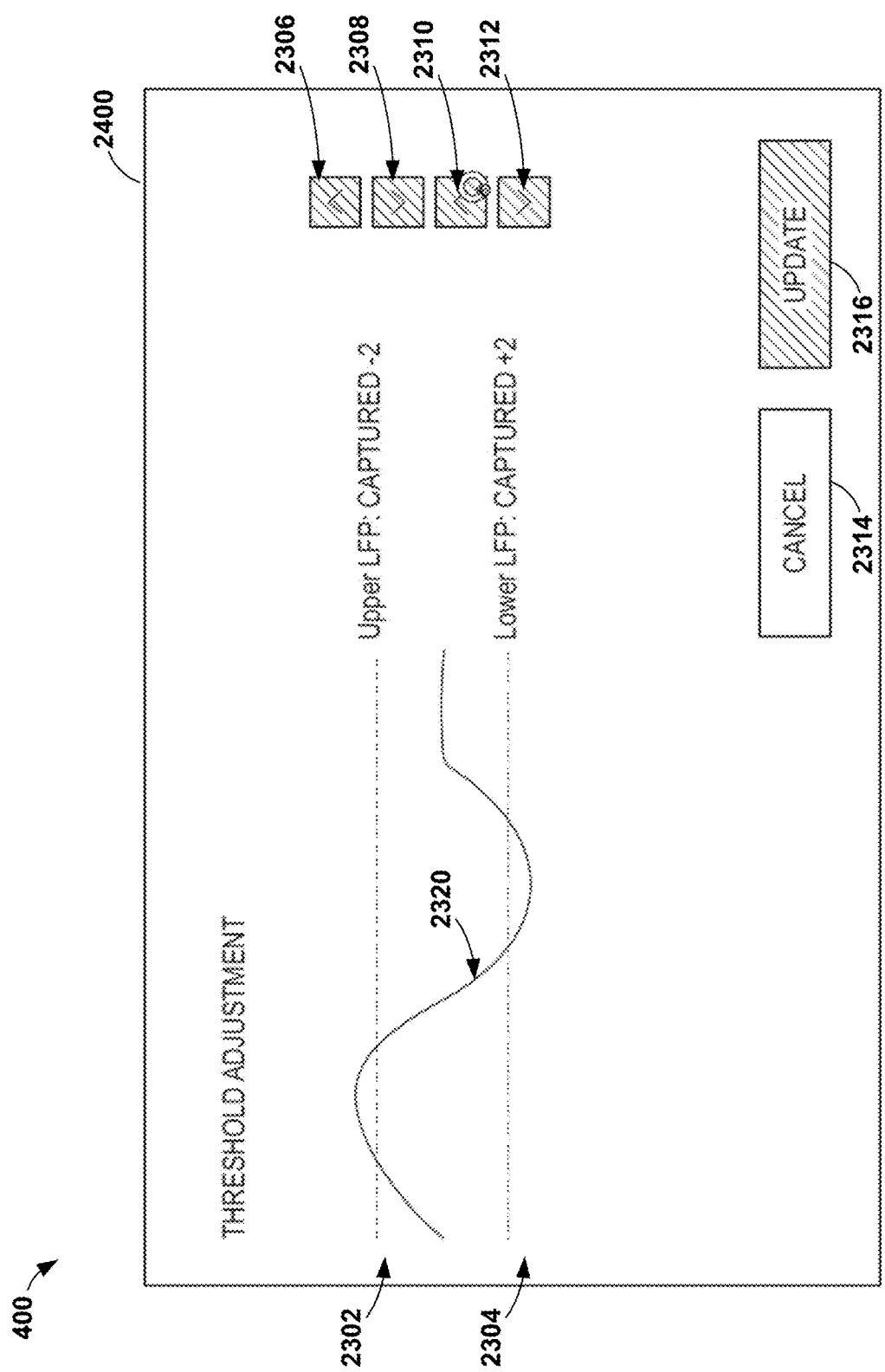

FIGS. 23 and 24 are conceptual diagrams illustrating example screens for manually adjusting one or more thresholds associated with adaptive DBS therapy. In the example screen 2300 of FIG. 23, arrow buttons 2306, 2308, 2310, and 2312 are provided to receive user increase or decrease of either the upper threshold 2302 or lower threshold 2304. The LFP signal is represented by curve 2320. In this manner, processing circuitry 310 may be configured to receive user input requesting manual adjustment to one or both of the thresholds via user interface 400 and then adjust the respective threshold. FIG. 24 includes example screen 2400 which indicates that the user reduced the upper threshold by 2 steps and increases the lower threshold by 2 steps. User selection of cancel button 2314 will cancel the adjustment to the LFP thresholds. User selection of update button 2316 will cause programmer 104 to change the LFP thresholds as indicated in screen 2400.

The system can increase or decrease either threshold. In some examples, the adjustment to the threshold is a relative adjustment to one or both thresholds. For example, the amplitude value separating the upper and lower threshold may be divided into equal steps such that each increase or decrease to the respective threshold causes a normalized change to the threshold. In one example, the magnitude between the thresholds is divided by 100 steps (or some other predetermined number of steps), and each press of the up or down button increases or decreases the threshold by one step. In other examples, each press of the button may change the threshold by a percentage or other relative value for the thresholds.

Figure 25:
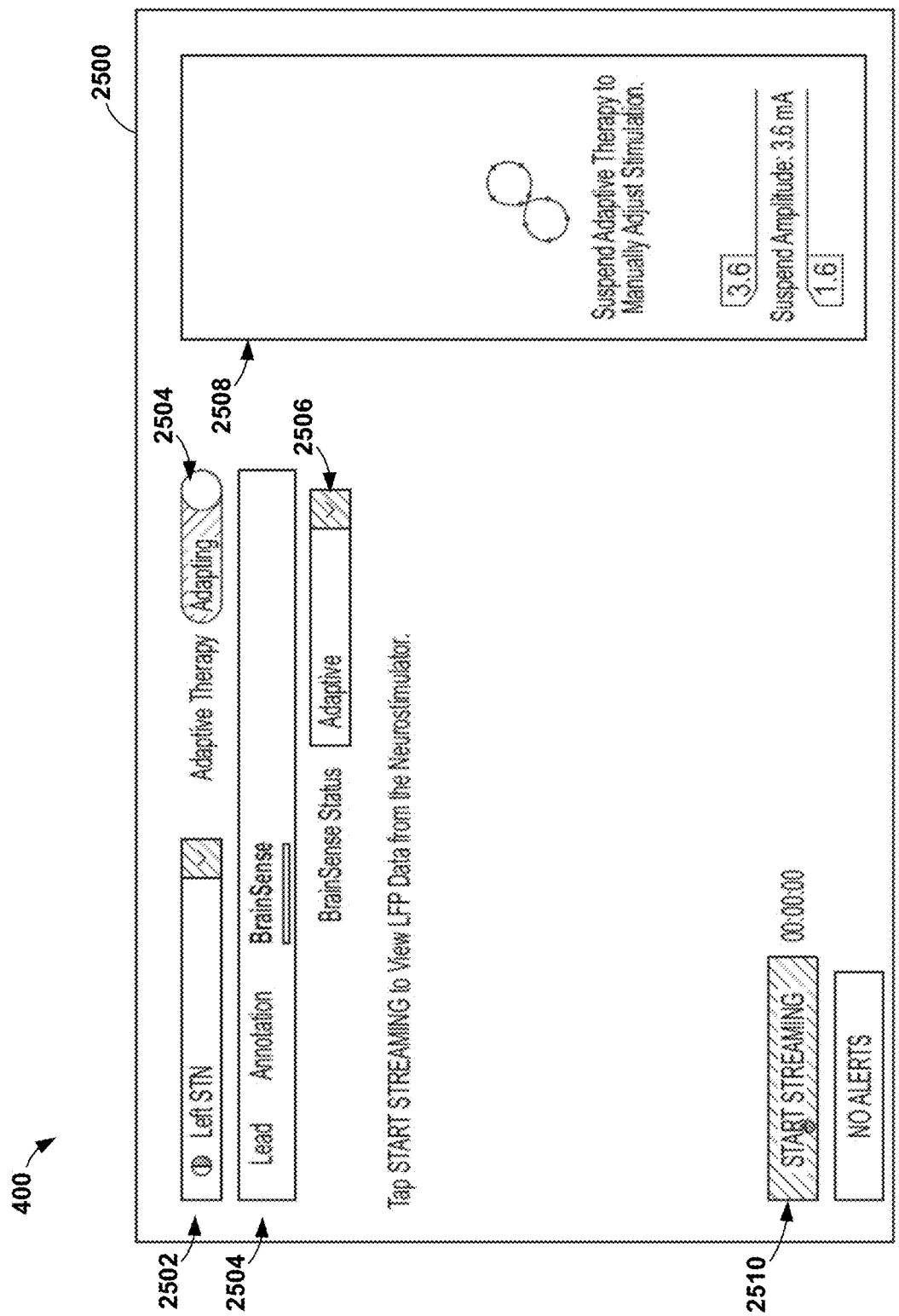
FIGS. 25-30 are conceptual diagrams illustrating example screens for displaying sensed brain signals with one or more stimulation parameters defining delivered DBS therapy.

FIGS. 25-30 are conceptual diagrams illustrating example screens for displaying sensed brain signals with one or more stimulation parameters defining delivered DBS therapy. FIG. 25 illustrates a screen 2500 in which a selectable "start streaming" button 2510 enables a user to start streaming near-real time brain information, such as LFP Power, and stimulation amplitude simultaneously. Processing circuitry 310 may be configured to display and/or store the streamed LFP information to a memory. Screen 2500 also includes hemisphere selection 2502, adaptive therapy toggle 2504 to turn adaptive therapy on or off, and menu 2504 which indicates the type of setup screen is current. Adaptive status 2506 indicates what type of stimulation is being delivered. Parameter field 2508 indicates selected amplitude limits, but adaptive stimulation must be suspended before manual parameter value adjustments can be made.

Figure 26:
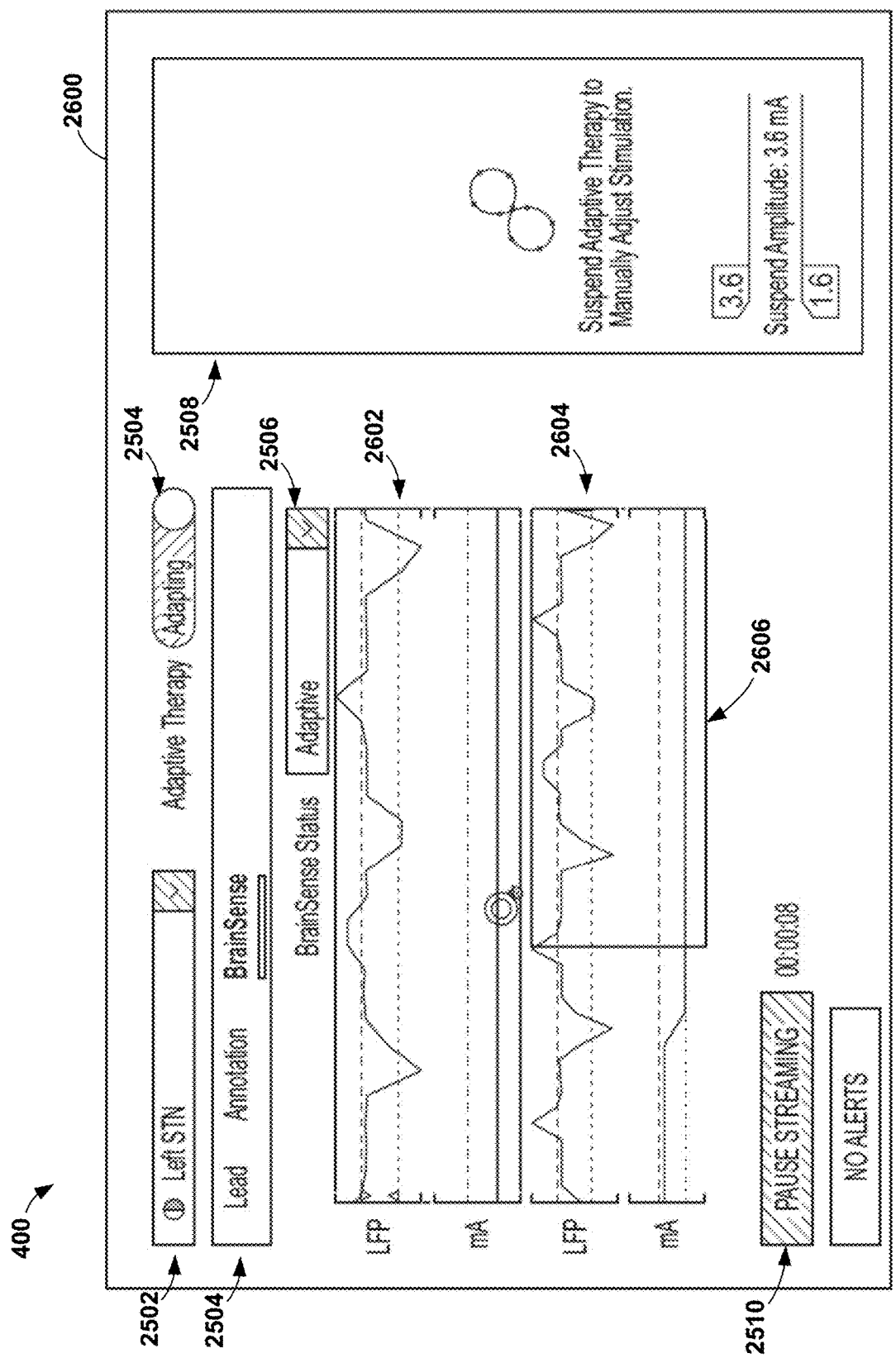
Figure 27:
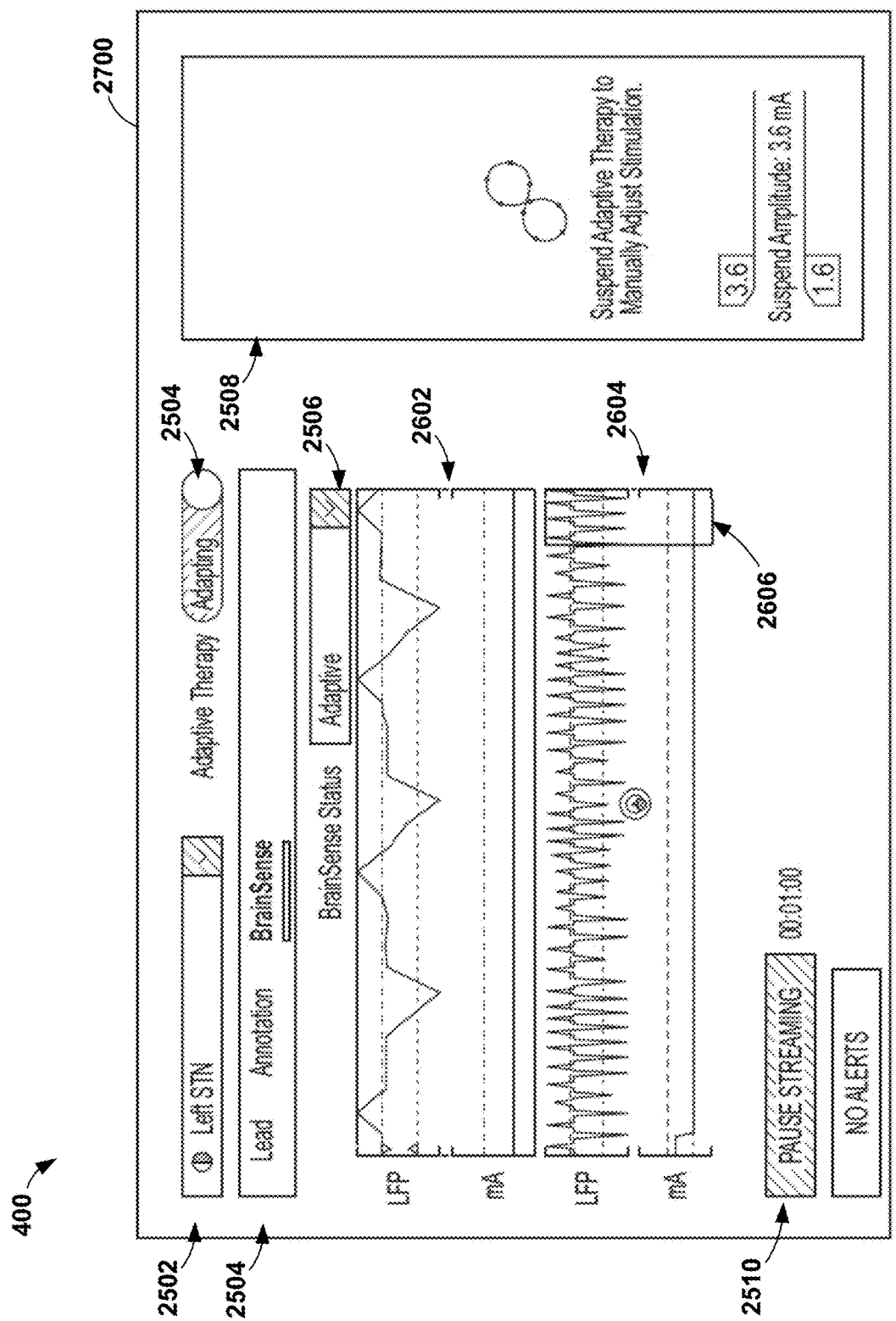

Once the start streaming button 2510 is selected, processing circuitry 310 begins streaming LFP power information to be displayed in user interface 400. As shown in FIG. 26, the screen 2600 of user interface 400 includes two graphs 2602 and 2604. Each graph displays the LFP power values with respect to the current amplitude value used to deliver stimulation at the same time the LFP power was obtained. The lower graph 2604 may include all data streamed since streaming started. The upper graph 2602 may include the data streamed within a shorter period of time. Box 2606 indicates the period of time from lower graph 2604 from which upper graph 2602 displays the LFP data. In this manner, the lower graph 2604 may cover a larger period of time than the upper graph 2602, with the lower graph 2604 including the information presented in the upper graph 2602. In this manner, each graph provides a different time frame for the displayed information. FIG. 27 illustrates screen 2700 in which the graphs 2602 and 2604 will change over time when more data is captured, where the upper graph 2602 maintains a certain time period, and the lower graph time period increases as more data is streamed. As shown, box 2606 decreases in size as more time of LFP data is added to lower graph 2604.

Figure 28:
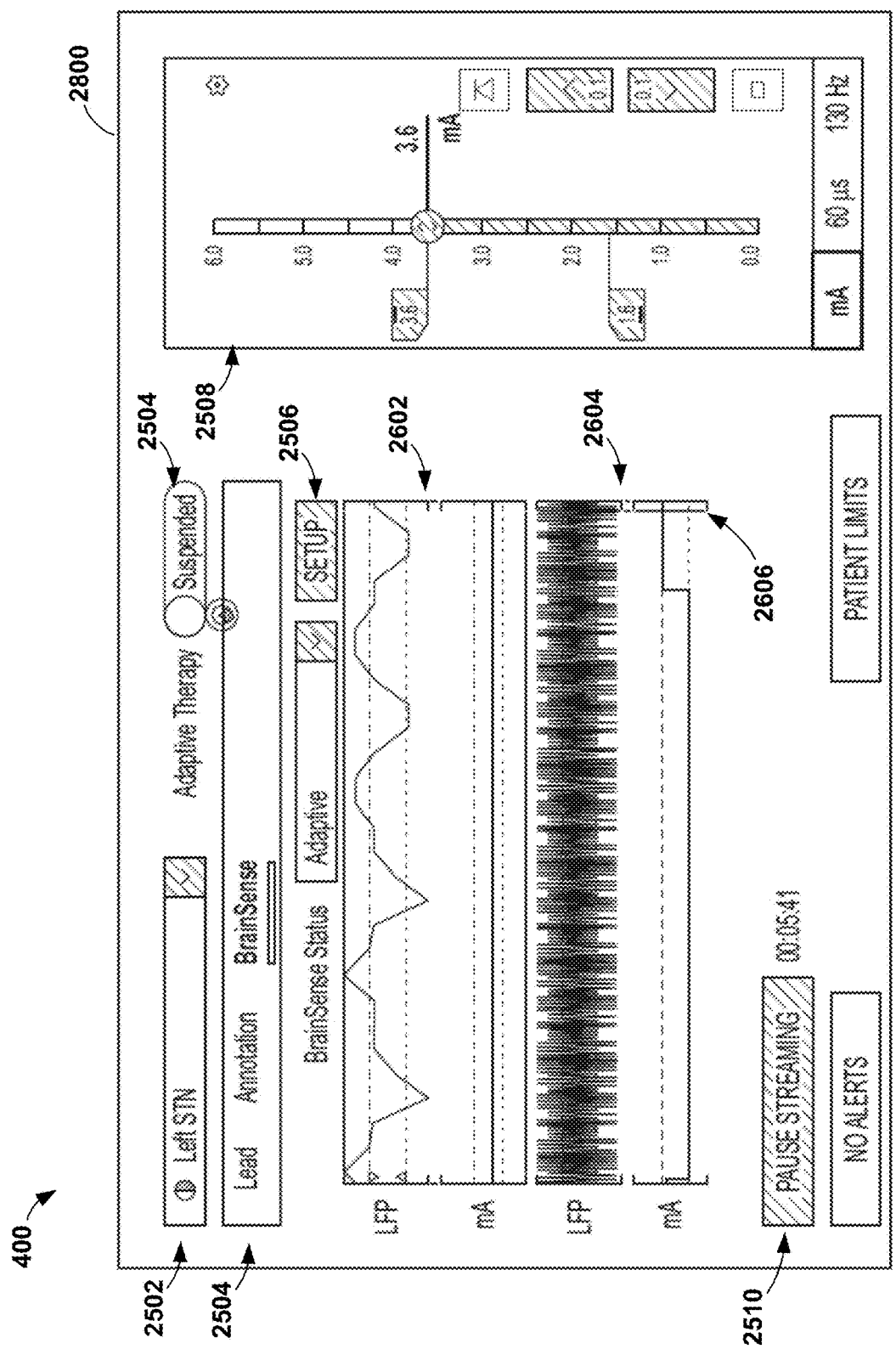
Figure 29:
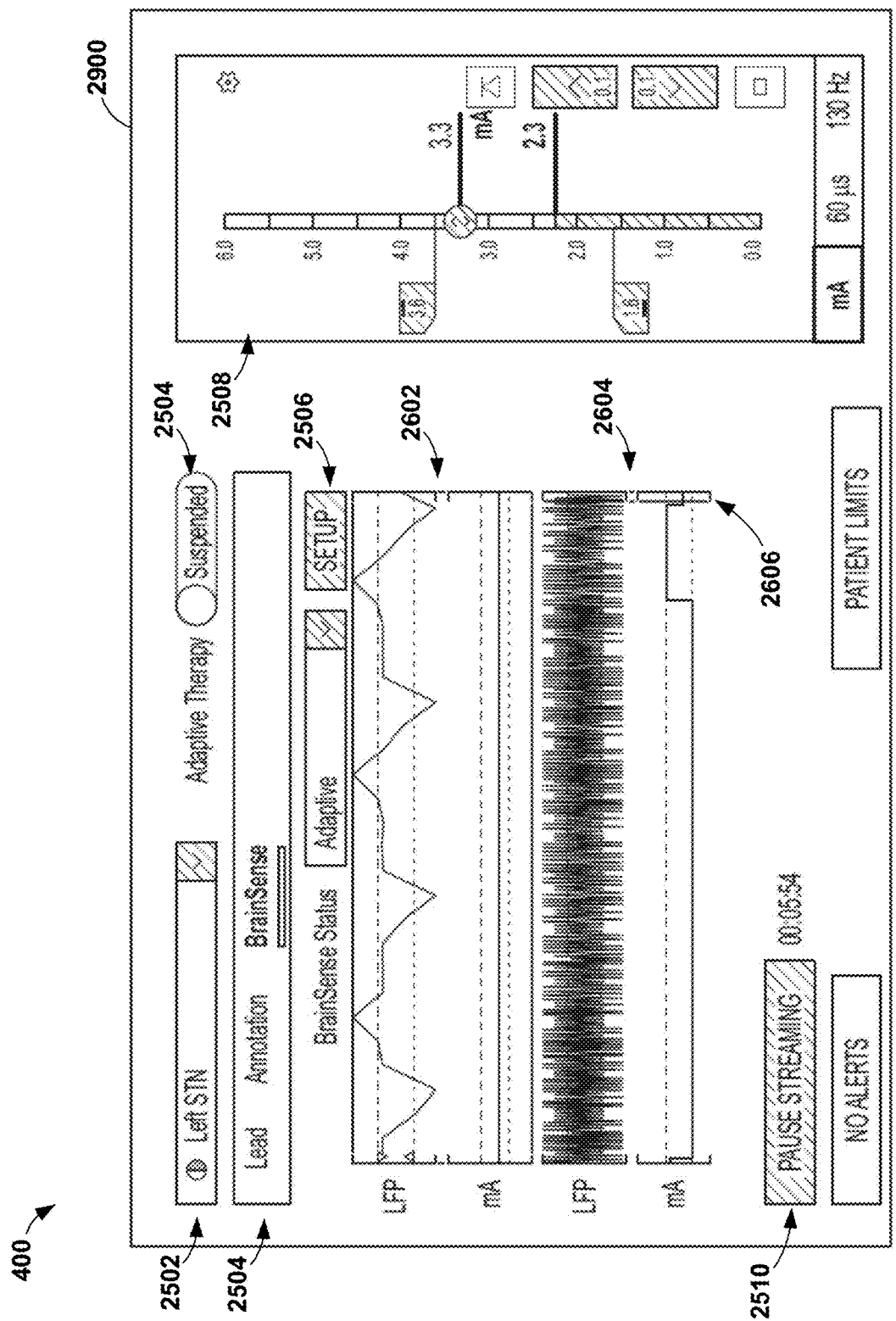

The graphs 2602 and 2604 will display any observed changes to the LFP power and the current amplitude. In addition, each graph may include the upper and lower threshold with the LFP power data and the upper and lower limit with the current amplitude. In this manner, the streaming shown in FIG. 26 enables the user to view how changes to the current amplitude affects the LFP power at the frequency selected for that sensing electrode configuration. In some examples, processing circuitry 310 may automatically calculate the vertical height of the streamed data graph based on threshold and limit values. In other to sense the LFP power while stimulation is delivered, processing circuitry 310 may blank the sensing channel during the time when the stimulation signal is delivered to the patient. Although user interface 400 may prevent the user from adjusting stimulation parameters or thresholds manually via the screen 2600 of FIG. 26, other examples may provide such ability to manually change one or more thresholds or parameter limits alongside real-time sensing data. In this manner, the clinician can monitor direct changes to LFP power (or another type of brain signal) caused by electrical stimulation and any changes to the electrical stimulation. For example, as shown in FIG. 28, the screen 2800 provides input buttons (within stimulation field 2508) that enable the user to change current amplitude while streaming the LFP power data and the stimulation parameter value. FIG. 29 illustrates an example screen 2900 in which adaptive therapy has been suspended as indicated by adaptive therapy toggle 2504, but a manual limit on current amplitude has been set (3.3. mA).

Figure 30:
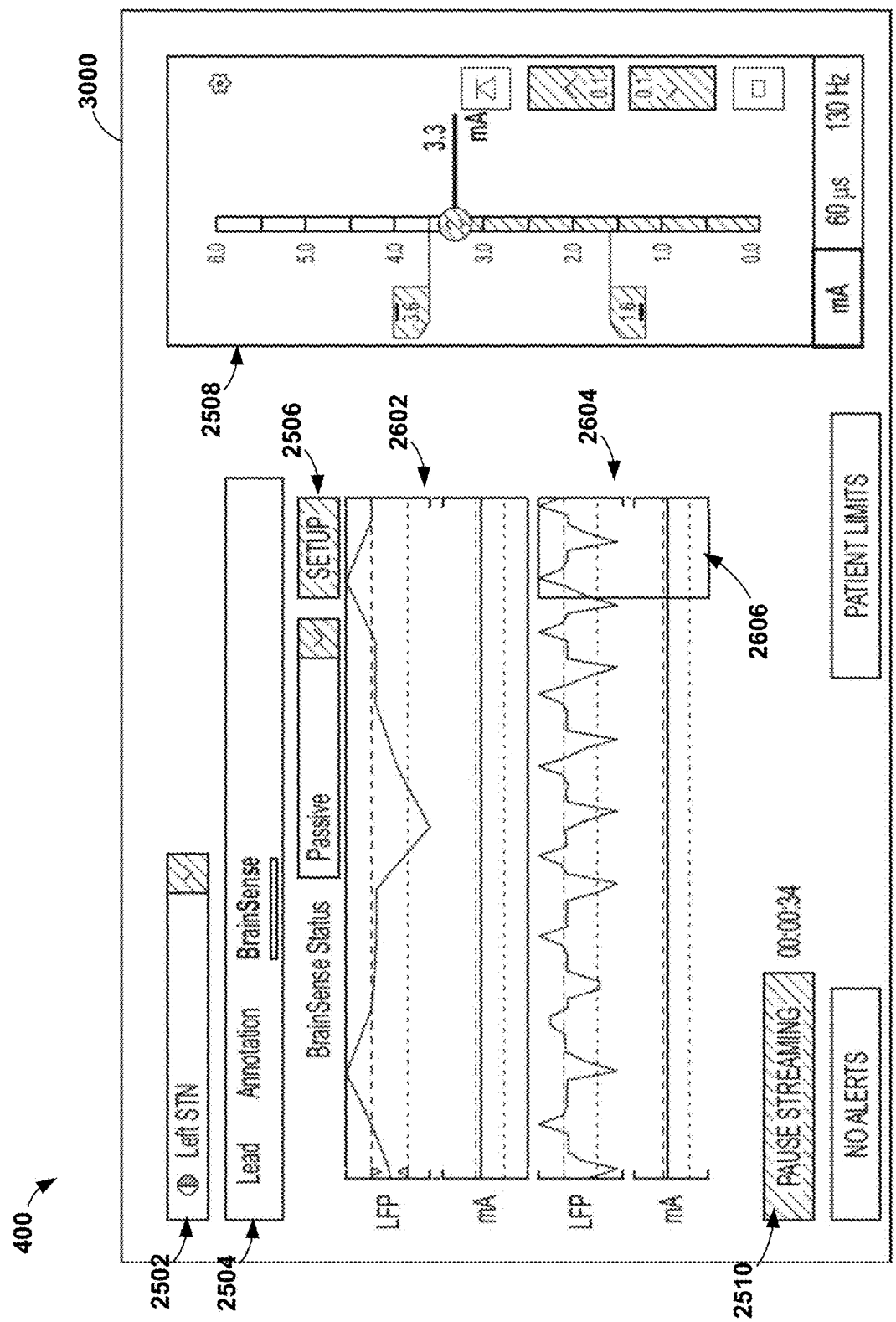

FIGS. 25 through 29 illustrate example screens for adaptive stimulation. However, the user may switch to passive stimulation as shown in screen 3000 of FIG. 30. In the screen 3000 of FIG. 30, LFP power and stimulation amplitude are still displayed. The user can also adjust stimulation amplitude to identify how those adjustments can affect the LFP power. In addition, as shown in FIG. 30, selection of the patient limits button will cause processing circuitry 310 to present a screen from which the user can adjust the upper or lower limits on current amplitude. The vertical height of each graph may be calculated based on the thresholds and limits.

As shown in FIGS. 25-30, user interface 400 provides real time streaming of LFP data on programmer 104. Once a signal/config has been configured, the system can enable a signal to be streamed in clinic while programming occurs in order to understand the real time response of the signal to stim changes. In this manner, short and long term trends of a selected signal can be displayed, which can be included with stimulation amplitude, adjustment of one or more stimulation parameter values (e.g., amplitude, frequency, and pulse rate). Programmer 104 may store the real time data offline in memory for later analysis and/or review by the user.

In some examples, user interface 400 may include input mechanisms to receive user input indicative of events or other annotations related to the streaming of data and time of stimulation for the patient. In some examples, user interface 400 may receive input adjusting the time scale of the presented data and/or compare data from different period of times. In other examples, user interface 400 may present real time power spectrum data, multiple signals of interest, or real time analytics. User interface 400 may present information regarding the relative suppression of LFP signal compared to baseline, for example.

FIGS. 25 through 30 show LFP data streaming from one electrode combination for sensing. In other examples, processing circuitry 310 may store brain signal information (e.g., LFP power) from multiple different electrode combinations. Processing circuitry 310 may then present stored brain signal information from the different electrode combinations together on the same screen to enable the user to identify which electrode combination provides the sensing of brain signals desired by the user.

Figure 31:
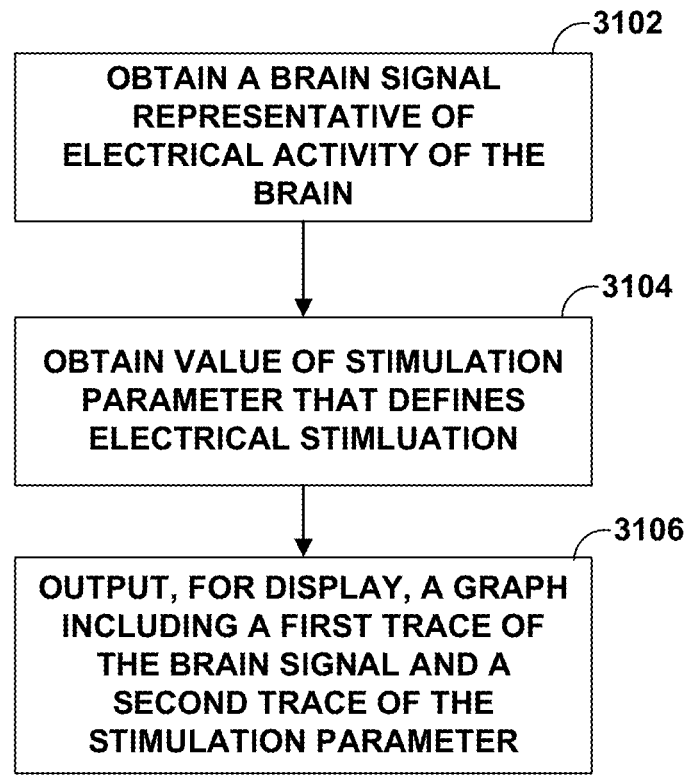
FIG. 31 is a flowchart illustrating an example technique for displaying sensed brain signals with one or more stimulation parameters defining delivered DBS therapy.

FIG. 31 is a flowchart illustrating an example technique for displaying sensed brain signals with one or more stimulation parameters defining delivered DBS therapy, as illustrated in FIGS. 25-30. As shown in the example of FIG. 31, processing circuitry 310 may obtain a brain signal representative of electrical activity of a brain of a patient (3102). Processing circuitry 310 then obtains one or more values of a stimulation parameter that at least partially defines electrical stimulation deliverable to a portion of the brain of the patient (3104). Processing circuitry then outputs, for display by user interface 400, a graph comprising a first trace of the brain signal for a period of time and a second trace of the one or more values of the stimulation parameter for the period of time (3106). The presentation of this information may be in real-time.

Figure 32:
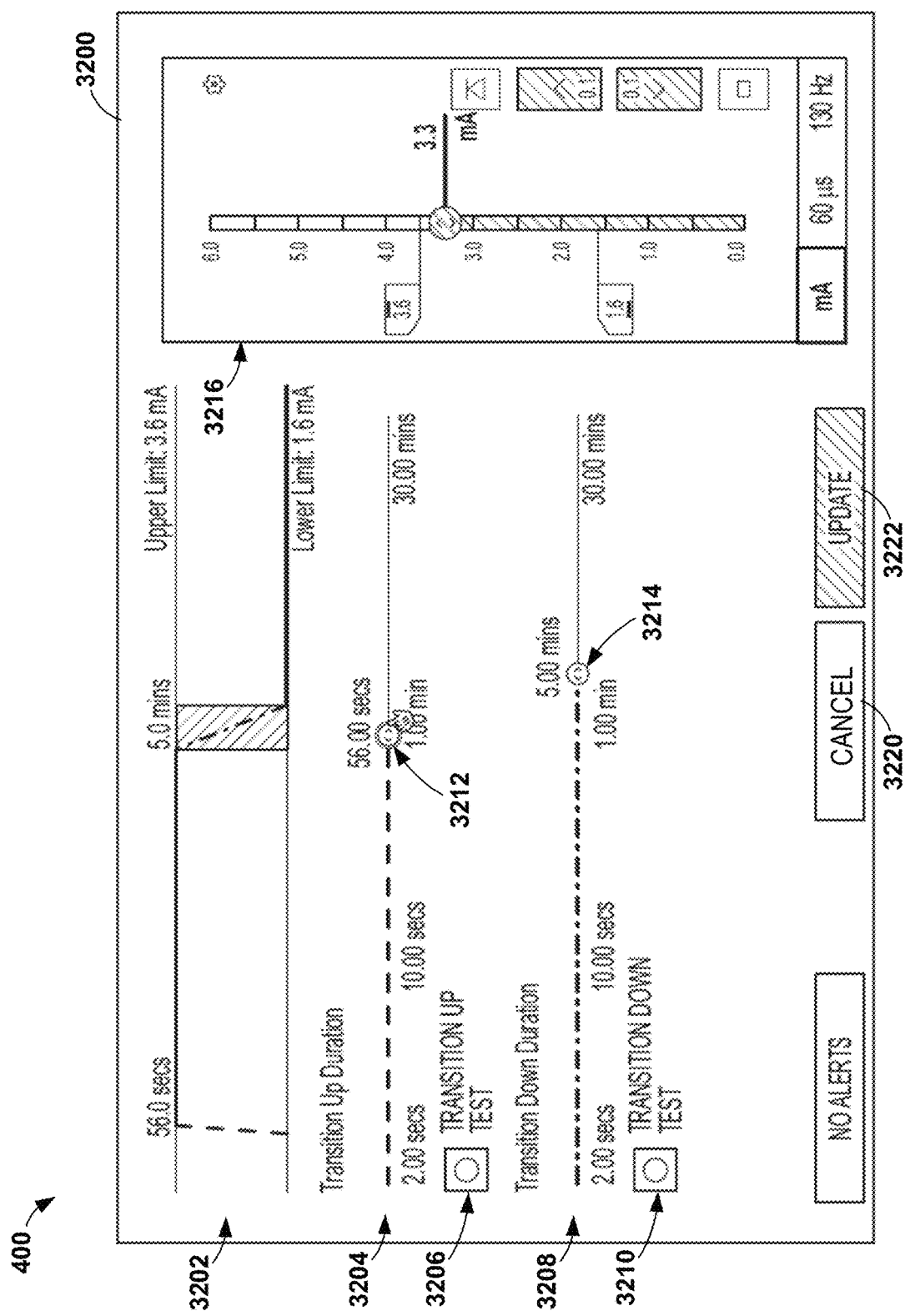
FIGS. 32 and 33 are conceptual diagrams illustrating example screens for adjusting transitions between upper and lower stimulation parameter limits.
Figure 33:
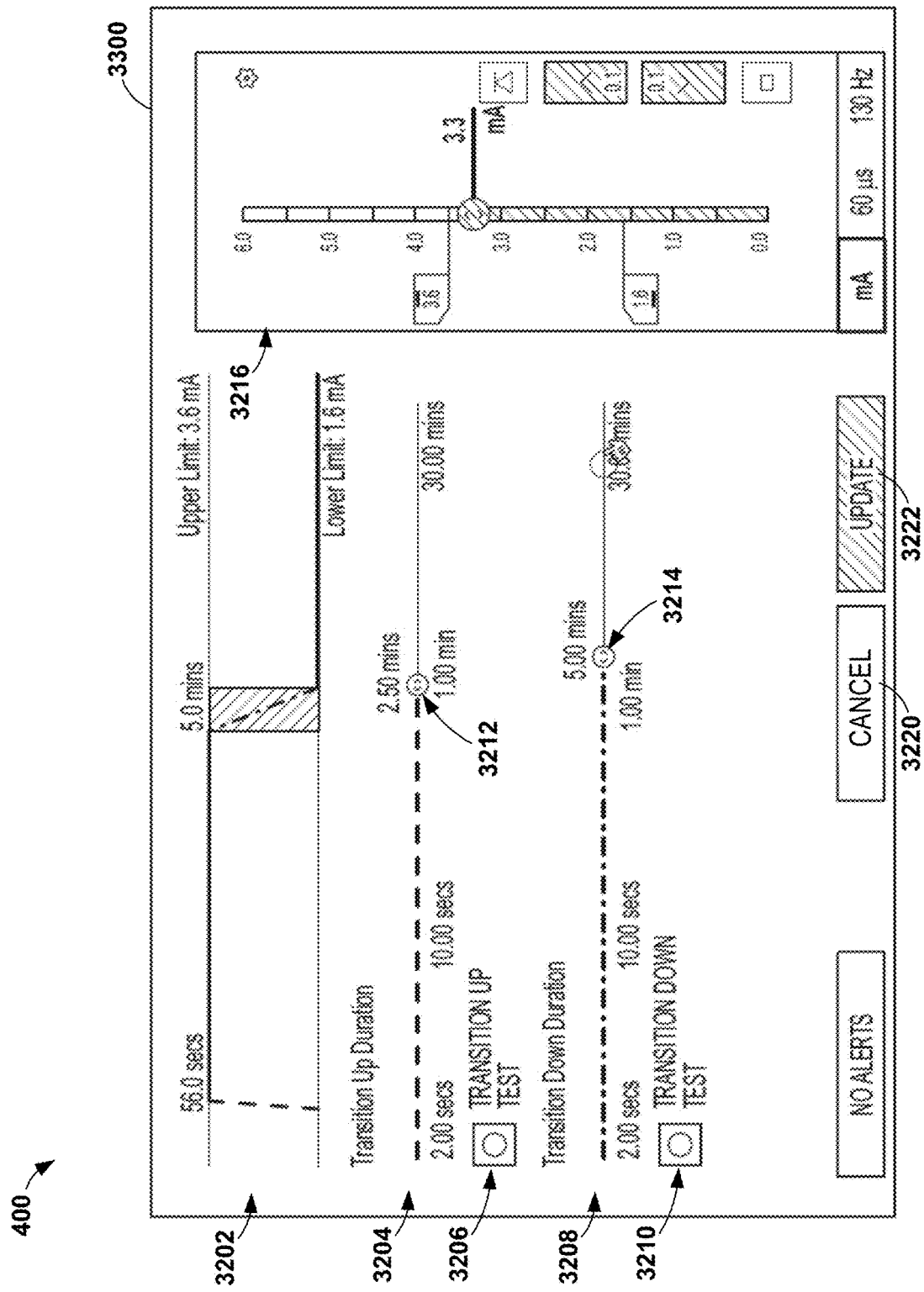

FIGS. 32 and 33 are conceptual diagrams illustrating example screens for adjusting transitions between upper and lower stimulation parameter limits. As shown in FIGS. 32 and 33, user interface 400 provides screens 3200 and 3300 that enable a user to test aDBS Transition and adjust how the transition occurs. Transition curve 3202 indicates the currently set transition times. Parameter field 3216 provides amplitude limits, current values, and adjustment inputs. Transition up adjustment 3204 represents the current up duration of time, which can be adjusted by moving slider 3212. Transition down adjustment 3208 represents the current down duration of time, which can be adjusted by moving slider 3214. Using this transition test, the user can evaluate whether there is an elevated potential for side effects due to rapid transition from stimulation on to off or stimulation off to on. For example, the transition up test button 3206 or the transition down test button 3210 can be selected to initiate simulation of an adaptive therapy transition for all or part of the therapeutic window in the respective direction. Processing circuitry 310 may send the complete command to perform the entire transition up or down to IMD 106 in order to avoid communication delays on each step during the transition. In this manner, IMD 106 will perform the test transition as it would be done automatically by IMD 106 during adaptive DBS.

Each of the ramps up and down on the top graph, and/or sliders 3212 and 3214 on the timelines below, may be selectable by the user to drag the ramp shorter or longer in time. In one example, processing circuitry 310 can initiate the ramp up or down from any starting amplitude. However, in other examples, processing circuitry 310 may require starting at the lower amplitude and ramping up fully before ramping down fully. Selection of cancel button 3220 cancels any changes to the transition durations. Selection of update button 3222 confirms any changes to the transition durations.

Figure 34:
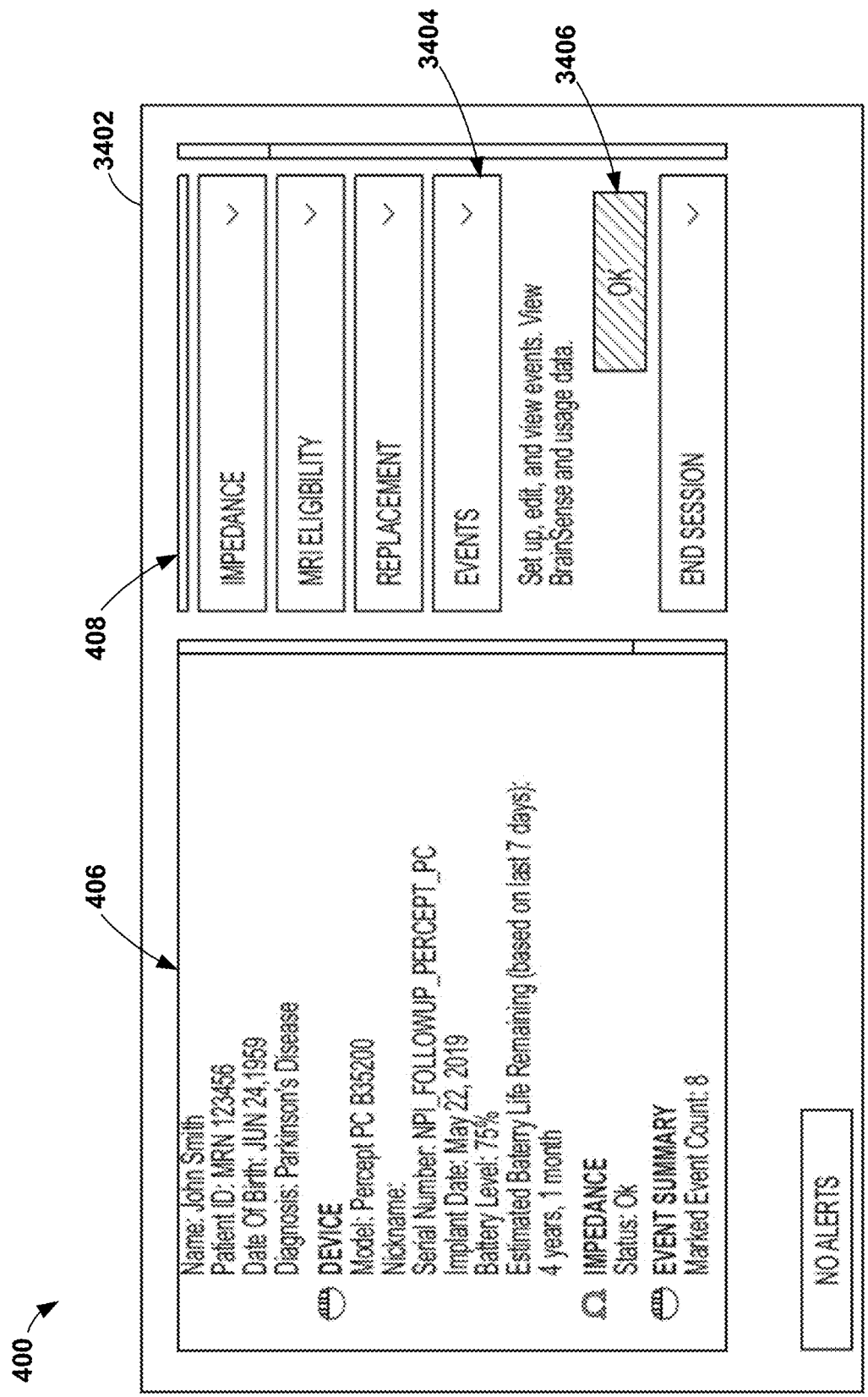
FIG. 34 is a conceptual diagram illustrating an example home screen for navigating to view stored patient event data.

FIG. 34 is a conceptual diagram illustrating an example home screen 3402 of user interface 400 for navigating to view stored patient event data, which may be similar to screen 402. When the user selects event button 3404 on the menu screen 3402, user interface 400 expands the event button and displays a confirmation button 3406 that must be selected by the user before processing circuitry 310 moves to the event set of screens shown in FIGS. 35-42.

Figure 35:
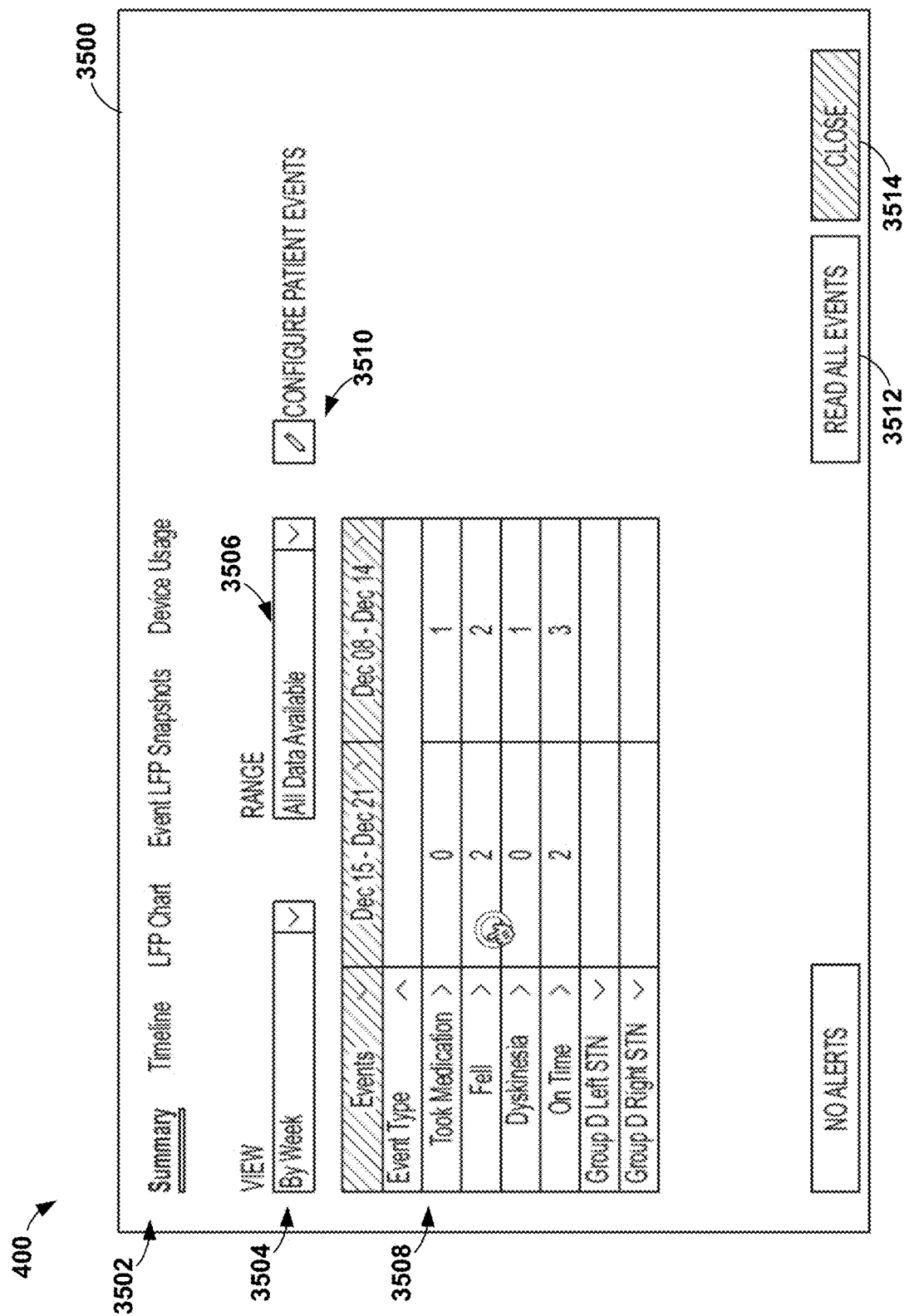
FIGS. 35-42 are conceptual diagrams illustrating example screens for displaying patient event data arranged by user selectable times.

FIGS. 35-42 are conceptual diagrams illustrating example screens for displaying patient event data arranged by user selectable times. FIGS. 35-39 illustrate example screens that show a number of each type of events that occurred during one or more periods of time. FIG. 35 illustrates an example screen 3500 in which four different events are shown for two different period of time (e.g., respective weeks of time) in table 3508. The example events include "took medication," "fell," "dyskinesia," and "on time." These events may be patient events that are indicated by the patient when they occur, such as the took medication, fell, dyskinesia events, and "on time." The "on time" may be the number of times in which the patient felt well and symptoms have been reduced or eliminated. The timing and number of each event may help a clinician evaluate the efficacy of stimulation therapy for the patient. Menu 3502 indicates which type of information is being displayed, which indicates that the summary is displayed in screen 3500. View selection 3504 indicates the time frame for each column of data (e.g., day, week, month, hours, etc.). Range selector 3506 indicates which data will be used to populate table 3508. Event selector 3510 can be selected so that the user can select which type of events are shown in table 3508. The user can read all events by selecting button 3512 or close screen 3500 by selecting close button 3514.

Figure 36:
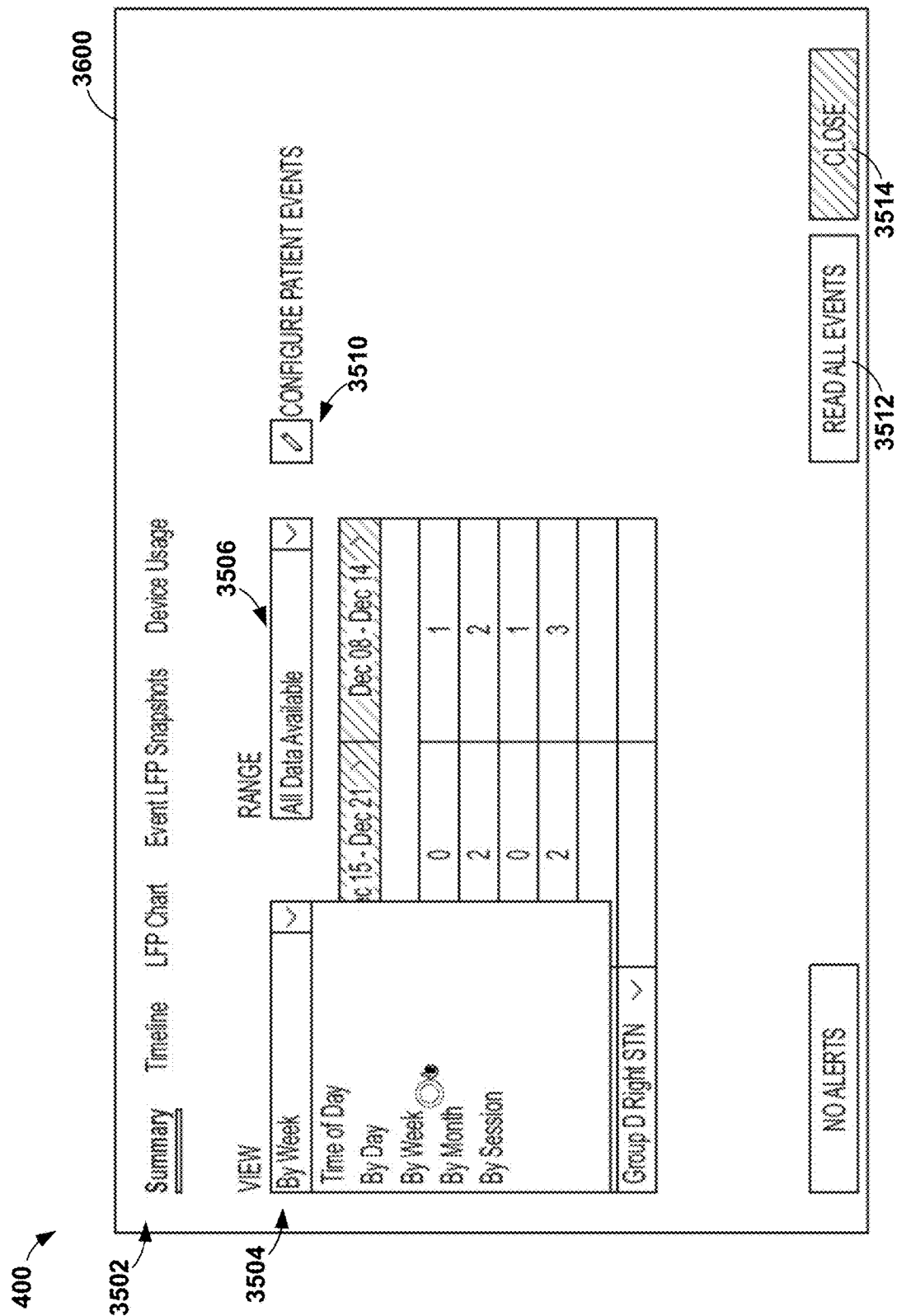
Figure 37:
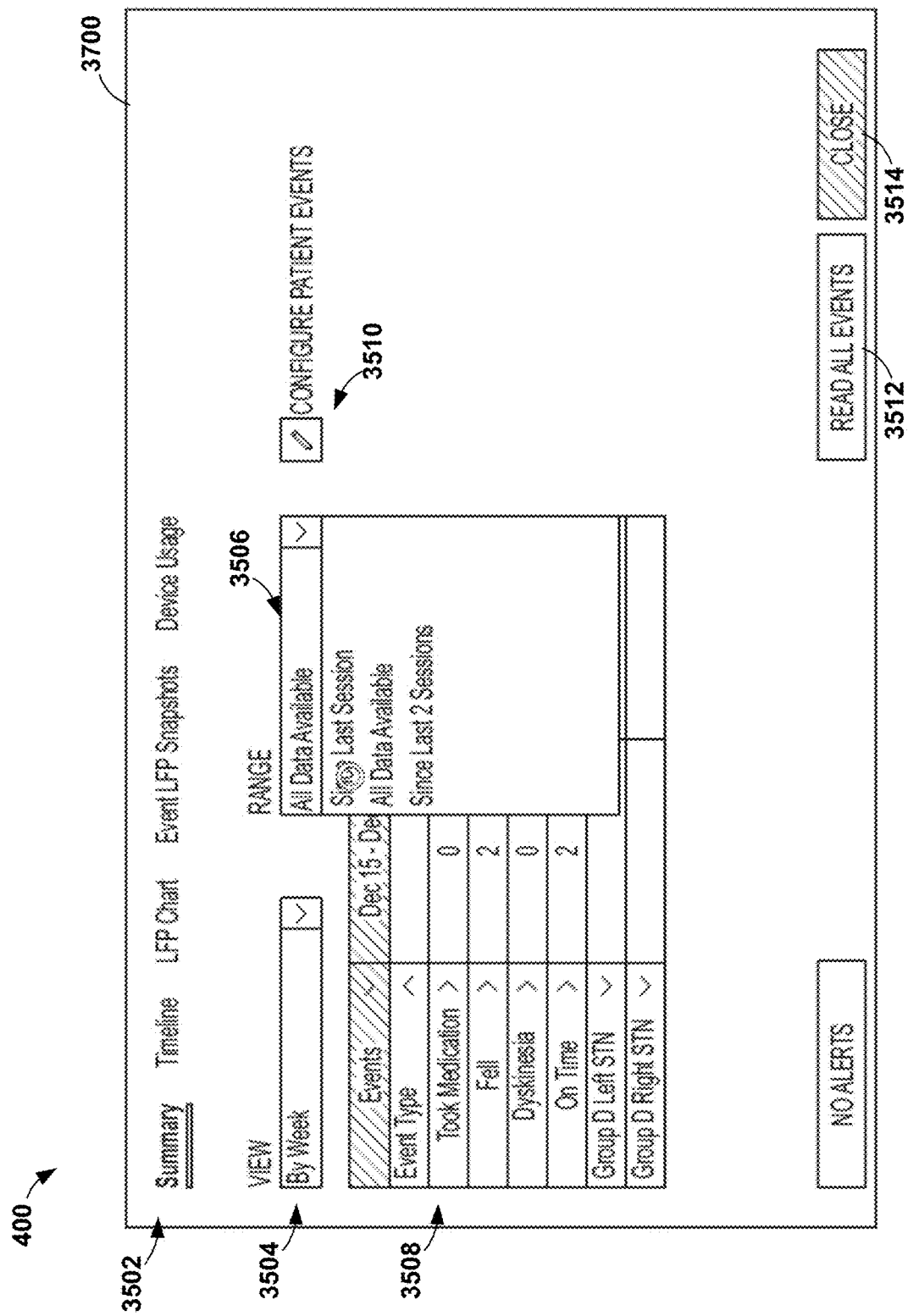
Figure 38:
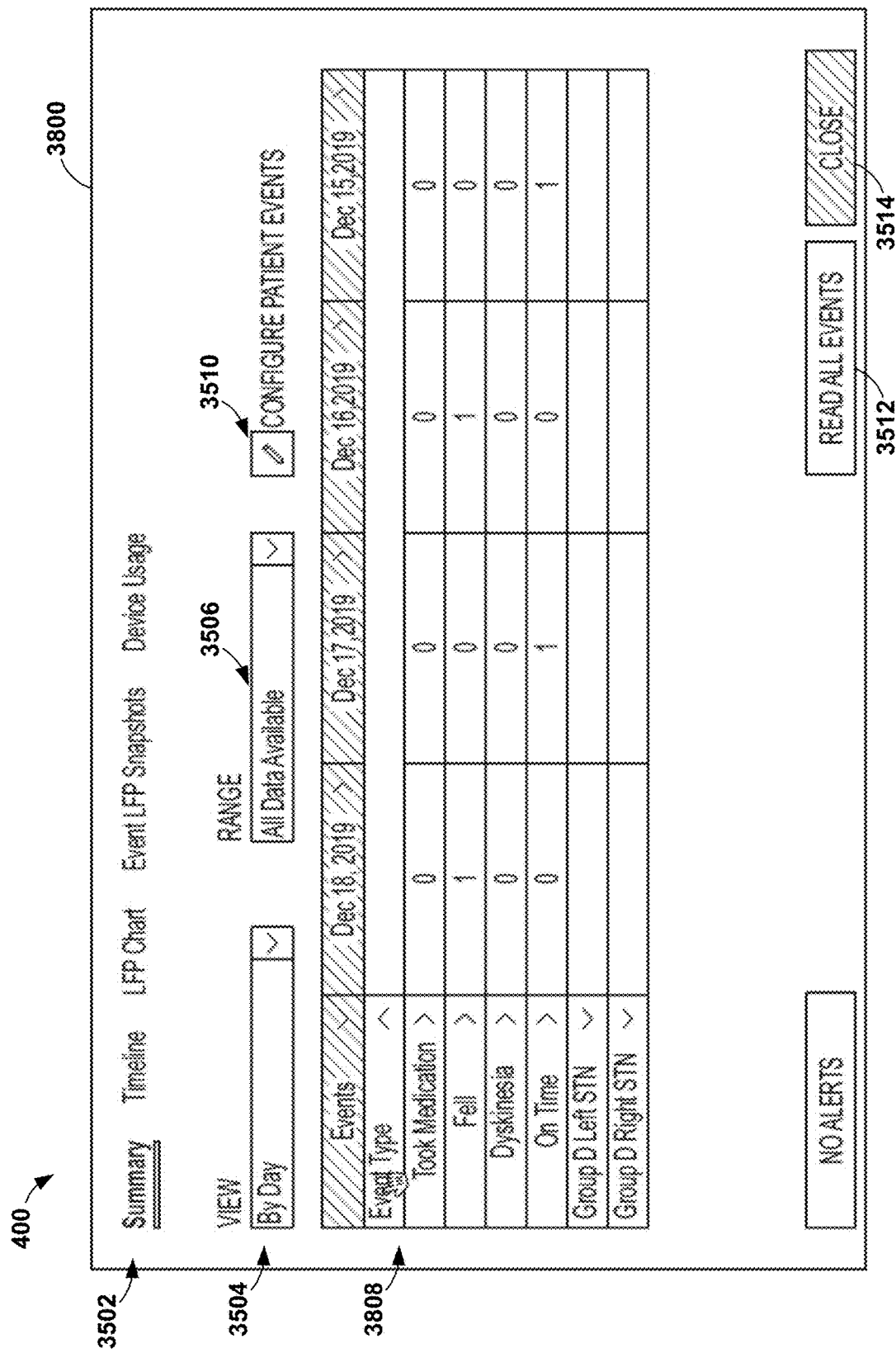
Figure 39:
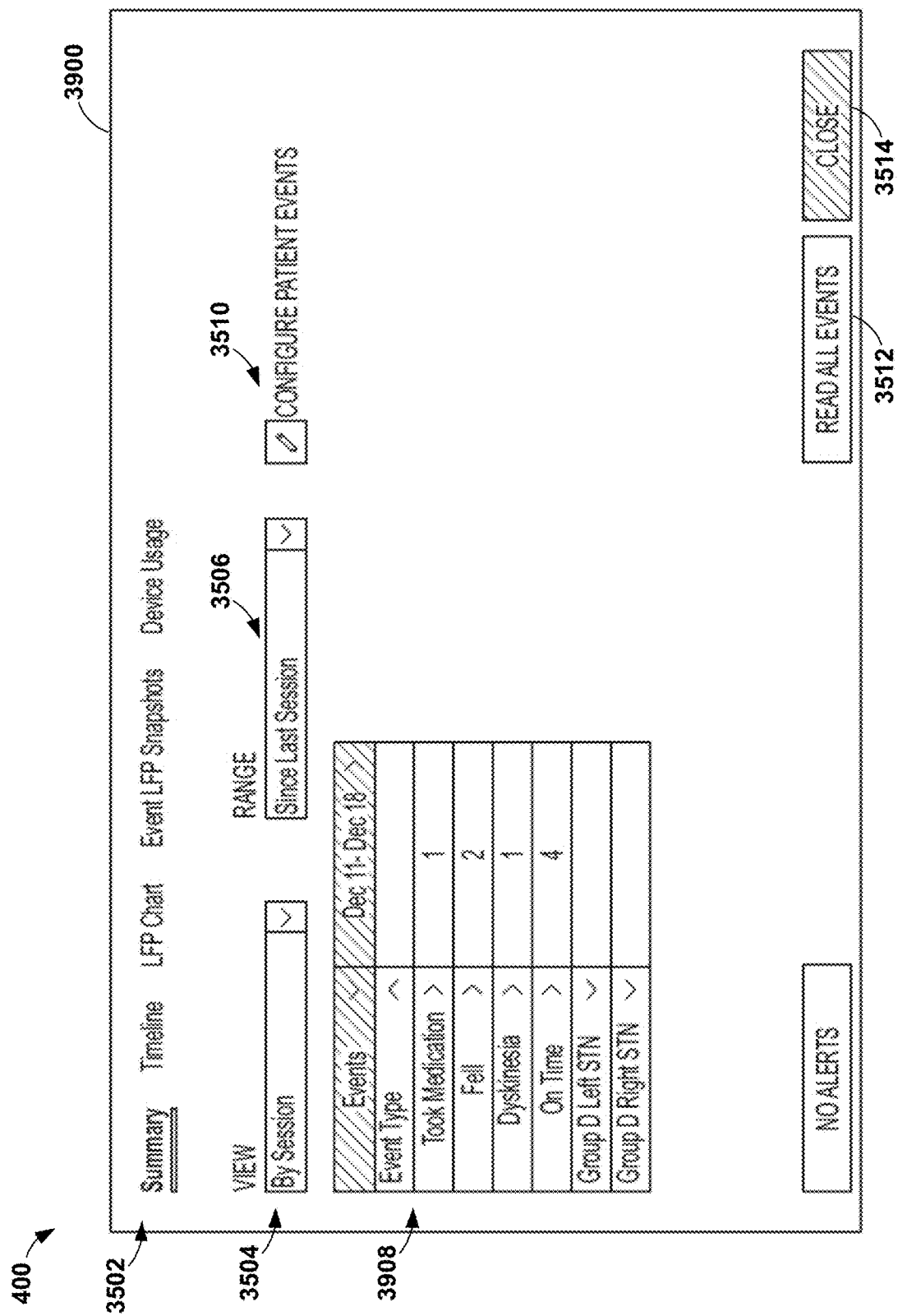

FIG. 36 illustrates screen 3600 which includes a drop down menu for view selector 3504 from which the user can select different periods of time for which the events can be parsed. FIG. 37 illustrates screen 3700 which includes a drop down menu for range selector 3506 from which the user can select which data to use in the chart. FIG. 38 includes an example screen 3800 in which the events are shown for each day in table 3808. FIG. 39 includes an example screen 3900 in which the events are shown since the last session with the clinician in table 3908.

Figure 40:
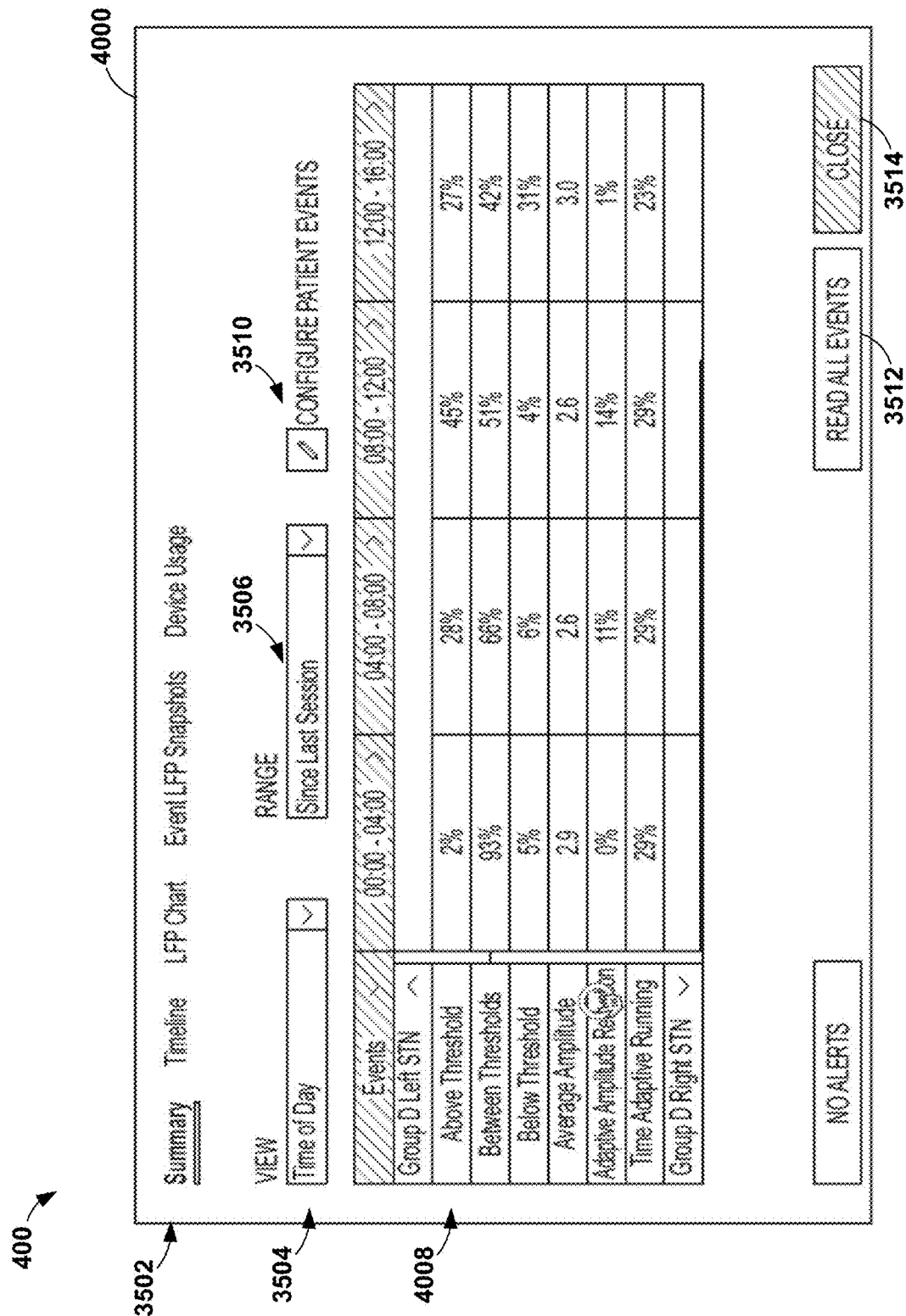

FIG. 40 illustrates an example screen 4000 that displays LFP classifications determined by processing circuitry 310 in chart 4008. Processing circuitry 310 may classify brain state over user selectable ranges and bins based upon measured thresholds. For example, the chart 4008 of FIG. 40 includes classification of amount of time the LFP amplitude was above the upper threshold, the amount of time the LFP amplitude was below the lower threshold, and the amount of time the LFP amplitude was between the upper and lower thresholds. This amount of time is shown in percentage of time, but could be displayed minutes, hours, or other absolute measurement of time. Using these indications, a clinician can view how effective stimulation has been in keeping the LFP amplitude between the upper and lower thresholds. This may be an objective measure of efficacy of adaptive DBS.

In addition, the chart 4008 of FIG. 40 illustrates the average amplitude of the stimulation parameter during stimulation and the adaptive amplitude reduction metric to show how adaptive therapy is impacting the amount of stimulation the patient is receiving. When adaptive therapy is running, processing circuitry 310 may calculate and display the average reduction in amplitude between the adaptive amplitude and the continuous stimulation default amplitude value. Higher percentages indicate that adaptive DBS is reducing the amount of stimulation that is delivered and thus reducing the power consumption of the battery of the IMD 106. The chart 4008 may also include the amount of time the adaptive DBS was running for the period of time indicated in the chart.

Figure 41:
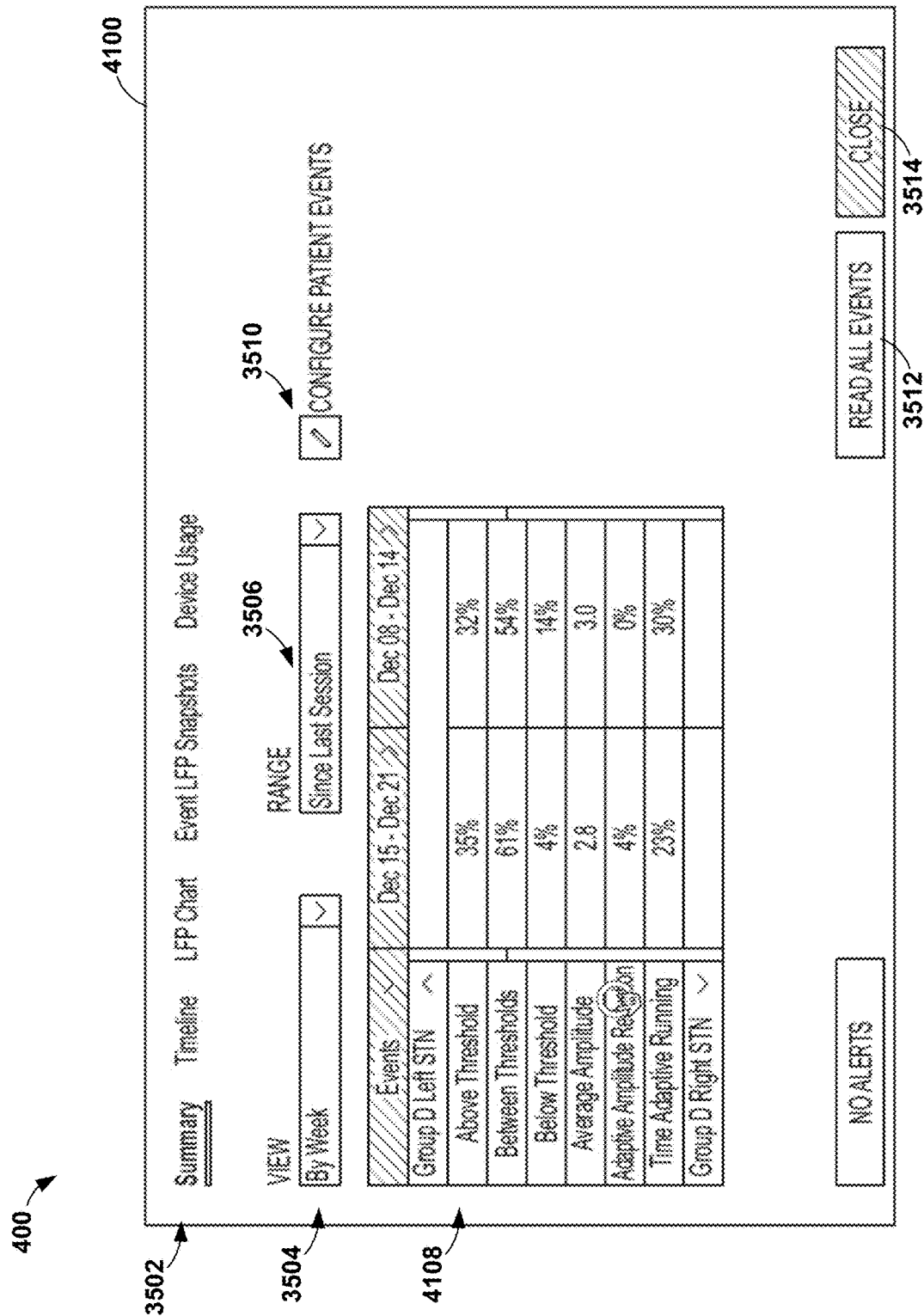

In some examples, the chart 4008 of FIG. 40 may flag incomplete or otherwise bad data or indicate trends in therapy or sensing over the different time periods. FIG. 41 shows a screen 4100 that includes two different weeks and corresponding LFP classifications in example chart 4108.

Figure 42:
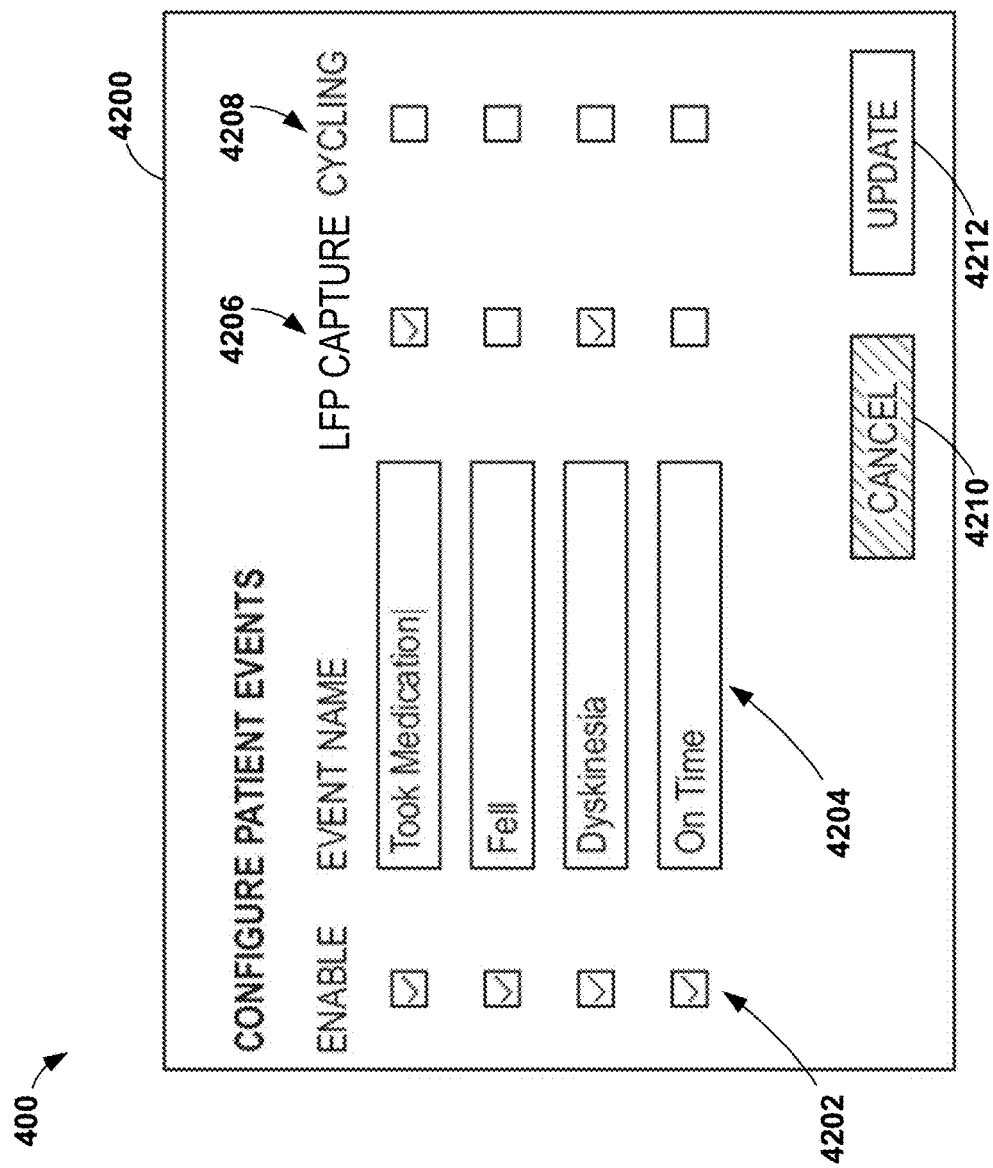

FIG. 42 presents a screen 4200 in which the user can specify which patient events can be indicated by the patient and whether or not LFP data should be captured in response to the user indicating that the patient event occurred. Screen 4200 may be entered by selecting configure event selector 3510 from screen 4100, for example. The user can select the appropriate one of boxes 4202 to select which one or more of events 4202 to include in the displayed data. For each of the events, LFP capture 4206 indicates whether LFPs were captured for that event or whether stimulation cycling 4208 was used for that event. Selection of cancel button 4210 will not save any changes to the patient events, but selection of update button 4212 will cause programmer 104 to change how patient events are shows as selected. In some examples, the language of patient programmer user interface can be different than the physician programmer language. A medical translator could enter events, group names, or other information in the language of the patient for the patient programmer, while the clinician programmer can maintain the language used by the clinician.

User interface 400 can present information related to patient events in numerous different ways. As described herein, once a sensing electrical combination has been configured and used for sensing, the system allows a patient or other user to mark an event contemporaneously or after its occurrence. Programmer 104 may control IMD 106 to capture a signature of the sensed brain signal after that event (and prior to the event by using a sensing buffer that temporarily stores brain signals). Programmer 104 may control user interface 400 to presenting one event with other similar or different events. In this manner, user interface 400 can help a user understand real world response of brain states to medications, stimulation, and other daily activities to inform future therapy management which can include available stimulation parameter values and/or improvements to closed-loop control of stimulation. Example screens of user interface 400 that can provide this information are included in FIGS. 42-47.

User interface 400 can provide various structure and functionality for presenting patient events. For example, user interface 400 can accept input naming different event types, selection of one or more actions (e.g., recording data and/or stimulation adjustments) that should occur in response to detection of a particular patient event or event type, request for a comparison view of multiple events or event types, input requesting analysis of the data such as the frequency of events, number of events, or severity of events, or any other type of input. In addition, user interface 400 may enable a user to filter (e.g., add or remove) events, event types, time periods, or other information to customize the view of stored information.

In some examples, programmer 104 may perform statistical analyses on various data within or between events. For example, programmer 104 may determine an average peak frequency for different events or type of events, average peak magnitudes for different events or types of events, correlations of events to different LFP data, etc. Programmer 104 may also cluster events together based on the similarity of one or more characteristics of the sensed brain signal sensed during the events. For example, programmer 104 may cluster events together that have a peak at a similar frequency in the beta band and that these events occur at a similar time of day (e.g., in the morning on weekdays) or have other similarities such as similar accelerometer data. Programmer 104 may then control user interface 400 to present these statistical conclusions, clustered events, etc.

FIGS. 43-47 are conceptual diagrams illustrating example screens for displaying brain signal graphs for respective patient events. The brain signal information (e.g., spectral information for a brain signal) can be obtained by IMD 106 in response to the user providing input indicating that a patient event occurred. IMD 106 may capture Beta and/or Gamma band data for each event. The clinician can determine which bands or frequencies are good biomarkers for that type of event that happened based on the captured brain signal information for that event. This functionality may also be beneficial for the patient since medication takes a long time to wear off and may not occur during a clinic visit.

In response to the user pressing a button on the patient programmer or clinician programmer, the programmer may control IMD 106 to capture LFP information for a period of time (e.g., 25 seconds). This LFP information may be sensed after the event has been indicated. However, in other examples, IMD 106 may maintain a rolling buffer and capture LFP information before, during, and after the event was indicated to occur. In other examples when LFP data is stored for long periods of time, the user may be able to go back and mark an event that occurred hours or days before, and the system may capture the LFP information recorded at the time of the indicated event. The LFP information captured may include time domain information and/or an FFT transform of recorded LFP data. In some examples, processing circuitry 310 may select a certain number of power values across the frequency domain, such as 100 power values. However, more or less data may be stored for each sample of LFP information in other examples. The LFP data may be stored on the patient programmer or IMD 106. In other examples, the LFP information may be transmitted to the cloud or other device for storage. In some examples, the LFP information may be directly transmitted to a clinician.

Figure 43:
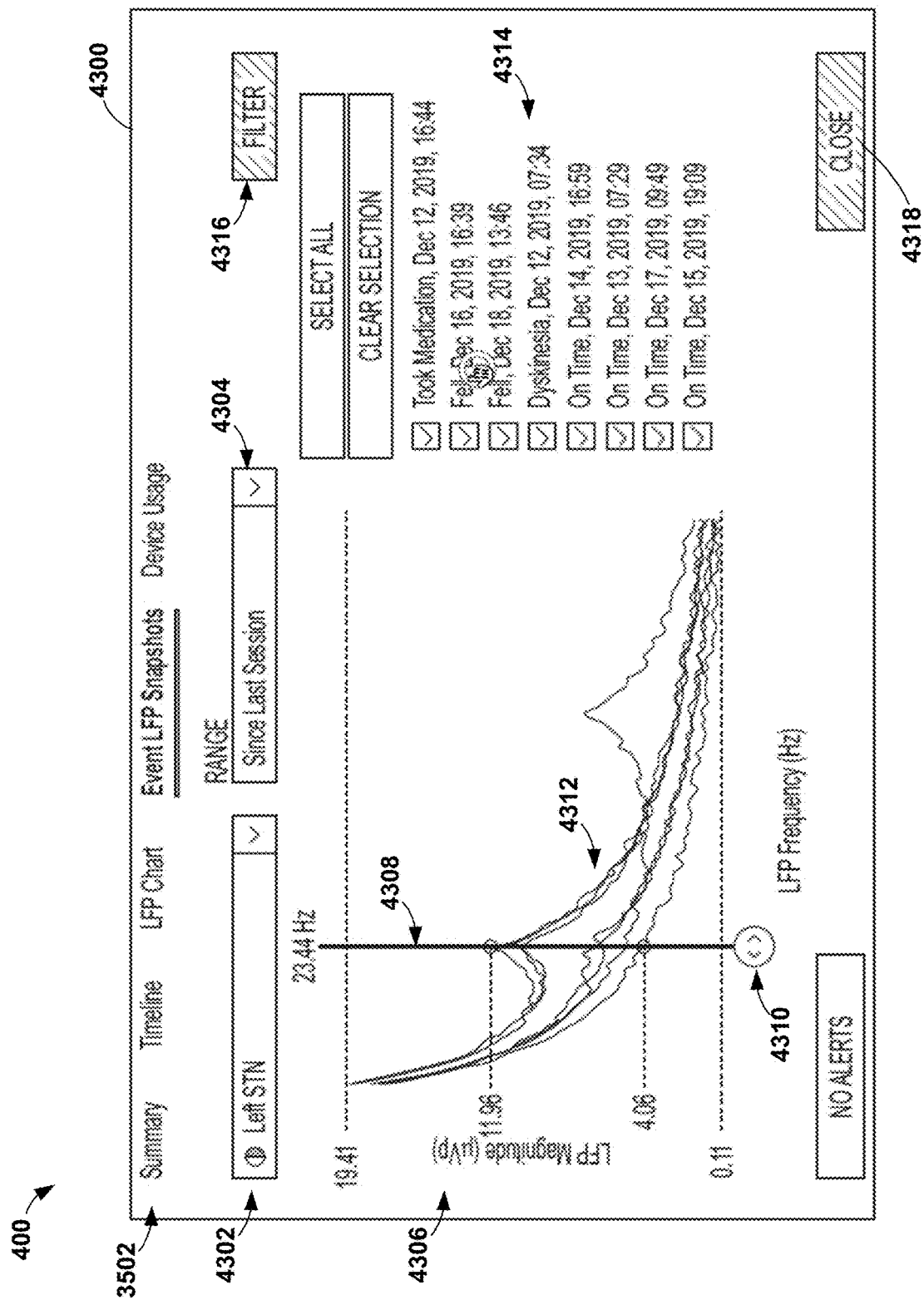
FIGS. 43-47 are conceptual diagrams illustrating example screens for displaying brain signal graphs for respective patient events.

FIG. 43 illustrates a screen 4300 showing patient events and corresponding LFP information displayed on a graph 4306 of LFP power vs. frequency. Traces 4312 are the LFP powers for each event shown in event list 4314. Hemisphere selector 4302 can be selected to switch between signals sensed from different leads, and range selector 4304 can be selected to switch between different dates for sensed data. Although four event types are shown as selectable in this example (from FIG. 42), fewer or greater types of events may be indicated by the user in other examples. The screen 4300 of FIG. 43 provides a slider 4310 that the user can move to adjust frequency bar 4308 and identify the frequency and/or power of any part of each trace. On the right of the screen 4300, the event list 4314 of each event is provided. In response to the user deselecting an event (e.g., by unchecking the respective check box), user interface 400 will remove that specific trace for that event from the graph 4306. In this manner, the user can choose to evaluate any events and compare any events. In other examples, other types of information could be captured for each event, such as medication status, accelerometer data, stimulation delivery status, etc. Each of these types of information may be presented on the same graph or different graphs for each type of information. Selection of close button 4318 will close screen 4300.

Figure 44:
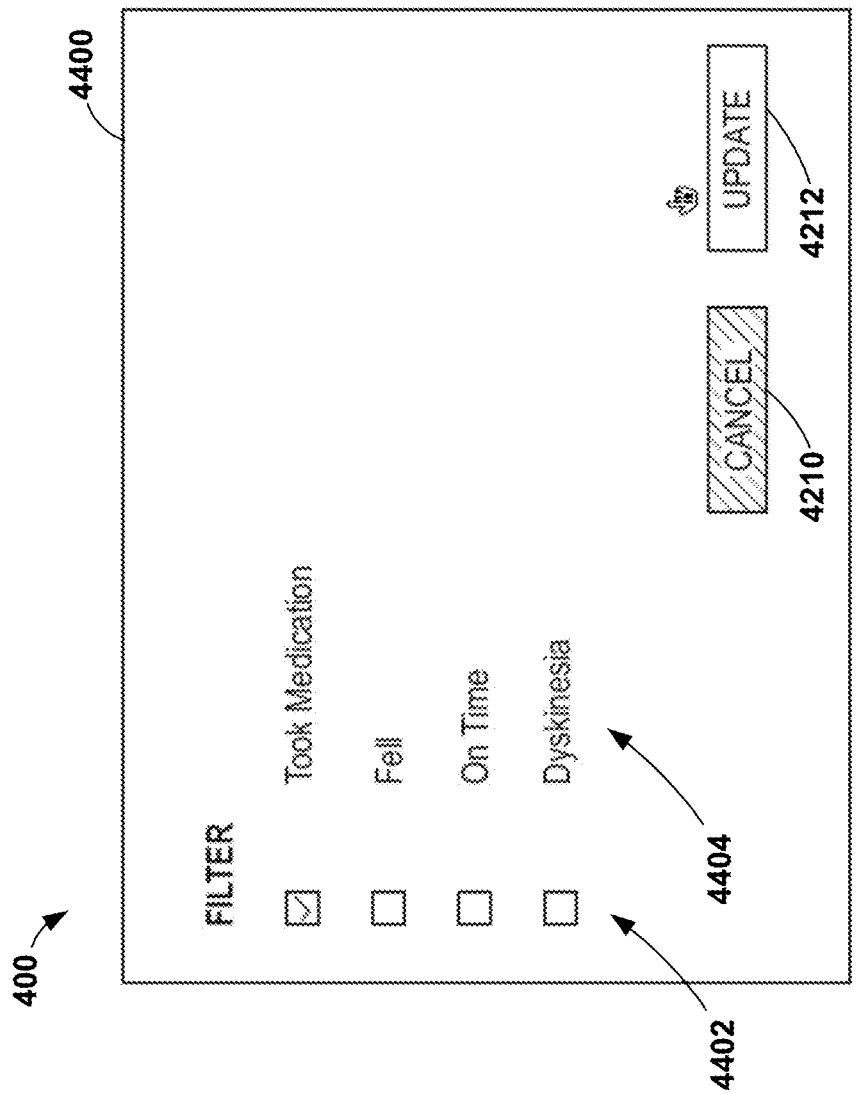
Figure 45:
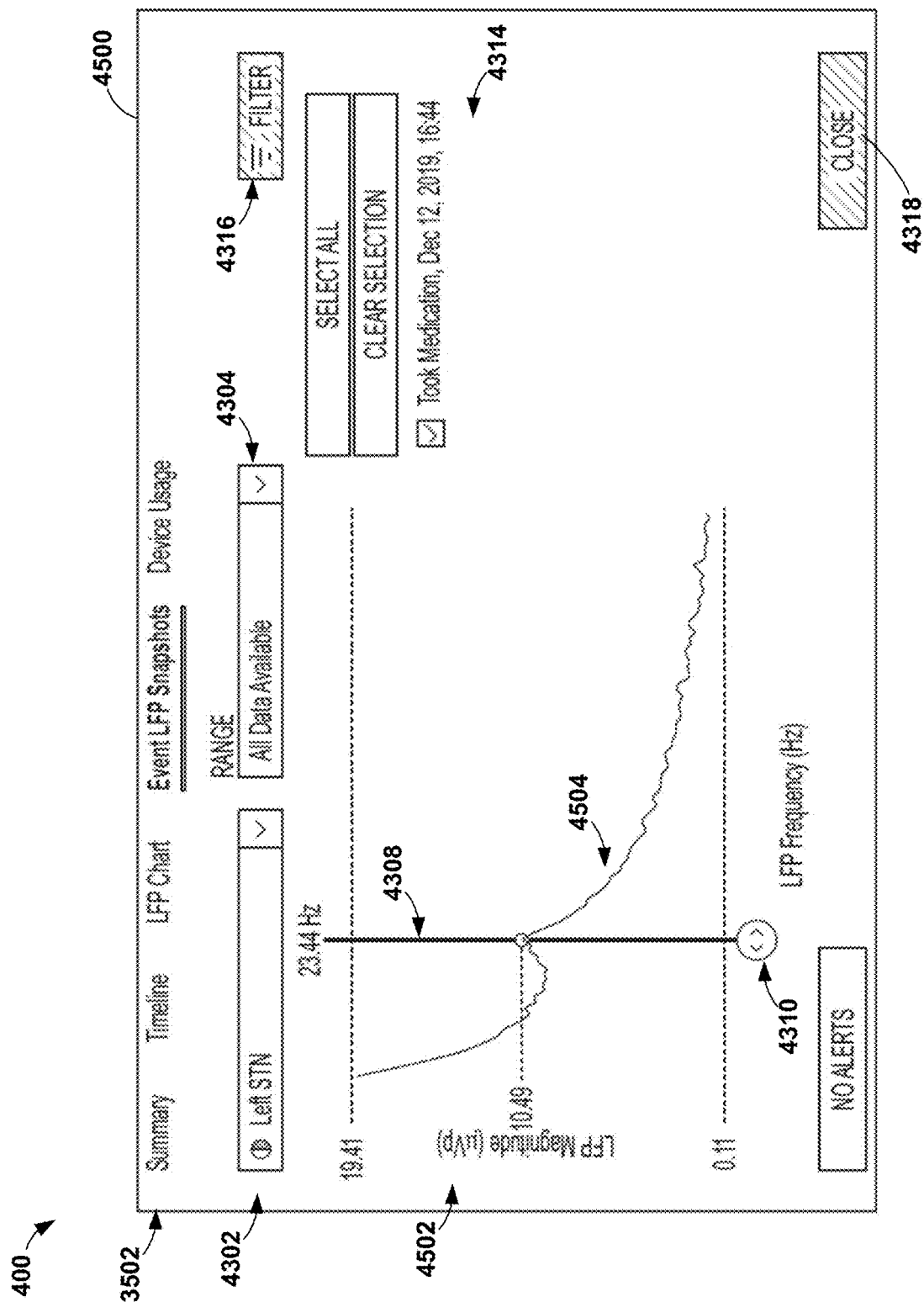
Figure 46:
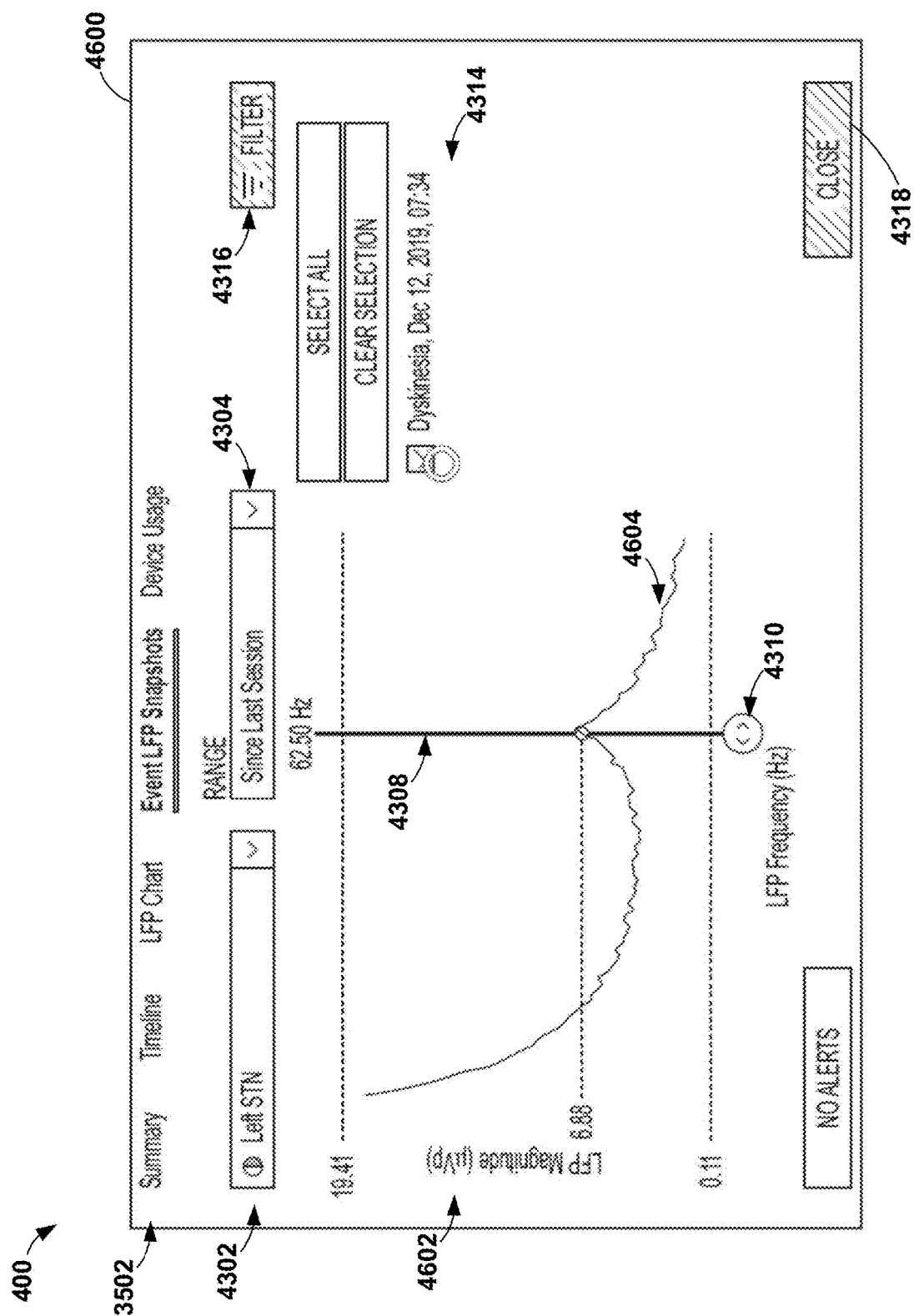
Figure 47:
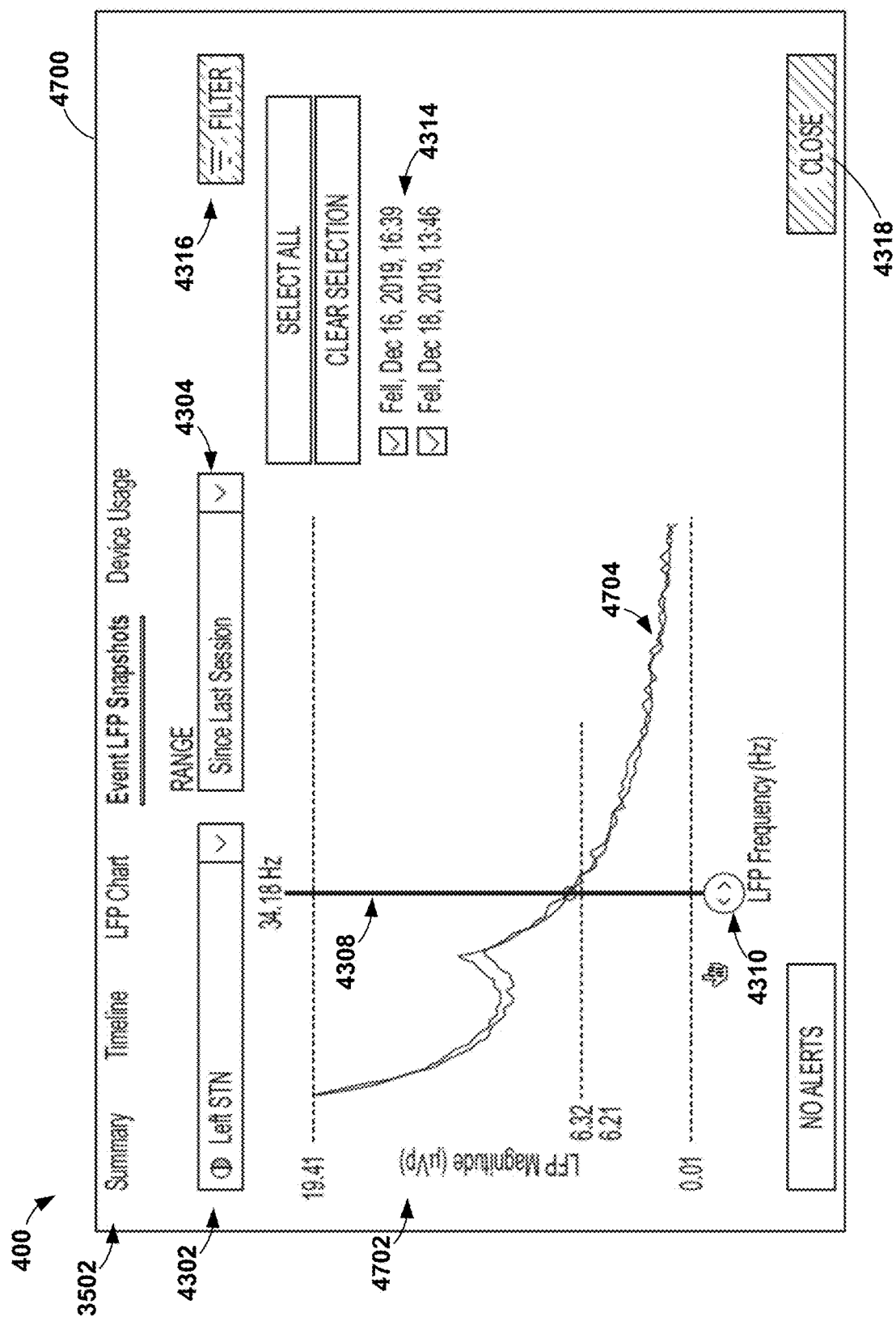

FIG. 44 shows a pop up window 4400 that is shown in response to selection of filter button 4316 in screen 4300. In pop up window 4400, the user can select the type of event to show on the screen. The types of event 4404 are shown and can be selected or unselected via the respective check box 4402. Selection of cancel button 4210 will cancel the changes and selection of update button 4212 will change the event types shown in the next screen. FIG. 45 includes screen 4500 which indicates a took medication event and corresponding LFP trace 4504 in graph 4502 selected by the user from the window 4400 of FIG. 44. FIG. 46 illustrates an example screen 4600 in which a dyskinesia event was identified and the corresponding trace 4604 is shown in graph 4602. In some examples, programmer 104 may automatically place frequency bar 4308 at the peak in frequency, but the user can always move slider 4310 to the peak on trace 4604. FIG. 47 illustrates an example screen 4700 in which fall events (e.g., all events within the fall event type) were identified and the corresponding LFP data are shown as traces 4704 in graph 4702.

Figure 48:
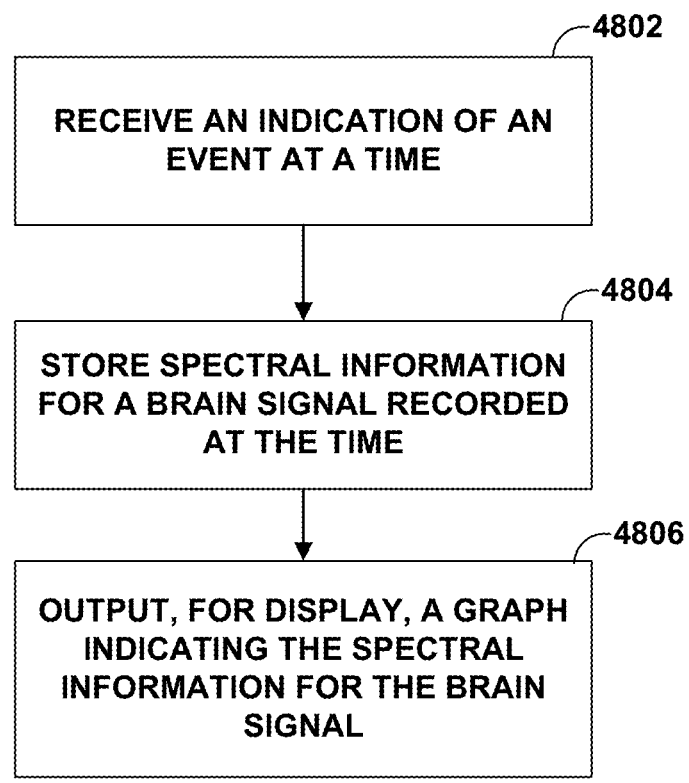
FIG. 48 is a flowchart illustrating an example technique for generating and displaying brain signal graphs for respective patient events.

FIG. 48 is a flowchart illustrating an example technique for generating and displaying brain signal graphs for respective patient events, such as the screens of FIGS. 42-47. In the example of FIG. 48, processing circuitry 310 receives an indication of an event at a time (4802) and, responsive to receiving the indication of the event, stores spectral information for a brain signal recorded at the time (4804). In some examples, the stored spectral information may have been obtained only after receiving the indication of the event. In other examples, processing circuitry 310 may retrieve spectral information obtained prior to the event from a buffer in memory. Processing circuitry 310 then outputs, for display by a user interface, a graph indicating the spectral information for the brain signal recorded at the time (4806). Processing circuitry 310 can then control user interface 400 to adjust the displayed events and corresponding traces or other information in response to user requests.

Figure 49:
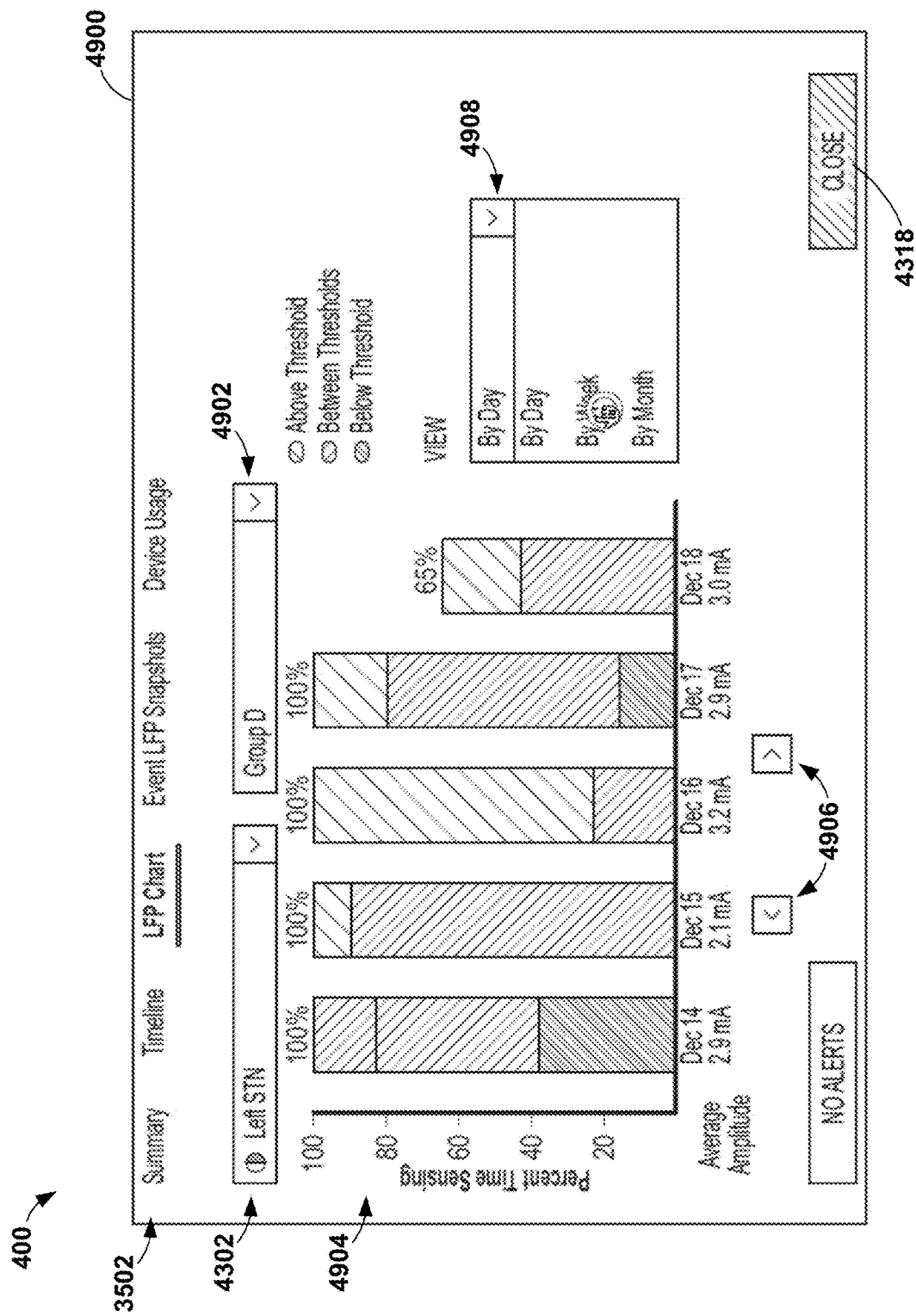
FIG. 49 is a conceptual diagram illustrating an example screen for displaying amounts of time a brain signal characteristic is within a respective range of brain signal values.

FIG. 49 is a conceptual diagram illustrating an example screen 4900 for displaying amounts of time a brain signal characteristic is within a respective range of brain signal values. As shown in FIG. 49, screen 4900 shows bar graphs 4904 of the amount of time the brain signal (e.g., LFP power) is above an upper threshold, below a lower threshold, and between the upper and lower thresholds. This information can be viewed for different periods of time, such as by day, week, or month. Selection of the period of time can be made via time selection 4908, which may be a drop down menu. Data selector 4902 can enable a user to select the type of data, such as type of stimulation delivered or group of data that was stored. Arrows 4906 can be selected to move to different days or to view data for other time periods that do not fit within the graph.

FIGS. 50-55 are conceptual diagrams illustrating example screens for displaying a graph of brain signal characteristics and stimulation parameter values from DBS therapy over time. This information may be stored over time and similar to an electronic motor diary. Stored information may include brain signal information (e.g., LFP power), stimulation parameter values, patient events, and/or system events. This type of information may allow a clinician to review stored brain signal information over time that was collected outside of the clinical setting.

Once a sensing electrode combination has been configured, the system can record the sensed signal continuously (e.g., in memory of IMD 106 and or until offloaded to programmer 104 or another device). Programmer 104 than controls user interface 400 to display the data for review at a clinical or follow up visit, for example. The goal of presenting this data may be to help a user understand real world response of brain state to medications, stimulation, and other daily activities to inform future therapy management. In some examples, the display may show trends of the stored LFP signal, trends of the stimulation parameter values (such as amplitude), any events sensed or marked by the patient during that time, one or more stimulation parameter values used to deliver stimulation during this time, one or more hemispheres (e.g., one or two leads), LFP thresholds, stimulation limits, or any other information related to stored data.

In some examples, user interface 400 may enable the user to reduce or increase the time period of displayed data (e.g., change from showing minutes, hours, days, weeks, or months). In some examples, programmer 104 may control user interface 400 may identify days with similar events or stored data, cluster days or other time periods together, or determine statistical measures. Example statistical measures may include an average day, an average night, trends observed before and/or after an event, observed trends before and/or after a stimulation parameter value change, or comparisons between different stimulation programs.

Figure 50:
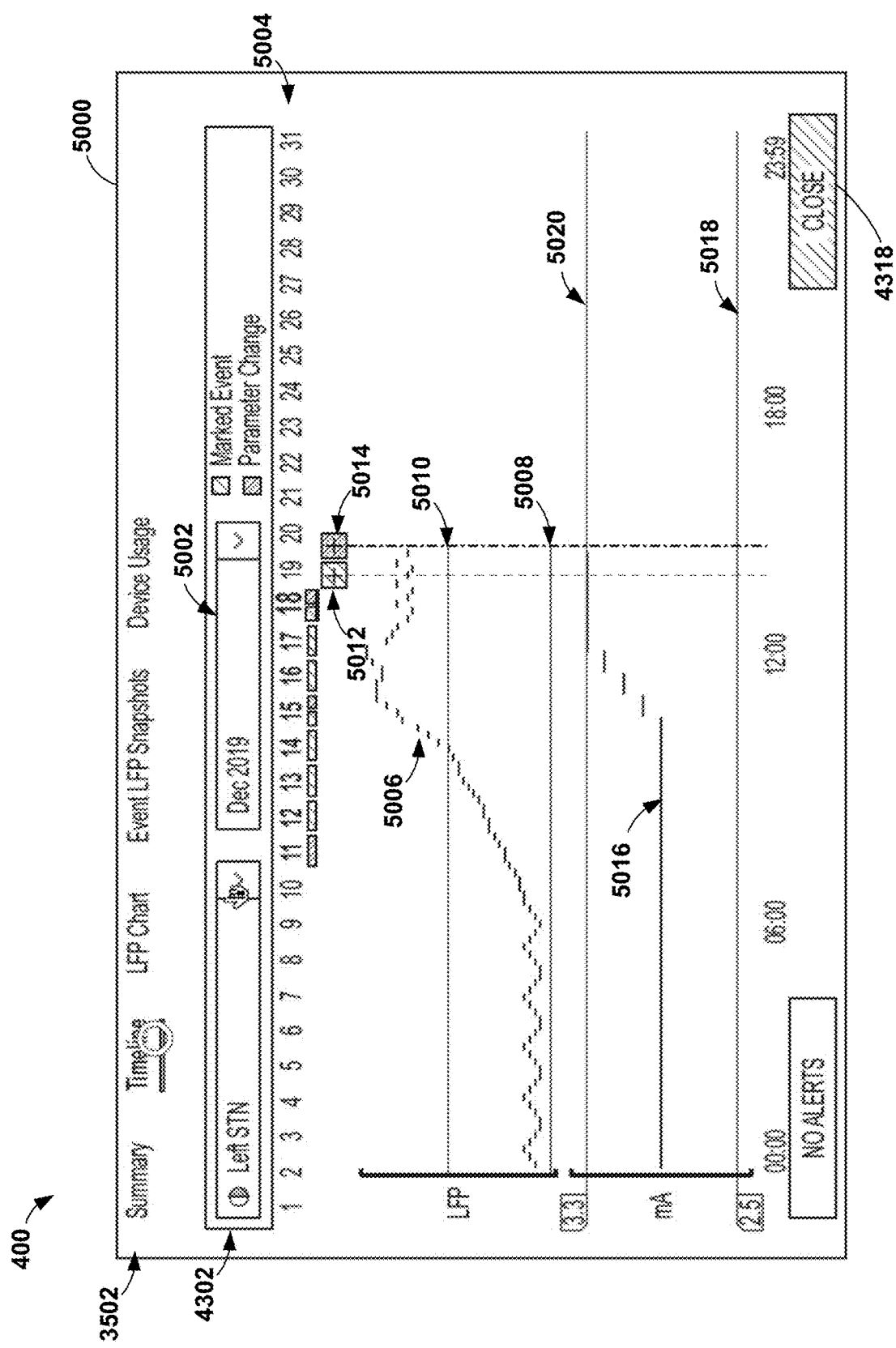
FIGS. 50-55 are conceptual diagrams illustrating example screens for displaying a graph of brain signal characteristics and stimulation parameter values from DBS therapy over time.

In the example screen 5000 of FIG. 50, LFP power over time is shown as a trace 5006 of a graph in conjunction with a trace 5016 of current amplitude over the same time for one lead in one hemisphere of the patient. Although the upper limit 5020 and lower limit 5018 of the stimulation parameter are shown in the graph, the limits or thresholds may not be presented in other examples. Upper and/or lower thresholds for LFP data may also be shown. Screen 5000 in FIG. 50 also indicates patient event 5012 (e.g., a patient marked event) and system event 5014 (e.g., a parameter value change) that were identified and displays them at the time at which they were identified. The patient event 5012 and system event 5014 may be identified using different colors. User selection of patient event 5012 or system event 5014 may open a window that includes additional information related to that event, such as more specific LFP data or what parameter value changes were made. Using this timeline, the clinician can view historical brain signal information, stimulation information, and event information on the same graph. The timeline 5004 above the graph indicates days of the month. Therefore, the graph of FIG. 50 can present data for an entire month in one screen. In other examples, the timeline may be shrunk to weeks or days or expanded to multiple months or years. Time selector 5002 may be selected to choose a different period of time to show data. Each LFP and stimulation data point may be sampled at a certain rate, such as six times per hour. However, higher or lower sample rates may be used depending on data storage capabilities and types of graph to be presented.

Figure 51:
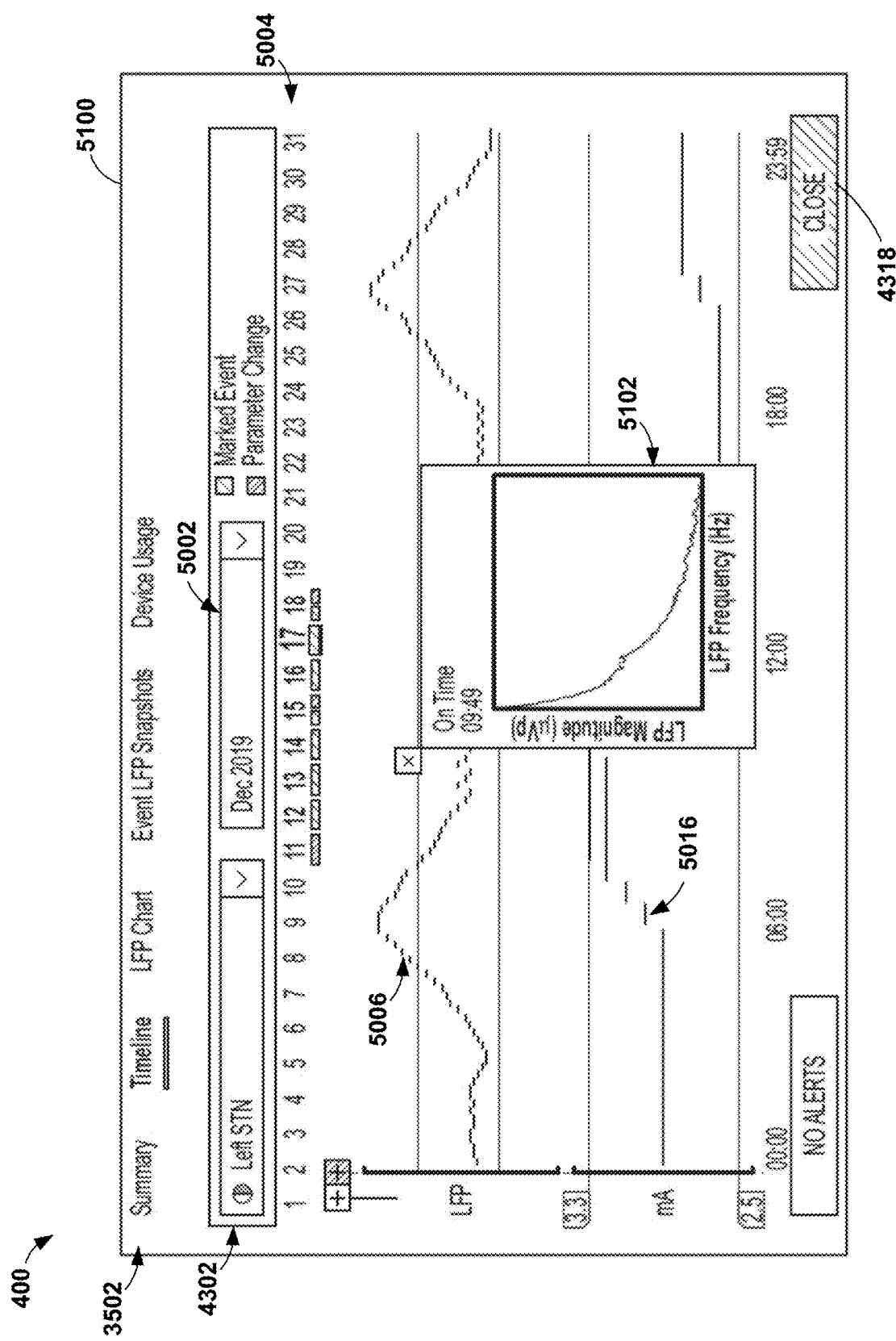

FIG. 51 includes screen 5100 that indicates that selecting of the patient event causes processing circuitry 310 to present a snapshot 5102 of the LFP spectral information stored at the same time of the patient event. A clinician can then identify if anything unusual occurred during that event or identify a certain frequency of the brain signal that may be useful for preventing, or encouraging, that patient event in the future. The "on time" flag for this patient event indicates the patient felt good at this time.

Figure 52:
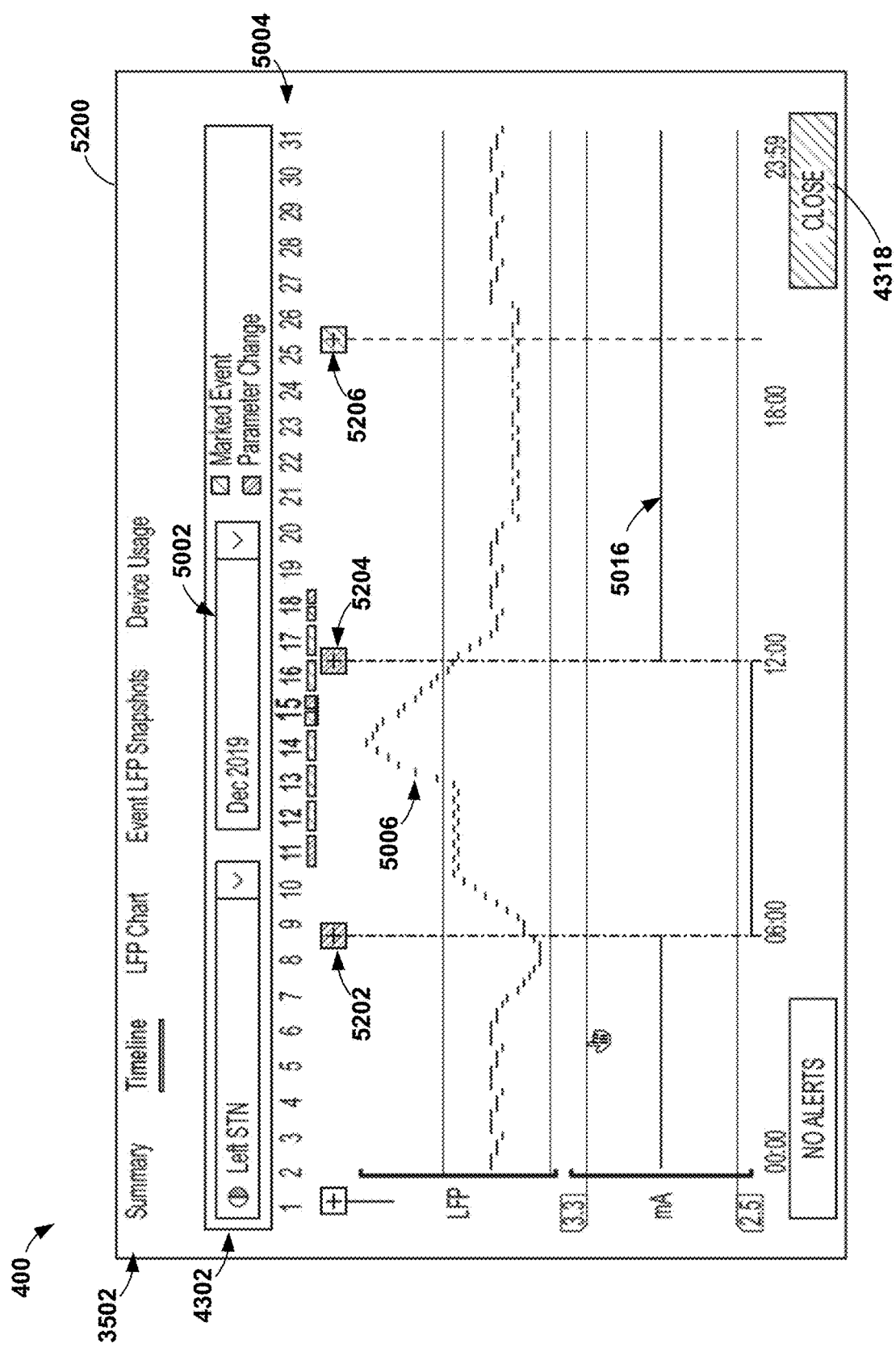
Figure 53:
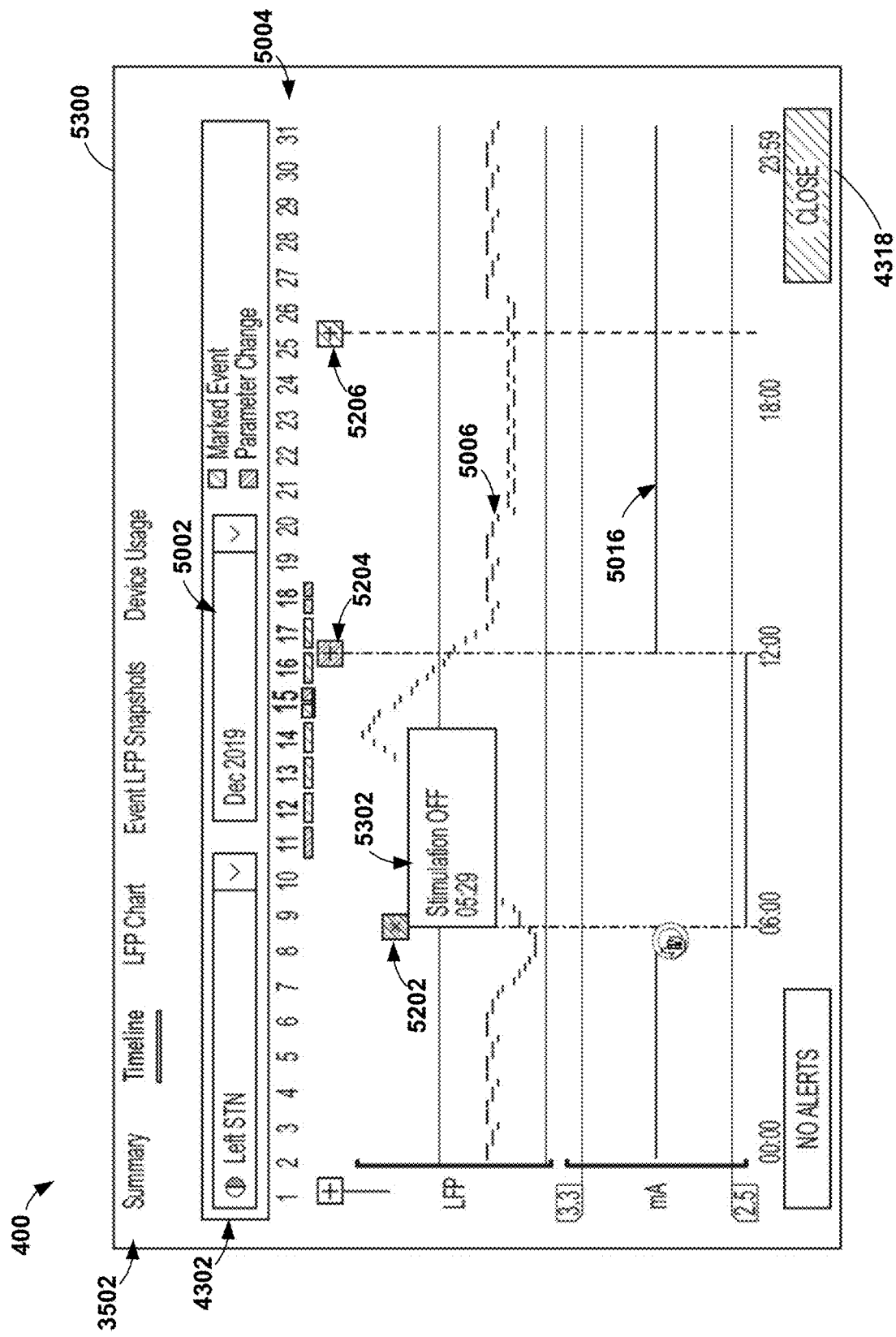
Figure 54:
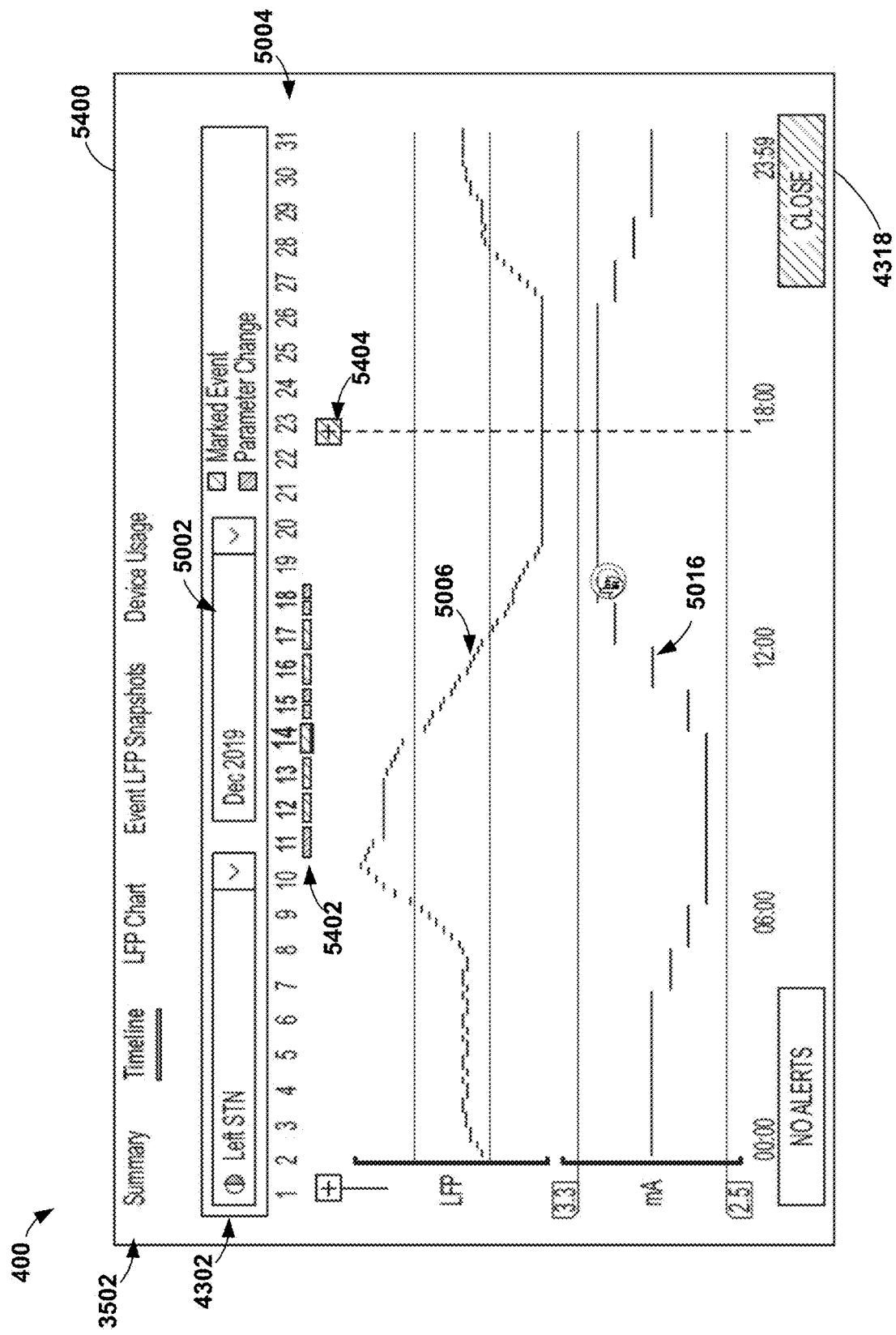
Figure 55:
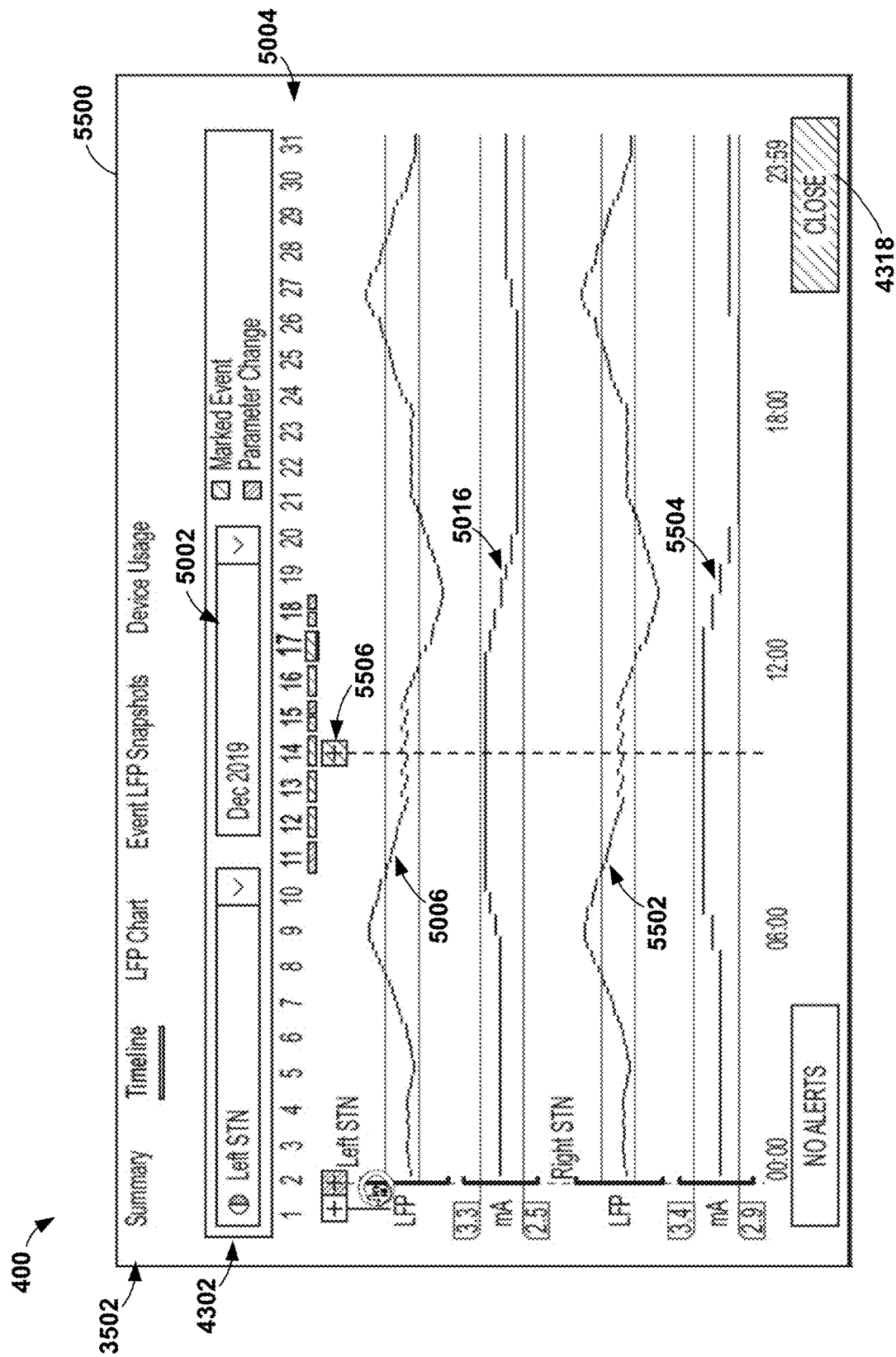

FIG. 52 illustrates a screen 5200 in which system events, which include changes to stimulation parameters, are marked in the data. The system events 5202 and 5204 show stopping and starting stimulation. As can be seen in FIG. 52, stimulation was turned on in response to detecting that the LFP power exceeded the upper threshold. Patient event 5206 is also shown in the graph. As shown in screen 5300 of FIG. 53, the user can click on either of the system events 5202 or 5204 to expand the event to show what event occurred. As shown in the window 5302, the system event was that stimulation was turned off at that particular time of day listed. FIG. 54 illustrates a screen 5400 in which a patient event 5404 was marked when the LFP power was below the lower threshold, likely due to side effects from stimulation. Marker identifiers 5402 indicate which days of the month had events recorded, and which type of events (patient events or system events) were recorded via color coding. FIG. 55 illustrates a screen 5500 in which LFP power and stimulation parameter values for both hemispheres of the brain are shown together. The stimulation parameter could be the same or different for each hemisphere. Although brain signals typically move together, diverging signals from separate hemispheres may indicate another issue for the patient. Patient event 5506 is shown in conjunction with.

As shown in FIG. 55, the graph can present a full day worth of objective LFP information and correlated stimulation parameter data on the same screen. In addition, the same screen may show stimulation changes and patient-reported events such as feeling well, feeling side effects, taking medication, etc. in some examples, all data is stored on the programmer, so no network connection is required to present this information. However, in other examples, the programmer may send data to, for viewing on, a digital health platform for the clinician. In some examples, the screens of FIGS. 50-55 may enable a user to filter events by type of event, LFP power ranges, stimulation events, threshold crossings, etc.

Figure 56:
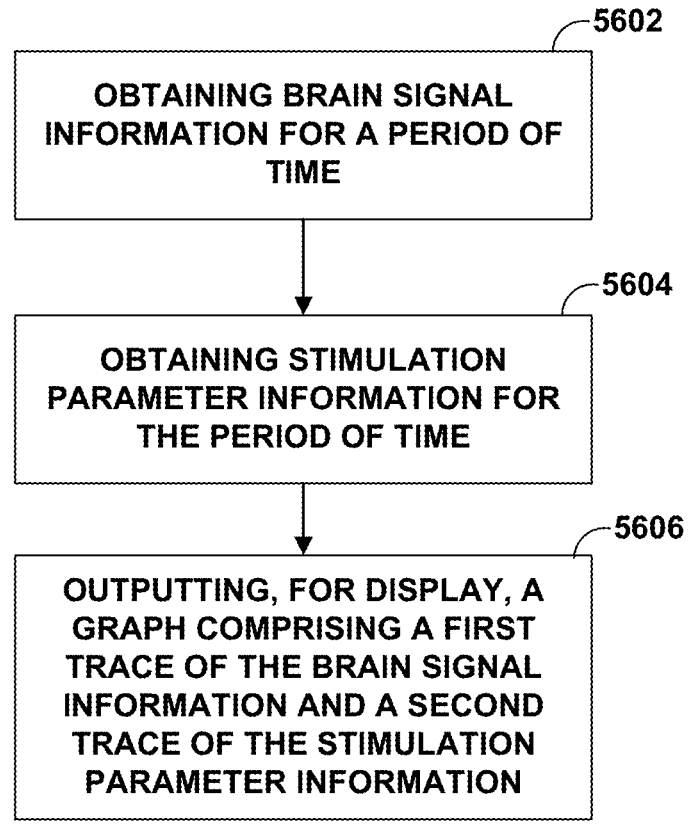
FIG. 56 is a flowchart illustrating an example technique for generating and displaying a graph of brain signal characteristics and stimulation parameter values from DBS therapy over time.

FIG. 56 is a flowchart illustrating an example technique for generating and displaying a graph of brain signal characteristics and stimulation parameter values from DBS therapy over time. The process of FIG. 56 may correspond to the user interface 400 described with respect to and of FIGS. 50-55. FIG. 56 is a flowchart illustrating an example technique for displaying sensed brain signals with one or more stimulation parameters defining delivered DBS therapy from historical data. As shown in FIG. 56, processing circuitry 310 may obtain a brain signal representative of electrical activity of a brain of a patient for a period of time (5602). Processing circuitry 310 then obtains stimulation parameter information that at least partially defines electrical stimulation deliverable to a portion of the brain of the patient during the period of time (5604). Processing circuitry 310 then outputs, for display by user interface 400, a graph comprising a first trace of the brain signal for a period of time and a second trace of the one or more values of the stimulation parameter information for the period of time (5606).

Figure 57:
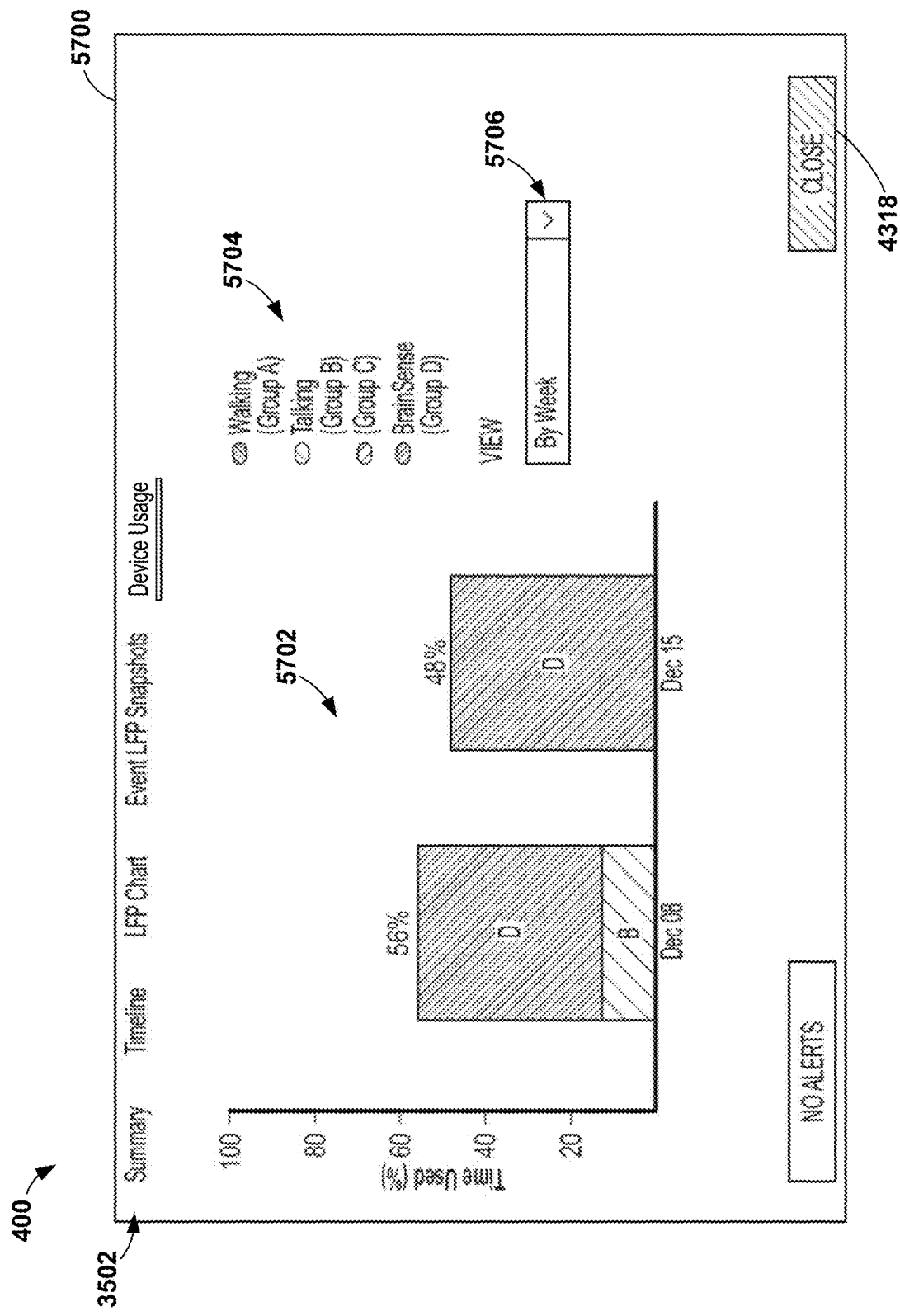
FIG. 57 is a conceptual diagram illustrating an example screen for displaying an amount of time different types of DBS therapy were delivered for respective dates.

FIG. 57 is a conceptual diagram illustrating an example screen 5700 for displaying an amount of time different types of DBS therapy were delivered for respective dates. As shown in FIG. 57, user interface 400 may display device usage for each type of stimulation program in bar graph 5702, such as adaptive stimulation or talking. This information can be viewed by different periods of time, such as day, week, or month, which can be selected via time selector 5706. Key 5704 indicates the types of therapy that was used as shown in bar graph 5702.

Figure 58:
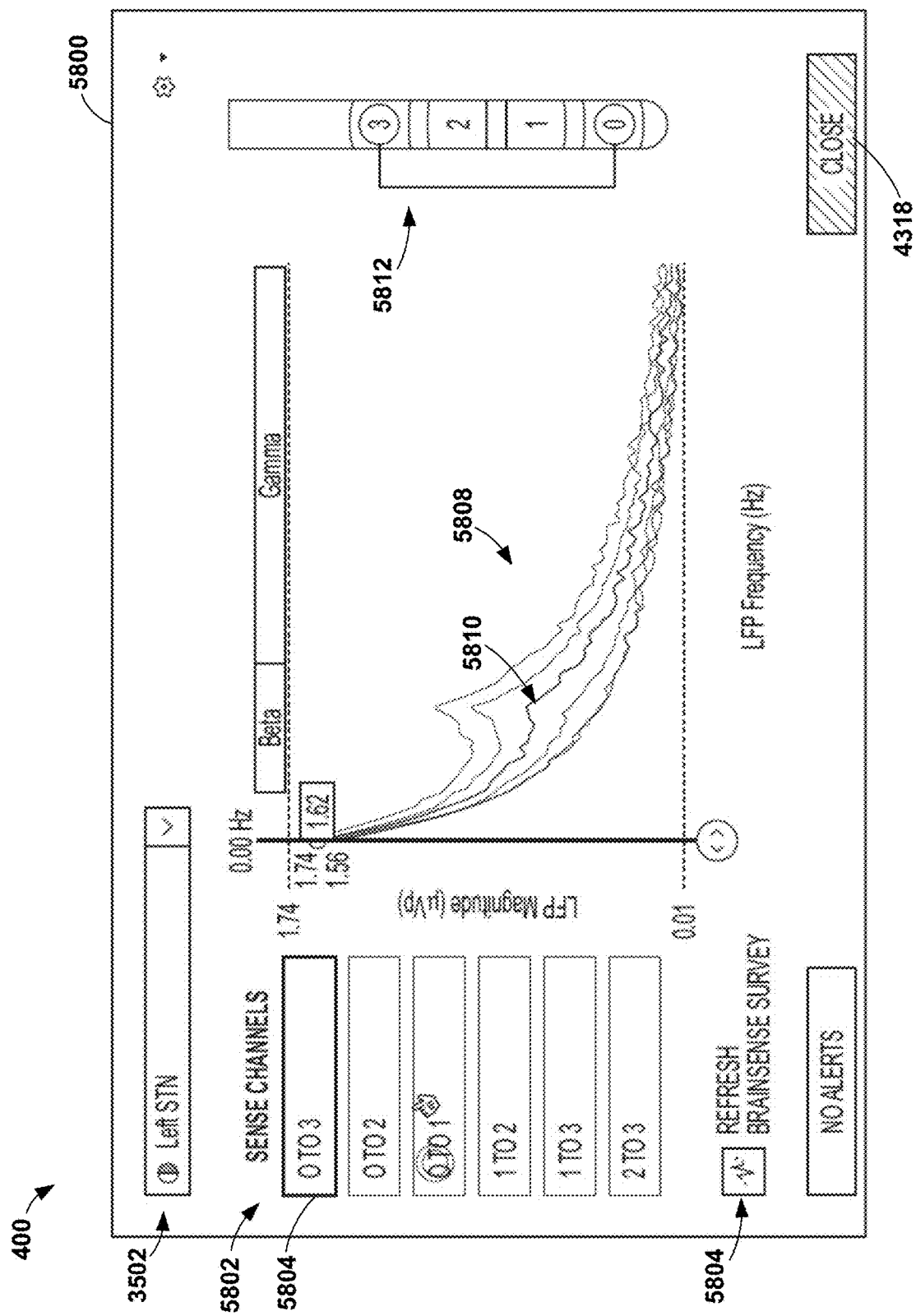
FIGS. 58 and 59 are conceptual diagrams illustrating example screens for displaying graphs of brain signal power for respective electrode combinations of a lead.
Figure 59:
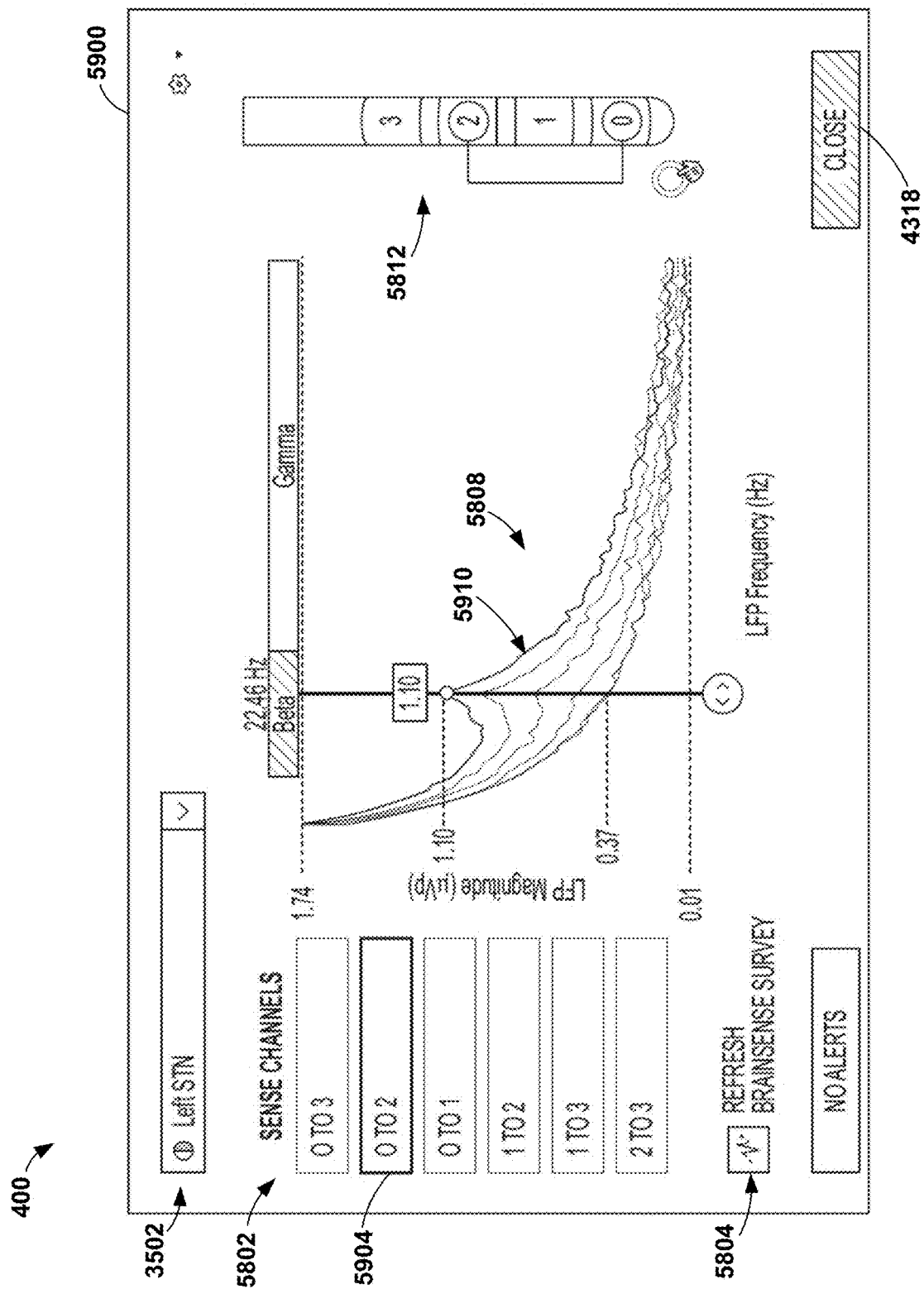

FIGS. 58 and 59 are conceptual diagrams illustrating example screens 5800 and 5900 for displaying graphs of brain signal power for respective electrode combinations of a lead. The graph of screen 5800 of FIG. 58 may include LFP information 5808 (e.g., traces) recorded for each electrode combination (channel) available. Typically, the best electrode combinations are those with peaks present at a certain frequency as shown in the LFP power vs. frequency graph. This screen 5800 enables the user to select different sense channels 5802 to highlight the corresponding trace for that channel within the group of all traces for all channels. In screen 5800, the user has selected sense channel 5804, and lead 5812 shows the electrodes of the lead used for this particular sense channel. LFP information 5808 shows all of the traces for the sense channels 5802. Trace 5810 may be highlighted (e.g., using a thicker line, dotted line, different color, etc.) and indicates the LFP data saved for selected sense channel 5804. The user can select refresh brainsense survey 5804 to cause programmer 104 to initiate new sensing of LFP information for all of sense channels 5802. FIG. 59 includes screen 5900 which illustrates that the user has selected sense channel 5904 (e.g., electrodes "0 to 2") which corresponds to the trace 5910 with the highest peak in the Beta frequency band for all of LFP information 5808. Lead 5812 provides a visual indication of the electrodes used for sense channel 5904.

As discussed herein, programmer 104 may initiate an automatic scan of brain signals from all or most sense channels available to enable programmer 104 or a user to identify where signals might be located (which hemisphere, which region of a lead, which specific combinations of contacts) for the purpose of understanding such signals, the integrity or quality of the recording system, and then guiding sensing configuration and/or stimulation parameters values. Screen 5800 of FIG. 58 shows a specific list of contacts to be scanned, and programmer 104 may use the finite sensing resources of IMD 106 to capture all signals "close" to synchronously so that they can be compared directly on relative scales. Once the LFP data are captured during scanning, programmer 104 ma calculate a power spectrum for each sensing channel and control user interface 400 to creates an interactive display of this LFP data.

In this manner, user interface 400 can provide a view of all signals in a hemisphere simultaneously and enable selection of one signal to be compared to the others. Programmer 104 may measure aspects of the signal (e.g., difference between maximum and/or minimum at a specific frequency of interest). Programmer 104 may enable IMD 106 to continuously record a subset of signals. In some examples, programmer 104 may perform statistical comparisons (e.g., an energy in a region of frequencies compared to the energy at a specific peak, the relative amplitude above 1/frequency of the curve, the width of the peak, or simultaneous comparison or measurement of two or more peaks. In some examples, user interface 400 may provide additional views for leads having electrodes at different locations around a perimeter of a lead (e.g., directional leads). User interface 400 may also provide visualization of anatomic structures or other reference in combination with a signal location (e.g., whether or not a signal is in or out of target, or if a signal is medial or lateral from an anatomical structure).

Figure 60:
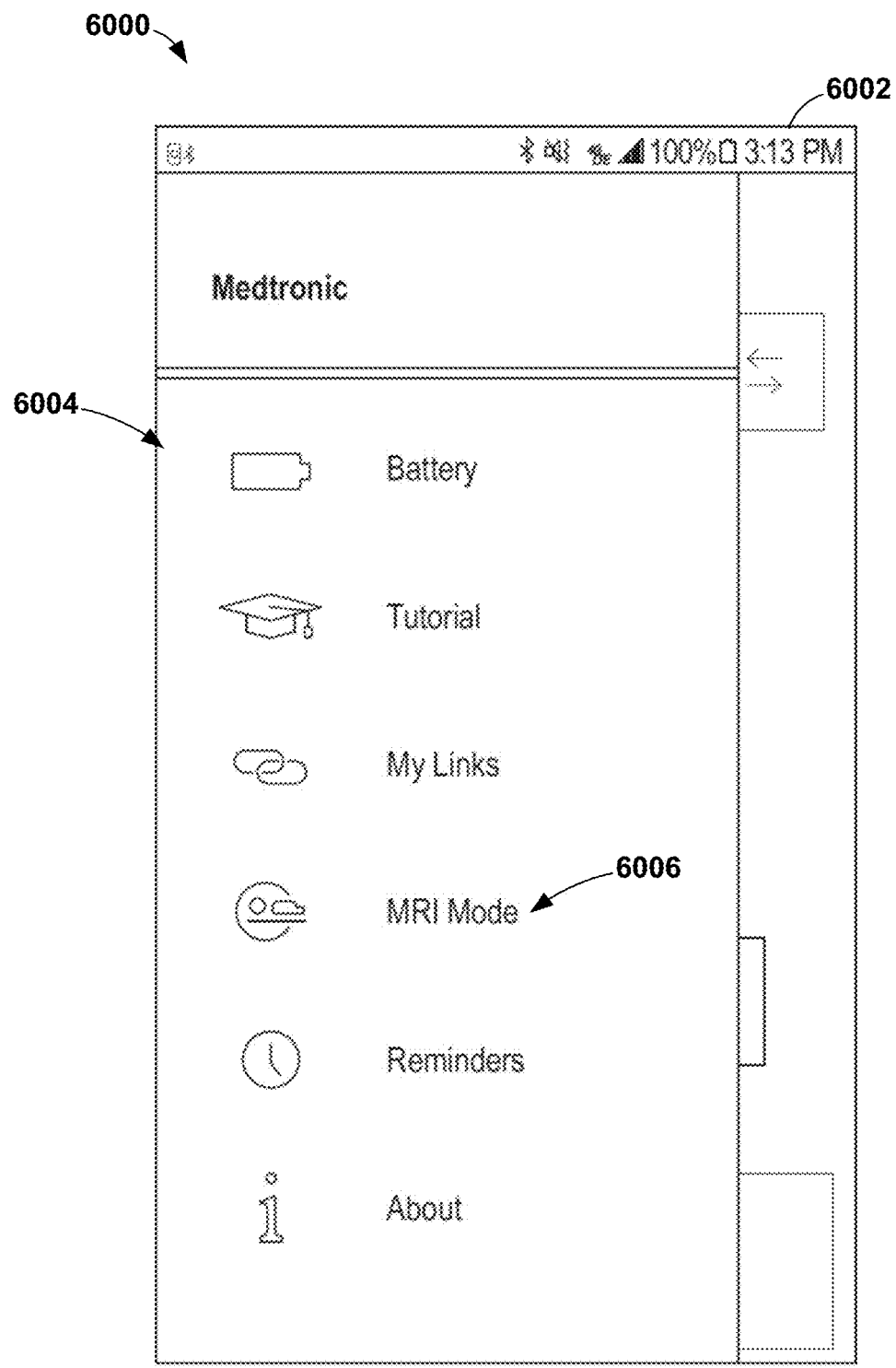
FIGS. 60-69 are conceptual diagrams illustrating example screens of a user interface associated with entering an MRI mode for a medical device.
Figure 61:
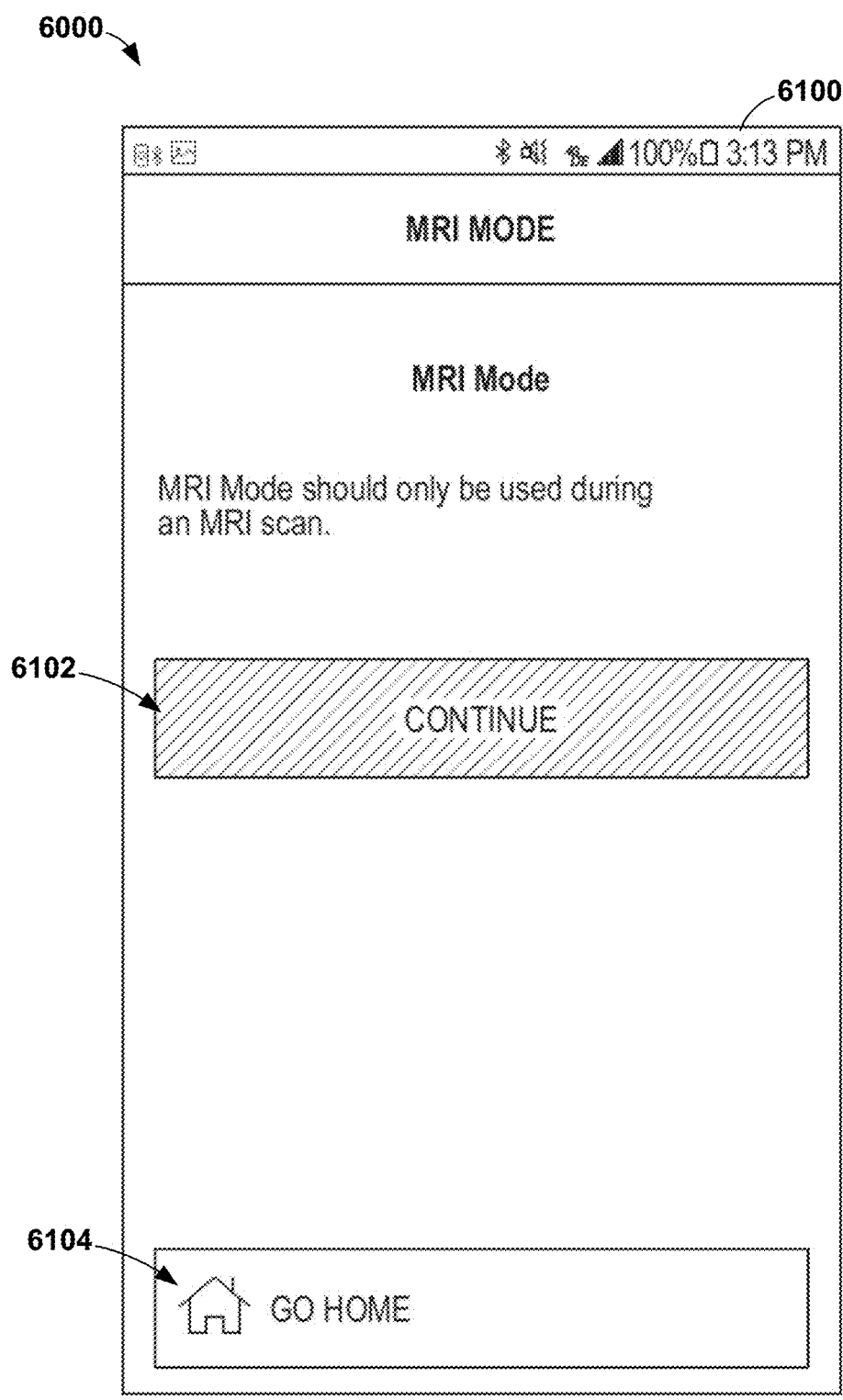
Figure 62:
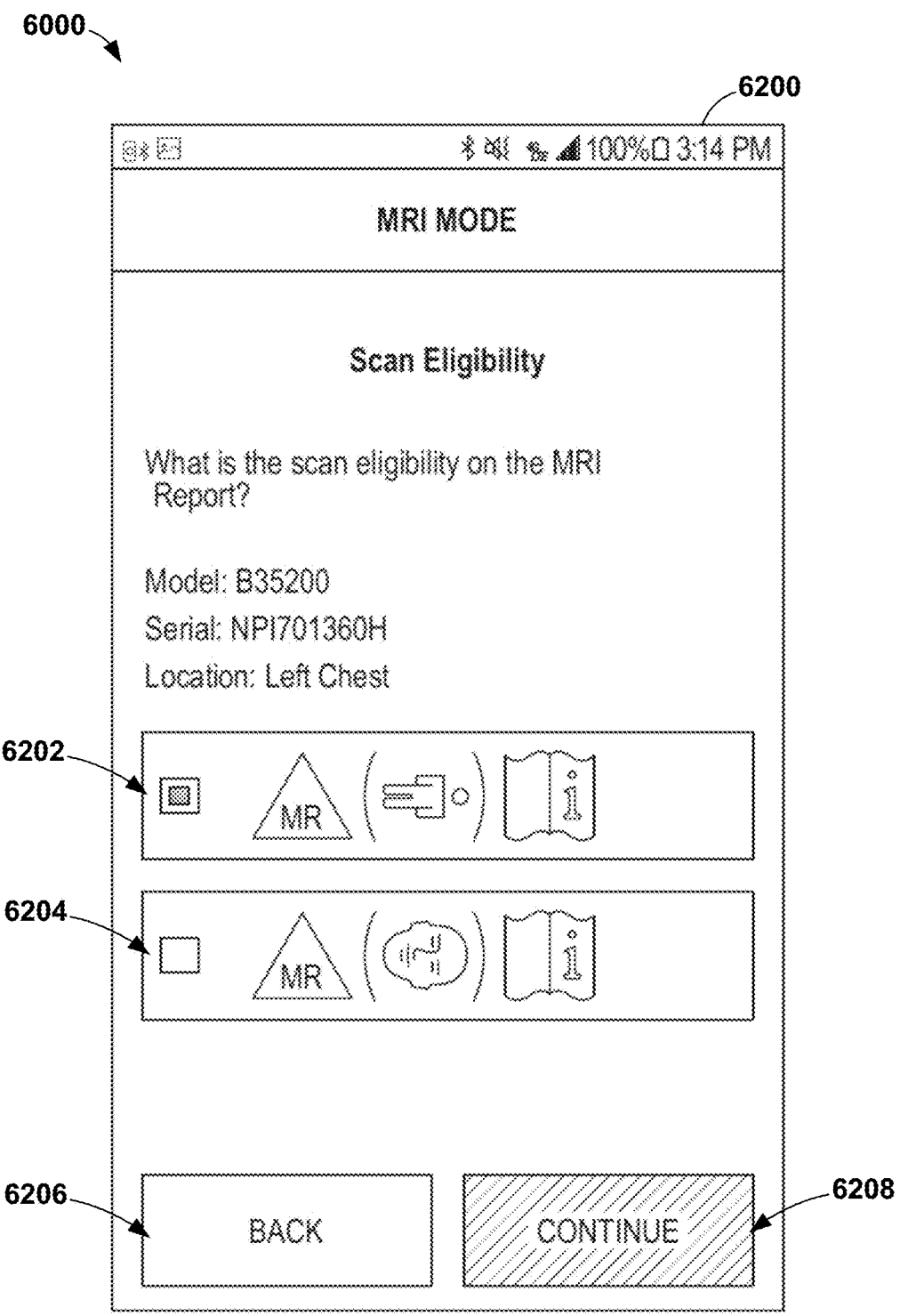
Figure 63:
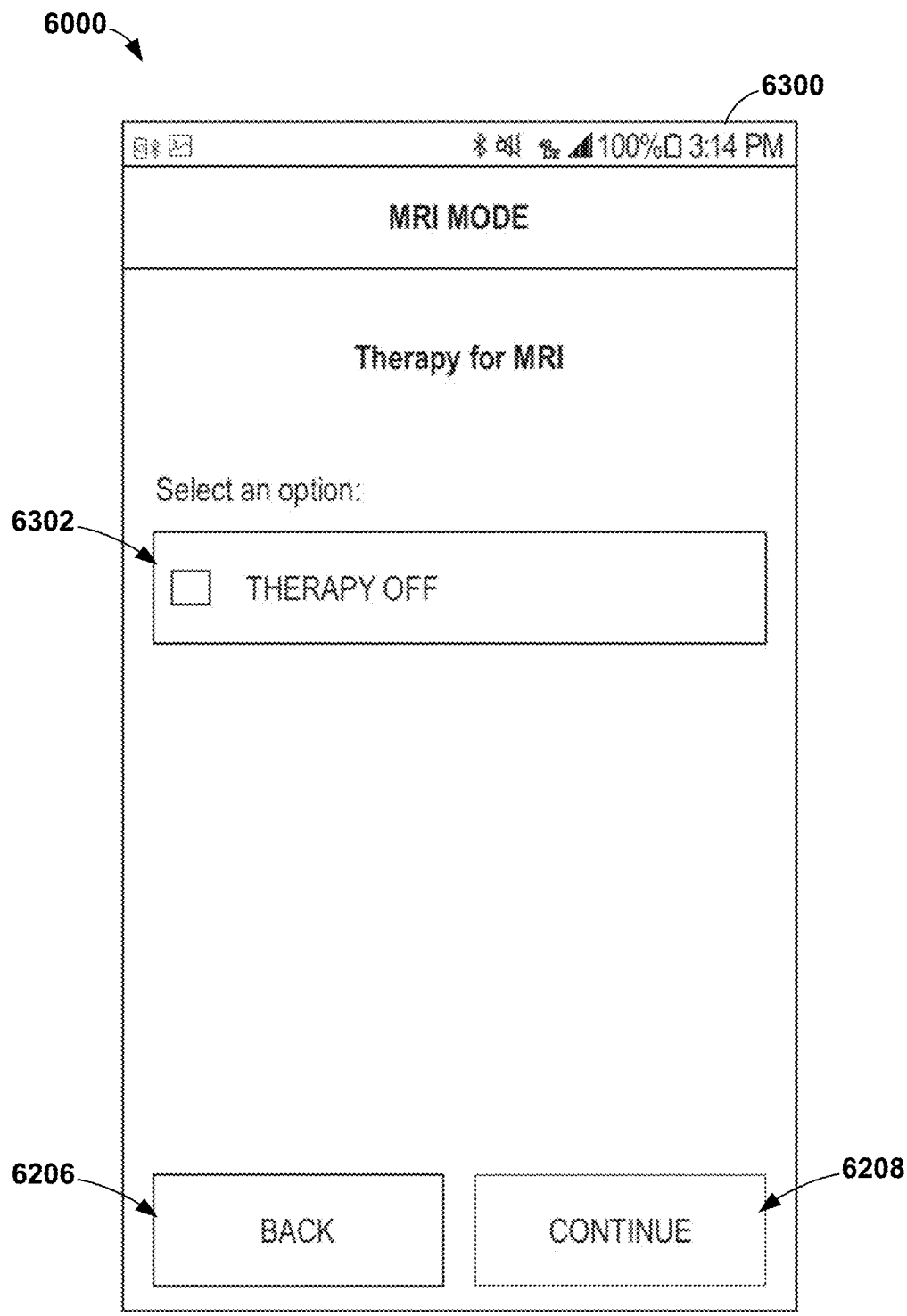
Figure 64:
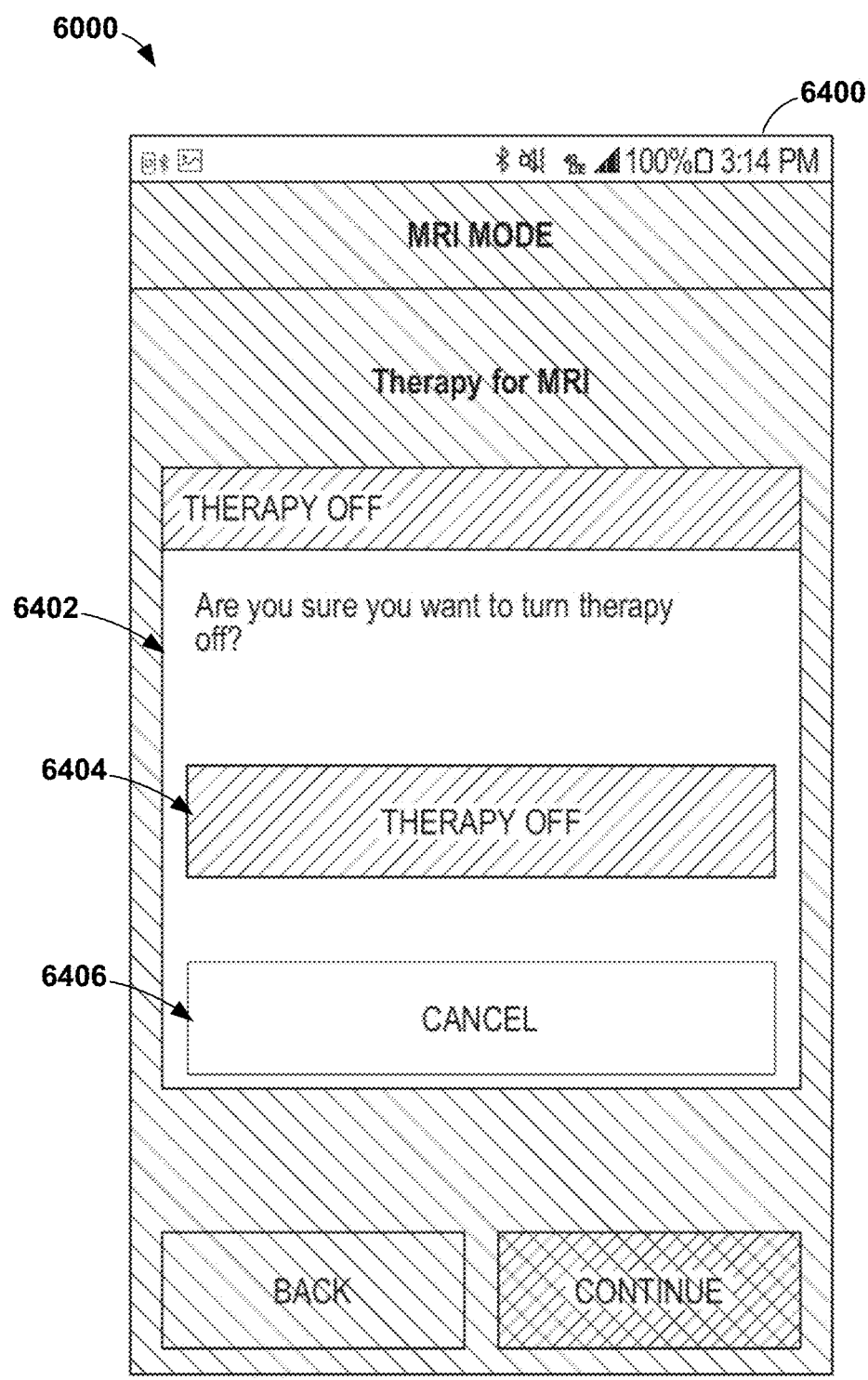

FIGS. 60-69 are conceptual diagrams illustrating example screens of a user interface for a patient programmer associated with entering an MRI mode for a medical device. FIG. 60 illustrates a screen 6002 that includes a navigation menu 6004 from which the user can enter the "MRI mode" by selecting MRI mode button 6006. This mode is used to check the MRI eligibility for IMD 106 implanted within the patient and enable the patient to directly enter the MRI mode if eligible, using the patient programmer. Upon selecting the "MRI mode" button 6006 in FIG. 60, the user interface presents FIG. 61 in which screen 6100 prompts the user to continue into MRI mode using continue button 6102. Home button 6104 can be selected to leave the MRI mode process. FIG. 62 includes a screen 6200 to prompt the use to select the device to be checked. Button 6202 indicates a device located in the body (such as the left chest), and button 6204 indicates a device located in the head. Back button 6206 takes the user back to the previous screen 6100, and continue button 6208 moves to the next screen in the process. The screen 6300 of FIG. 63 enables the user to turn therapy off directly from the MRI eligibility check without navigating to different screens via therapy off button 6302. If the user selects to turn off therapy, the user interface prompts the user to confirm that the therapy should be turned off in screen 6400 of FIG. 64. For example, pop up window 6402 includes a therapy off button 6404 which must be selected to turn off therapy. Selection of cancel button 6406 returns to the previous screen and therapy remains on.

Figure 65:
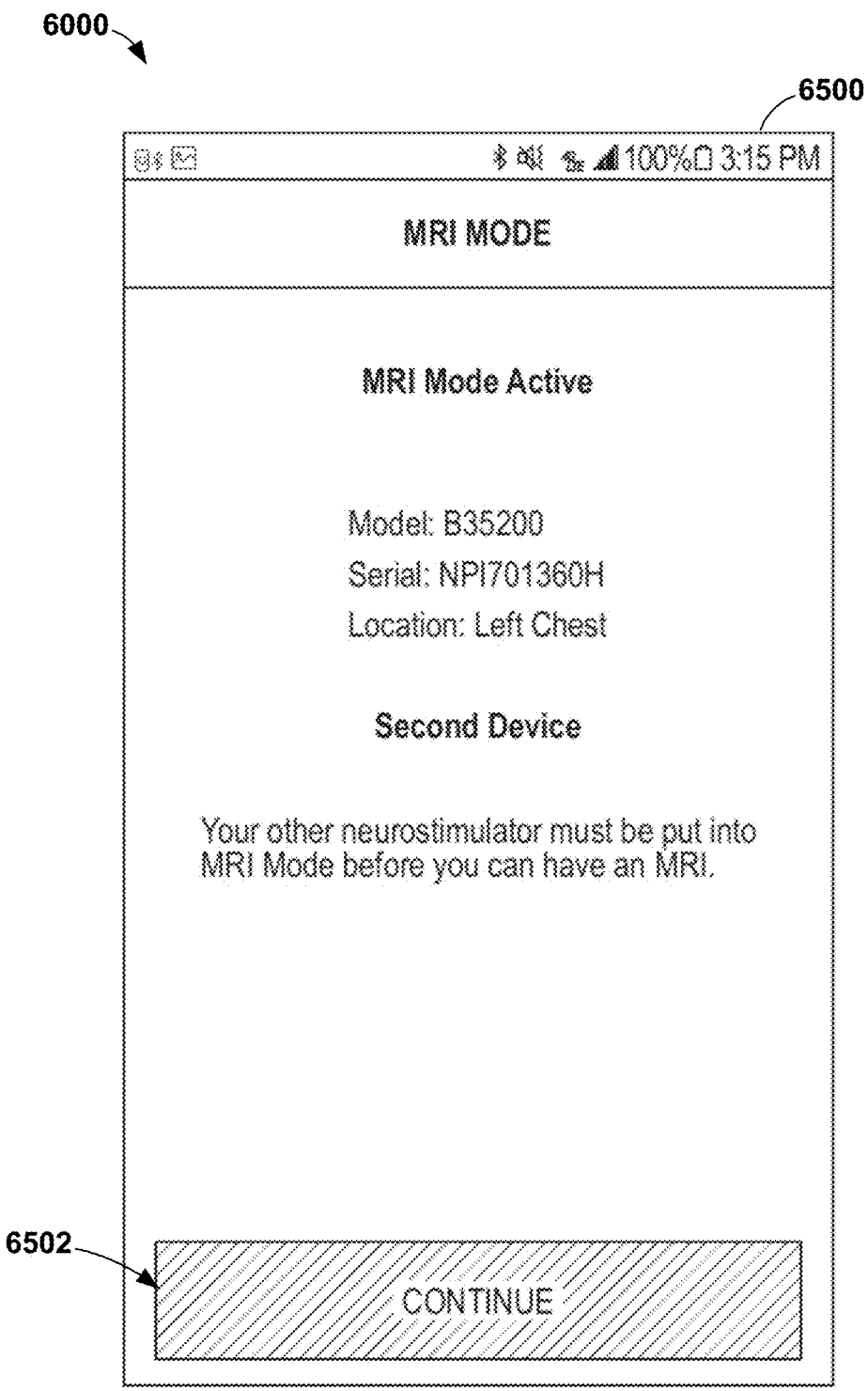
Figure 66:
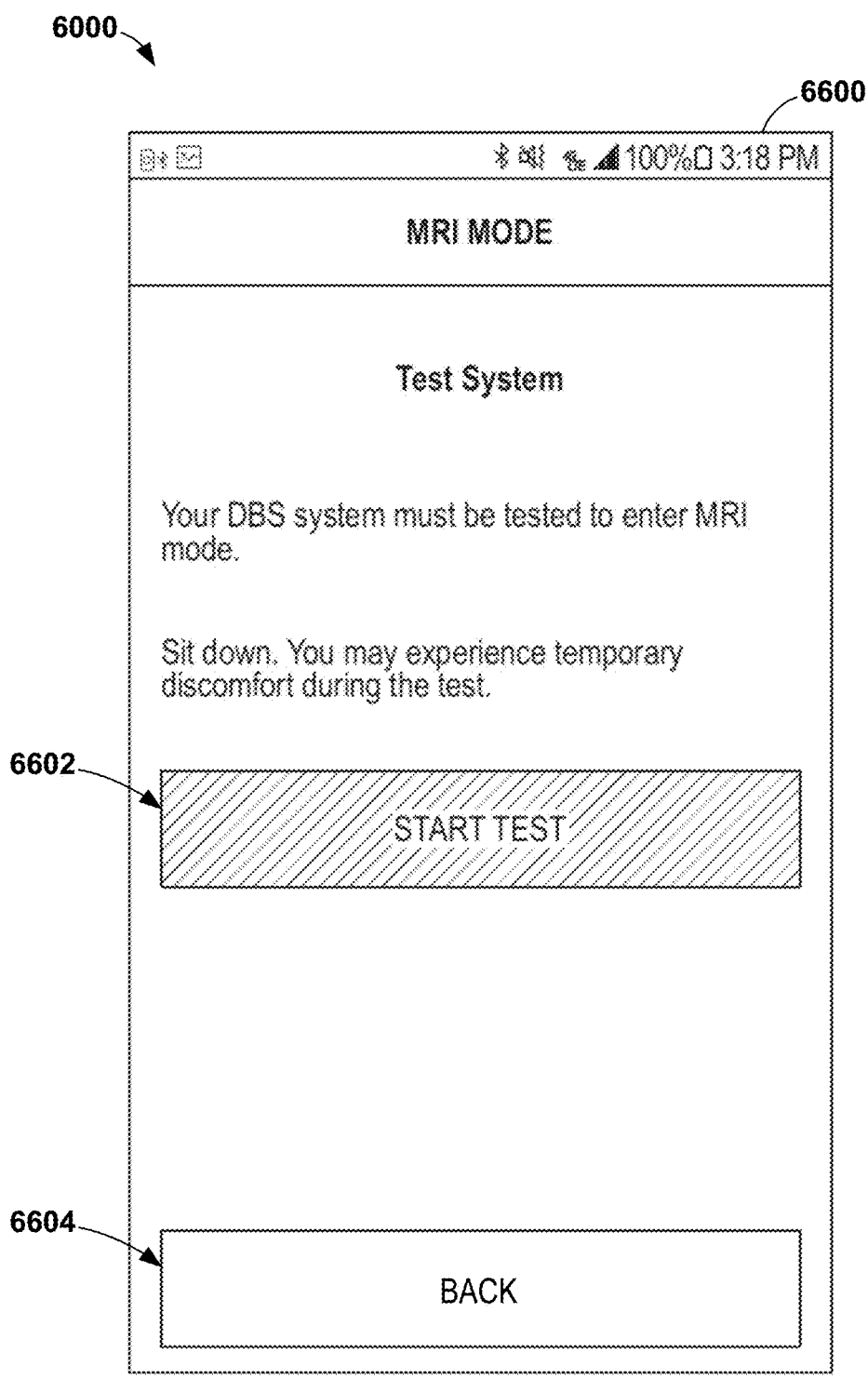
Figure 67:
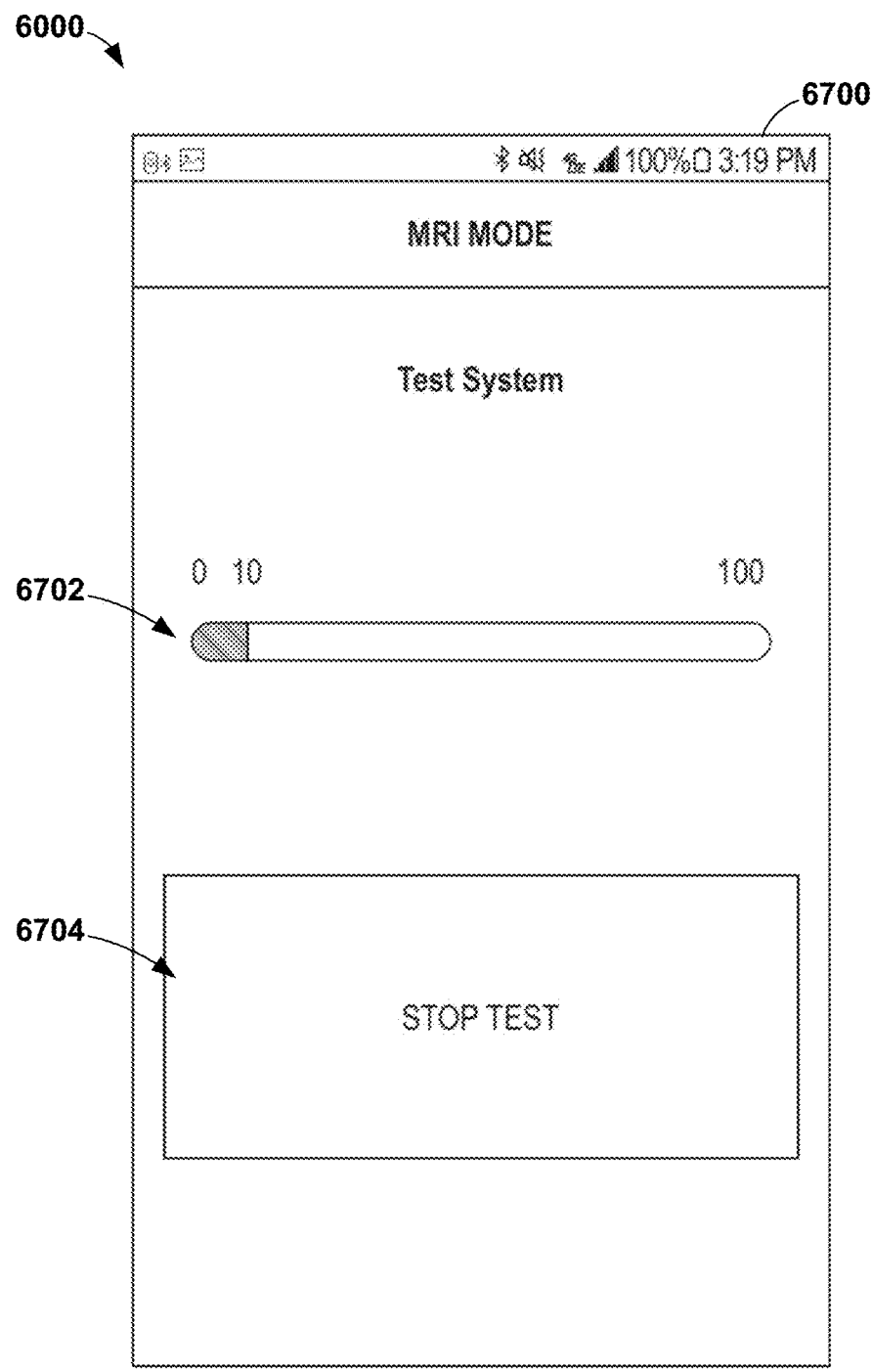
Figure 68:
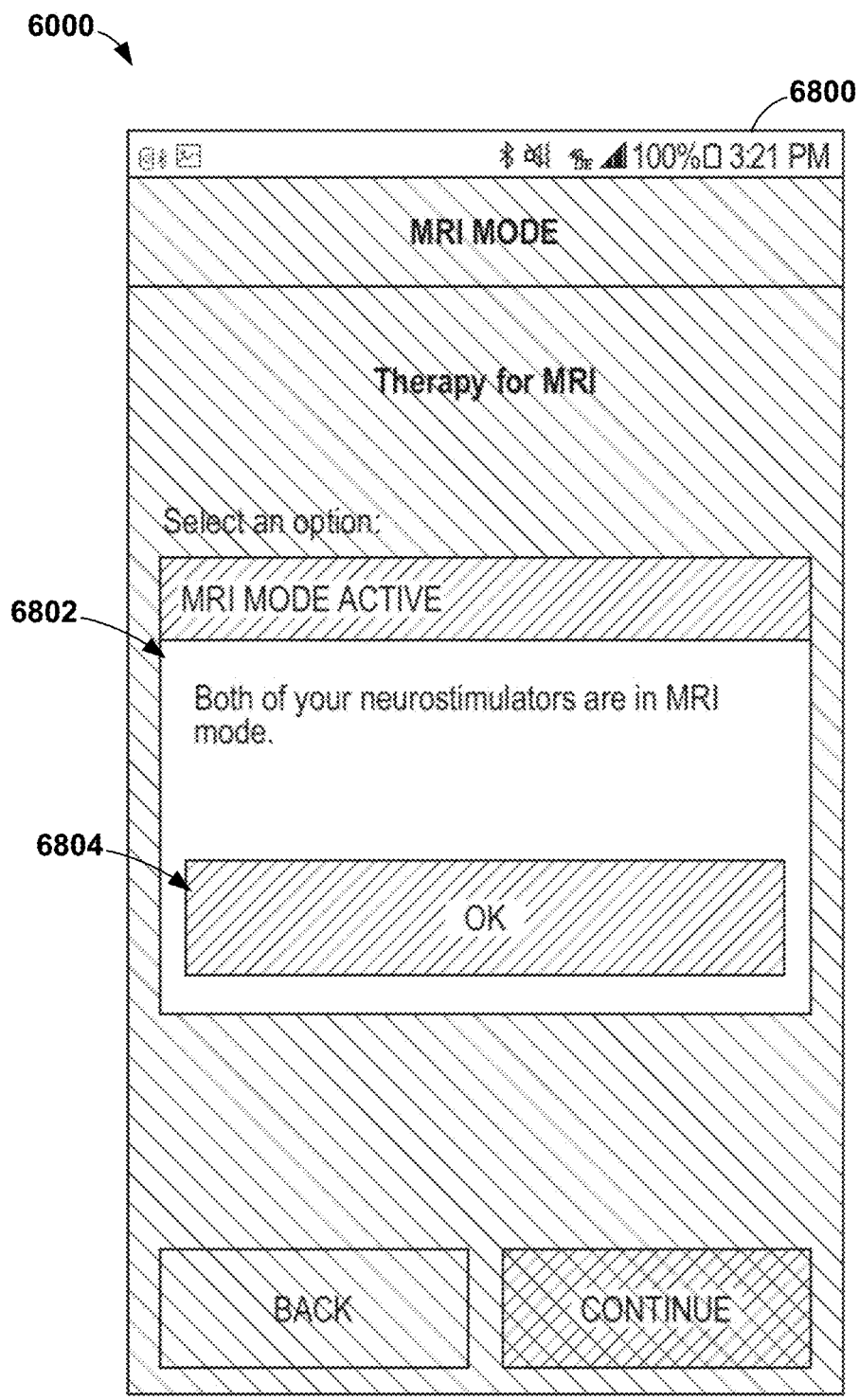
Figure 69:
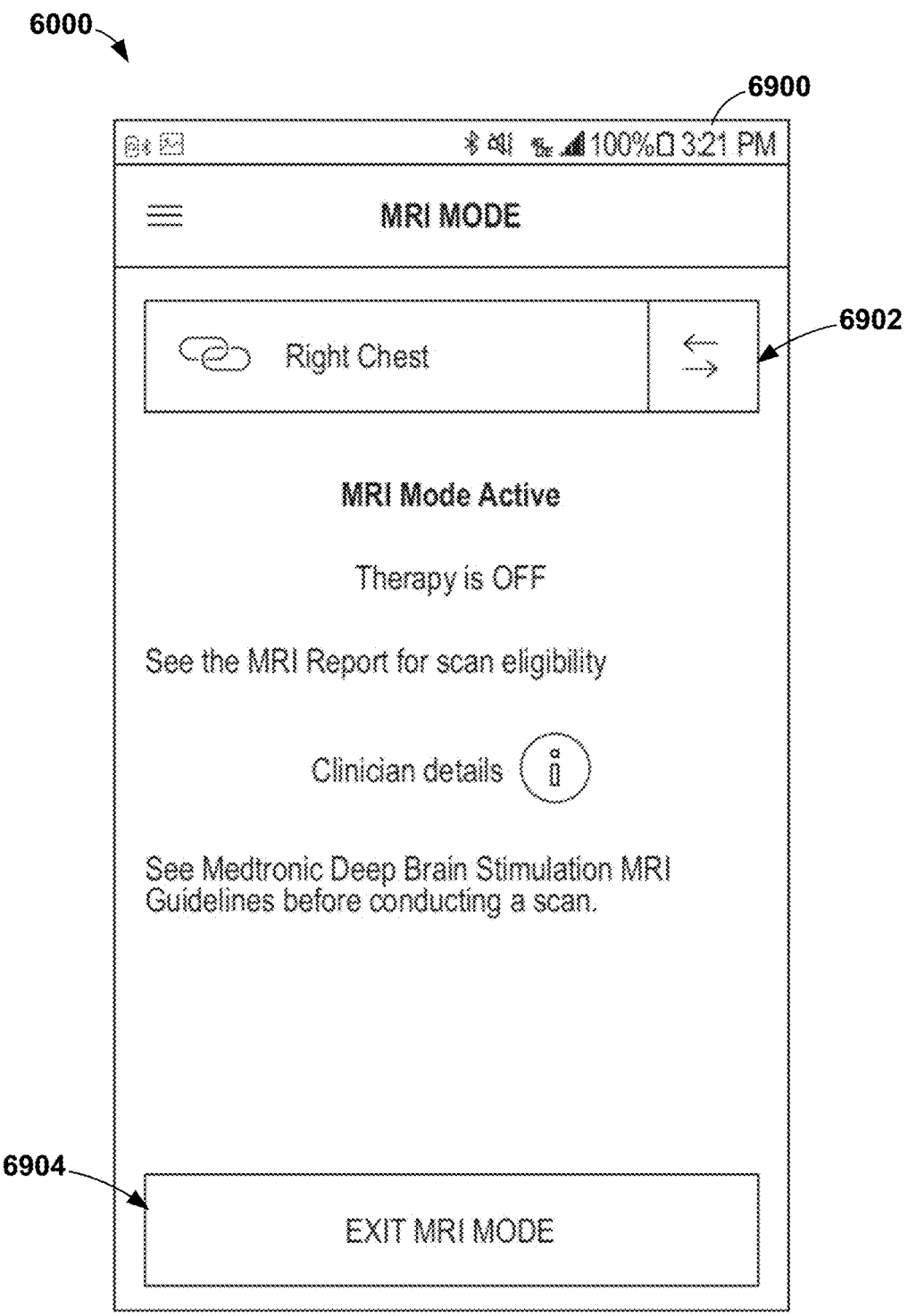

FIG. 65 includes a screen 6500 in which the user is prompted to turn any other devices into MRI mode as well. Upon selecting continue button 6502, screen 6600 of FIG. 66 is shown and prompts the user to start the MRI eligibility check by selecting start test button 6602. Selecting back button 6604 returns to a previous screen. Responsive to receiving selection of the "start test" button 6602, the user interface moves to the screen 6700 in FIG. 67 that indicates the status of the MRI eligibility test via status bar 6702 (e.g., showing a percentage of the process). From this screen, the user can select to stop the test if desired via stop test button 6704. If the test is successful, FIG. 68 indicates that the programmer has put the one or more neurostimulators into MRI mode. In pop up window 6802 of screen 6800, the user can select OK button 6904 to proceed in MRI mode. Once in MRI mode, screen 6900 of FIG. 69 indicates that the user interface will present a button 6904 that, when pressed, will cause the programmer to control the implanted devices to exit the MRI mode. Button 6902 can toggle between different devices in different locations of the patient.

Figure 70:
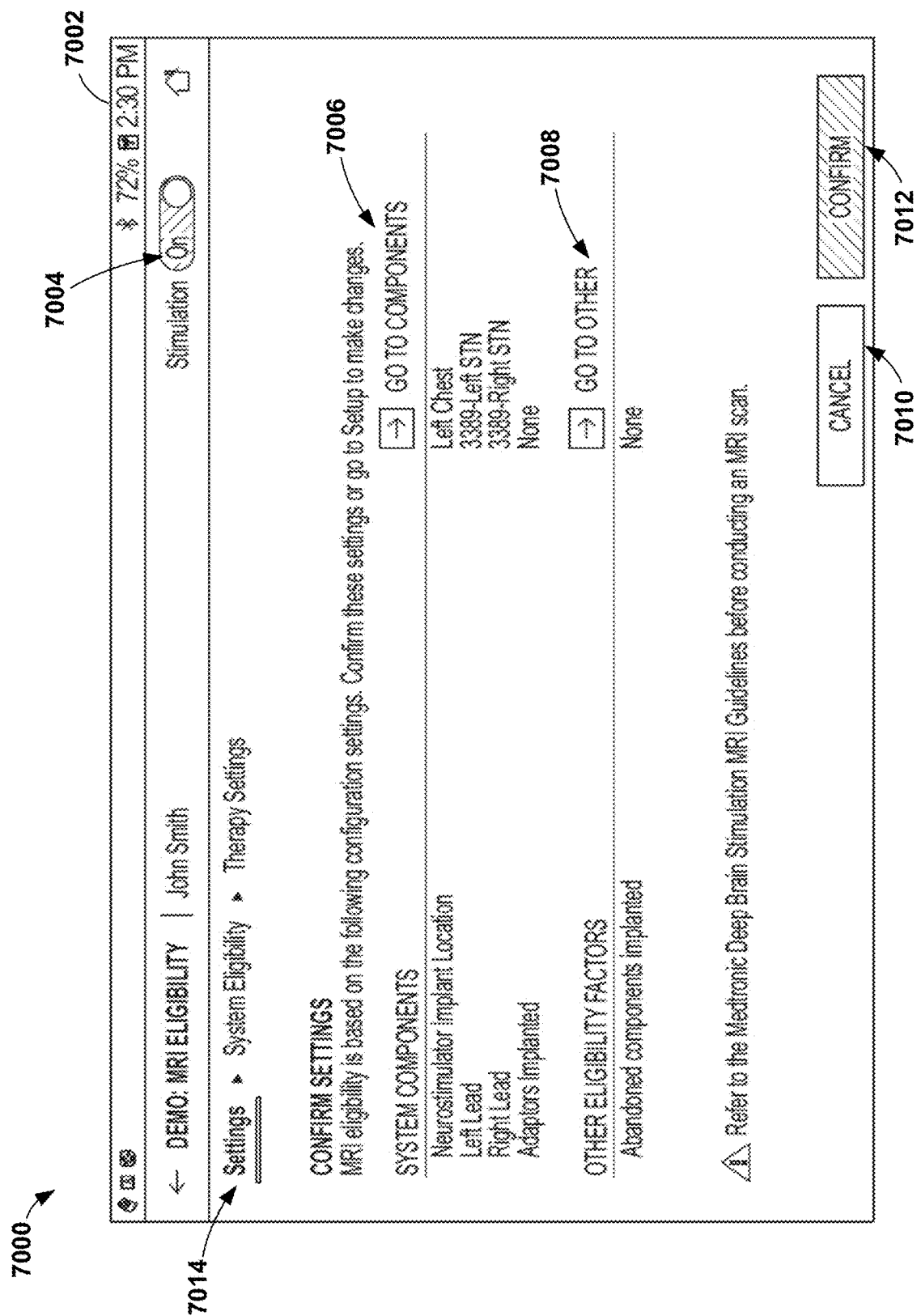
FIGS. 70-74 are conceptual diagrams illustrating example screens of a user interface associated with entering an MM mode for a medical device.
Figure 71:
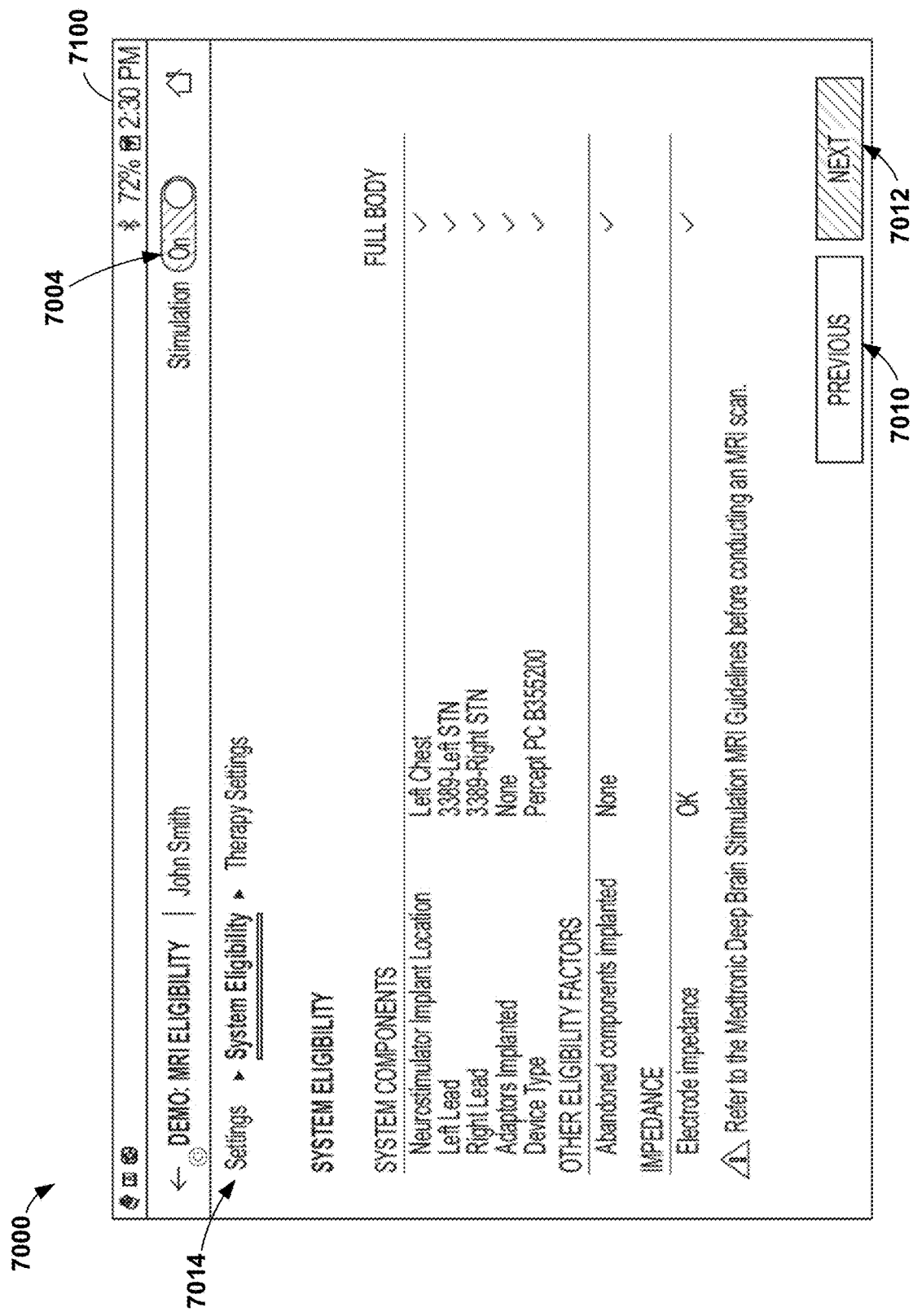
Figure 72:
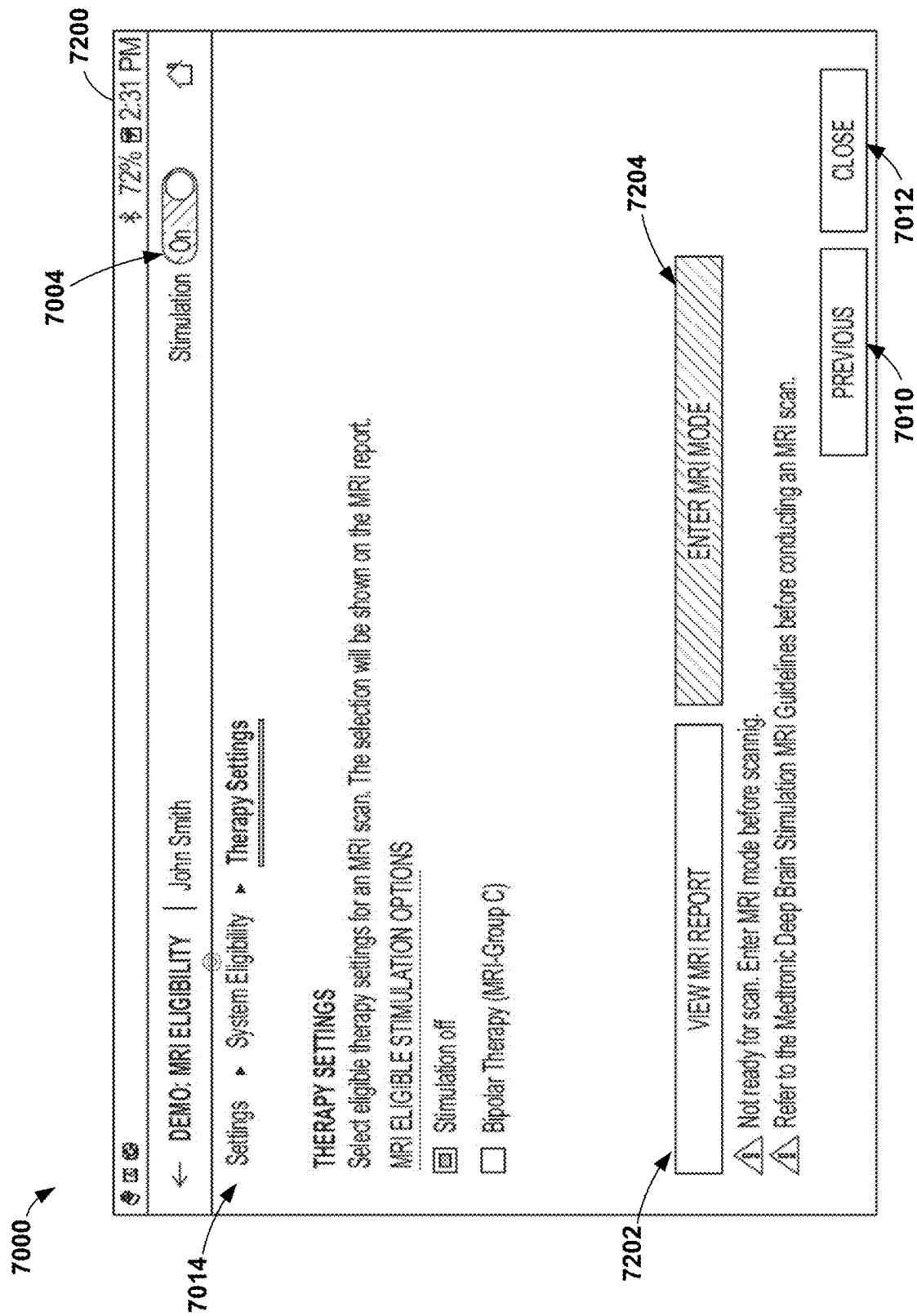
Figure 73:
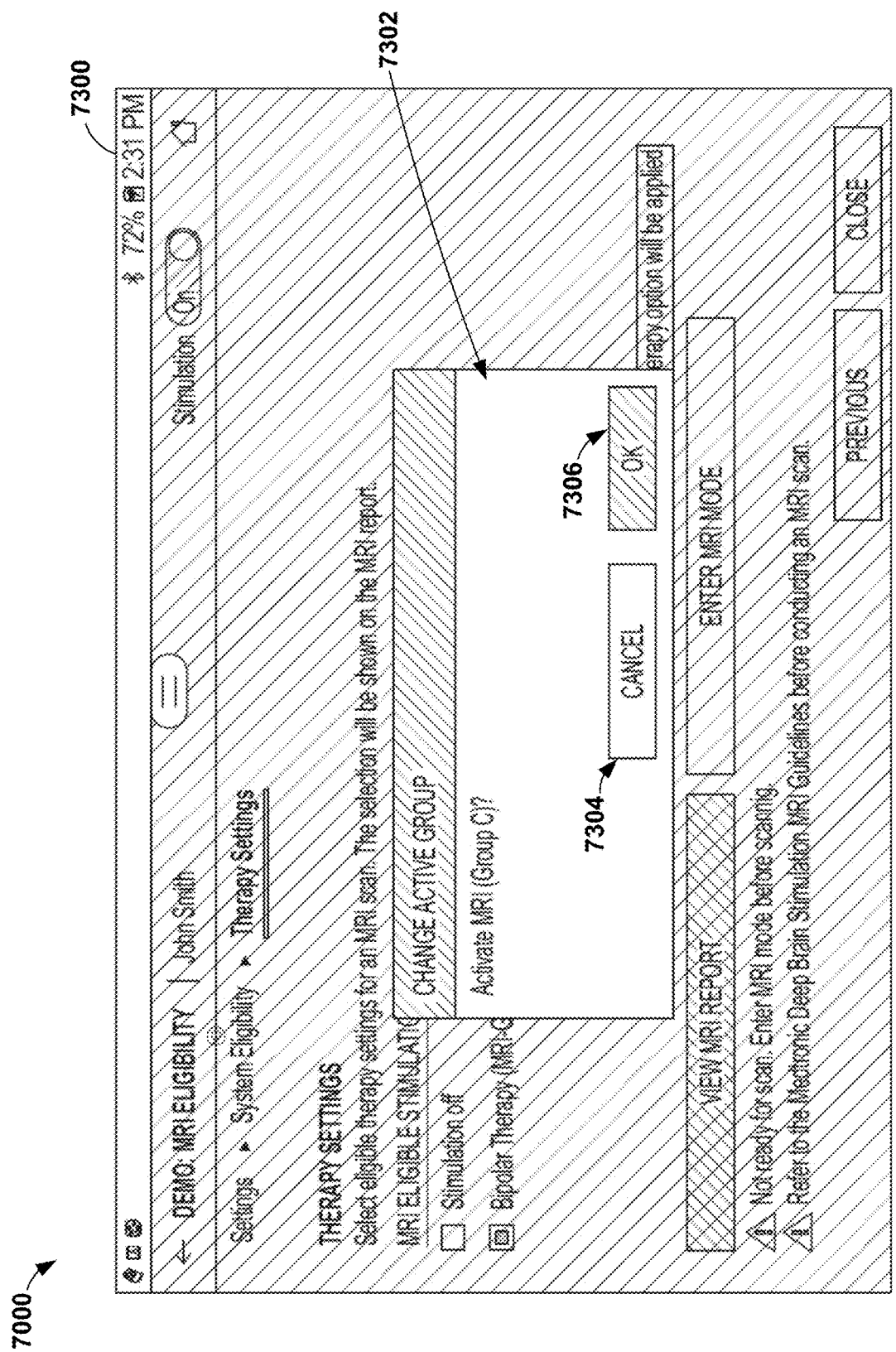
Figure 74:
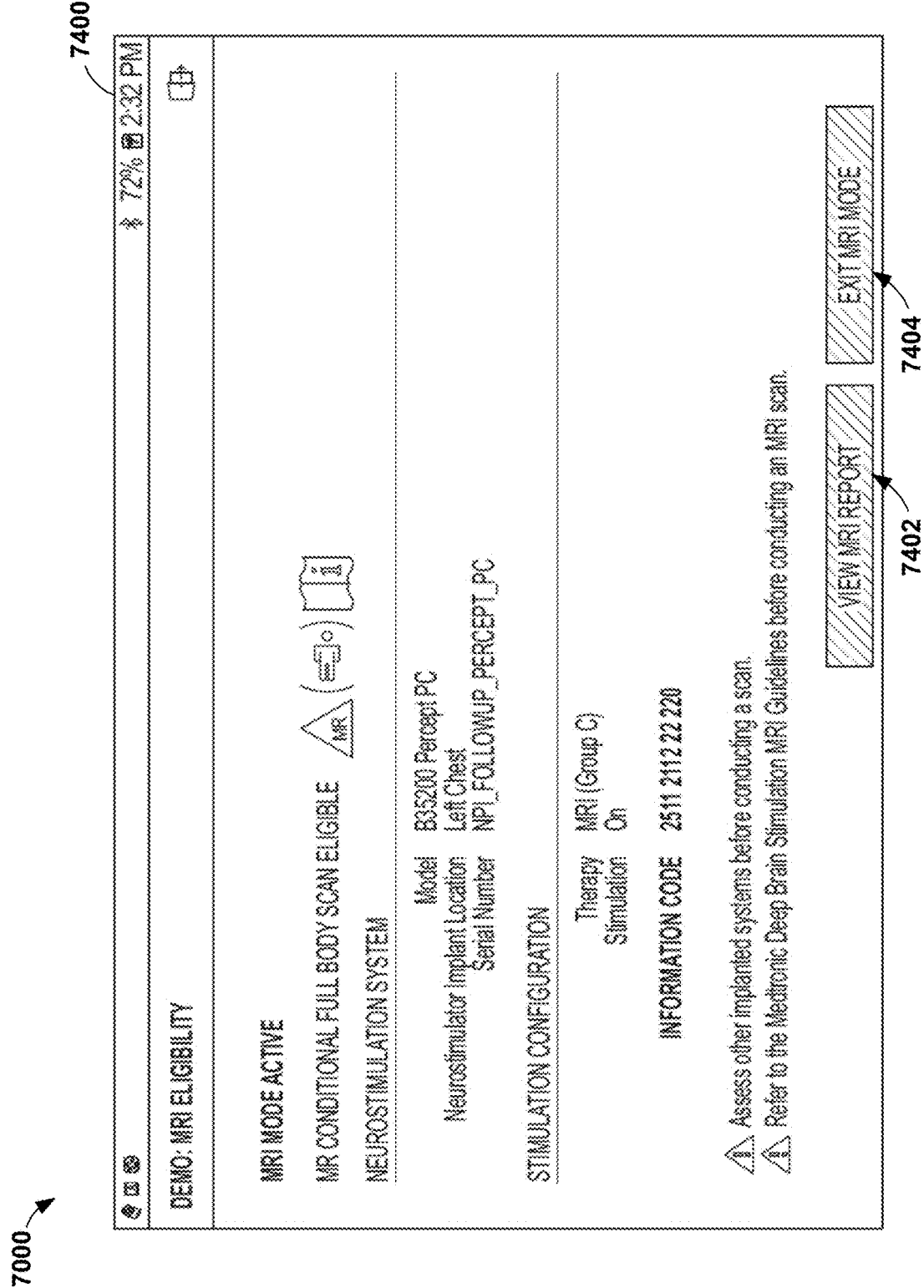

FIGS. 70-75 are conceptual diagrams illustrating example screens of a user interface associated with entering an MRI mode for a medical device. In the examples of FIGS. 70-75, the clinician programmer may enter an MRI mode for stimulation devices. FIG. 70 illustrates a screen 7002 where the clinician can confirm system components and any other eligibility factors for MRI eligibility. Stimulation toggle 7004 enables a user to turn stimulation on or off. Menu 7014 provides the different screens in which information related to the device can be viewed. Components button 7006 can show the user additional components associated with the patient, and button 7008 can show additional factors related to MRI eligibility. Cancel button 7010 will cancel this portion of the MRI check. Selection of confirm button 7012 will confirm that MRI test can proceed. FIG. 71 illustrates a screen 7100 showing the system eligibility for each component of the system. The screen 7200 of FIG. 72 is configured to receive user input turning stimulation off or on for MRI imaging. In addition, FIG. 72 provides an enter MRI mode button 7204 that, when selected, causes the programmer to place the IMD into the MRI mode. Report button 7202 will cause user interface 400 to present a report regarding the MRI eligibility for the patient. FIG. 73 includes screen 7300 which indicates a pop-up screen 7302 in which the user can confirm that the system should enter the therapy mode eligible for MRI scans by selecting OK button 7306. Cancel button 7304 will cancel the MRI setting. FIG. 74 provides a screen 7400 that indicates that the IMD is in MRI mode. Report button 7402 will cause user interface 400 to present a report regarding the MRI mode for the patient. Programmer 106 will control the IMD to exit the MRI mode in response to the user selecting the exit MRI mode button 7404.

Figure 75:
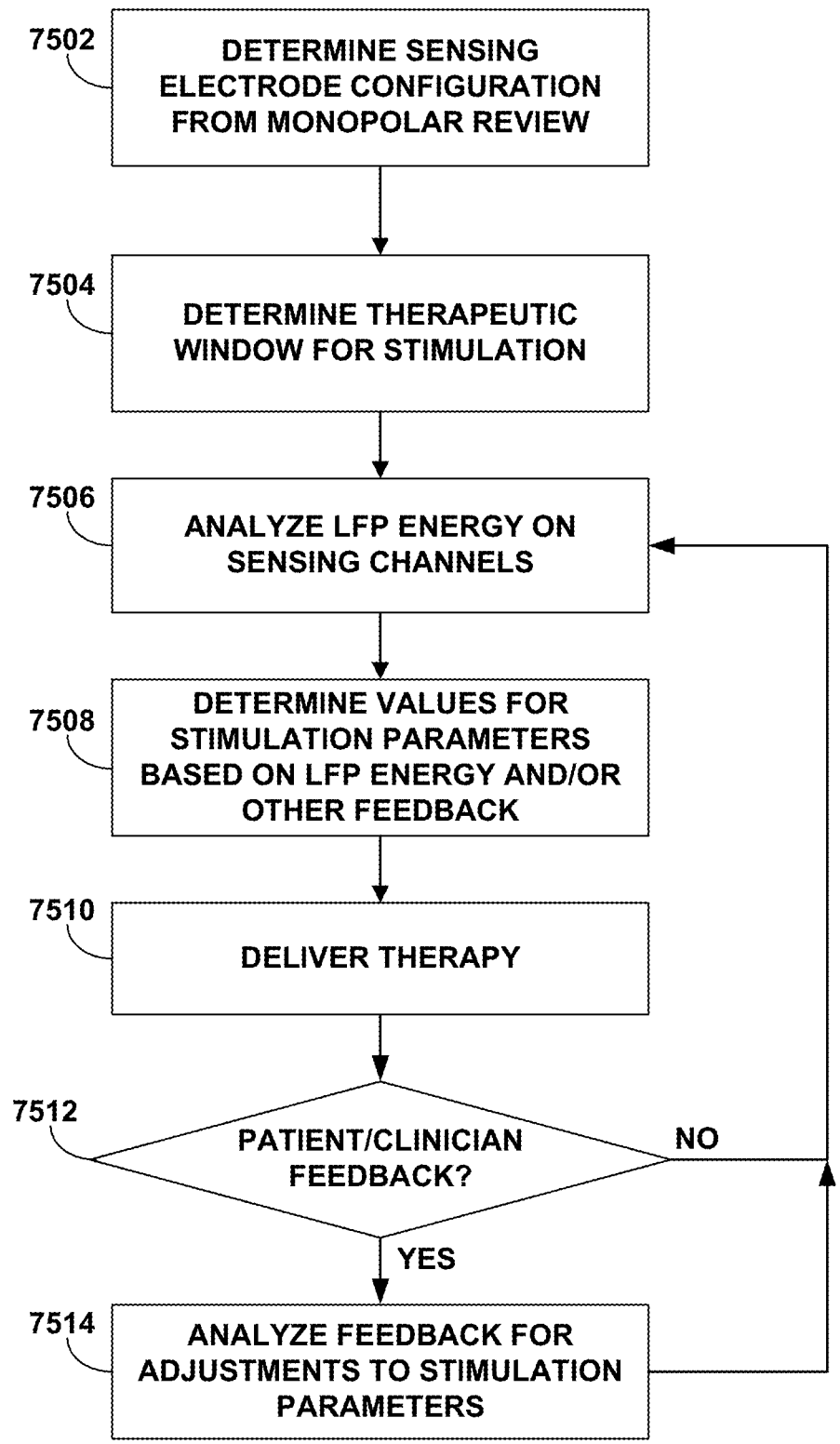
FIG. 75 is a flowchart illustrating an example technique for managing the sensing of brain signals.

FIG. 75 is a flowchart illustrating an example technique for managing the sensing of brain signals. As shown in the example flowchart of FIG. 75, LFP power can be recorded and presented to a user in order to adjust settings for therapy that is not automatically adjusted. For example, processing circuitry 310 of programmer 104 may determine a sensing electrode configuration from monopolar review of electrode combinations (7502). Processing circuitry 310 then determines the therapeutic window for stimulation (7504). This process may be automated or performed with input from a user. Processing circuitry 310 then analyzes LFP energy sensed on the different sensing channels (7506).

Based on the LFP energy, processing circuitry 310 determines values for stimulation parameters and/or other feedback, such as feedback from the patient or clinician (7508). Processing circuitry 310 then controls IMD 106 to deliver therapy using these stimulation parameter values (7510). If there is no patient or clinician feedback ("No" branch of block 7512), processing circuitry 310 continues to analyze LFP energy and adjust stimulation parameter values as need to adapt stimulation to changing brain states (7506). This automated process for referring the LFP signals enables adaptive stimulation for the patient. If processing circuitry 310 determines that there is patient or clinician feedback ("YES" branch of block 7512), processing circuitry 310 analyzes the feedback for any adjustments to make to one or more stimulation parameters (7514). For example, feedback indicating that the patient experiences dyskinesia at some times may cause processing circuitry 310 to reduce the upper limit of stimulation amplitude.

Figure 76:
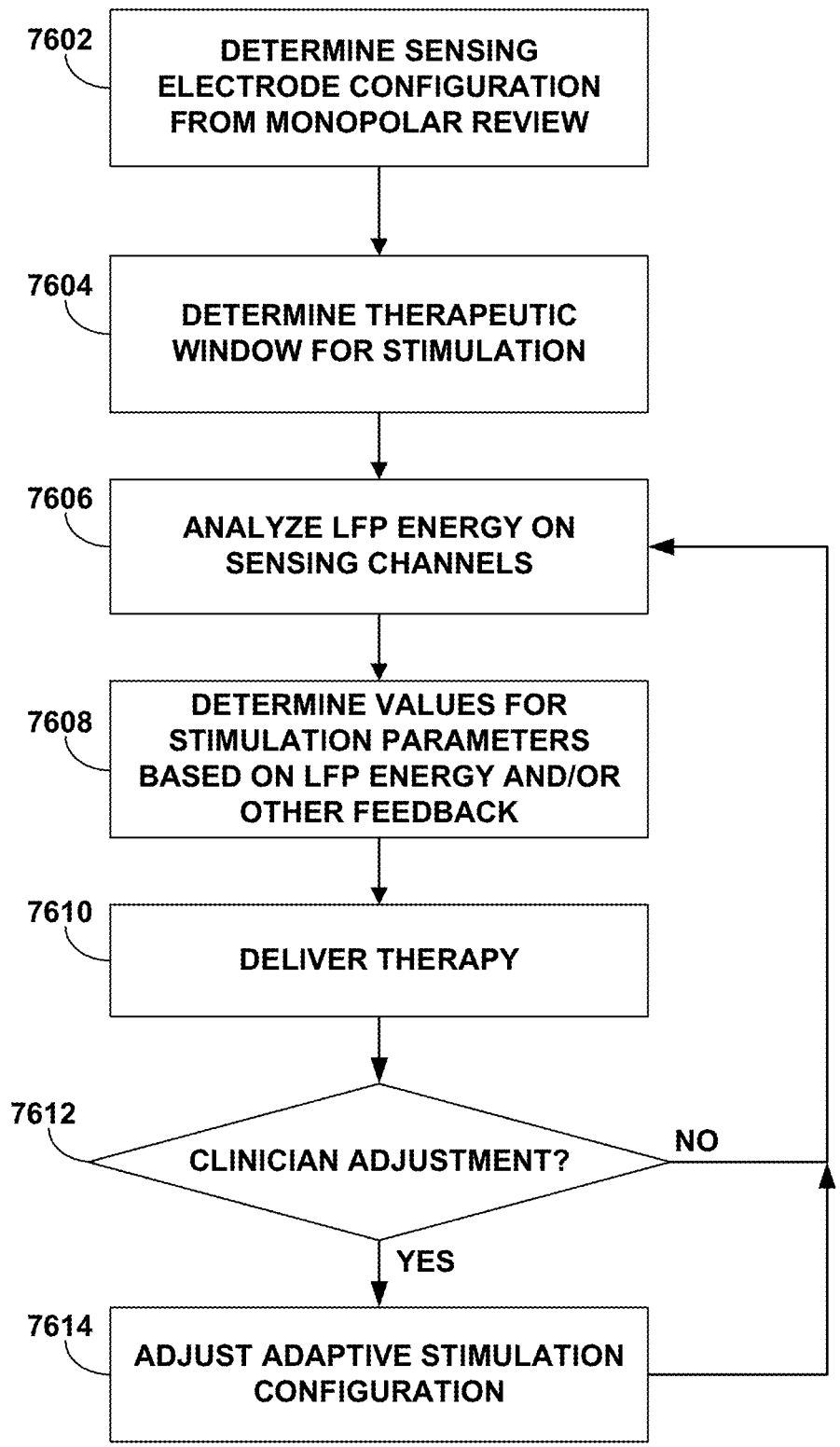
FIG. 76 is a flowchart illustrating an example technique for setting up and managing adaptive stimulation using brain signals.

FIG. 76 is a flowchart illustrating an example technique for setting up and managing adaptive stimulation using brain signals. As shown in the example flowchart of FIG. 76, an IMD can employ LFP power to automatically adjust one or more stimulation parameters in order to maintain the LFP power at appropriate levels with respect to one or more thresholds. For example, processing circuitry 310 of programmer 104 may determine a sensing electrode configuration from monopolar review of electrode combinations (7602). Processing circuitry 310 then determines the therapeutic window for stimulation (7604). This process may be automated or performed with input from a user. Processing circuitry 310 then analyzes LFP energy sensed on the different sensing channels (7606).

Based on the LFP energy, processing circuitry 310 determines values for stimulation parameters and/or other feedback, such as feedback from the patient or clinician (7608). Processing circuitry 310 then controls IMD 106 to deliver therapy using these stimulation parameter values (7610). If there is no clinician adjustment made during an office visit or other clinician intervention ("No" branch of block 7612), processing circuitry 310 continues to analyze LFP energy and adjust stimulation parameter values as need to adapt stimulation to changing brain states (7606). This automated process for referring the LFP signals enables adaptive stimulation for the patient. If processing circuitry 310 determines that there is clinician adjustment ("YES" branch of block 7612), processing circuitry 310 analyzes the feedback for any adjustments to make to one or more stimulation parameters (7614). For example, the clinician may review data and request an adjustment to LFP thresholds and/or stimulation limits.

The following examples are described herein. Example 1. A method comprising: obtaining, by processing circuitry, brain signal information for at least one electrode combination of a plurality of electrode combinations of one or more electrical leads; determining, by the processing circuitry and based on the brain signal information, a respective frequency for the at least one electrode combination; outputting, for display, a plurality of selectable lead icons, wherein each selectable lead icon of the plurality of selectable lead icons represents a different electrode combination of the plurality of electrode combinations; outputting, for display, the respective frequency determined for the at least one electrode combination in association with the respective selectable lead icon associated with the at least one electrode combination; receiving user input selecting one selectable lead icon of the plurality of selectable lead icons; and responsive to receiving the user input, selecting, by the processing circuitry and for subsequent brain signal sensing, a sense electrode combination associated with the one selectable lead icon selected by the user input.

Example 2. The method of example 1, further comprising: outputting, for display, a selectable signal test icon; receiving user input selecting the selectable signal test icon; and responsive to receiving the user input selecting the selectable signal test icon, controlling a medical device to obtain brain signal information for at least one electrode combination of the plurality of electrode combinations.

Example 3. The method of any of examples 1 though 2, wherein the plurality of electrode combinations comprises all electrode combinations possible for the one or more electrical leads implanted within a patient.

Example 4. The method of any of examples 1 though 3, further comprising: analyzing the brain signal information for presence of an artifact associated with at least one of electrocardiogram sensing or motion of the one or more electrical leads; determining that the artifact is not present in the brain signal information; and responsive to determining that the artifact is not present, approving the one or more electrode combinations for selection by a user for subsequent brain signal sensing.

Example 5. The method of example 4, wherein analyzing the brain signal information for presence of the artifact comprises applying a logistic regression classifier to at least a portion of the brain signal information.

Example 6. The method of example 5, further comprising determining a plurality of signal features from the brain signal information, the plurality of signal features comprise entropies for a plurality of frequency bands within the brain signal information and a plurality of time domain threshold crossing features, wherein applying the logistic regression classifier to the portion of the brain signal information comprises applying the logistic regression classifier to the plurality of signal features.

Example 7. The method of any of examples 4 though 6, wherein analyzing the brain signal information for presence of the artifact associated with the electrocardiogram comprises analyzing the brain signal information for a fast Fourier transform (FFT) amplitude separation at approximately 8 Hz between a first brain signal detected during delivery of electrical stimulation and a second brain signal detecting during an absence of electrical stimulation delivery; and wherein the FFT amplitude separation less than a separation threshold indicates that the artifact is not present.

Example 8. The method of any of examples 1 though 7, wherein the brain signal information comprises one or more local field potential signals.

Example 9. The method of any of examples 1 though 8, wherein an external programmer comprises the processing circuitry, the external programmer configured to control an implantable medical device configured to be coupled to the one or more electrical leads.

Example 10. An external programmer comprising: processing circuitry configured to: obtain brain signal information for at least one electrode combination of a plurality of electrode combinations of one or more electrical leads; determine, based on the brain signal information, a respective frequency for the at least one electrode combination; output, for display, a plurality of selectable lead icons, wherein each selectable lead icon of the plurality of selectable lead icons represents a different electrode combination of the plurality of electrode combinations; output, for display, the respective frequency determined for the at least one electrode combination in association with the respective selectable lead icon associated with the at least one electrode combination; receive user input selecting one selectable lead icon of the plurality of selectable lead icons; and responsive to receiving the user input, selecting, for subsequent brain signal sensing, a sense electrode combination associated with the one selectable lead icon selected by the user input.

Example 11. The external programmer of example 10, wherein the processing circuitry is further configured to: output, for display, a selectable signal test icon; receive user input selecting the selectable signal test icon; and responsive to receiving the user input selecting the selectable signal test icon, control a medical device to obtain brain signal information for at least one electrode combination of the plurality of electrode combinations.

Example 12. The external programmer of any of examples 10 though 11, wherein the plurality of electrode combinations comprises all electrode combinations possible for the one or more electrical leads implanted within a patient.

Example 13. The external programmer of any of examples 10 though 12, wherein the processing circuitry is further configured to: analyze the brain signal information for presence of an artifact associated with at least one of electrocardiogram sensing or motion of the one or more electrical leads; determine that the artifact is not present in the brain signal information; and responsive to determining that the artifact is not present, approve the one or more electrode combinations for selection by a user for subsequent brain signal sensing.

Example 14. The external programmer of example 13, wherein the processing circuitry is configured to analyze the brain signal information for presence of the artifact by at least applying a logistic regression classifier to at least a portion of the brain signal information.

Example 15. The external programmer of example 14, wherein the processing circuitry is further configured to determine a plurality of signal features from the brain signal information, the plurality of signal features comprise entropies for a plurality of frequency bands within the brain signal information and a plurality of time domain threshold crossing features, wherein the processing circuitry is configured to apply the logistic regression classifier to the portion of the brain signal information by at least applying the logistic regression classifier to the plurality of signal features.

Example 16. The external programmer of any of examples 13 though 15, wherein the processing circuitry is configured to analyze the brain signal information for presence of the artifact associated with the electrocardiogram by at least analyzing the brain signal information for a fast Fourier transform (FFT) amplitude separation at approximately 8 Hz between a first brain signal detected during delivery of electrical stimulation and a second brain signal detecting during an absence of electrical stimulation delivery; and wherein the FFT amplitude separation less than a separation threshold indicates that the artifact is not present.

Example 17. The external programmer of any of examples 10 though 16, wherein the brain signal information comprises one or more local field potential signals.

Example 18. The external programmer of any of examples 1 though 17, wherein the external programmer is configured to control an implantable medical device configured to be coupled to the one or more electrical leads.

Example 19. An external programmer comprising means for performing the method of any of examples 1 though 9.

Example 20. A non-transitory computer-readable medium comprising instructions that, when executed, control processing circuitry to obtain brain signal information for at least one electrode combination of a plurality of electrode combinations of one or more electrical leads; determine, based on the brain signal information, a respective frequency for the at least one electrode combination; output, for display, a plurality of selectable lead icons, wherein each selectable lead icon of the plurality of selectable lead icons represents a different electrode combination of the plurality of electrode combinations; output, for display, the respective frequency determined for the at least one electrode combination in association with the respective selectable lead icon associated with the at least one electrode combination; receive user input selecting one selectable lead icon of the plurality of selectable lead icons; and responsive to receiving the user input, selecting, for subsequent brain signal sensing, a sense electrode combination associated with the one selectable lead icon selected by the user input.

Example 21. A method comprising: obtaining, by processing circuitry, a brain signal representative of electrical activity of a brain of a patient; controlling, by the processing circuitry, a medical device to deliver electrical stimulation defined by at least a first value of a stimulation parameter; adjusting, by the processing circuitry, the first value of the stimulation parameter to a second value of the stimulation parameter at which a patient condition is identified; and determining, by the processing circuitry, a threshold value for the brain signal associated with the patient condition, wherein the medical device is configured to limit automatic adjustment of the stimulation parameter to the second value associated with the threshold value.

Example 22. The method of example 21, wherein the threshold value for the brain signal is associated with one of an upper threshold associated with a therapeutic benefit or a lower threshold for the brain signal associated with a side effect.

Example 23. The method of any of examples 21 and 22, wherein the patient condition comprises a therapeutic benefit and the threshold value comprises a first threshold value associated with an upper threshold, further comprising: adjusting the stimulation parameter to a third value at which a side effect is identified, the third value different than the second value; and determining a second threshold value for the brain signal associated with the side effect, the second threshold value associated with a lower threshold, wherein the medical device is configured to limit automatic adjustment of the stimulation parameter to between the second value and the third value such that the brain signal remains between the upper threshold and the lower threshold.

Example 24. The method of any of examples 21 though 23, further comprising controlling a user interface to: display the upper threshold and the lower threshold on a first graph; and display the second value and the third value on a second graph.

Example 25. The method of example 24, wherein the upper threshold and the second value are represented with a first color, and wherein the lower threshold and the third value are represented with a second color different than the first color.

Example 26. The method of any of examples 21 though 25, wherein adjusting the first value of the stimulation parameter to the second value of the stimulation parameter comprises: receiving, via a user interface, user input requesting an adjustment from the first value to the second value; and responsive to receiving the user input, adjusting the first value to the second value.

Example 27. The method of any of examples 21 though 26, wherein determining the threshold value for the brain signal comprises: receiving, via a user interface, user input requesting capture of the threshold value; and identifying the threshold value of the brain signal corresponding to an amplitude value of the brain signal obtained at a time the user input was received.

Example 28. The method of any of examples 21 though 27, wherein the threshold value comprises a first threshold value, wherein the method further comprising: receiving, via a user interface, user input requesting a manual adjustment to the first threshold value; and adjusting the first threshold value to a second threshold value according to the user input.

Example 29. The method of any of examples 21 though 28, further comprising controlling a user interface to: display the threshold value of the brain signal on a first graph; display the second value of the stimulation parameter on a second graph; display a representation of electrodes via which the electrical stimulation is delivered; and display a stimulation field representing the electrical stimulation with respect to the representation of the electrodes.

Example 30. The method of any of examples 21 though 29, wherein the brain signal comprises one or more local field potential signals.

Example 31. The method of any of examples 21 though 30, wherein an external programmer comprises the processing circuitry, the external programmer configured to control the medical device configured to be coupled to the one or more electrical leads.

Example 32. An external programmer configured to perform the method of any of examples 21 though 31.

Example 33. An external programmer comprising means for performing the method of any of examples 21 though 31.

Example 34. A non-transitory computer-readable medium comprising instructions that, when executed, control processing circuitry to perform the method of any of examples 21 through 32.

Example 41. A method comprising: obtaining, by processing circuitry, a brain signal representative of electrical activity of a brain of a patient; obtaining, by the processing circuitry, one or more values of a stimulation parameter that at least partially defines electrical stimulation deliverable to a portion of the brain of the patient; and outputting, for display by a user interface, a graph comprising a first trace of the brain signal for a period of time and a second trace of the one or more values of the stimulation parameter for the period of time.

Example 42. The method of example 41, wherein the graph is a first graph and the period of time is a first period of time, and wherein the method further comprises: outputting, for display by the user interface, a second graph comprising a third trace of the brain signal for a second period of time and a fourth trace of the one or more values of the stimulation parameter for the second period of time, wherein the second period of time is greater than the first period of time, and wherein the second period of time comprises the first period of time.

Example 43. The method of any of examples 41 and 42, further comprising outputting, for display by the user interface, at least one of an upper threshold for the brain signal or a lower threshold for the brain signal on the graph.

Example 44. The method of any of examples 41 though 43, further comprising, outputting, for display by the user interface, at least one of a lower limit for the stimulation parameter or an upper limit for the stimulation parameter on the graph.

Example 45. The method of any of examples 41 though 44, further comprising controlling a medical device to limit the stimulation parameter between at least one of a lower limit of the stimulation parameter corresponding to an upper threshold of the brain signal or an upper limit of the stimulation parameter corresponding to a lower threshold of the brain signal.

Example 46. The method of any of examples 41 though 45, wherein the first trace of the brain signal for a period of time and the second trace of the one or more values of the stimulation parameter for the period of time comprise near real-time values for the brain signal and the stimulation parameter.

Example 47. The method of any of examples 41 though 46, wherein the brain signal comprises one or more local field potential signals.

Example 48. The method of any of examples 41 though 47, wherein an external programmer comprises the processing circuitry, the external programmer configured to control the medical device configured to be coupled to the one or more electrical leads.

Example 49. An external programmer configured to perform the method of any of examples 41 though 48.

Example 50. An external programmer comprising means for performing the method of any of examples 41 though 48.

Example 51. A non-transitory computer-readable medium comprising instructions that, when executed, control processing circuitry to perform the method of any of examples 41 through 48.

Example 61. A method comprising: obtaining, by processing circuitry and from a first memory, brain signal information representative of electrical activity of a brain of a patient over a period of time; obtaining, by the processing circuitry, stimulation parameter information comprising one or more values of a stimulation parameter that at least partially defines electrical stimulation delivered to a portion of the brain of the patient during the period of time; and outputting, for display by a user interface, a graph comprising a first trace of the brain signal information for the period of time and a second trace of the one or more values of the stimulation parameter for the period of time.

Example 62. The method of example 61, further comprising: obtaining one or more patient events corresponding to a respective user input received during the period of time; and outputting, for display by the user interface, one or more respective first markers representing the one or more patient events on the graph, wherein the one or more respective first markers are located at a corresponding time at which the respective user input was received along a time axis of the graph.

Example 63. The method of any of examples 61 and 62, further comprising: obtaining one or more system identified events corresponding to respective automatically identified events during the period of time; and outputting, for display by the user interface, one or more respective second markers representing the one or more patient events on the graph, wherein the one or more respective second markers are located at a corresponding time at which the respective user input was received along a time axis of the graph.

Example 64. The method of example 61, further comprising: obtaining one or more patient events corresponding to a respective user input received during the period of time; outputting, for display by the user interface, one or more respective first markers representing the one or more patient events on the graph, wherein the one or more respective first markers are located at a corresponding time at which the respective user input was received along a time axis of the graph; obtaining one or more system identified events corresponding to respective automatically identified events during the period of time; and outputting, for display by the user interface, one or more respective second markers representing the one or more patient events on the graph, wherein the one or more respective second markers are located at a corresponding time at which the respective user input was received along a time axis of the graph.

Example 65. The method of any of examples 61 though 63, further comprising: receiving user input selecting a marker presented on the graph; and responsive to receiving the user input, displaying a pop up graph of the brain signal information corresponding to a time associated with the marker, the pop up graph comprising a spectral graph of the brain signal information at the time associated with the marker.

Example 66. The method of any of examples 61 though 65, wherein: the brain signal information comprises electrical activity of a first hemisphere of the brain and a second hemisphere of the brain over the period of time, the stimulation parameter information comprises one or more values of a first stimulation parameter that at least partially defines electrical stimulation delivered to the first hemisphere of the brain and one or more values of a second stimulation parameter that at least partially defines electrical stimulation delivered to the second hemisphere of the brain during the period of time; and the graph is a first graph comprising the first trace of the brain signal information comprising electrical activity of the first hemisphere for the period of time and the second trace of the one or more values of the first stimulation parameter for the period of time, and wherein the method further comprises: outputting, for display by the user interface, a second graph on a same screen as the first graph, wherein the second graph comprises a third trace of the brain signal information comprising electrical activity of the second hemisphere for the period of time and a fourth trace of the one or more values of the second stimulation parameter for the period of time.

Example 67. The method of any of examples 61 and 66, wherein the graph comprises: at least one of an upper threshold or a lower threshold displayed with the first trace of the brain signal information; and at least one of a lower limit or an upper limit displayed with the second trace of the one or more values of the stimulation parameter.

Example 68. The method of any of examples 61 though 67, wherein the brain signal comprises one or more local field potential signals.

Example 69. The method of any of examples 61 though 68, wherein an external programmer comprises the processing circuitry, the external programmer configured to control the medical device configured to be coupled to the one or more electrical leads.

Example 70. An external programmer comprising: a first memory; and processing circuitry configured to: obtain, from the first memory, brain signal information representative of electrical activity of a brain of a patient over a period of time; obtain stimulation parameter information comprising one or more values of a stimulation parameter that at least partially defines electrical stimulation delivered to a portion of the brain of the patient during the period of time; and output, for display by a user interface, a graph comprising a first trace of the brain signal information for the period of time and a second trace of the one or more values of the stimulation parameter for the period of time.

Example 71. The external programmer of example 70, wherein the processing circuitry is further configured to: obtain one or more patient events corresponding to a respective user input received during the period of time; and output, for display by the user interface, one or more respective first markers representing the one or more patient events on the graph, wherein the one or more respective first markers are located at a corresponding time at which the respective user input was received along a time axis of the graph.

Example 72. The external programmer of any of examples 70 and 71, wherein the processing circuitry is further configured to: obtain one or more system identified events corresponding to respective automatically identified events during the period of time; and output, for display by the user interface, one or more respective second markers representing the one or more patient events on the graph, wherein the one or more respective second markers are located at a corresponding time at which the respective user input was received along a time axis of the graph.

Example 73. The external programmer of any of examples 70 though 72, wherein the processing circuitry is further configured to: obtain one or more patient events corresponding to a respective user input received during the period of time; output, for display by the user interface, one or more respective first markers representing the one or more patient events on the graph, wherein the one or more respective first markers are located at a corresponding time at which the respective user input was received along a time axis of the graph; obtain one or more system identified events corresponding to respective automatically identified events during the period of time; and output, for display by the user interface, one or more respective second markers representing the one or more patient events on the graph, wherein the one or more respective second markers are located at a corresponding time at which the respective user input was received along a time axis of the graph.

Example 74. The external programmer of any of examples 70 though 73, wherein the processing circuitry is further configured to: receive user input selecting a marker presented on the graph; and responsive to receiving the user input, control a display to display a pop up graph of the brain signal information corresponding to a time associated with the marker, the pop up graph comprising a spectral graph of the brain signal information at the time associated with the marker.

Example 75. The external programmer of any of examples 70 though 74, wherein: the brain signal information comprises electrical activity of a first hemisphere of the brain and a second hemisphere of the brain over the period of time, the stimulation parameter information comprises one or more values of a first stimulation parameter that at least partially defines electrical stimulation delivered to the first hemisphere of the brain and one or more values of a second stimulation parameter that at least partially defines electrical stimulation delivered to the second hemisphere of the brain during the period of time; and the graph is a first graph comprising the first trace of the brain signal information comprising electrical activity of the first hemisphere for the period of time and the second trace of the one or more values of the first stimulation parameter for the period of time, and wherein the processing circuitry is further configured to: output, for display by the user interface, a second graph on a same screen as the first graph, wherein the second graph comprises a third trace of the brain signal information comprising electrical activity of the second hemisphere for the period of time and a fourth trace of the one or more values of the second stimulation parameter for the period of time.

Example 76. The external programmer of any of examples 70 through and 75, wherein the graph comprises: at least one of an upper threshold or a lower threshold displayed with the first trace of the brain signal information; and at least one of a lower limit or an upper limit displayed with the second trace of the one or more values of the stimulation parameter.

Example 77. The external programmer of any of examples 70 though 76, wherein the brain signal comprises one or more local field potential signals.

Example 78. The external programmer of any of examples 70 though 77, wherein the external programmer is configured to control a medical device configured to be coupled to the one or more electrical leads.

Example 79. An external programmer comprising means for performing the method of any of examples 61 though 69.

Example 80. A non-transitory computer-readable medium comprising instructions that, when executed, control processing circuitry to obtain, from a first memory, brain signal information representative of electrical activity of a brain of a patient over a period of time; obtain stimulation parameter information comprising one or more values of a stimulation parameter that at least partially defines electrical stimulation delivered to a portion of the brain of the patient during the period of time; and output, for display by a user interface, a graph comprising a first trace of the brain signal information for the period of time and a second trace of the one or more values of the stimulation parameter for the period of time.

Example 81. A method comprising: obtaining, by processing circuitry, brain signal information representative of electrical activity of a brain of a patient over a period of time; determining, by the processing circuitry, a first amount of time an amplitude of the brain signal information was greater than an upper threshold during the period of time; determining, by the processing circuitry, a second amount of time the amplitude of the brain signal information was less than a lower threshold during the period of time; determining, by the processing circuitry, a third amount of time the amplitude of the brain signal information was between the upper threshold and the lower threshold during the period of time; and outputting, for display via a user interface, a representation of the first amount of time, the second amount of time, and the third amount of time.

Example 82. The method of example 81, wherein the amplitude of the brain signal information above the upper threshold indicates ineffective electrical stimulation for treating a symptom of the patient.

Example 83. The method of any of examples 81 and 82, wherein the amplitude of the brain signal information below the lower threshold indicates a side effect caused by the electrical stimulation delivered to the patient.

Example 84. The method of any of examples 81 though 83, wherein the representation comprises a table having respective entries for each of the first amount of time, the second amount of time, and the third amount of time.

Example 85. The method of any of examples 81 though 84, wherein the representation comprises a graph illustrating each of the first amount of time, the second amount of time, and the third amount of time.

Example 86. The method of any of examples 81 though 85, further comprising outputting, as part of the representation, at least one of an average amplitude of stimulation, an amount of time stimulation was turned off due to adaptive stimulation being delivered to the patient, or an amount of time adaptive stimulation was delivered to the patient during the period of time.

Example 87. The method of any of examples 81 though 86, wherein the brain signal information comprises one or more local field potential signals.

Example 88. The method of any of examples 81 though 87, wherein an external programmer comprises the processing circuitry, the external programmer configured to control the medical device configured to be coupled to the one or more electrical leads.

Example 89. An external programmer configured to perform the method of any of examples 81 though 88.

Example 90. An external programmer comprising means for performing the method of any of examples 81 though 88.

Example 91. A non-transitory computer-readable medium comprising instructions that, when executed, control processing circuitry to perform the method of any of examples 81 through 88.

Example 101. A method comprising: receiving, by processing circuitry, an indication of an event at a time; responsive to receiving the indication of the event, storing spectral information for a brain signal recorded at the time; and outputting, for display by a user interface, a graph indicating the spectral information for the brain signal recorded at the time.

Example 102. The method of example 101, wherein the indication is a first indication, the event is a first event, the brain signal is a first brain signal, and the time is a first time, and wherein the method further comprises: receiving, by processing circuitry, a second indication of a second event at a second time; responsive to receiving the second indication of the second event, storing spectral information for a second brain signal recorded at the second time; and outputting, for display by a user interface, the graph indicating the spectral information for the first brain signal recorded at the first time and spectral information for the second brain signal recorded at the second time.

Example 103. The method of any of examples 101 and 102, wherein receiving the indication of the event comprises receiving, via a user interface, user input indicating the event.

Example 104. The method of any of examples 101 though 103, further comprising: responsive to receiving the indication of the event, recording the brain signal; and subsequent to recording the brain signal, generating the spectral information for the brain signal.

Example 105. The method of any of examples 101 though 104, wherein storing the spectral information for the brain signal recorded at the time comprises selecting the brain signal from a rolling buffer comprising brain signals sensed over a period comprising the time.

Example 106. The method of any of examples 101 though 105, wherein receiving the indication of the event comprises automatically identifying, by the processing circuitry, the event from at least one of brain signal information or an electrical stimulation status.

Example 107. The method of any of examples 101 though 106, wherein the event comprises at least one of a patient fall, a medication time, a patient symptom, or a stimulation delivery event.

Example 108. The method of any of examples 101 though 107, wherein the brain signal recorded at the time is a one brain signal of a plurality of brain signals recorded at respective times, and wherein the method further comprises: receiving user input selecting at least the one brain signal from the plurality of brain signals; and outputting, for display via the user interface, the spectral information for the at least one brain signal selected according to the user input.

Example 109. The method of any of examples 101 though 108, wherein the graph displays the spectral information as a magnitude of the brain signal vs. frequency of the brain signal.

Example 110. The method of any of examples 101 though 109, wherein the brain signal comprises one or more local field potential signals.

Example 111. The method of any of examples 101 though 110, wherein an external programmer comprises the processing circuitry, the external programmer configured to control the medical device configured to be coupled to the one or more electrical leads.

Example 112. An external programmer configured to perform the method of any of examples 101 through 111.

Example 113. An external programmer comprising means for performing the method of any of examples 101 through 111.

Example 114. A non-transitory computer-readable medium comprising instructions that, when executed, control processing circuitry to perform the method of any of examples 101 through 111.

Example 115. A system comprising an implantable deep brain stimulation device and the external programmer of any of examples 10, 11, 32, 33, 49, 50, 69, 70, 89, 90, 112, and 113.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
obtaining, by processing circuitry and from a memory, brain signal information representative of electrical activity of a brain of a patient over a period of time;
obtaining, by the processing circuitry, stimulation parameter information comprising one or more values of a stimulation parameter used to generate electrical stimulation delivered to a portion of the brain of the patient during the period of time; and
outputting, for display by a user interface, a graph comprising a first trace of the brain signal information for the period of time and a second trace of the one or more values of the stimulation parameter for the period of time.

2. The method of claim 1, further comprising:
obtaining one or more patient events corresponding to a respective user input received during the period of time; and
outputting, for display by the user interface, one or more respective first markers representing the one or more patient events on the graph, wherein the one or more respective first markers are located at a corresponding time at which the respective user input was received along a time axis of the graph.

3. The method of claim 1, further comprising:
obtaining one or more system identified events corresponding to respective automatically identified events during the period of time; and
outputting, for display by the user interface, one or more respective second markers representing the one or more system identified events on the graph, wherein the one or more respective second markers are located at a corresponding time at which the respective automatically identified events occurred along a time axis of the graph.

4. The method of claim 1, further comprising:
obtaining one or more patient events corresponding to a respective user input received during the period of time;
outputting, for display by the user interface, one or more respective first markers representing the one or more patient events on the graph, wherein the one or more respective first markers are located at a corresponding time at which the respective user input was received along a time axis of the graph;
obtaining one or more system identified events corresponding to respective automatically identified events during the period of time; and
outputting, for display by the user interface, one or more respective second markers representing the one or more system identified events on the graph, wherein the one or more respective second markers are located at a corresponding time at which the respective automatically identified events occurred along a time axis of the graph.

5. The method of claim 1, further comprising:
receiving user input selecting a marker presented on the graph; and
responsive to receiving the user input, displaying a pop up graph of the brain signal information corresponding to a time associated with the marker, the pop up graph comprising a spectral graph of the brain signal information at the time associated with the marker.

6. The method of claim 1, wherein:
the brain signal information comprises electrical activity of a first hemisphere of the brain and a second hemisphere of the brain over the period of time,
the stimulation parameter information comprises one or more values of a first stimulation parameter used to generate electrical stimulation delivered to the first hemisphere of the brain and one or more values of a second stimulation parameter used to generate electrical stimulation delivered to the second hemisphere of the brain during the period of time; and
the graph is a first graph comprising the first trace of the brain signal information comprising electrical activity of the first hemisphere for the period of time and the second trace of the one or more values of the first stimulation parameter for the period of time, and wherein the method further comprises:

outputting, for display by the user interface, a second graph on a same screen as the first graph, wherein the second graph comprises a third trace of the brain signal information comprising electrical activity of the second hemisphere for the period of time and a fourth trace of the one or more values of the second stimulation parameter for the period of time.

7. The method of claim 1, wherein the graph comprises:
at least one of an upper threshold or a lower threshold displayed with the first trace of the brain signal information; and
at least one of a lower limit or an upper limit displayed with the second trace of the one or more values of the stimulation parameter.

8. The method of claim 1, wherein the brain signal comprises one or more local field potential signals.

9. The method of claim 1, wherein an external programmer comprises the processing circuitry, the external programmer configured to control a medical device configured to be coupled to the one or more electrical leads configured to deliver the electrical stimulation.

10. An external programmer comprising:
a memory; and
processing circuitry configured to:
  obtain, from the memory, brain signal information representative of electrical activity of a brain of a patient over a period of time;
  obtain stimulation parameter information comprising one or more values of a stimulation parameter used to generate electrical stimulation delivered to a portion of the brain of the patient during the period of time; and
  output, for display by a user interface, a graph comprising a first trace of the brain signal information for the period of time and a second trace of the one or more values of the stimulation parameter for the period of time.

11. The external programmer of claim 10, wherein the processing circuitry is further configured to:
obtain one or more patient events corresponding to a respective user input received during the period of time; and
output, for display by the user interface, one or more respective first markers representing the one or more patient events on the graph, wherein the one or more respective first markers are located at a corresponding time at which the respective user input was received along a time axis of the graph.

12. The external programmer of claim 10, wherein the processing circuitry is further configured to:
obtain one or more system identified events corresponding to respective automatically identified events during the period of time; and
output, for display by the user interface, one or more respective second markers representing the one or more system identified events on the graph, wherein the one or more respective second markers are located at a corresponding time at which the respective automatically identified events occurred along a time axis of the graph.

13. The external programmer of claim 10, wherein the processing circuitry is further configured to:
obtain one or more patient events corresponding to a respective user input received during the period of time;

output, for display by the user interface, one or more respective first markers representing the one or more patient events on the graph, wherein the one or more respective first markers are located at a corresponding time at which the respective user input was received along a time axis of the graph;
obtain one or more system identified events corresponding to respective automatically identified events during the period of time; and
output, for display by the user interface, one or more respective second markers representing the one or more system identified events on the graph, wherein the one or more respective second markers are located at a corresponding time at which the respective automatically identified events occurred along a time axis of the graph.

14. The external programmer of claim 10, wherein the processing circuitry is further configured to:
receive user input selecting a marker presented on the graph; and
responsive to receiving the user input, control a display to display a pop up graph of the brain signal information corresponding to a time associated with the marker, the pop up graph comprising a spectral graph of the brain signal information at the time associated with the marker.

15. The external programmer of claim 10, wherein:
the brain signal information comprises electrical activity of a first hemisphere of the brain and a second hemisphere of the brain over the period of time,
the stimulation parameter information comprises one or more values of a first stimulation parameter used to generate electrical stimulation delivered to the first hemisphere of the brain and one or more values of a second stimulation parameter used to generate electrical stimulation delivered to the second hemisphere of the brain during the period of time; and
the graph is a first graph comprising the first trace of the brain signal information comprising electrical activity of the first hemisphere for the period of time and the second trace of the one or more values of the first stimulation parameter for the period of time, and wherein the processing circuitry is further configured to:
output, for display by the user interface, a second graph on a same screen as the first graph, wherein the second graph comprises a third trace of the brain signal information comprising electrical activity of the second hemisphere for the period of time and a fourth trace of the one or more values of the second stimulation parameter for the period of time.

16. The external programmer of claim 10, wherein the graph comprises:
at least one of an upper threshold or a lower threshold displayed with the first trace of the brain signal information; and
at least one of a lower limit or an upper limit displayed with the second trace of the one or more values of the stimulation parameter.

17. The external programmer of claim 10, wherein the brain signal comprises one or more local field potential signals.

18. The external programmer of claim 10, wherein the external programmer is configured to control a medical device configured to be coupled to the one or more electrical leads.

19. A non-transitory computer-readable medium comprising instructions that, when executed, control processing circuitry to:
- obtain, from a memory, brain signal information representative of electrical activity of a brain of a patient over a period of time;
- obtain stimulation parameter information comprising one or more values of a stimulation parameter used to generate electrical stimulation delivered to a portion of the brain of the patient during the period of time; and
- output, for display by a user interface, a graph comprising a first trace of the brain signal information for the period of time and a second trace of the one or more values of the stimulation parameter for the period of time.

20. The non-transitory computer-readable medium of claim 19, further comprising instructions that cause the processing circuitry to:
- obtain one or more patient events corresponding to a respective user input received during the period of time; and
- output, for display by the user interface, one or more respective first markers representing the one or more patient events on the graph, wherein the one or more respective first markers are located at a corresponding time at which the respective user input was received along a time axis of the graph.

* * * * *